United States Patent
Nagase et al.

(10) Patent No.: US 9,815,787 B2
(45) Date of Patent: Nov. 14, 2017

(54) SULFONAMIDE DERIVATIVE OR PHARMACEUTICALLY ACCEPTABLE ACID ADDITION SALT THEREOF

(71) Applicant: UNIVERSITY OF TSUKUBA, Tsukuba-shi, Ibaraki (JP)

(72) Inventors: Hiroshi Nagase, Tsukuba (JP); Takashi Nagahara, Yokohama (JP)

(73) Assignee: University of Tsukuba, Tsukuba (JP)

( * ) Notice: Subject to any disclaimer, the term of this patent is extended or adjusted under 35 U.S.C. 154(b) by 0 days.

(21) Appl. No.: 15/103,085

(22) PCT Filed: Dec. 12, 2014

(86) PCT No.: PCT/JP2014/082961
§ 371 (c)(1),
(2) Date: Jun. 9, 2016

(87) PCT Pub. No.: WO2015/088000
PCT Pub. Date: Jun. 18, 2015

(65) Prior Publication Data
US 2016/0362376 A1 Dec. 15, 2016

(30) Foreign Application Priority Data
Dec. 12, 2013 (JP) .................................. 2013-257523

(51) Int. Cl.
| | |
|---|---|
| *C07D 205/04* | (2006.01) |
| *C07D 207/04* | (2006.01) |
| *C07D 211/16* | (2006.01) |
| *C07D 213/81* | (2006.01) |
| *C07D 213/82* | (2006.01) |
| *C07D 231/14* | (2006.01) |
| *C07D 233/90* | (2006.01) |
| *C07D 307/68* | (2006.01) |
| *C07D 333/38* | (2006.01) |
| *C07D 401/12* | (2006.01) |
| *C07D 409/12* | (2006.01) |
| *C07C 311/44* | (2006.01) |
| *C07C 311/21* | (2006.01) |
| *C07C 311/29* | (2006.01) |
| *C07D 213/34* | (2006.01) |
| *C07D 213/61* | (2006.01) |
| *C07D 213/64* | (2006.01) |
| *C07D 295/192* | (2006.01) |

(52) U.S. Cl.
CPC .......... *C07D 213/81* (2013.01); *C07C 311/21* (2013.01); *C07C 311/29* (2013.01); *C07C 311/44* (2013.01); *C07D 205/04* (2013.01); *C07D 207/04* (2013.01); *C07D 211/16* (2013.01); *C07D 213/34* (2013.01); *C07D 213/61* (2013.01); *C07D 213/64* (2013.01); *C07D 213/82* (2013.01); *C07D 231/14* (2013.01); *C07D 233/90* (2013.01); *C07D 295/192* (2013.01); *C07D 307/68* (2013.01); *C07D 333/38* (2013.01); *C07D 401/12* (2013.01); *C07D 409/12* (2013.01)

(58) Field of Classification Search
CPC .. C07D 205/04; C07D 207/04; C07D 211/16; C07D 213/81; C07D 213/82; C07D 231/14; C07D 233/90; C07D 307/68; C07D 333/38; C07D 401/12; C07D 409/12; C07C 311/44
See application file for complete search history.

(56) References Cited

U.S. PATENT DOCUMENTS

| | | |
|---|---|---|
| 8,258,163 B2 | 9/2012 | Yanagisawa |
| 2009/0186920 A1* | 7/2009 | Knust et al. ......... C07D 207/06 514/330 |

(Continued)

FOREIGN PATENT DOCUMENTS

| | | |
|---|---|---|
| JP | 2009-503106 A | 1/2009 |
| JP | 2011-510037 A | 3/2011 |

(Continued)

OTHER PUBLICATIONS

Chemelli et al., *Cell*, 98(4): 437-451 (1999).

(Continued)

*Primary Examiner* — Timothy R Rozof
(74) *Attorney, Agent, or Firm* — Leydig, Voit & Mayer, Ltd.

(57) ABSTRACT

The present invention aims to provide a novel low-molecular-weight compound having an orexin agonist activity, which is expected to be useful as a superior agent for the treatment or prophylaxis of narcolepsy. The present invention provides a compound showing superior orexin agonist activity which is represented by the formula (I)

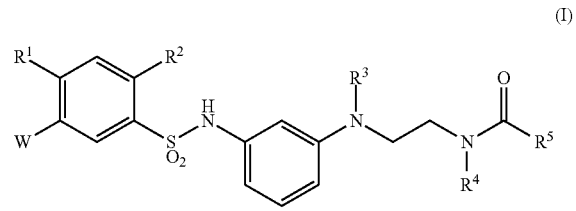

(I)

wherein each symbol is as defined in the DESCRIPTION, and a pharmaceutically acceptable acid addition salt thereof, as well as an orexin agonist containing the compound or a pharmaceutically acceptable acid addition salt thereof.

2 Claims, No Drawings

(56) References Cited

U.S. PATENT DOCUMENTS

2009/0258903 A1 10/2009 Coleman et al.
2011/0190351 A1 8/2011 Ohtani et al.
2011/0207747 A1 8/2011 Bergman et al.

FOREIGN PATENT DOCUMENTS

JP 2011-529903 A 12/2011
JP 2012-507539 A 3/2012

OTHER PUBLICATIONS

De Lecea et al., *Proceedings of the National Academy of Sciences of the United States of America*, 95(1): 322-327 (1998).
Funato et al., *Cell Metabolism*, 9(1): 64-76 (2009).
Lin et al., *Cell*, 98(3): 365-376 (1999).
Mignot et al., *Archives of Neurology*, 59(10): 1553-1562 (2002).
Nagahara et al., *Journal of Medicinal Chemistry*, 58(20): 7931-7937 (2015).
Nagase et al., "Design and synthesis of orexin 2 receptor agonist," 36th Annual Meeting of Japanese Narcotic Research Conference, p. 19, abstract S2-3 (Aug. 19-20, 2016).
Saitoh et al., "Creation of orexin receptor agonist and clarification of pharmacological action," Research grant relating to clarification of etiology and pathology of adult diseases (TMFC), 22nd Research Presentation, p. 70, Poster Session II, item 10 (Jul. 2-3, 2016).
Saitoh et al., "Development of non-peptide orexin receptor agonists for controlling sleep/wake cycle," The 96th CSJ Annual Meeting, Presentation 4A4-08 (Mar. 24, 2016).
Saitoh et al., "Discovery of novel orexin receptor agonists for controlling sleep/awake cycle," 2015 International Chemical Congress of Pacific Basin Societies, Honolulu, Hawaii, Abstract 2186 (Dec. 15-20, 2015).
Saitoh et al., *Medchem News*, 26(7): 90-96 (2016).
Saitoh et al., *The 33rd Medicinal Chemistry Symposium*, p. 134, Abstract 2P-08 (2015).
Saitoh et al., *Wako Junyaku Jiho*, 84(3): 2-5 (2016).
Sakurai et al., *Cell*, 92(4): 573-585 (1998).
Tominaga et al., "YNT-185, a novel small-molecule orexin type 2 receptor agonist, ameliorates narcolepsy-cataplexy symptoms in model mice," The 89th Annual Meeting of The Japanese Pharmacological Society (Mar. 9, 2016).
Willie et al., *Neuron*, 38(5): 715-730 (2003).
Yamanaka et al., *Neuron*, 38(5): 701-713 (2003).

\* cited by examiner

SULFONAMIDE DERIVATIVE OR PHARMACEUTICALLY ACCEPTABLE ACID ADDITION SALT THEREOF

CROSS-REFERENCE TO RELATED APPLICATIONS

This patent application is the U.S. national phase of International Patent Application No. PCT/JP2014/082961, filed Dec. 12, 2014, which claims the benefit of Japanese Patent Application No. 2013-257523, filed on Dec. 12, 2013, which are incorporated by reference in their entireties herein.

TECHNICAL FIELD

The present invention aims to provide a novel compound useful as a superior orexin agonist.

BACKGROUND ART

Narcolepsy is a sleeping disorder caused by the inability of the brain to control the sleep-wake cycle. The major symptoms of narcolepsy includes, for example, excessive daytime sleepiness during the day, cataplexy induced by emotion (particularly strong joy and surprise), hypnagogic hallucination, and hypnagogic paralysis, and narcolepsy patients are under serious influence in general social life. The prevalence of narcolepsy is assumed to be 0.05-0.2% (0.16-0.18% in Japan), and the prevalence indicates that the disease is not rare.

The therapy of narcolepsy mainly includes a drug therapy and life guidance. For drug therapy, methylphenidate, modafinil and pemoline are used to suppress daytime sleepiness, and tricyclic antidepressant, selective serotonin reuptake inhibitor (SSRI), and serotonin and noradrenaline reuptake inhibitor (SNRI) are used to control cataplexy. While these treatment methods are symptomatic therapy of narcolepsy, they are not basic treatment methods.

In recent years, the relationship between narcolepsy and orexin system dysfunction is attracting attention. Orexins are neuropeptides present in the lateral hypothalamic area, which are two kinds of peptide of orexin-A and orexin-B (hypocretin 1, hypocretin 2 (non-patent document 1)). They bind to orexin 1 receptor (hereinafter to be also referred to as OX1R) and orexin 2 receptor (hereinafter to be also referred to as OX2R), which are G-protein coupled receptors (non-patent document 2). It was suggested from model experiments using mouse and dog that lack of orexin receptor (both OX1R and OX2R are expressed), or lack of OX2R causes narcolepsy (non-patent document 3). Furthermore, it was suggested from model experiments using mouse that the function of OX2R is important for maintaining wakefulness (non-patent document 4, non-patent document 5).

On the other hand, many narcolepsy patients were confirmed to show disappearance of orexin neuron, and decreased orexin concentration (non-patent document 6). Therefore, it is strongly suggested that narcolepsy is highly possibly caused by the lack of orexin.

The orexin receptor is widely expressed in the brain. Orexins are peptides, and are not useful for pharmaceutical use since permeability through the blood-brain barrier is extremely low. Therefore, a low molecule orexin receptor agonist has been desired. In recent years, a compound with a cyclic guanidine skeleton is reported as a small-molecule OX2R agonist (patent document 1).

In addition, orexin system is considered to not only control the above-mentioned sleep-wake but also appropriately control feeding behavior with emotion and energy balance. A mouse under fasting increases the amount of behavior for searching food by increasing the waking time and decreasing the sleep hours. On the other hand, it was clarified that the waking time and the amount of behavior do not increase in orexin receptor-deficient mouse (non-patent document 7). Moreover, it was suggested that an increase of the leptin sensitivity by OX2R regulates the homeostasis of body weight (non-patent document 8). From these findings, an orexin receptor (particularly OX2R) agonist is a potential therapeutic drug for not only narcolepsy but also diabetes, obesity and metabolic syndrome.

DOCUMENT LIST

Patent Document patent document 1: U.S. Pat. No. 8,258,163

Non-Patent Documents non-patent document 1: Proc. Natl. Acad. Sci. USA, 95, 322-327 (1998)
non-patent document 2: Cell, 92, 573-585 (1998)
non-patent document 3: Cell, 98, 365-376 (1999)
non-patent document 4: Cell, 98, 437-451 (1999)
non-patent document 5: Neuron, 38, 715-730 (2003)
non-patent document 6: Arch. Neurol., 59, 1553-1562 (2002)
non-patent document 7: Neuron, 38, 701-713 (2003)
non-patent document 8: Cell Metab., 9, 64-76 (2009)

SUMMARY OF THE INVENTION

Problems to be Solved by the Invention

The present invention aims to provide a novel low-molecular-weight compound showing an orexin agonist activity, which is expected to be useful as a superior therapeutic or prophylactic agent for narcolepsy.

Means of Solving the Problems

The present inventors have conducted intensive studies in an attempt to solve the aforementioned problems and found a compound represented by the formula (I) mentioned below and having a superior OX2R agonist activity, which resulted in the completion of the present invention.

That is, the present invention provides

[1] A compound represented by the formula (I)

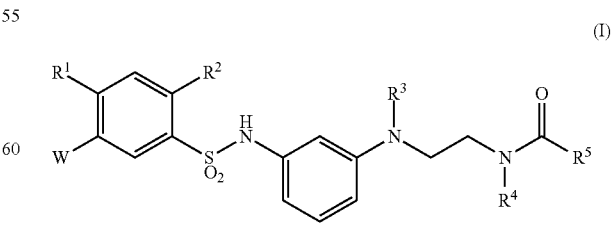

wherein
$R^1$ is a hydrogen atom, alkyl having 1 to 4 carbon atoms or halogen, $R^2$ is a hydrogen atom, alkyl having 1 to 4 carbon atoms, alkoxy having 1 to 4 carbon atoms, halogen, —OH, —NR$^{2a}$R$^{2b}$ (wherein R$^{2a}$ is a hydrogen atom, alkyl having 1 to 6 carbon atoms or cycloalkyl having 3 to 8 carbon atoms, R$^{2b}$ is a hydrogen atom, alkyl having 1 to 6 carbon atoms or cycloalkyl having 3 to 8 carbon atoms), or the formula (a) or (b)

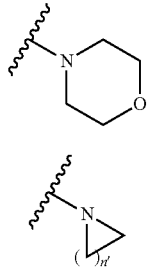
(a)

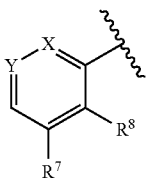
(b)

(wherein n' is an integer of 1 to 4)
$R^3$ is a hydrogen atom or alkyl having 1 to 4 carbon atoms,
$R^4$ is a hydrogen atom or alkyl having 1 to 4 carbon atoms,
$R^5$ is aryl or heteroaryl (wherein aryl or heteroaryl is optionally substituted by optionally selected 1 to 4 $R^6$),
$R^6$ is a hydrogen atom, alkyl having 1 to 4 carbon atoms, alkoxy having 1 to 4 carbon atoms, halogen, —CN, —CF$_3$, —CH$_2$F, —CHF$_2$, —OCF$_3$, —OH, —NO$_2$ or —NR$^{6a}$R$^{6b}$ (wherein R$^{6a}$ is a hydrogen atom, alkyl having 1 to 4 carbon atoms, —CH$_2$CH$_2$OMe or —CH$_2$CH$_2$OEt, R$^{6b}$ is a hydrogen atom, alkyl having 1 to 4 carbon atoms, —CH$_2$CH$_2$OMe or —CH$_2$CH$_2$OEt).
W is the formula (II):

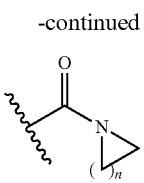
(II)

(wherein
$R^7$ is a hydrogen atom, alkyl having 1 to 4 carbon atoms, alkoxy having 1 to 4 carbon atoms or halogen,
$R^8$ is a hydrogen atom, alkyl having 1 to 4 carbon atoms, alkoxy having 1 to 4 carbon atoms or halogen,
X is —N= or —CR$^9$=,
Y is —N= or —CR$^9$=,
$R^9$ is a hydrogen atom, alkyl having 1 to 4 carbon atoms, alkoxy having 1 to 4 carbon atoms, halogen, —OH, —NH$_2$, —NR$^{10}$R$^{11}$, —CH$_2$OR$^{10}$, —CF$_3$, —OCF$_3$, —CN, —C(O)OR$^{10}$, —C(O)NR$^{10}$R$^{11}$, the formula (III) or (IV),

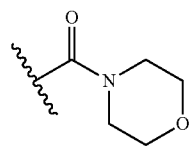
(III)

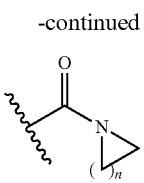
(IV)

(wherein n is an integer of 1 to 4)
X and Y are —CR$^9$=, each R$^9$ may be the same or different,
$R^{10}$ is a hydrogen atom, alkyl having 1 to 4 carbon atoms, —CH$_2$CF$_3$, —CH$_2$CH$_2$OH or —CH$_2$CH$_2$OMe,
$R^{11}$ is a hydrogen atom, alkyl having 1 to 4 carbon atoms, —CH$_2$CF$_3$, —CH$_2$CH$_2$OH or —CH$_2$CH$_2$OMe,
or a pharmaceutically acceptable acid addition salt thereof,
[1'] a compound represented by the formula (I)

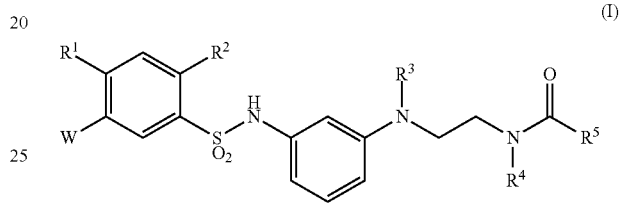
(I)

wherein
$R^1$ is a hydrogen atom, alkyl having 1 to 4 carbon atoms or halogen,
$R^2$ is a hydrogen atom, alkyl having 1 to 4 carbon atoms, alkoxy having 1 to 4 carbon atoms or halogen,
$R^3$ is a hydrogen atom or alkyl having 1 to 4 carbon atoms,
$R^4$ is a hydrogen atom or alkyl having 1 to 4 carbon atoms,
$R^5$ is aryl or heteroaryl (wherein aryl or heteroaryl is optionally substituted by optionally selected 1 to 4 $R^6$),
$R^6$ is a hydrogen atom, alkyl having 1 to 4 carbon atoms, alkoxy having 1 to 4 carbon atoms, halogen, —CN, —CF$_3$, —CH$_2$F, —CHF$_2$, —OCF$_3$, —OH, —NO$_2$ or —NR$^a$R$^b$ (wherein R$^a$ is a hydrogen atom, alkyl having 1 to 4 carbon atoms, —CH$_2$CH$_2$OMe or —CH$_2$CH$_2$OEt, R$^b$ is a hydrogen atom, alkyl having 1 to 4 carbon atoms, —CH$_2$CH$_2$OMe or —CH$_2$CH$_2$OEt,
W is the formula (II):

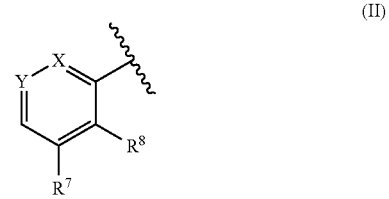
(II)

(wherein
$R^7$ is a hydrogen atom, alkyl having 1 to 4 carbon atoms, alkoxy having 1 to 4 carbon atoms or halogen,
$R^8$ is a hydrogen atom, alkyl having 1 to 4 carbon atoms, alkoxy having 1 to 4 carbon atoms or halogen,
X is —N= or —CR$^9$=,
Y is —N= or —CR$^9$=,
$R^9$ is a hydrogen atom, alkyl having 1 to 4 carbon atoms, alkoxy having 1 to 4 carbon atoms, halogen, —OH, —NH$_2$, —NR$^{10}$R$^{11}$, —CH$_2$OR$^{10}$, —CF$_3$, —OCF$_3$, —CN, —C(O)OR$^{10}$, —C(O)NR$^{10}$R$^{11}$, the formula (III) or (IV),

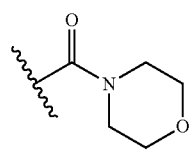
(III)

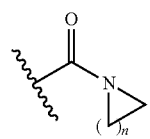
(IV)

(wherein n is an integer of 1 to 4)

when X and Y are —CR⁹═, each $R^9$ may be the same or different, $R^{10}$ is a hydrogen atom, alkyl having 1 to 4 carbon atoms, —CH$_2$CF$_3$, —CH$_2$CH$_2$OH or —CH$_2$CH$_2$OMe, and $R^{11}$ is a hydrogen atom, alkyl having 1 to 4 carbon atoms, —CH$_2$CF$_3$, —CH$_2$CH$_2$OH or —CH$_2$CH$_2$OMe, or a pharmaceutically acceptable acid addition salt thereof,

[2] the compound of the above-mentioned [1] or [1'], wherein $R^1$ is a hydrogen atom, methyl, ethyl, a fluorine atom or a chlorine atom, $R^2$ is a hydrogen atom, methyl, ethyl, methoxy, ethoxy, a fluorine atom, a chlorine atom, —OH, —NH$_2$, —NH (Me) or —N(Me)$_2$, $R^3$ is a hydrogen atom or methyl, $R^4$ is a hydrogen atom or methyl, $R^5$ is any group selected from the formulas (V) to (XV)

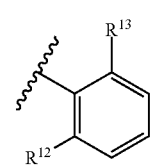
(V)

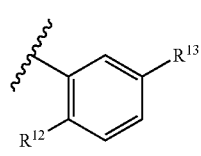
(VI)

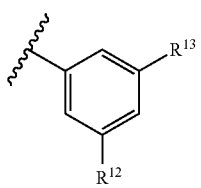
(VII)

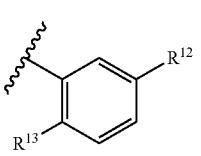
(VIII)

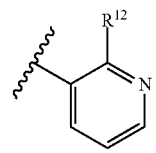
(IX)

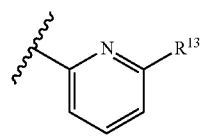
(X)

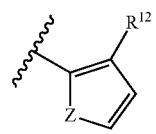
(XI)

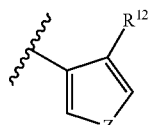
(XII)

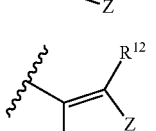
(XIII)

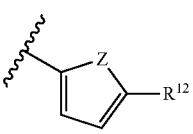
(XIV)

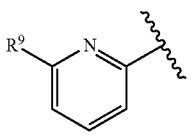
(XV)

(wherein $R^{12}$ is methyl, ethyl, n-propyl, isopropyl, tert-butyl, methoxy, ethoxy, a fluorine atom, a chlorine atom, —CH$_2$F, —CHF$_2$, —CF$_3$ or —CN, $R^{13}$ is a hydrogen atom, methyl, ethyl, methoxy, ethoxy, a fluorine atom or a chlorine atom, Z is an oxygen atom or a sulfur atom, W is any group selected from the formulas (XVI) to (XX)

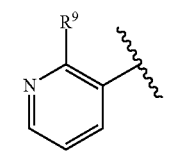
(XVI)

(XVII)

-continued

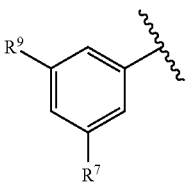 (XVIII)

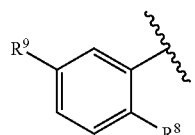 (XIX)

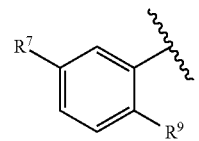 (XX)

(wherein
$R^7$ is a hydrogen atom, methyl, ethyl, methoxy, ethoxy, a fluorine atom or a chlorine atom,
$R^8$ is a hydrogen atom, methyl, ethyl, methoxy, ethoxy, a fluorine atom or a chlorine atom,
$R^9$ is a hydrogen atom, methyl, ethyl, n-propyl, isopropyl, methoxy, ethoxy, n-propoxy, isopropoxy, a fluorine atom, a chlorine atom, —OH, —NR$^{10}$R$^{11}$, —CH$_2$OR$^{10}$, —CF$_3$, —OCF$_3$, —CN, —C(O)NR$^{10}$R$^{11}$, the formula (III) or (IV),
$R^{10}$ is a hydrogen atom, methyl, ethyl, n-propyl, isopropyl, tert-butyl, isobutyl or —CH$_2$CH$_2$OMe,
$R^{11}$ is a hydrogen atom, methyl, ethyl, n-propyl, isopropyl, tert-butyl, isobutyl or —CH$_2$CH$_2$OMe,
n is an integer of 2 to 4,
or a pharmaceutically acceptable acid addition salt thereof,
[2'] the compound of the above-mentioned [1] or [1'], wherein
$R^1$ is a hydrogen atom or alkyl having 1 to 4 carbon atoms,
$R^2$ is a hydrogen atom, alkyl having 1 to 4 carbon atoms, alkoxy having 1 to 4 carbon atoms or halogen,
$R^6$ is alkyl having 1 to 4 carbon atoms, alkoxy having 1 to 4 carbon atoms, halogen, —CN, —CF$_3$, —OH or —NR$^{6a}$R$^{6b}$ (wherein R$^{6a}$ is alkyl having 1 to 4 carbon atoms, R$^{6b}$ is alkyl having 1 to 4 carbon atoms),
W is a compound of the formula (II):

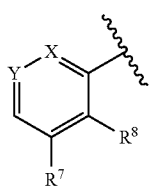 (II)

(wherein
$R^7$ is a hydrogen atom, alkoxy having 1 to 4 carbon atoms or halogen,
$R^8$ is a hydrogen atom, alkyl having 1 to 4 carbon atoms, alkoxy having 1 to 4 carbon atoms or halogen,
X is —CR$^9$= or —N=,
Y is or —N=, $R^9$ is a hydrogen atom, alkyl having 1 to 4 carbon atoms, alkoxy having 1 to 4 carbon atoms, halogen, —OH, —NR$^{10}$R$^{11}$, —CH$_2$OH, —C(O)OR$^{10}$, —C(O)NR$^{10}$R$^{11}$ or the formula (IV):

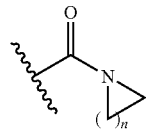 (IV)

(wherein n is an integer of 1 to 4),
$R^{10}$ is a hydrogen atom, alkyl having 1 to 4 carbon atoms, —CH$_2$CF$_3$, —CH$_2$CH$_2$OH or —CH$_2$CH$_2$OMe, and
$R^{11}$ is a hydrogen atom, alkyl having 1 to 4 carbon atoms, —CH$_2$CF$_3$, —CH$_2$CH$_2$OH or —CH$_2$CH$_2$OMe,
or a pharmaceutically acceptable acid addition salt thereof,
[3] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XVI)
(wherein
$R^9$ is a hydrogen atom, methyl, ethyl, methoxy, ethoxy, a fluorine atom or a chlorine atom),
$R^{12}$ is methyl, ethyl, methoxy, a fluorine atom or a chlorine atom,
$R^{13}$ is a hydrogen atom, methyl, methoxy, a fluorine atom or a chlorine atom,
or a pharmaceutically acceptable acid addition salt thereof,
[4] the compound of the above-mentioned [3], wherein
$R^2$ is methoxy, and
$R^5$ is the formula (V), (VIII), (IX) or (X)
(wherein
$R^{13}$ is a hydrogen atom or a fluorine atom),
or a pharmaceutically acceptable acid addition salt thereof,
[5] the compound of the above-mentioned [2], wherein
$R^1$ is a hydrogen atom,
$R^2$ is methoxy or ethoxy,
$R^3$ is a hydrogen atom,
$R^4$ is a hydrogen atom,
W is the formula (XVI)
(wherein
$R^9$ is —C(O)NR$^{10}$R$^{11}$ or the formula (IV),
$R^{10}$ is a hydrogen atom, methyl or ethyl,
$R^{11}$ is a hydrogen atom, methyl or ethyl,
n is an integer of 2 to 3),
$R^{12}$ is methyl, ethyl, methoxy, a fluorine atom or a chlorine atom,
$R^{13}$ is a hydrogen atom, methyl, methoxy, a fluorine atom or a chlorine atom,
or a pharmaceutically acceptable acid addition salt thereof,
[6] the compound of the above-mentioned [5], wherein
$R^2$ is methoxy,
$R^5$ is the formula (V), (VIII), (IX) or (X)
(wherein
$R^{13}$ is a hydrogen atom),
or a pharmaceutically acceptable acid addition salt thereof,
[7] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XVII), (wherein
$R^9$ is a hydrogen atom, methyl, methoxy, a fluorine atom or a chlorine atom)
$R^{12}$ is methyl, ethyl, methoxy, a fluorine atom or a chlorine atom,
$R^{13}$ is a hydrogen atom, methyl, methoxy, a fluorine atom or a chlorine atom,
or a pharmaceutically acceptable acid addition salt thereof,
[8] the compound of the above-mentioned [7], wherein
$R^1$ is a hydrogen atom,
$R^2$ is methoxy,
$R^5$ is the formula (V), (VIII), (IX), (X) or (XI),
(wherein
$R^{12}$ is methyl, methoxy, a fluorine atom or a chlorine atom,
$R^{13}$ is a hydrogen atom or a fluorine atom)
$R^9$ is a hydrogen atom or a fluorine atom,
or a pharmaceutically acceptable acid addition salt thereof,
[9] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XVIII),
(wherein
$R^7$ is a hydrogen atom, methyl, ethyl, methoxy, ethoxy, a fluorine atom or a chlorine atom,
$R^9$ is a hydrogen atom, methyl, ethyl, methoxy, ethoxy, a fluorine atom, a chlorine atom, —$CF_3$ or —$NR^{10}R^{11}$,
$R^{10}$ is a hydrogen atom, methyl, ethyl, n-propyl, isopropyl or isobutyl,
$R^{11}$ is a hydrogen atom or methyl)
$R^{12}$ is methyl, ethyl, methoxy, a fluorine atom or a chlorine atom,
$R^{13}$ is a hydrogen atom, methyl, methoxy, a fluorine atom or a chlorine atom,
or a pharmaceutically acceptable acid addition salt thereof,
[10] the compound of the above-mentioned [9], wherein
$R^2$ is methoxy,
$R^5$ is the formula (V), (VIII), (IX) or (X),
(wherein
$R^{12}$ is methyl, methoxy, a fluorine atom or a chlorine atom,
$R^{13}$ is a hydrogen atom or a fluorine atom)
$R^9$ is methoxy, ethoxy, a fluorine atom or a chlorine atom,
or a pharmaceutically acceptable acid addition salt thereof,
[11] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XVIII),
(wherein
$R^7$ is a hydrogen atom or a fluorine atom,
$R^9$ is —$C(O)NR^{10}R^{11}$ or the formula (IV),
$R^{10}$ is a hydrogen atom, methyl, ethyl, n-propyl, isopropyl or tert-butyl,
$R^{11}$ is a hydrogen atom, methyl or ethyl,
n is an integer of 2 to 4)
$R^{12}$ is methyl, ethyl, methoxy, a fluorine atom, a chlorine atom, —$CF_3$ or —CN,
$R^{13}$ is a hydrogen atom, methyl, ethyl, methoxy, ethoxy, a fluorine atom or a chlorine atom,
or a pharmaceutically acceptable acid addition salt thereof,
[12] the compound of the above-mentioned [11], wherein
$R^2$ is methoxy,
$R^5$ is the formula (V), (VIII), (IX), (X) or (XI), (wherein
$R^{12}$ is methyl, methoxy, a fluorine atom or a chlorine atom,
$R^{13}$ is a hydrogen atom or a fluorine atom,
Z is a sulfur atom), and
$R^7$ is a hydrogen atom,
or a pharmaceutically acceptable acid addition salt thereof,
[13] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XIX),
(wherein
$R^8$ is methyl, ethyl, methoxy, ethoxy, a fluorine atom or a chlorine atom,
$R^9$ is methyl, ethyl, methoxy, ethoxy, a fluorine atom, a chlorine atom or —$NR^{10}R^{11}$,
$R^{10}$ is a hydrogen atom, methyl, ethyl, n-propyl, isopropyl or isobutyl,
$R^{11}$ is a hydrogen atom or methyl)
$R^{12}$ is methyl, ethyl, methoxy, a fluorine atom or a chlorine atom,
$R^{13}$ is a hydrogen atom, methyl, methoxy, a fluorine atom or a chlorine atom,
or a pharmaceutically acceptable acid addition salt thereof,
[14] the compound of the above-mentioned [13], wherein
$R^2$ is methoxy,
$R^5$ is the formula (V), (VIII), (IX) or (X)
(wherein
$R^{12}$ is methyl, methoxy, a fluorine atom or a chlorine atom,
$R^{13}$ is a hydrogen atom, a fluorine atom or a chlorine atom),
or a pharmaceutically acceptable acid addition salt thereof,
[15] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XIX),
(wherein
$R^8$ is a fluorine atom,
$R^9$ is —$C(O)NR^{10}R^{11}$ or the formula (IV),
$R^{10}$ is a hydrogen atom, methyl, ethyl, n-propyl, isopropyl or tert-butyl,
$R^{11}$ is a hydrogen atom, methyl or ethyl,
n is an integer of 2 to 4)
$R^{12}$ is methyl, ethyl, methoxy, a fluorine atom or a chlorine atom,
$R^{13}$ is a hydrogen atom, methyl, ethyl, methoxy, ethoxy, a fluorine atom or a chlorine atom,
or a pharmaceutically acceptable acid addition salt thereof,
[16] the compound of the above-mentioned [15], wherein
$R^1$ is a hydrogen atom,
$R^2$ is methoxy,
$R^5$ is the formula (V), (VIII), (IX) or (X),
(wherein
$R^{13}$ is a hydrogen atom or a fluorine atom),
or a pharmaceutically acceptable acid addition salt thereof,
[17] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XX),
(wherein
$R^7$ is a hydrogen atom, methyl, ethyl, methoxy, ethoxy, a fluorine atom or a chlorine atom,
$R^9$ is a hydrogen atom, methyl, ethyl, methoxy, ethoxy, a fluorine atom, a chlorine atom or —$CF_3$)

$R^{12}$ is methyl, ethyl, methoxy, a fluorine atom or a chlorine atom,
$R^{13}$ is a hydrogen atom, methyl, methoxy, a fluorine atom or a chlorine atom,
or a pharmaceutically acceptable acid addition salt thereof,
[18] the compound of the above-mentioned [17], wherein
$R^2$ is methoxy,
$R^5$ is the formula (V), (VIII), (IX) or (X),
(wherein
$R^{12}$ is methyl, methoxy, a fluorine atom or a chlorine atom,
$R^{13}$ is a hydrogen atom or a fluorine atom)
$R^7$ is a hydrogen atom,
or a pharmaceutically acceptable acid addition salt thereof,
[19] the compound of the above-mentioned [2], wherein
$R^1$ is a hydrogen atom or methyl,
$R^2$ is methyl, methoxy, ethoxy or a fluorine atom,
$R^3$ is a hydrogen atom,
$R^4$ is a hydrogen atom,
W is the formula (XX),
(wherein
$R^7$ is a hydrogen atom or a fluorine atom,
$R^9$ is —C(O)NR$^{10}$R$^{11}$,
$R^{10}$ is a hydrogen atom, methyl, ethyl, n-propyl, isopropyl or tert-butyl,
$R^{11}$ is a hydrogen atom, methyl or ethyl)
$R^{12}$ is methyl, ethyl, methoxy, a fluorine atom or a chlorine atom, and
$R^{13}$ is a hydrogen atom, methyl, ethyl, methoxy, ethoxy, a fluorine atom or a chlorine atom,
or a pharmaceutically acceptable acid addition salt thereof,
[20] the compound of the above-mentioned [19], wherein
$R^2$ is methoxy,
$R^5$ is the formula (V), (VIII), (IX) or (X)
(wherein
$R^{12}$ is methyl, methoxy, a fluorine atom or a chlorine atom,
$R^{13}$ is a hydrogen atom or a fluorine atom), and
$R^{10}$ is methyl or ethyl,
or a pharmaceutically acceptable acid addition salt thereof,
[21] a medicament comprising the compound of any of the above-mentioned [1] to [20] or a pharmaceutically acceptable acid addition salt thereof,
[22] an orexin receptor agonist comprising the compound of any of the above-mentioned [1] to [20] or a pharmaceutically acceptable acid addition salt thereof,
[23] an anti-narcolepsy agent comprising the compound of any of the above-mentioned [1] to [20] or a pharmaceutically acceptable acid addition salt thereof,
[24] an agent for the treatment or prophylaxis of narcolepsy, comprising the compound of any of the above-mentioned [1] to [20] or a pharmaceutically acceptable acid addition salt thereof,
[25] a method for the treatment or prophylaxis of narcolepsy, comprising administering an effective amount of the compound of any of the above-mentioned [1] to [20] or a pharmaceutically acceptable acid addition salt thereof, and
[26] the compound of any of the above-mentioned [1] to [20] or a pharmaceutically acceptable acid addition salt thereof, for the treatment or prophylaxis of narcolepsy.

Effect of the Invention

The compound represented by the formula (I) or a pharmaceutically acceptable acid addition salt thereof of the present invention has a superior OX2R agonist activity.

DESCRIPTION OF EMBODIMENTS

The following terms used in the present specification are as defined below unless otherwise specified.

The "alkyl" in the present specification means a monovalent straight chain or branched saturated hydrocarbon group composed of a carbon atom and a hydrogen atom. For example, methyl, ethyl, n-propyl, isopropyl, n-butyl, isobutyl, sec-butyl, tert-butyl, pentyl, hexyl and the like can be mentioned.

The "alkoxy" in the present specification means an oxy group to which the above-mentioned "alkyl" is bonded. For example, methoxy, ethoxy, n-propoxy, isopropoxy, n-butoxy, isobutoxy, tert-butoxy and the like can be mentioned.

The "halogen" in the present specification means a fluorine atom, a chlorine atom, a bromine atom or an iodine atom.

The "cycloalkyl" in the present specification means a monocyclic aliphatic carbon cyclic group having 3 to 8 carbon atoms. For example, cyclopropyl, cyclobutyl, cyclopentyl, cyclohexyl, cycloheptyl, cyclooctyl and the like can be mentioned.

The "aryl" in the present specification means a monocyclic or fused aromatic carbon cyclic group having 6 to 10 carbon atoms. For example, phenyl, 1-naphthyl, 2-naphthyl and the like can be mentioned.

The "heteroaryl" in the present specification means a 5- to 10-membered monocyclic or bicyclic aromatic heterocyclic group containing, as a ring-constituting atom besides carbon atom, one or two kinds of 1 to 4 hetero atoms selected from oxygen atom, sulfur atom and nitrogen atom. For example, thienyl, furyl, pyrrolyl, imidazolyl, pyrazolyl, triazolyl, tetrazolyl, oxazolyl, isoxazolyl, thiazolyl, isothiazolyl, pyridyl, pyridazinyl, pyrimidinyl, furazanyl, pyrazinyl, thiadiazolyl, oxadiazolyl, benzofuryl, benzothienyl, benzimidazolyl, benzothiazolyl, quinolyl, isoquinolyl, cinnolyl, quinazolyl, quinoxalyl, phthalazinyl, 1H-indazolyl and the like can be mentioned.

The "anti-narcolepsy agent" in the present specification means an agent for the treatment or prophylaxis of narcolepsy.

The definition of each symbol in the formula (I) is explained in detail below.

Examples of the "alkyl having 1 to 4 carbon atoms" for $R^1$, $R^2$, $R^3$, $R^4$, $R^6$, $R^7$, $R^8$, $R^9$, $R^{10}$, $R^{11}$, $R^a$ or $R^b$ include methyl, ethyl, n-propyl, isopropyl, n-butyl, isobutyl, sec-butyl, tert-butyl and the like; however, these are not limitative.

Examples of the "halogen" for $R^1$, $R^2$, $R^6$, $R^7$, $R^8$ or $R^9$ include a fluorine atom, a chlorine atom, a bromine atom, an iodine atom and the like; however, these are not limitative.

Examples of the "alkoxy having 1 to 4 carbon atoms" for $R^2$, $R^6$, $R^7$, $R^8$ or $R^9$ include methoxy, ethoxy, n-propoxy, isopropoxy, n-butoxy, tert-butoxy and the like can be mentioned; however, these are not limitative.

Preferable embodiment of each symbol in the formula (I) is explained below.

As $R^1$, a hydrogen atom, methyl, ethyl, a fluorine atom or a chlorine atom is preferable, and a hydrogen atom or methyl is particularly preferable.

As $R^2$, a hydrogen atom, methyl, ethyl, methoxy, ethoxy, a fluorine atom or a chlorine atom is preferable, methyl, methoxy, ethoxy or a fluorine atom is further preferable, and methoxy is particularly preferable.

As $R^{2a}$ and $R^{2b}$, each is independently preferably a hydrogen atom, methyl, ethyl, n-propyl, isopropyl, n-butyl, isobutyl, sec-butyl or tert-butyl, and a hydrogen atom or methyl is particularly preferable.

As $R^3$, a hydrogen atom, methyl or ethyl is preferable, a hydrogen atom or methyl is further preferable, and a hydrogen atom is particularly preferable.

As $R^4$, a hydrogen atom, methyl or ethyl is preferable, a hydrogen atom or methyl is further preferable, and a hydrogen atom is particularly preferable.

As $R^5$, phenyl, naphthyl, pyridyl, thienyl, furyl or pyrazolyl is preferable, phenyl, pyridyl or thienyl is further preferable, and phenyl or pyridyl is particularly preferable.

As $R^6$, methyl, ethyl, methoxy, ethoxy, a fluorine atom or a chlorine atom is preferable, methyl, methoxy, a fluorine atom or a chlorine atom is further preferable, and methoxy or a chlorine atom is particularly preferable.

As $R^{6a}$ and $R^{6b}$, each is independently preferably a hydrogen atom, methyl or ethyl, and a hydrogen atom or methyl is particularly preferable.

In the structure of W shown by the above-mentioned formula (II), $R^7$ is preferably a hydrogen atom, methyl, ethyl, methoxy, ethoxy, a fluorine atom or a chlorine atom, further preferably a hydrogen atom or a fluorine atom, particularly preferably a hydrogen atom.

As $R^8$, a hydrogen atom, methyl, ethyl, methoxy, ethoxy, a fluorine atom or a chlorine atom is preferable, and a hydrogen atom or a fluorine atom is particularly preferable.

As $R^9$, methyl, ethyl, methoxy, ethoxy, a fluorine atom, a chlorine atom, —$CF_3$, —CN, —$NR^{10}R^{11}$, —$C(O)NR^{10}R^{11}$ or the formula (IV) is preferable, methoxy, a fluorine atom, a chlorine atom, —$C(O)NR^{10}R^{11}$ or the formula (IV) is further preferable, and methoxy or —$C(O)NR^{10}R^{11}$ is particularly preferable.

As $R^{10}$, a hydrogen atom, methyl, ethyl, n-propyl, isopropyl, isobutyl or tert-butyl is preferable, and methyl, ethyl or isopropyl is particularly preferable.

As $R^{11}$, a hydrogen atom, methyl, ethyl, n-propyl, isopropyl, isobutyl or tert-butyl is preferable, a hydrogen atom, methyl or ethyl is further preferable, and a hydrogen atom or methyl is particularly preferable.

As $R^{12}$, methyl, ethyl, n-propyl, isopropyl, tert-butyl, methoxy, ethoxy, a fluorine atom, a chlorine atom, trifluoromethyl or cyano is preferable, methyl, ethyl, methoxy, ethoxy, fluoro or chloro is further preferable, and methyl, methoxy, fluoro or chloro is particularly preferable.

As $R^{13}$, a hydrogen atom, methyl, ethyl, methoxy, ethoxy, a fluorine atom or a chlorine atom is preferable, a hydrogen atom, methyl, methoxy, a fluorine atom or a chlorine atom is further preferable, and a hydrogen atom or a fluorine atom is particularly preferable.

In the structure of $R^9$ shown by the above-mentioned formula (IV), as n, 2, 3 or 4 is preferable, and 2 or 3 is particularly preferable.

As a preferable example of the compound represented by the above-mentioned formula (I) of the present invention, the following compound can be mentioned.

[Compound A]
Compound (I) wherein
$R^1$ is a hydrogen atom or alkyl having 1 to 4 carbon atoms (e.g., methyl),
$R^2$ is a hydrogen atom, alkyl having 1 to 4 carbon atoms (e.g., methyl), alkoxy having 1 to 4 carbon atoms (e.g., methoxy or ethoxy) or halogen (e.g., fluorine atom),
$R^3$ is a hydrogen atom or alkyl having 1 to 4 carbon atoms (e.g., methyl),
$R^4$ is a hydrogen atom or alkyl having 1 to 4 carbon atoms (e.g., methyl), $R^5$ is aryl (e.g., phenyl) or heteroaryl (e.g., pyridyl, pyrazolyl, thienyl, imidazolyl, furyl) (wherein aryl or heteroaryl is optionally substituted by optionally selected 1 to 4 $R^6$),
$R^6$ is alkyl having 1 to 4 carbon atoms (e.g., methyl), alkoxy having 1 to 4 carbon atoms (e.g., methoxy), halogen (e.g., a fluorine atom, a chlorine atom, a bromine atom), —CN, —$CF_3$, —OH or —$NR^{6a}R^{6b}$ (wherein $R^{6a}$ is alkyl having 1 to 4 carbon atoms (e.g., methyl), $R^{6b}$ is alkyl having 1 to 4 carbon atoms (e.g., methyl)),
W is the formula (II):

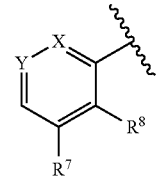

(II)

(wherein
$R^7$ is a hydrogen atom, alkoxy having 1 to 4 carbon atoms (e.g., methoxy) or halogen (e.g., a fluorine atom, a chlorine atom),
$R^8$ is a hydrogen atom, alkyl having 1 to 4 carbon atoms (e.g., methyl), alkoxy having 1 to 4 carbon atoms (e.g., methoxy) or halogen (e.g., a fluorine atom, a chlorine atom),
X is —$CR^9$= or —N=,
Y is —$CR^9$= or —N=,
$R^9$ is a hydrogen atom, alkyl having 1 to 4 carbon atoms (e.g., methyl), alkoxy having 1 to 4 carbon atoms (e.g., methoxy), halogen (e.g., a fluorine atom, a chlorine atom), —OH, —$NR^{10}R^{11}$, —$CH_2OH$, —$C(O)OR^{10}$, —$C(O)NR^{10}R^{11}$ or the formula (IV):

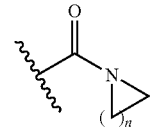

(IV)

(wherein n is an integer of 1 to 4) (e.g., azetidine-1-carbonyl, pyrrolidine-1-carbonyl, piperidine-1-carbonyl),
$R^{10}$ is a hydrogen atom, alkyl having 1 to 4 carbon atoms (e.g., methyl, isobutyl, tert-butyl), —$CH_2CF_3$, —$CH_2CH_2OH$ or —$CH_2CH_2OMe$, and
$R^{11}$ is a hydrogen atom, alkyl having 1 to 4 carbon atoms (e.g., methyl, isobutyl, tert-butyl), —$CH_2CF_3$, —$CH_2CH_2OH$ or —$CH_2CH_2OMe$), or a pharmaceutically acceptable acid addition salt thereof.

As a pharmaceutically acceptable acid addition salt of the compound of the formula (I) of the present invention, inorganic acid salts such as hydrochloride, sulfate, nitrate, hydrobromide, hydroiodide, phosphate and the like, organic carbonates such as acetate, lactate, citrate, oxalate, glutarate, malate, tartrate, fumarate, mandelate, maleate, benzoate, phthalate and the like, organic sulfonates such as methanesulfonate, ethanesulfonate, benzenesulfonate, p-toluenesulfonate, camphorsulfonate and the like, and the like can be mentioned; however, these are not limitative. Of these, hydrochloride, hydrobromide, phosphate, tartrate, methanesulfonate or camphorsulfonate is preferable, and hydrochloride, tartrate or methanesulfonate is further preferably used; however, these are also not limitative.
Of the compounds of the formula (I) of the present invention, specific preferable examples thereof are shown in Table 1 to Table 8; however, they do not limit the present invention.
TABLE 1
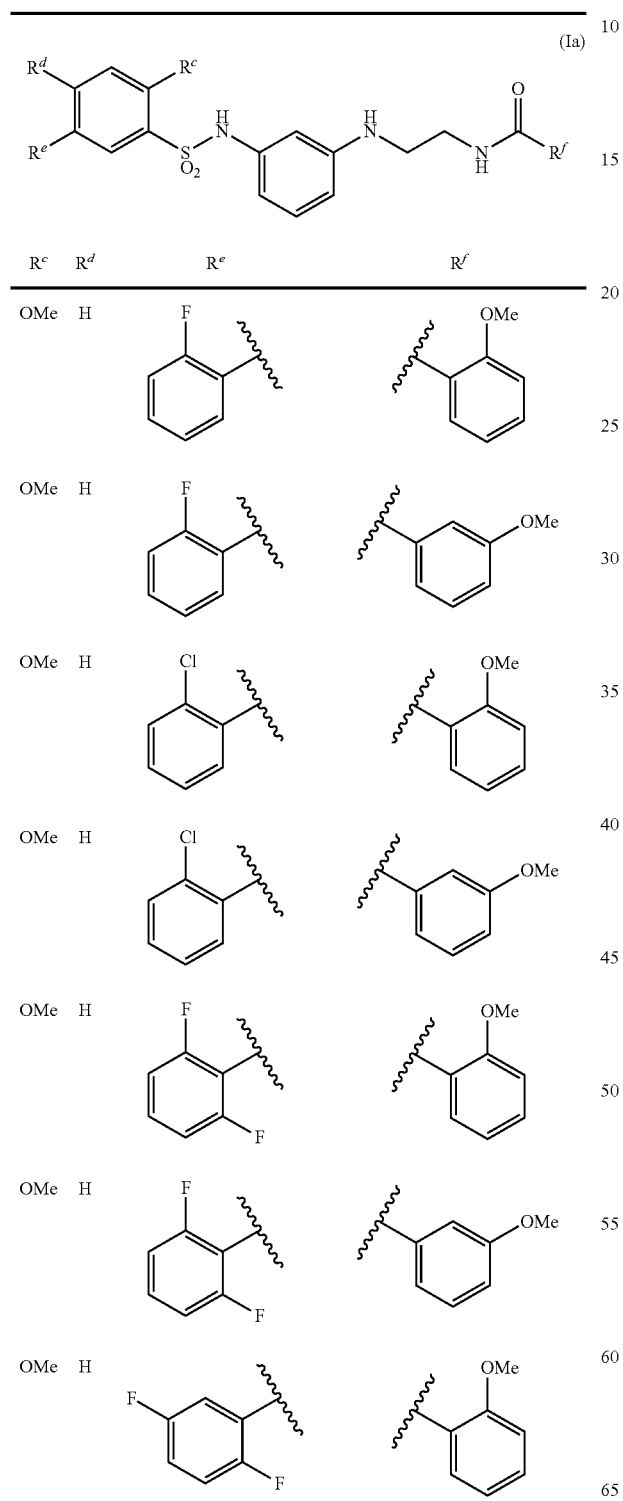
TABLE 1-continued
TABLE 2
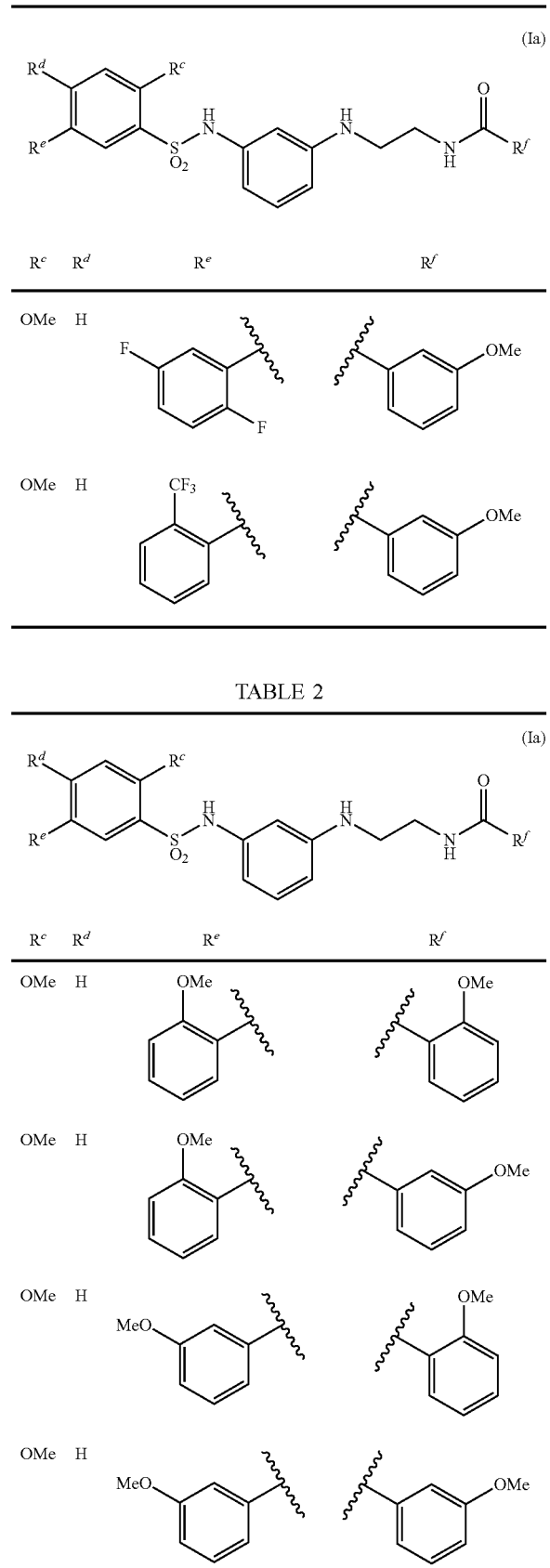

TABLE 2-continued

| Rc | Rd | Re | Rf |
|---|---|---|---|
| OMe | H | 3,5-dimethoxyphenyl | 2-methoxyphenyl |
| OMe | H | 3,5-dimethoxyphenyl | 3-methoxyphenyl |
| OMe | H | 5-methoxy-2-fluorophenyl | 2-methoxyphenyl |
| OMe | H | 5-methoxy-2-fluorophenyl | 3-methoxyphenyl |

TABLE 3

| Rc | Rd | Re | Rf |
|---|---|---|---|
| OMe | H | 3-fluoropyridin-2-yl | 2-methoxyphenyl |
| OMe | H | 3-fluoropyridin-2-yl | 3-methoxyphenyl |
| OMe | H | 6-methoxypyridin-2-yl | 2-methoxyphenyl |
| OMe | H | 6-methoxypyridin-2-yl | 3-methoxyphenyl |
| OMe | H | pyridin-3-yl | 2-methoxyphenyl |
| OMe | H | pyridin-3-yl | 3-methoxyphenyl |
| OMe | H | pyridin-3-yl | 2-chlorophenyl |
| OMe | H | pyridin-3-yl | 2-methoxypyridin-3-yl |

(Structural diagrams for formula (Ia) and substituents are shown in the original table.)

TABLE 4

(Ia)

| $R^c$ | $R^d$ | $R^e$ | $R^f$ |
|---|---|---|---|
| OMe | H | 2-(Me₂NC(O))-phenyl | 2-methoxyphenyl |
| OMe | H | 2-(Me₂NC(O))-phenyl | 3-methoxyphenyl |
| OMe | H | 3-(MeNHC(O))-phenyl | 2-methoxyphenyl |
| OMe | H | 3-(MeNHC(O))-phenyl | 3-methoxyphenyl |
| OMe | H | 3-(Me₂NC(O))-phenyl | 2-methoxyphenyl |
| OMe | H | 3-(Me₂NC(O))-phenyl | 3-methoxyphenyl |
| OMe | H | 3-(Me₂NC(O))-4-fluorophenyl | 2-methoxyphenyl |
| OMe | H | 3-(Me₂NC(O))-4-fluorophenyl | 3-methoxyphenyl |

TABLE 5

(Ia)

| $R^c$ | $R^d$ | $R^e$ | $R^f$ |
|---|---|---|---|
| OMe | Me | 3-(MeNHC(O))-phenyl | 2-fluorophenyl |
| OMe | H | 3-(MeNHC(O))-phenyl | 2-chlorophenyl |
| OMe | Me | 3-(MeNHC(O))-phenyl | 2-methoxy-3-pyridyl |
| OMe | H | 3-(Me₂NC(O))-phenyl | 2-chlorophenyl |
| OMe | H | 3-(Me₂NC(O))-phenyl | 2-methoxy-3-pyridyl |
| OMe | H | 3-(Me₂NC(O))-phenyl | 2-chloro-3-thienyl |
| OMe | Me | 3-(Me₂NC(O))-phenyl | 2-chlorophenyl |
| OMe | Me | 3-(Me₂NC(O))-phenyl | 3-methoxyphenyl |

TABLE 6 / TABLE 7 — chemical structure tables (structures not transcribed as text).

TABLE 8

(Ia)

| $R^c$ | $R^d$ | $R^e$ | $R^f$ |
|---|---|---|---|
| OMe | H | pyrrolidinyl-C(O)-phenyl | 2-Cl-phenyl |
| OMe | H | pyrrolidinyl-C(O)-phenyl | 2-F-phenyl |
| OMe | H | pyrrolidinyl-C(O)-phenyl | 2-OMe-pyridinyl |
| OMe | H | piperidinyl-C(O)-phenyl | 2-OMe-phenyl |
| OMe | H | piperidinyl-C(O)-phenyl | 3-OMe-phenyl |
| OMe | H | piperidinyl-C(O)-phenyl | 2-Cl-phenyl |
| OMe | H | piperidinyl-C(O)-phenyl | 2-F-phenyl |
| OMe | H | piperidinyl-C(O)-phenyl | 2-OMe-pyridinyl |

The compound of the above-mentioned formula (I) of the present invention can be produced by an appropriate method based on the characteristics derived from the basic skeleton and substituents thereof. While the starting materials and reagents to be used for the production of these compounds are generally available or can be synthesized by a method known to those of ordinary skill in the art, which follows the procedures described in reference documents such as Organic Reactions (Wiley&Sons), Fieser and Fieser's Reagent for Organic Synthesis (Wiley&Sons) and the like.

As a specific production method of the compound of the above-mentioned formula (I) of the present invention, for example, the methods shown in Schemes 1 to 4 can be mentioned.

Scheme 1

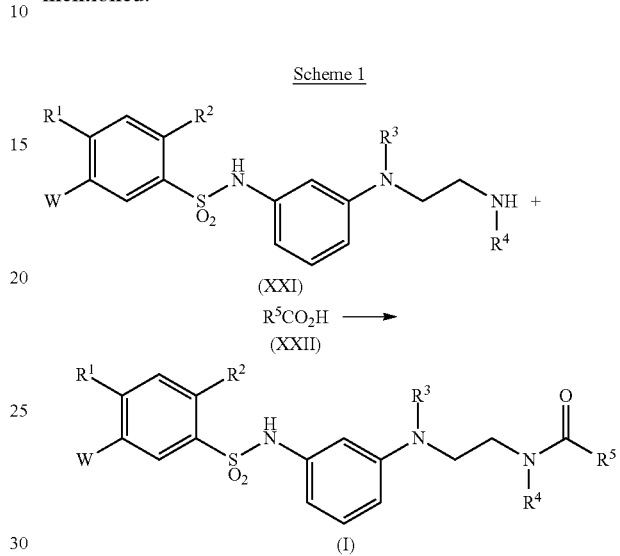

(I)

wherein $R^1$, $R^2$, $R^3$, $R^4$, $R^5$ and W are as defined above.

Specifically, the compound of the formula (I) can be obtained by, for example, amidating an amine derivative represented by the formula (XXI) with a carboxylic acid represented by the formula (XXII).

As a solvent, halogenated solvents such as dichloromethane, chloroform, 1,2-dichloroethane and the like, ether solvents such as diethyl ether, tetrahydrofuran (THF), 1,2-dimethoxyethane (DME), dioxane and the like, aprotic polar solvents such as N,N-dimethylformamide (DMF), dimethyl sulfoxide (DMSO) and the like, alcohol solvents such as methanol, ethanol, propanol and the like or a mixed solvent thereof can be used. In general, dichloromethane or THF is preferably used. Carboxylic acid (XXII) is used in an amount of 0.5-20 equivalents, preferably 0.5-10 equivalents, relative to amine derivative (XXI).

As the condensing agent, dicyclohexylcarbodiimide, 1-ethyl-3-(3-dimethylaminopropyl)carbodiimide hydrochloride (EDCI), benzotriazol-1-yloxytris(dimethylamino)phosphonium hexafluorophosphate (BOP) reagent and the like can be used, and a BOP reagent is particularly preferably used. The condensing agent is used in an amount of 1.0-100 equivalents, preferably 1.0-10 equivalents, relative to amine derivative (XXI).

When a base is used, triethylamine, diisopropylethylamine, pyridine, N-methylmorpholine and the like can be used, and triethylamine or diisopropylethylamine is preferably used. The base is used in an amount of 3.0-100 equivalents, preferably 3.0-10 equivalents, relative to amine derivative (XXI).

The reaction temperature is generally −40-150° C., preferably 0-60° C. While the reaction time is appropriately selected according to the conditions such as reaction temperature and the like, it is generally about 20 min-48 hr.

While the concentration of substrate (XXI) in the reaction system is not particularly limited, it is generally preferably 0.001 mmol/L-1 mol/L.

Scheme 2

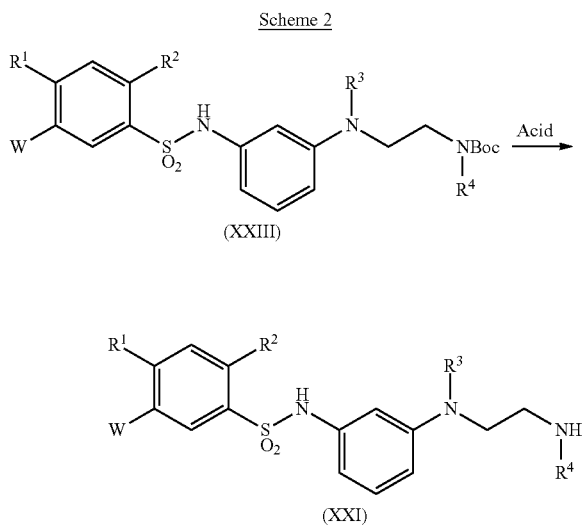

(XXIII)

(XXI)

wherein $R^1$, $R^2$, $R^3$, $R^4$ and W are as defined above.

The amine derivative of the formula (XXI) can be obtained by, for example, deprotecting a tert-butoxycarbonyl (Boc) group of the derivative represented by the formula (XXIII) under acidic conditions.

As a solvent, halogenated solvents such as dichloromethane, chloroform, 1,2-dichloroethane and the like, ether solvents such as THF, DME, dioxane and the like, alcohol solvents such as methanol, ethanol, propanol and the like or a mixed solvent thereof can be used. In general, dichloromethane or dioxane is preferably used.

As the acid, organic acids such as trifluoroacetic acid, methanesulfonic acid, p-toluenesulfonic acid, trifluoromethanesulfonic acid and the like, or inorganic acids such as hydrochloric acid, hydrobromic acid, hydroiodic acid, sulfuric acid, nitric acid, phosphoric acid and the like can be used. In general, trifluoroacetic acid or hydrochloric acid is preferably used. In another method, a hydrogen chloride-methanol solution, a hydrogen chloride-THF solution, a hydrogen chloride-ethyl acetate solution, or a hydrogen chloride-dioxane solution obtained by dissolving hydrogen chloride in an organic solvent is each independently used. In this case, particularly, preferable results are obtained by using a hydrogen chloride-methanol solution or a hydrogen chloride-THF solution. The acid is used in an amount of 1.0-100 equivalents, preferably 3.0-10 equivalents, relative to the formula (XXIII).

The reaction temperature is generally −40-150° C., preferably 0-80° C. While the reaction time is appropriately selected according to the conditions such as reaction temperature and the like, it is generally about 20 min-48 hr. While the concentration of substrate (XXIII) in the reaction system is not particularly limited, it is generally preferably 0.001 mmol/L-1 mol/L.

Scheme 3

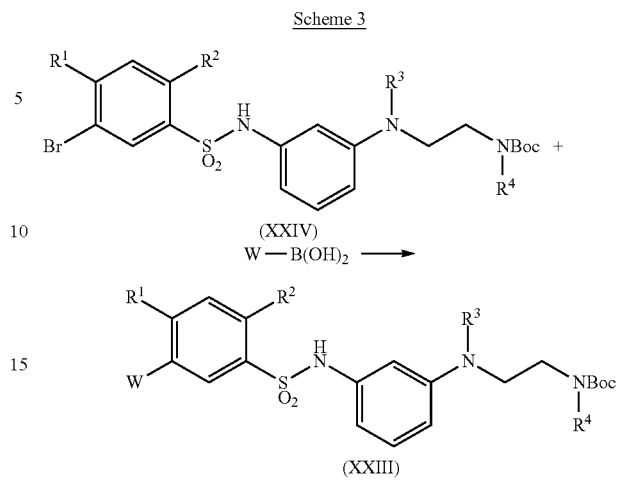

(XXIV)

W—B(OH)₂ ⟶

(XXIII)

wherein $R^1$, $R^2$, $R^3$, $R^4$ and W are as defined above.

The derivative represented by the formula (XXIII) can be obtained by, for example, a Suzuki coupling of a derivative represented by the formula (XXIV) with a boronic acid derivative represented by the formula (XXV).

The Suzuki coupling reaction is performed in the presence of a palladium catalyst and a base, in the presence or absence of a phosphine ligand in a suitable solvent.

As a solvent, ether solvents such as THF, DME, dioxane and the like, aprotic polar solvents such as DMF, DMSO and the like, alcohol solvents such as methanol, ethanol, propanol and the like, aromatic solvents such as benzene, toluene, xylene and the like, water or a mixed solvent thereof can be used. In general, dioxane, DME, a mixed solvent of dioxane and water or a mixed solvent of DME and water is preferably used.

As boronic acid derivative (XXV), not only boronic acid but also boronates such as boronic acid pinacol ester, N-methyliminodiacetic acid (MIDA) boronate and the like, or potassium trifluoroborate salt can be used. Particularly, boronic acid or boronic acid pinacol ester is preferably used. The boronic acid derivative (XXV) is used in an amount of 1.0-20 equivalents, preferably 1.0-10 equivalents, relative to the derivative of the formula (XXIV).

Examples of the palladium catalyst include tetrakis(triphenylphosphine)palladium, palladiumacetate, bis(triphenylphosphine)palladiumdichloride, bis(dibenzylideneacetone)palladium, bis(diphenylphosphino)ferrocenepalladiumdichloride and the like, and tetrakis(triphenylphosphine)palladium or bis(diphenylphosphino)ferrocene palladium dichloride is preferably used. The palladium catalyst is used in an amount of 0.001-1 equivalent, preferably 0.005-0.5 equivalent, relative to the derivative of the formula (XXIV).

Examples of the base include sodium carbonate, potassium carbonate, cesium carbonate, potassium phosphate, sodium hydroxide, potassium hydroxide, barium hydroxide, triethylamine, diisopropylethylamine and the like, and sodium carbonate or potassium carbonate is preferably used.

The reaction temperature is generally −40-150° C., preferably 20-110° C. While the reaction time is appropriately selected according to the conditions such as reaction temperature and the like, it is generally about 20 min-48 hr. While the concentration of substrate (XXIV) in the reaction system is not particularly limited, it is generally preferably 0.001 mmol/L-1 mol/L.

Scheme 4

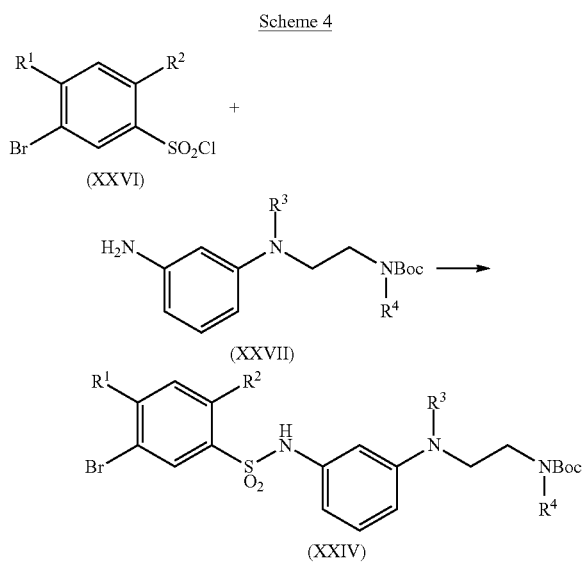

wherein $R^1$, $R^2$, $R^3$ and $R^4$ are as defined above.

The derivative represented by the formula (XXIV) can be obtained by, for example, amidating the sulfonic acid chloride derivative of the formula (XXVI) with the amine derivative of the formula (XXVII).

As a solvent, halogenated solvents such as dichloromethane, chloroform, 1,2-dichloroethane and the like, ether solvents such as diethyl ether, THF, DME, dioxane and the like, aprotic polar solvents such as DMF, DMSO and the like or a mixed solvent thereof can be used. In general, dichloromethane or THF is preferably used. The sulfonic acid chloride derivative (XXVI) is used in an amount of 0.5-20 equivalents, preferably 1.0-10 equivalents, relative to amine derivative (XXVII).

Examples of the base include sodium carbonate, potassium carbonate, cesium carbonate, potassium phosphate, sodium hydroxide, potassium hydroxide, barium hydroxide, triethylamine, diisopropylethylamine, pyridine, 4-dimethylaminopyridine and the like can be mentioned, triethylamine or pyridine is preferably used.

The reaction temperature is generally −40-150° C., preferably 0-80° C. While the reaction time is appropriately selected according to the conditions such as reaction temperature and the like, it is generally about 10 min-48 hr. While the concentration of substrate (XXVII) in the reaction system is not particularly limited, it is generally preferably 0.001 mmol/L-1 mol/L.

An orexin agonist containing the compound of the present invention is effective for not only human but also mammals other than human, for example, mouse, rat, hamster, rabbit, cat, dog, bovine, sheep, monkey and the like.

Also, the compound of the present invention is used not only as an agent for the treatment or prophylaxis of narcolepsy as mentioned above but also can be used as a method for the treatment or prophylaxis of narcolepsy, or for the production of a medicament for the treatment or prophylaxis of narcolepsy.

Furthermore, the compound of the present invention can also be used as an agent for the treatment or prophylaxis of various neurological disorders related to an orexin receptor, such as sleeping sickness, sleeping disorder, waking disorder, jet lag, obesity, metabolic syndrome and the like.

When the compound of the present invention is clinically used as an agent for the treatment or prophylaxis of narcolepsy, the medicament may be a free form of the compound of the present invention or an acid addition salt thereof, or additives such as excipient, stabilizer, preservative, buffering agent, solubilizing agent, emulsifier, diluent, isotonicity agent and the like may be mixed as appropriate. Examples of the administration form include oral preparations such as tablet, capsule, granule, powder, syrup and the like, parenteral agents such as injection, suppository, liquid and the like, topical administration of ointment, cream, adhesive preparation and the like, and the like.

The agent for the treatment or prophylaxis of narcolepsy of the present invention desirably contains 0.001-90 wt %, preferably 0.01-70 wt %, of the above-mentioned active ingredient. The amount thereof to be used is appropriately determined according to the symptom, age, body weight, and administration method. In the case of injection for an adult, the amount of the active ingredient is 0.1 µg-1 g per day, 1 µg-1 g in the case of an oral preparation, and 1 µg-10 g in the case of an adhesive preparation, each of which can be administered in one to several portions.

In addition, the agent for the treatment or prophylaxis of narcolepsy of the present invention can also be used in combination with an agent for the treatment or prophylaxis of strong sleepiness and dozing during the day, an agent for the treatment or prophylaxis of deep sleep disorder, or an agent for the treatment or prophylaxis of cataplexy.

As an agent for the treatment or prophylaxis of strong sleepiness and dozing during the day, central nervous system stimulants such as methylphenidate, pemoline, modafinil and the like, and the like can be mentioned.

As an agent for the treatment or prophylaxis of deep sleep disorder, tricyclic antidepressants such as triazolam, vegetamin B and the like, antianxiety drug and the like can be mentioned.

As an agent for the treatment or prophylaxis of cataplexy, tricyclic antidepressants such as clomipramine hydrochloride, brotizolam, imipramine hydrochloride and the like, selective serotonin reuptake inhibitors (SSRI) such as fluvoxamine maleate, paroxetine, hydrochloride and the like, serotonin and noradrenaline reuptake inhibitors (SNRI) such as milnacipran hydrochloride, duloxetine hydrochloride and the like, and the like can be mentioned.

EXAMPLES

The present invention is specifically explained in the following by referring to Examples. In the following Examples, the following abbreviations are used.
Boc: tert-butoxycarbonyl
Bn: benzyl
MIDA: N-methyliminodiacetic acid
PMB: p-methoxybenzyl Reference Example 1 tert-butyl (2-((3-nitrophenyl)amino)ethyl)carbamate

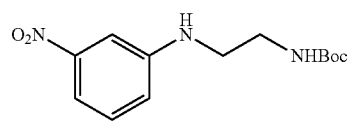 [SMILES: CC(C)(C)OC(=O)NCCNc1cccc([N+](=O)[O-])c1]

Under an argon atmosphere, to 3-fluoronitrobenzene (3.21 mL) was added ethylenediamine (25.0 mL), and the mixture was stirred at 100° C. for 24 hr. To this reaction mixture was added saturated aqueous sodium hydrogen carbonate solution, and the mixture was extracted with chloroform. The organic layer was dried over sodium sulfate, filtered, and the filtrate was concentrated. To a solution of the obtained residue in dichloromethane (50 mL) were added triethylamine (4.60 mL), di-tert-butyl dicarbonate (6.55 g), and the mixture was stirred at room temperature for 2 hr. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/4→1/3) to give tert-butyl (2-((3-nitrophenyl)amino)ethyl)carbamate (5.31 g).

Reference Example 2 tert-butyl (2-((3-aminophenyl)(benzyl)amino)ethyl) carbamate

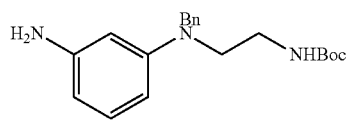 [SMILES: CC(C)(C)OC(=O)NCCN(Cc1ccccc1)c1cccc(N)c1]

(1) Under an argon atmosphere, to a solution of tert-butyl (2-((3-nitrophenyl)amino)ethyl)carbamate (4.46 g) in dichloromethane (30 mL) were added 50 wt % aqueous sodium hydroxide solution (10 mL), benzyl bromide (2.84 mL) and tetrabutylammoniumiodide (587 mg), and the mixture was stirred at 20-30° C. for 48 hr. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/6→1/4) to give tert-butyl (2-(benzyl(3-nitrophenyl)amino)ethyl)carbamate (4.62 g).

(2) Under an argon atmosphere, to a mixed suspension of tert-butyl (2-(benzyl(3-nitrophenyl)amino)ethyl)carbamate in ethanol (50 mL) and water (20 mL) were added ammonium chloride (6.69 g) and iron powder (4.86 g), and the mixture was heated under reflux for 2 hr. The reaction mixture was filtered through celite, the filtrate was concentrated, saturated aqueous sodium hydrogen carbonate solution was added, and the mixture was extracted with chloroform. The organic layer was dried over sodium sulfate, filtered, and the filtrate was concentrated. The obtained residue was purified by amine silica gel column chromatography (eluate: chloroform/ethyl acetate=2/1) to give tert-butyl (2-((3-aminophenyl)(benzyl)amino)ethyl)carbamate (4.58 g).

Reference Example 3 tert-butyl (2-((3-aminophenyl)(4-methoxybenzyl) amino)ethyl)carbamate

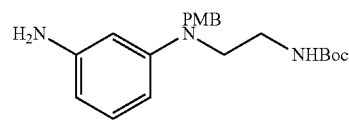

(1) Under an argon atmosphere, to a solution of tert-butyl (2-((3-nitrophenyl)amino)ethyl)carbamate (4.46 g) in DMF (30 mL) were added potassium carbonate (1.21 g), sodium iodide (1.01 g) and 4-methoxybenzylchloride (1.00 mL), and the mixture was stirred at 60° C. overnight. To this reaction mixture was added saturated brine, and the mixture was extracted with ethyl acetate. The organic layer was washed with water, dried over sodium sulfate, filtered, and the filtrate was concentrated. The obtained residue was purified by silica gel column chromatography (eluate: ethyl acetate/hexane=1/3→1/2→1/1) to give tert-butyl (2-(4-methoxybenzyl(3-nitrophenyl)amino)ethyl)carbamate (2.78 g).

(2) To a solution of tert-butyl (2-(4-methoxybenzyl(3-nitrophenyl)amino)ethyl)carbamate (1.13 g) in methanol (20 mL) was added 10% palladium/carbon (339 mg), and the mixture was stirred under a hydrogen atmosphere at room temperature for 1 hr. The reaction mixture was filtered through celite, and the filtrate was concentrated. The obtained residue was purified by amine silica gel column chromatography (eluate: ethyl acetate) to give tert-butyl (2-((3-aminophenyl)(4-methoxybenzyl)amino)ethyl)carbamate (848 mg).

Reference Example 4 tert-butyl (2-((benzyl) (3-(5-bromo-2-methoxyphenylsulfonamide)phenyl)amino)ethyl) carbamate

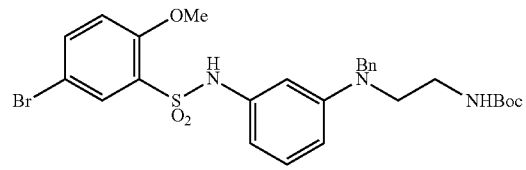 [SMILES: COc1ccc(Br)cc1S(=O)(=O)Nc1cccc(N(CCNC(=O)OC(C)(C)C)Cc2ccccc2)c1]

Under an argon atmosphere, to a solution of tert-butyl (2-((3-aminophenyl)(benzyl)amino)ethyl)carbamate (1.59 g) in dichloromethane (20 mL) were added pyridine (0.413 mL) and 5-bromo-2-methoxybenzenesulfonyl chloride (1.33 g), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/2) to give tert-butyl (2-((benzyl) (3-(5-bromo-2-methoxyphenylsulfonamide)phenyl)amino)ethyl)carbamate (2.53 g).

Reference Example 5 tert-butyl (2-((3-(5-bromo-2-methoxyphenylsulfonamide)phenyl) (4-methoxybenzyl)amino)ethyl)carbamate

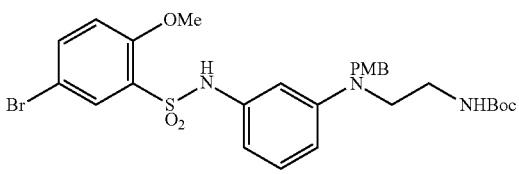

Under an argon atmosphere, to a solution of tert-butyl (2-((3-aminophenyl)(4-methoxybenzyl)amino)ethyl)carbamate (848 mg) in dichloromethane (30 mL) were added pyridine (0.202 mL) and 5-bromo-2-methoxybenzenesulfonyl chloride (651 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=2/3→1/1) to give tert-butyl (2-((3-(5-bromo-2-methoxyphenylsulfonamide)phenyl)(4-methoxybenzyl)amino)ethyl)carbamate (1.15 g).

Reference Example 6

N-(3-((2-aminoethyl)amino)phenyl)-2'-fluoro-4-methoxy-[1,1'-biphenyl]-3-sulfonamide dihydrochloride

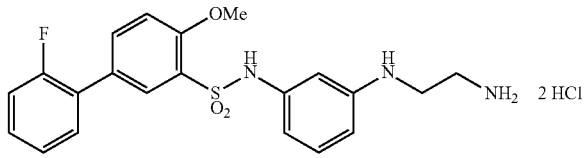 [SMILES: COc1ccc(-c2ccccc2F)cc1S(=O)(=O)Nc1cccc(NCCN)c1]

(1) Under an argon atmosphere, to a solution of tert-butyl (2-((benzyl) (3-(5-bromo-2-methoxyphenylsulfonamide)phenyl)amino)ethyl)carbamate (2.26 g) in DME (30 mL) were added 2-fluorophenylboronic acid (748 mg), sodium carbonate (811 mg), water (3.83 mL) and tetrakis(triphenylphosphine)palladium (221 mg), and the mixture was heated under reflux overnight. The reaction mixture was filtered through celite, and the filtrate was concentrated. The obtained residue was purified by silica gel column chromatography (eluate: ethyl acetate/hexane=1/2→1/1) to give tert-butyl (2-((benzyl)(3-(2'-fluoro-4-methoxy-[1,1'-biphenyl]-3-ylsulfonamide)phenyl)amino)ethyl)carbamate (2.15 g).
(2) To a solution of tert-butyl (2-(benzyl(3-(2'-fluoro-4-ylsulfonamide)phenyl)amino)ethyl) carbamate (2.15 g) in methanol (40 mL) was added 10% palladium/carbon (645 mg), and the mixture was stirred under a hydrogen atmosphere at room temperature for 3 hr. The reaction mixture was filtered through celite, and the filtrate was concentrated. The obtained residue was purified by silica gel column chromatography (eluate: ethyl acetate/hexane-1/1) to give tert-butyl (2-((3-(2'-fluoro-4-methoxy-[1,1'-biphenyl]-3-ylsulfonamide)phenyl)amino)ethyl)carbamate (1.61 g).
(3) To tert-butyl (2-((3-(2'-fluoro-4-methoxy-[1,1'-biphenyl]-3-ylsulfonamide)phenyl)amino)ethyl)carbamate (1.61 g) was added 10% hydrogen chloride-methanol solution (20 mL), and the mixture was stirred at 50° C. for 3 hr. The reaction mixture was concentrated to give N-(3-((2-aminoethyl)amino)phenyl)-2'-fluoro-4-methoxy-[1,1'-biphenyl]-3-sulfonamide dihydrochloride (1.55 g).

Reference Example 7

N-(3-((2-aminoethyl)amino)phenyl)-2'-chloro-4-methoxy-[1,1'-biphenyl]-3-sulfonamide dihydrochloride

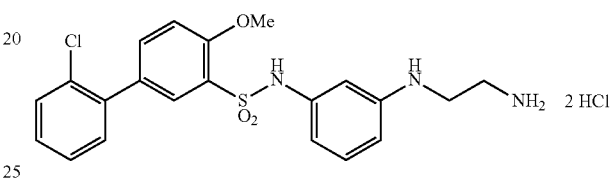

(1) To a suspension of tert-butyl (2-((3-nitrophenyl)amino) ethyl)carbamate (1.07 g) in methanol (15 mL) was added 10% palladium/carbon (321 mg), and the mixture was stirred under a hydrogen atmosphere at room temperature overnight. The reaction mixture was filtered through celite, and the filtrate was concentrated. The obtained residue was purified by amine silica gel column chromatography (eluate: ethyl acetate/hexane=2/1), methanol (1.5 mL) and 10% hydrogen chloride-methanol solution (1.5 mL) were further added, and the mixture was stirred at room temperature for 30 min. The reaction mixture was concentrated to give tert-butyl (2-((3-aminophenyl)amino)ethyl)carbamate dihydrochloride (845 mg).
(2) Under an argon atmosphere, to a suspension of tert-butyl (2-((3-aminophenyl)amino)ethyl)carbamate dihydrochloride (143 mg) in dichloromethane (5.0 ml) were added pyridine (0.133 mL) and 5-bromo-2-methoxybenzenesulfonyl chloride (143 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/1) to give tert-butyl(2-((3-(5-bromo-2-methoxyphenylsulfonamide)phenyl)amino)ethyl)carbamate (133 mg).
(3) Under an argon atmosphere, to a solution of tert-butyl (2-((3-(5-bromo-2-methoxyphenylsulfonamide)phenyl) amino)ethyl)carbamate (79.4 mg) in DME (2.0 mL) were added 2-chlorophenylboronic acid (34.2 mg), sodium carbonate (33.9 mg), water (0.160 mL) and tetrakis(triphenylphosphine)palladium (9.2 mg), and the mixture was heated under reflux overnight. The reaction mixture was filtered through celite, and the filtrate was concentrated. The obtained residue was purified by preparative thin layer chromatography (eluate: chloroform/methanol=40/1) to give tert-butyl (2-((3-(2'-chloro-4-methoxy-[1,1'-biphenyl]-3-ylsulfonamide)phenyl)amino)ethyl)carbamate (53.6 mg).
(4) To tert-butyl (2-((3-(2'-chloro-4-methoxy-[1,1'-biphenyl]-3-ylsulfonamide)phenyl)amino)ethyl)carbamate (53.6 mg) was added 10% hydrogen chloride-methanol solution (1.0 mL), and the mixture was stirred at 50° C. for 3 hr. The reaction mixture was concentrated to give N-(3-((2-aminoethyl)amino)phenyl)-2'-chloro-4-methoxy-[1,1'-biphenyl]-3-sulfonamide dihydrochloride (49.9 mg).

Reference Example 8 tert-butyl (2-((3-(2',4-dimethoxy-[1,1'-biphenyl]-3-ylsulfonamide)phenyl)(4-methoxybenzyl)amino)ethyl)carbamate

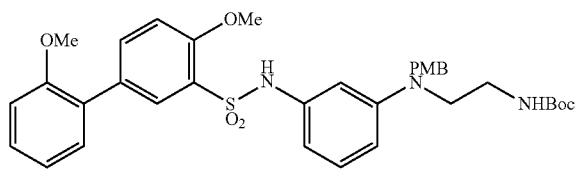

Under an argon atmosphere, to a solution of tert-butyl (2-((3-(5-bromo-2-methoxyphenylsulfonamide)phenyl)(4-methoxybenzyl)amino)ethyl)carbamate (124 mg) in n-propanol (2.0 mL) were added 2-methoxyphenyltrifluoroborate potassium salt (51.4 mg), triethylamine (0.084 mL) and bis(diphenylphosphino)ferrocenepalladium dichloride dichloromethane complex (4.9 mg), and the mixture was heated under reflux overnight. The reaction mixture was filtered through celite, and the filtrate was concentrated. The obtained residue was purified by silica gel column chromatography (eluate: ethyl acetate/hexane=1/1) to give tert-butyl (2-((3-(2',4-dimethoxy-[1,1'-biphenyl]-3-ylsulfonamide)phenyl)(4-methoxybenzyl)amino)ethyl)carbamate (116 mg).

Reference Example 9 tert-butyl (2-((3-(2',6'-difluoro-4-methoxy-[1,1'-biphenyl]-3-ylsulfonamide)phenyl)(4-methoxybenzyl)amino)ethyl)carbamate

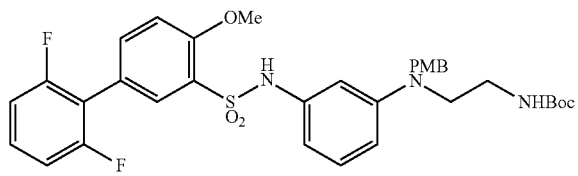

Under an argon atmosphere, to a solution of tert-butyl (2-((3-(5-bromo-2-methoxyphenylsulfonamide)phenyl)(4-methoxybenzyl)amino)ethyl)carbamate (100 mg) in DME (2.0 mL) were added 2,6-difluorophenyltrifluoroborate potassium salt (41.8 mg), triethylamine (0.067 mL) and bis(diphenylphosphino)ferrocene palladium dichloride dichloromethane complex (3.9 mg), and the mixture was heated under reflux overnight. The reaction mixture was filtered through celite, and the filtrate was concentrated. The obtained residue was purified by preparative thin layer column chromatography (eluate: ammonia-saturated chloroform) to give tert-butyl (2-((3-(2',6'-difluoro-4-methoxy-[1,1'-biphenyl]-3-ylsulfonamide)phenyl)(4-methoxybenzyl)amino)ethyl)carbamate (69.6 mg).

Reference Example 10 tert-butyl (2-((3-(2',5'-difluoro-4-methoxy-[1,1'-biphenyl]-3-ylsulfonamide)phenyl)(4-methoxybenzyl)amino)ethyl)carbamate

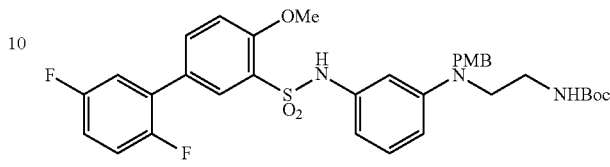

Under an argon atmosphere, to a solution of tert-butyl (2-((3-(5-bromo-2-methoxyphenylsulfonamide)phenyl)(4-methoxybenzyl)amino)ethyl)carbamate (124 mg) in DME (4.0 mL) were added 2,5-difluorophenylboronic acid (344 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by preparative thin layer chromatography (eluate: chloroform/methanol=40/1) to give tert-butyl (2-((3-(2',5'-difluoro-4-methoxy-[1,1'-biphenyl]-3-ylsulfonamide)phenyl)(4-methoxybenzyl)amino)ethyl) carbamate (70.1 mg).

Reference Example 11 tert-butyl (2-((3-(4-methoxy-2'-methyl-[1,1'-biphenyl]-3-ylsulfonamide)phenyl)amino)ethyl) carbamate

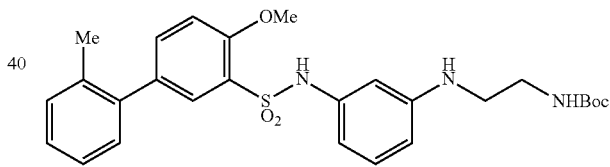

(1) Under an argon atmosphere, to a solution of tert-butyl (2-((benzyl) (3-(5-bromo-2-methoxyphenylsulfonamide)phenyl)amino)ethyl)carbamate (94.5 mg) in DME (4.0 mL) were added 2-trifluoromethylphenylboronic acid (41.8 mg), sodium carbonate (33.9 mg), water (0.160 mL) and tetrakis(triphenylphosphine)palladium (9.2 mg), and the mixture was heated under reflux overnight. The reaction mixture was filtered through celite, and the filtrate was concentrated. The obtained residue was purified by silica gel column chromatography (eluate: ethyl acetate/hexane=1/1) to give tert-butyl (2-((benzyl)(3-(4-methoxy-2'-(trifluoromethyl)-[1,1'-biphenyl]-3-ylsulfonamide)phenyl)amino)ethyl)carbamate (91.0 mg).

(2) To a solution of tert-butyl (2-((benzyl) (3-(4-methoxy-2'-(trifluoromethyl)-[1,1'-biphenyl]-3-ylsulfonamide)phenyl)amino)ethyl)carbamate (91.0 mg) in methanol (3.0 mL) was added 10% palladium/carbon (27.3 mg), and the mixture was stirred under a hydrogen atmosphere at room temperature overnight. The reaction mixture was filtered through celite, and the filtrate was concentrated. The obtained residue was purified by preparative thin layer chromatography (eluate: ammonia-saturated chloroform) to give tert-butyl (2-((3-(4-methoxy-2'-methyl-[1,1'-biphenyl]-3-ylsulfonamide)phenyl)amino)ethyl)carbamate (11.7 mg).

Reference Example 12 tert-butyl (2-((3-(2'-hydroxy-4-methoxy-[1,1'-biphenyl]-3-ylsulfonamide)phenyl)amino)ethyl)carbamate

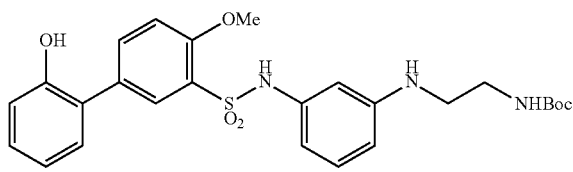 [SMILES: COc1ccc(-c2ccccc2O)cc1S(=O)(=O)Nc1cccc(NCCNC(=O)OC(C)(C)C)c1]

(1) Under an argon atmosphere, to a solution of tert-butyl (2-((benzyl)(3-(5-bromo-2-methoxyphenylsulfonamide)phenyl)amino)ethyl)carbamate (94.5 mg) in DME (4.0 mL) were added 2-benzyloxyphenylboronic acid (51.1 mg), sodium carbonate (33.9 mg), water (0.160 mL) and tetrakis(triphenylphosphine)palladium (9.2 mg), and the mixture was heated under reflux overnight. The reaction mixture was filtered through celite, and the filtrate was concentrated. The obtained residue was purified by silica gel column chromatography (eluate: ethyl acetate/hexane=1/2) to give tert-butyl (2-((benzyl)(3-(2'-(benzyloxy)-4-methoxy-[1,1'-biphenyl]-3-ylsulfonamide)phenyl)amino)ethyl)carbamate (96.0 mg).
(2) To a solution of tert-butyl (2-((benzyl)(3-(2'-(benzyloxy)-4-methoxy-[1,1'-biphenyl]-3-ylsulfonamide)phenyl)amino)ethyl) carbamate (96.0 mg) in methanol (3.0 mL) was added 10% palladium/carbon (67.2 mg), and the mixture was stirred under a hydrogen atmosphere at room temperature overnight. The reaction mixture was filtered through celite, and the filtrate was concentrated. The obtained residue was purified by preparative thin layer chromatography (eluate: chloroform/methanol=40/1) to give tert-butyl (2-((3-(2'-hydroxy-4-methoxy-[1,1'-biphenyl]-3-ylsulfonamide)phenyl)amino)ethyl)carbamate (7.2 mg).

Reference Example 13

N-(3-((2-aminoethyl)amino)phenyl)-2'-fluoro-4,6'-dimethoxy-[1,1'-biphenyl]-3-sulfonamide dihydrochloride

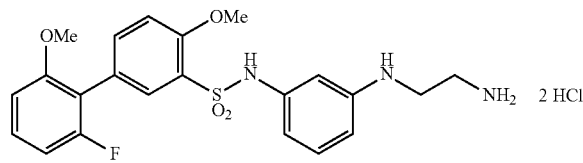 [SMILES: COc1ccc(-c2c(F)cccc2OC)cc1S(=O)(=O)Nc1cccc(NCCN)c1]

(1) Under an argon atmosphere, to a solution of tert-butyl (2-((benzyl) (3-(5-bromo-2-methoxyphenylsulfonamide)phenyl)amino)ethyl)carbamate (118 mg) in DME (4.0 mL) were added 2-fluoro-6-methoxyphenylboronic acid (47.6 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by silica gel column chromatography (eluate: ethyl acetate/hexane=1/1).

To a solution of the obtained purified product in methanol (3.0 mL) was added 10% palladium/carbon (38.4 mg), and the mixture was stirred under a hydrogen atmosphere at room temperature overnight. The reaction mixture was filtered through celite, and the filtrate was concentrated. The obtained residue was purified by preparative thin layer chromatography (eluate: ammonia-saturated chloroform/ethyl acetate=6/1) to give tert-butyl (2-((3-(2'-fluoro-4,6'-dimethoxy-[1,1'-biphenyl]-3-ylsulfonamide)phenyl)amino)ethyl) carbamate (34.6 mg).
(2) To tert-butyl (2-((3-(2'-fluoro-4,6'-dimethoxy-[1,1'-biphenyl]-3-ylsulfonamide)phenyl)amino)ethyl)carbamate (34.6 mg) was added 10% hydrogen chloride-methanol (1.0 mL), and the mixture was stirred at 50° C. for 2 hr. The reaction mixture was concentrated to give N-(3-((2-aminoethyl)amino)phenyl)-2'-fluoro-4,6'-dimethoxy-[1,1'-biphenyl]-3-sulfonamide dihydrochloride (36.6 mg).

Reference Example 14 tert-butyl (2-((3-(4-methoxy-2'-(trifluoromethyl)-[1,1'-biphenyl]-3-ylsulfonamide)phenyl) (4-methoxybenzyl)amino)ethyl)carbamate

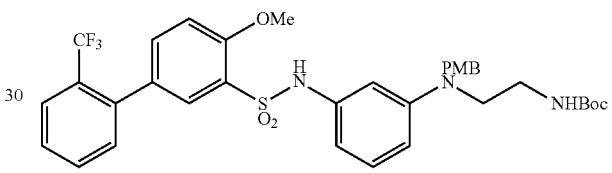

Under an argon atmosphere, to a solution of tert-butyl (2-((3-(5-bromo-2-methoxyphenylsulfonamide)phenyl)(4-methoxybenzyl)amino)ethyl)carbamate (160 mg) in DME (4.0 mL) were added 2-trifluoromethylphenylboronic acid (68.4 mg), sodium carbonate (55.1 mg), water (0.260 mL) and tetrakis(triphenylphosphine)palladium (15.0 mg), and the mixture was heated under reflux overnight. The reaction mixture was filtered through celite, and the filtrate was concentrated. The obtained residue was purified by preparative thin layer chromatography (eluate: ammonia-saturated chloroform) to give tert-butyl (2-((3-(4-methoxy-2'-(trifluoromethyl)-[1,1'-biphenyl]-3-ylsulfonamide)phenyl) (4-methoxybenzyl)amino)ethyl)carbamate (76.1 mg).

Reference Example 15 tert-butyl (2-((3-(2',5'-dichloro-4-methoxy-[1,1'-biphenyl]-3-ylsulfonamide)phenyl)(4-methoxybenzyl)amino)ethyl)carbamate

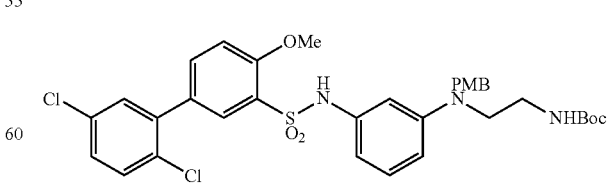

Under an argon atmosphere, to a solution of tert-butyl (2-((3-(5-bromo-2-methoxyphenylsulfonamide)phenyl) (4-methoxybenzyl)amino)ethyl)carbamate (165 mg) in DME (4.0 mL) were added 2,5-dichlorophenylboronic acid (70.6 mg), sodium carbonate (56.2 mg), water (0.270 mL) and tetrakis(triphenylphosphine)palladium (15.0 mg), and the mixture was heated under reflux overnight. The reaction mixture was filtered through celite, and the filtrate was concentrated. The obtained residue was purified by preparative thin layer chromatography (eluate: ammonia-saturated chloroform) to give tert-butyl (2-((3-(2',5'-dichloro-4-methoxy-[1,1'-biphenyl]-3-ylsulfonamide)phenyl)(4-methoxybenzyl)amino)ethyl)carbamate (177 mg).

Reference Example 16 tert-butyl (2-((3-(3',5'-dichloro-4-methoxy-[1,1'-biphenyl]-3-ylsulfonamide)phenyl)(4-methoxybenzyl)amino)ethyl)carbamate

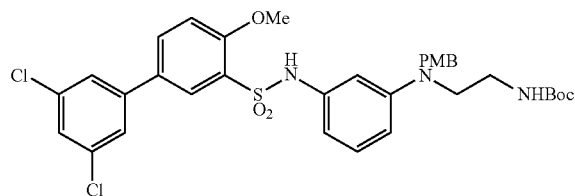

Under an argon atmosphere, to a solution of tert-butyl (2-((3-(5-bromo-2-methoxyphenylsulfonamide)phenyl)(4-methoxybenzyl)amino)ethyl)carbamate (165 mg) in DME (4.0 mL) were added 3,5-dichlorophenylboronic acid (70.6 mg), sodium carbonate (56.2 mg), water (0.270 mL) and tetrakis(triphenylphosphine)palladium (15.0 mg), and the mixture was heated under reflux overnight. The reaction mixture was filtered through celite, and the filtrate was concentrated. The obtained residue was purified by preparative thin layer chromatography (eluate: ammonia-saturated chloroform) to give tert-butyl (2-((3-(3',5'-dichloro-4-methoxy-[1,1'-biphenyl]-3-ylsulfonamide)phenyl)(4-methoxybenzyl)amino)ethyl)carbamate (137 mg).

Reference Example 17 tert-butyl (2-((3-(3'-chloro-4-methoxy-[1,1'-biphenyl]-3-ylsulfonamide)phenyl)(4-methoxybenzyl)amino)ethyl)carbamate

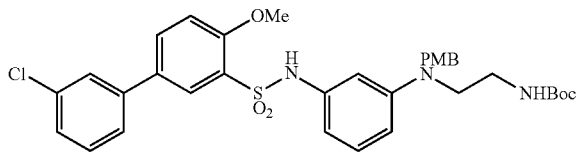

Under an argon atmosphere, to a solution of tert-butyl (2-((3-(5-bromo-2-methoxyphenylsulfonamide)phenyl)(4-methoxybenzyl)amino)ethyl)carbamate (124 mg) in DME (4.0 mL) were added 3-chlorophenylboronic acid (43.8 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by preparative thin layer chromatography (eluate: ammonia-saturated chloroform) to give tert-butyl (2-((3-(3'-chloro-4-methoxy-[1,1'-biphenyl]-3-ylsulfonamide)phenyl)(4-methoxybenzyl)amino)ethyl)carbamate (104 mg).

Reference Example 18

N-(3-((2-aminoethyl)amino)phenyl)-3',4-dimethoxy-[1,1'-biphenyl]-3-sulfonamide dihydrochloride

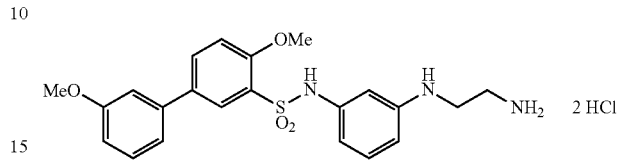

(1) Under an argon atmosphere, to a solution of tert-butyl (2-((benzyl) (3-(5-bromo-2-methoxyphenylsulfonamide)phenyl)amino)ethyl)carbamate (118 mg) in DME (4.0 mL) were added 3-methoxyphenylboronic acid (42.5 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by preparative thin layer chromatography (eluate: ammonia-saturated chloroform). To a solution of the obtained residue in methanol (2.0 mL) was added 10% palladium/carbon (28.0 mg), and the mixture was stirred under a hydrogen atmosphere at room temperature overnight. The reaction mixture was filtered through celite, and the filtrate was concentrated. The obtained residue was purified by silica gel column chromatography (eluate: ethyl acetate/hexane-1/1) to give tert-butyl (2-((3-(3',4-dimethoxy-[1,1'-biphenyl]-3-ylsulfonamide)phenyl)amino)ethyl)carbamate (43.0 mg).
(2) To tert-butyl(2-((3-(3',4-dimethoxy-[1,1'-biphenyl]-3-ylsulfonamide)phenyl)amino)ethyl)carbamate (43.0 mg) was added 10% hydrogen chloride-methanol (2.0 mL), and the mixture was stirred at 50° C. for 2 hr. The reaction mixture was concentrated to give N-(3-((2-aminoethyl)amino)phenyl)-3',4-dimethoxy-[1,1'-biphenyl]-3-sulfonamide dihydrochloride (33.8 mg).

Reference Example 19 tert-butyl (2-((3-(2'-chloro-5'-fluoro-4-methoxy-[1,1'-biphenyl]-3-ylsulfonamide)phenyl) (4-methoxybenzyl)amino)ethyl) carbamate

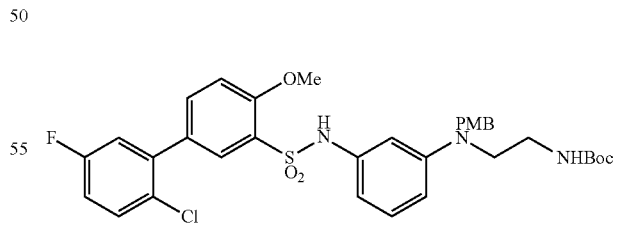

Under an argon atmosphere, to a solution of tert-butyl (2-((3-(5-bromo-2-methoxyphenylsulfonamide)phenyl)(4-methoxybenzyl)amino)ethyl)carbamate (124 mg) in DME (4.0 mL) were added 2-chloro-5-fluorophenylboronic acid (48.8 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by silica gel column chromatography (eluate: ethyl acetate/hexane=1/2) to give tert-butyl (2-((3-(2'-chloro-5'-fluoro-4-methoxy-[1,1'-biphenyl]-3-ylsulfonamide)phenyl)(4-methoxybenzyl)amino)ethyl)carbamate (127 mg).

Reference Example 20

N-(3-((2-aminoethyl)amino)phenyl)-2'-fluoro-4,5'-dimethoxy-[1,1'-biphenyl]-3-sulfonamide dihydrochloride

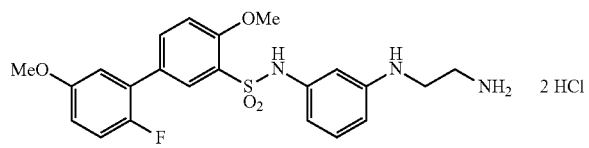 [SMILES: COc1ccc(F)c(-c2ccc(OC)c(S(=O)(=O)Nc3cccc(NCCN)c3)c2)c1]

(1) Under an argon atmosphere, to a solution of tert-butyl (2-((benzyl) (3-(5-bromo-2-methoxyphenylsulfonamide)phenyl)amino)ethyl)carbamate (118 mg) in DME (4.0 mL) were added 2-fluoro-5-methoxyphenylboronic acid (47.6 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by preparative thin layer chromatography (eluate: ammonia-saturated chloroform) to give tert-butyl (2-((benzyl)(3-(2'-fluoro-4,5'-ylsulfonamide)phenyl)amino)ethyl)carbamate (115 mg).
(2) To a solution of tert-butyl (2-((benzyl)(3-(2'-fluoro-4,5'-dimethoxy-[1,1'-biphenyl]-3-ylsulfonamide)phenyl)amino)ethyl)carbamate (115 mg) in methanol (2.0 mL) was added 10% palladium/carbon (57.5 mg), and the mixture was stirred under a hydrogen atmosphere at room temperature for 2 hr. The reaction mixture was filtered through celite, and the filtrate was concentrated. The obtained residue was purified by amine silica gel column chromatography (eluate: ethyl acetate) to give tert-butyl (2-((3-(2'-fluoro-4,5'-dimethoxy-[1,1'-biphenyl]-3-ylsulfonamide)phenyl)amino)ethyl)carbamate (95.4 mg).
(3) To tert-butyl (2-((3-(2'-fluoro-4,5'-dimethoxy-[1,1'-biphenyl]-3-ylsulfonamide)phenyl)amino)ethyl)carbamate (95.4 mg) was added 10% hydrogen chloride-methanol (2.0 mL), and the mixture was stirred at 50° C. for 2 hr. The reaction mixture was concentrated to give N-(3-((2-aminoethyl)amino)phenyl)-2'-fluoro-4,5'-dimethoxy-[1,1'-biphenyl]-3-sulfonamide dihydrochloride (80.5 mg).

Reference Example 21

N-(3-((2-aminoethyl)amino)phenyl)-3',4,5'-trimethoxy-[1,1'-biphenyl]-3-sulfonamide dihydrochloride

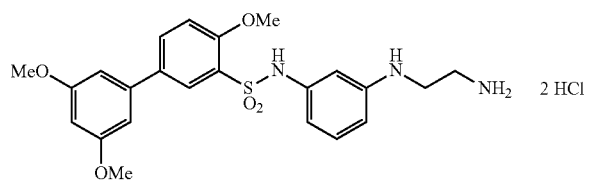 [SMILES: COc1cc(OC)cc(-c2ccc(OC)c(S(=O)(=O)Nc3cccc(NCCN)c3)c2)c1]

(1) Under an argon atmosphere, to a solution of tert-butyl (2-((benzyl) (3-(5-bromo-2-methoxyphenylsulfonamide)phenyl)amino)ethyl)carbamate (118 mg) in DME (4.0 mL) were added 3,5-dimethoxyphenylboronic acid (43.7 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by preparative thin layer chromatography (eluate: ammonia-saturated chloroform) to give tert-butyl (2-((benzyl)(3-(3',4,5'-ylsulfonamide)phenyl)amino)ethyl)carbamate (72.6 mg).
(2) To a solution of tert-butyl (2-((benzyl)(3-(3',4,5'-trimethoxy-[1,1'-biphenyl]-3-ylsulfonamide)phenyl)amino)ethyl)carbamate (72.6 mg) in methanol (2.0 mL) was added 10% palladium/carbon (21.8 mg), and the mixture was stirred under a hydrogen atmosphere at room temperature for 2 hr. The reaction mixture was filtered through celite, and the filtrate was concentrated. The obtained residue was purified by amine silica gel column chromatography (eluate: ethyl acetate) to give tert-butyl (2-((3-(3',4,5'-trimethoxy-[1,1'-biphenyl]-3-ylsulfonamide)phenyl)amino)ethyl)carbamate (59.4 mg).
(3) To tert-butyl (2-((3-(3',4,5'-trimethoxy-[1,1'-biphenyl]-3-ylsulfonamide)phenyl)amino)ethyl)carbamate (59.4 mg) was added 10% hydrogen chloride-methanol (2.0 mL), and the mixture was stirred at room temperature for 4 hr. The reaction mixture was concentrated to give N-(3-((2-aminoethyl)amino)phenyl)-3',4,5'-trimethoxy-[1,1'-biphenyl]-3-sulfonamide dihydrochloride (53.6 mg).

Reference Example 22

3'-amino-N-(3-((2-aminoethyl)amino)phenyl)-4-methoxy-[1,1'-biphenyl]-3-sulfonamide

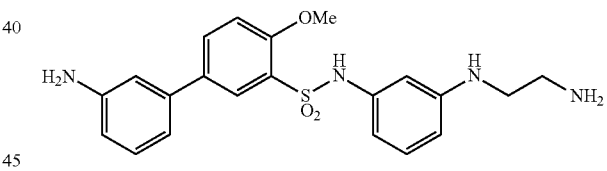

Under an argon atmosphere, to a solution of tert-butyl (2-((benzyl)(3-(5-bromo-2-methoxyphenylsulfonamide)phenyl)amino)ethyl)carbamate (162 mg) in dioxane (3.0 mL) were added 3-(N-Boc-amino)phenylboronic acid pinacol ester (122 mg), sodium carbonate (58.3 mg), water (0.275 mL) and bis(diphenylphosphino)ferrocenepalladium dichloride dichloromethane complex (11.4 mg), and the mixture was heated under reflux overnight. The reaction mixture was filtered through celite, and the filtrate was concentrated. The obtained residue was purified by silica gel column chromatography (eluate: ethyl acetate/hexane=1/2). To a solution of the obtained solid (171 mg) in 10% hydrogen chloride-methanol (2.0 mL) was added 10% palladium/carbon (51.3 mg), and the mixture was stirred under a hydrogen atmosphere at room temperature overnight. The reaction mixture was filtered through celite, and the filtrate was concentrated. The obtained residue was purified by amine silica gel column chromatography (eluate: ammonia-saturated chloroform/methanol=10/1) to give 3'-amino-N-(3-((2-aminoethyl)amino)phenyl)-4-methoxy-[1,1'-biphenyl]-3-sulfonamide (81.5 mg).

Reference Example 23

N-(3-((2-aminoethyl)amino)phenyl)-3'-(hydroxymethyl)-4-methoxy-[1,1'-biphenyl]-3-sulfonamide

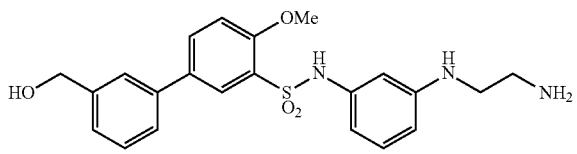 [SMILES: COc1ccc(-c2cccc(CO)c2)cc1S(=O)(=O)Nc1cccc(NCCN)c1]

(1) Under an argon atmosphere, to a solution of tert-butyl (2-((benzyl) (3-(5-bromo-2-methoxyphenylsulfonamide)phenyl)amino)ethyl)carbamate (118 mg) in dioxane (4.0 mL) were added 2-(3-hydroxymethylphenyl)boronic acid pinacol ester (65.5 mg), sodium carbonate (42.2 mg), water (0.200 mL) and bis(diphenylphosphino)ferrocene palladium dichloride dichloromethane complex (8.2 mg), and the mixture was heated under reflux overnight. The reaction mixture was filtered through celite, and the filtrate was concentrated. The obtained residue was purified by silica gel column chromatography (eluate: ethyl acetate/hexane=1/2→2/1) to give tert-butyl (2-((benzyl)(3-(3'-(hydroxymethyl)-4-methoxy-[1,1'-biphenyl]-3-ylsulfonamide)phenyl)amino)ethyl)carbamate (72.6 mg).

(2) To a solution of tert-butyl (2-((benzyl)(3-(3'-(hydroxymethyl)-4-methoxy-[1,1'-biphenyl]-3-ylsulfonamide)phenyl)amino)ethyl)carbamate (72.6 mg) in 10% hydrogen chloride-methanol (2.0 mL) was added 10% palladium/carbon (36.3 mg), and the mixture was stirred under a hydrogen atmosphere at room temperature overnight. The reaction mixture was filtered through celite, and the filtrate was concentrated. The obtained residue was purified by amine silica gel column chromatography (eluate: ammonia-saturated chloroform/methanol=10/1) to give N-(3-((2-aminoethyl)amino)phenyl)-3'-(hydroxymethyl)-4-methoxy-[1,1'-biphenyl]-3-sulfonamide (51.0 mg).

Reference Example 24 methyl 3'-(N-(3-((2-((tert-butoxycarbonyl)amino)ethyl)amino)phenyl)sulfamoyl)-4'-methoxy-[1,1'-biphenyl]-3-carboxylate

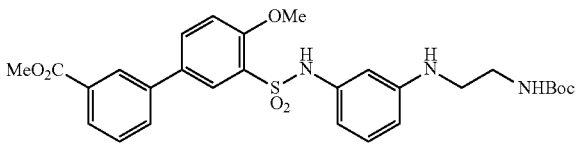 [SMILES: COC(=O)c1cccc(-c2ccc(OC)c(S(=O)(=O)Nc3cccc(NCCNC(=O)OC(C)(C)C)c3)c2)c1]

(1) Under an argon atmosphere, to a solution of tert-butyl (2-((benzyl) (3-(5-bromo-2-methoxyphenylsulfonamide)phenyl)amino)ethyl)carbamate (2.36 g) in dioxane (20.0 mL) were added 3-methoxycarbonylphenylboronic acid pinacol ester (1.26 g), sodium carbonate (828 mg), water (4.0 mL) and bis(diphenylphosphino)ferrocenepalladium dichloride dichloromethane complex (163 mg), and the mixture was heated under reflux overnight. The reaction mixture was filtered through celite, and the filtrate was concentrated. The obtained residue was purified by silica gel column chromatography (eluate: ethyl acetate/hexane=1/2) to give methyl 3'-(N-(3-((benzyl) (2-((tert-butoxycarbonyl)amino)ethyl)amino)phenyl)sulfamoyl)-4'-methoxy-[1,1'-biphenyl]-3-carboxylate (2.25 g).

(2) To a suspension of methyl 3'-(N-(3-((benzyl) ((tert-(2.25 g) in methanol (20 mL) was added 10% palladium/carbon (675 mg), and the mixture was stirred under a hydrogen atmosphere at room temperature for 5 hr. The reaction mixture was filtered through celite, and the filtrate was concentrated. The obtained residue was purified by amine silica gel column chromatography (eluate: ammonia-saturated chloroform/methanol=10/1) to give methyl 3'-(N-(3-((2-((tert-butoxycarbonyl)amino)ethyl)amino)phenyl)sulfamoyl)-4'-methoxy-[1,1'-biphenyl]-3-carboxylate (1.94 g).

Reference Example 25

3'-(N-(3-((2-((tert-butoxycarbonyl)amino)ethyl)amino)phenyl)sulfamoyl)-4'-methoxy-[1,1'-biphenyl]-3-carboxylic acid

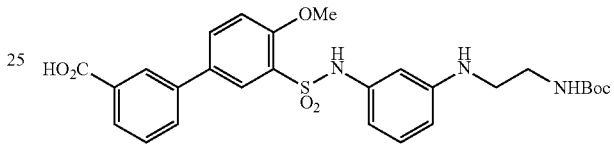

To a suspension of methyl 3'-(N-(3-((2-((tert-butoxycarbonyl)amino)ethyl)amino)phenyl)sulfamoyl)-4'-methoxy-[1,1'-biphenyl]-3-carboxylate (1.94 g) in methanol (30 mL) was added 1N aqueous sodium hydroxide solution (10.5 mL), and the mixture was stirred at 60° C. for 3 hr. To this reaction mixture was added 1N hydrochloric acid, and the mixture was extracted with a mixed solvent of chloroform and methanol (2/1). The organic layer was dried over sodium sulfate, filtered, and the filtrate was concentrated to give 3'-(N-(3-((2-((tert-butoxycarbonyl)amino)ethyl)amino)phenyl)sulfamoyl)-4'-methoxy-[1,1'-biphenyl]-3-carboxylic acid (1.77 g).

Reference Example 26

3'-(N-(3-((2-aminoethyl)amino)phenyl)sulfamoyl)-4'-methoxy-N,N-dimethyl-[1,1'-biphenyl]-3-carboxamide dihydrochloride

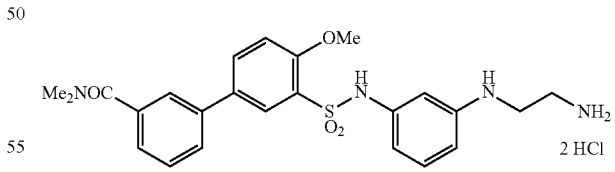

Under an argon atmosphere, to a suspension of 3'-(N-(3-((2-((tert-butoxycarbonyl)amino)ethyl)amino)phenyl)sulfamoyl)-4'-methoxy-[1,1'-biphenyl]-3-carboxylic acid (1.77 g) in dichloromethane (30 mL) were added dimethylamine hydrochloride (533 mg), triethylamine (1.59 mL) and BOP reagent (1.59 g), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/chloroform=4/1). To the obtained purified product was added 10% hydrogen chloride-methanol solution (10 mL), and the mixture was stirred at 50° C. for 2 hr. The reaction mixture was concentrated, and the obtained residue was purified by amine silica gel column chromatography (eluate: ammonia-saturated chloroform/methanol=1/0→100/1). To the obtained purified product was added 10% hydrogen chloride-methanol solution (5.0 mL), and the reaction mixture was concentrated to give 3'-(N-(3-((2-aminoethyl)amino)phenyl)sulfamoyl)-4'-methoxy-N,N-dimethyl-[1,1'-biphenyl]-3-carboxamide dihydrochloride (1.31 g).

Reference Example 27

3'-(N-(3-((2-aminoethyl)amino)phenyl)sulfamoyl)-4'-methoxy-N,N-dimethyl-[1,1'-biphenyl]-2-carboxamide dihydrochloride

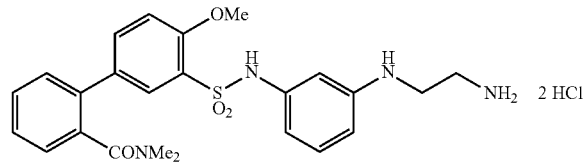

(1) Under an argon atmosphere, to a solution of tert-butyl (2-((benzyl)(3-(5-bromo-2-methoxyphenylsulfonamide)phenyl)amino)ethyl)carbamate (118 mg) in dioxane (4.0 mL) were added 2-ethoxycarbonylphenylboronic acid pinacol ester (66.3 mg), sodium carbonate (42.4 mg), water (0.200 mL) and bis(diphenylphosphino)ferrocenepalladium dichloride dichloromethane complex (8.2 mg), and the mixture was heated under reflux overnight. The reaction mixture was filtered through celite, and the filtrate was concentrated. The obtained residue was purified by silica gel column chromatography (eluate: ethyl acetate/hexane=1/2→1/1) to give ethyl 3'-(N-(3-((benzyl) (2-((tert-butoxycarbonyl)amino)ethyl)amino)phenyl)sulfamoyl)-4'-methoxy-[1,1'-biphenyl]-2-carboxylate (125 mg).

(2) To a suspension of ethyl 3'-(N-(3-((benzyl) (2-((tert-butoxycarbonyl)amino)ethyl)amino)phenyl)sulfamoyl)-4'-methoxy-[1,1'-biphenyl]-2-carboxylate (125 mg) in methanol (4.0 mL) was added 10% palladium/carbon (37.5 mg), and the mixture was stirred under a hydrogen atmosphere at room temperature for 3 hr. The reaction mixture was filtered through celite, and the filtrate was concentrated. The obtained residue was purified by amine silica gel column chromatography (eluate: chloroform/methanol=10/1) to give ethyl 3'-(N-(3-((2-((tert-butoxycarbonyl)amino)ethyl)amino)phenyl)sulfamoyl)-4'-methoxy-[1,1'-biphenyl]-2-carboxylate (95.4 mg).

(3) To a suspension of ethyl 3'-(N-(3-((2-((tert-butoxycarbonyl)amino)ethyl)amino)phenyl)sulfamoyl)-4'-methoxy-[1,1'-biphenyl]-2-carboxylate (95.4 mg) in methanol (3.0 mL) was added 1N aqueous sodium hydroxide solution (0.510 mL), and the mixture was stirred at 60° C. for 2 hr. To this reaction mixture was added 1N hydrochloric acid, and the mixture was extracted with chloroform. The organic layer was dried over sodium sulfate, filtered, and the filtrate was concentrated to give 3'-(N-(3-((2-((tert-butoxycarbonyl)amino)ethyl)amino)phenyl)sulfamoyl)-4'-methoxy-[1,1'-biphenyl]-2-carboxylic acid (100 mg).

(4) Under an argon atmosphere, to a suspension of 3'-(N-(3-((2-((tert-butoxycarbonyl)amino)ethyl)amino)phenyl)sulfamoyl)-4'-methoxy-[1,1'-biphenyl]-2-carboxylic acid (100 mg) in dichloromethane (2.0 mL) were added dimethylamine hydrochloride (30.2 mg), triethylamine (0.085 mL) and BOP reagent (88.5 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/1) to give tert-butyl (2-((3-(2'-(dimethylcarbamoyl)-4-methoxy-[1,1'-biphenyl]-3-ylsulfonamide)phenyl)amino)ethyl)carbamate (65.0 mg).

(5) To tert-butyl (2-((3-(2'-(dimethylcarbamoyl)-4-methoxy-[1,1'-biphenyl]-3-ylsulfonamide)phenyl)amino)ethyl)carbamate (65.0 mg) was added 10% hydrogen chloride-methanol solution (2.0 mL), and the mixture was stirred at 50° C. for 2 hr. The reaction mixture was concentrated to give 3'-(N-(3-((2-aminoethyl)amino)phenyl)sulfamoyl)-4'-methoxy-N,N-dimethyl-[1,1'-biphenyl]-2-carboxamide dihydrochloride (61.9 mg).

Reference Example 28

N-(3-((2-aminoethyl)amino)phenyl)-3'-(azetidine-1-carbonyl)-4-methoxy-[1,1'-biphenyl]-3-sulfonamide dihydrochloride

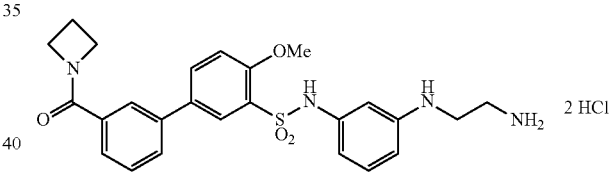

(1) Under an argon atmosphere, to a suspension of 3'-(N-(3-((2-((tert-butoxycarbonyl)amino)ethyl)amino)phenyl)sulfamoyl)-4'-methoxy-[1,1'-biphenyl]-3-carboxylic acid (130 mg) in dichloromethane (2.0 mL) were added azetidine hydrochloride (24.3 mg), triethylamine (0.074 mL) and BOP reagent (115 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate) to give tert-butyl (2-((3-(3'-(azetidine-1-carbonyl)-4-methoxy-[1,1'-biphenyl]-3-ylsulfonamide)phenyl)amino)ethyl)carbamate (109 mg).

(2) To tert-butyl (2-((3-(3'-(azetidine-1-carbonyl)-4-methoxy-[1,1'-biphenyl]-3-ylsulfonamide)phenyl)amino)ethyl)carbamate (109 mg) was added 10% hydrogen chloride-methanol solution (2.0 mL), and the mixture was stirred at room temperature overnight. The reaction mixture was concentrated to give N-(3-((2-aminoethyl)amino)phenyl)-3'-(azetidine-1-carbonyl)-4-methoxy-[1,1'-biphenyl]-3-sulfonamide dihydrochloride (96.1 mg).

Reference Example 29

N-(3-((2-aminoethyl)amino)phenyl)-4-methoxy-3'-(pyrrolidine-1-carbonyl)-[1,1'-biphenyl]-3-sulfonamide dihydrochloride

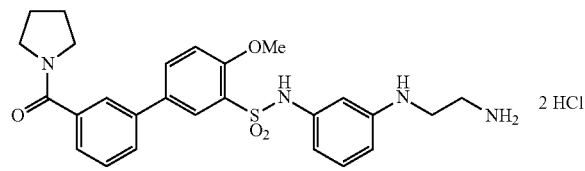 [SMILES: COc1ccc(-c2cccc(C(=O)N3CCCC3)c2)cc1S(=O)(=O)Nc1cccc(NCCN)c1]

(1) Under an argon atmosphere, to a suspension of 3'-(N-(3-((2-((tert-butoxycarbonyl)amino)ethyl)amino)phenyl)sulfamoyl)-4'-methoxy-[1,1'-biphenyl]-3-carboxylic acid (130 mg) in dichloromethane (2.0 mL) were added pyrrolidine (0.020 mL), triethylamine (0.036 mL) and BOP reagent (115 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate) to give tert-butyl (2-((3-(4-methoxy-3'-(pyrrolidine-1-carbonyl)-[1,1'-biphenyl]-3-ylsulfonamide)phenyl)amino)ethyl) carbamate (154 mg).

(2) To tert-butyl (2-((3-(4-methoxy-3'-(pyrrolidine-1-carbonyl)-[1,1'-biphenyl]-3-ylsulfonamide)phenyl)amino)ethyl) carbamate (154 mg) was added 10% hydrogen chloride-methanol solution (3.0 mL), and the mixture was stirred at 50° C. overnight. The reaction mixture was concentrated to give N-(3-((2-aminoethyl)amino)phenyl)-4-methoxy-3'-(pyrrolidine-1-carbonyl)-[1,1'-biphenyl]-3-sulfonamide dihydrochloride (125 mg).

Reference Example 30

N-(3-((2-aminoethyl)amino)phenyl)-4-methoxy-3'-(piperidine-1-carbonyl)-[1,1'-biphenyl]-3-sulfonamide dihydrochloride

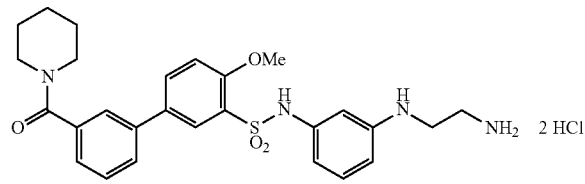 [SMILES: COc1ccc(-c2cccc(C(=O)N3CCCCC3)c2)cc1S(=O)(=O)Nc1cccc(NCCN)c1]

(1) Under an argon atmosphere, to a suspension of 3'-(N-(3-((2-((tert-butoxycarbonyl)amino)ethyl)amino)phenyl)sulfamoyl)-4'-methoxy-[1,1'-biphenyl]-3-carboxylic acid (130 mg) in dichloromethane (2.0 mL) were added piperidine (0.024 mL), triethylamine (0.036 mL) and BOP reagent (115 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate) to give tert-butyl (2-((3-(4-methoxy-3'-(piperidine-1-carbonyl)-[1,1'-biphenyl]-3-ylsulfonamide)phenyl)amino)ethyl)carbamate (129 mg).

(2) To tert-butyl (2-((3-(4-methoxy-3'-(pyrrolidine-1-carbonyl)-[1,1'-biphenyl]-3-ylsulfonamide)phenyl)amino)ethyl) carbamate (129 mg) was added 10% hydrogen chloride-methanol solution (3.0 mL), and the mixture was stirred at 50° C. overnight. The reaction mixture was concentrated to give N-(3-((2-aminoethyl)amino)phenyl)-4-methoxy-3'-(piperidine-1-carbonyl)-[1,1'-biphenyl]-3-sulfonamide dihydrochloride (112 mg).

Reference Example 31

N-(3-((2-aminoethyl)amino)phenyl)-5-(3-fluoropyridin-2-yl)-2-methoxybenzenesulfonamide trihydrochloride

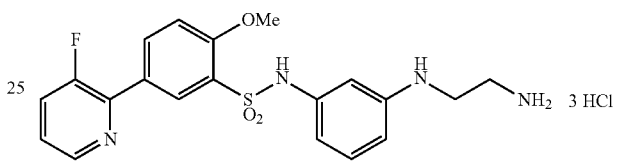

(1) Under an argon atmosphere, to a solution of tert-butyl (2-((benzyl) (3-(5-bromo-2-methoxyphenylsulfonamide)phenyl)amino)ethyl)carbamate (590 mg) in DMSO (2.0 mL) were added bis(pinacolato)diboron (305 mg), potassium acetate (294 mg) and bis(diphenylphosphino)ferrocene palladium dichloride dichloromethane complex (40.8 mg), and the mixture was stirred at 80° C. overnight. To this reaction mixture was added saturated aqueous sodium hydrogen carbonate solution, and the mixture was filtered through celite, and the filtrate was extracted with ethyl acetate. The organic layer was washed with water, dried over sodium sulfate, filtered, and the filtrate was concentrated. The obtained residue was purified by silica gel column chromatography (eluate: ethyl acetate/hexane=1/1). Under an argon atmosphere, to a solution of the obtained purified product (250 mg) in dioxane (4.0 mL) were added 2-bromo-3-fluoropyridine (0.056 mL), sodium carbonate (82.7 mg), water (0.390 mL) and bis(diphenylphosphino)ferrocene palladium dichloride dichloromethane complex (16.3 mg), and the mixture was heated under reflux overnight. The reaction mixture was filtered through celite, and the filtrate was concentrated. The obtained residue was purified by preparative thin layer chromatography (eluate: ethyl acetate/hexane=1/1) to give tert-butyl (2-((benzyl)(3-(5-(3-fluoropyridin-2-yl)-2-methoxyphenylsulfonamide)phenyl)amino) ethyl)carbamate (51.2 mg).

(2) To a suspension of tert-butyl (2-((benzyl) (3-(5-(3-fluoropyridin-2-yl)-2-methoxyphenylsulfonamide)phenyl)amino)ethyl)carbamate (51.2 mg) in methanol (2.0 mL) was added 10% palladium/carbon (15.4 mg), and the mixture was stirred under a hydrogen atmosphere at room temperature overnight. The reaction mixture was filtered through celite, and the filtrate was concentrated. The obtained residue was purified by amine silica gel column chromatography (eluate: ethyl acetate/hexane=1/1) to give tert-butyl (2-((3-(5-(3-fluoropyridin-2-yl)-2-methoxyphenylsulfonamide)phenyl)amino)ethyl) carbamate (18.8 mg).

(3) To tert-butyl (2-((3-(5-(3-fluoropyridin-2-yl)-2-methoxyphenylsulfonamide)phenyl)amino)ethyl)carbamate (18.8 mg) was added 10% hydrogen chloride-methanol solution (1.0 mL), and the mixture was stirred at 50° C. for 2 hr. The reaction mixture was concentrated to give N-(3-((2-aminoethyl)amino)phenyl)-5-(3-fluoropyridin-2-yl)-2-methoxybenzenesulfonamide trihydrochloride (16.8 mg).

Reference Example 32

N-(3-((2-aminoethyl)amino)phenyl)-2-methoxy-5-(6-methoxypyridin-2-yl)benzenesulfonamide

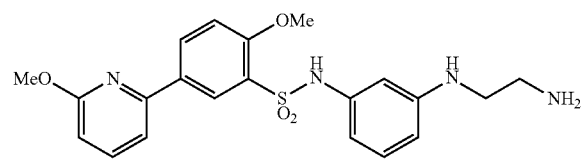 [SMILES: COc1cccc(-c2ccc(OC)c(S(=O)(=O)Nc3cccc(NCCN)c3)c2)n1]

(1) Under an argon atmosphere, to a solution of tert-butyl (2-((benzyl) (3-(5-bromo-2-methoxyphenylsulfonamide)phenyl)amino)ethyl)carbamate (118 mg) in dioxane (2.5 mL) were added 6-methoxy-2-pyridineboronic acid MIDA ester (52.8 mg), potassium phosphate (318 mg), water (0.500 mL), palladium acetate (2.2 mg) and 2-dicyclohexylphosphino-2',6'-dimethoxybiphenyl (Sphos) (8.2 mg), and the mixture was stirred at 60° C. overnight. To this reaction mixture was added 1N aqueous sodium hydroxide solution, and the mixture was extracted with ethyl acetate. The organic layer was dried over sodium sulfate, filtered, and the filtrate was concentrated. The obtained residue was purified by preparative thin layer chromatography (eluate: ammonia saturated-chloroform) to give tert-butyl (2-((benzyl) (3-(2-methoxy-5-(6-methoxypyridin-2-yl)phenylsulfonamide)phenyl)amino)ethyl)carbamate (72.7 mg).
(2) To a solution of tert-butyl (2-((benzyl)(3-(2-methoxy-5-(6-methoxypyridin-2-yl)phenylsulfonamide)phenyl)amino)ethyl)carbamate (72.7 mg) in 10% hydrogen chloride-methanol (4.0 mL) was added 10% palladium/carbon (36.4 mg), and the mixture was stirred under a hydrogen atmosphere at room temperature for 4 hr. The reaction mixture was filtered through celite, and the filtrate was concentrated. The obtained residue was purified by amine silica gel column chromatography (eluate: chloroform/methanol=10/1) to give N-(3-((2-aminoethyl)amino)phenyl)-2-methoxy-5-(6-methoxypyridin-2-yl)benzenesulfonamide (54.9 mg).

Reference Example 33

N-(3-((2-aminoethyl)amino)phenyl)-2-methoxy-5-(pyridin-3-yl)benzene sulfonamide

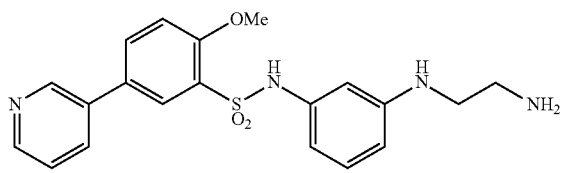 [SMILES: COc1ccc(-c2cccnc2)cc1S(=O)(=O)Nc1cccc(NCCN)c1]

(1) Under an argon atmosphere, to a solution of tert-butyl (2-((benzyl) (3-(5-bromo-2-methoxyphenylsulfonamide) phenyl)amino)ethyl)carbamate (118 mg) in dioxane (4.0 mL) were added 3-pyridylboronic acid (29.5 mg), sodium carbonate (42.4 mg), water (0.200 mL) and tetrakis(triphenylphosphine)palladium (11.6 mg), and the mixture was heated under reflux overnight. The reaction mixture was filtered through celite, and the filtrate was concentrated. The obtained residue was purified by silica gel column chromatography (eluate: ethyl acetate/hexane=3/2) to give tert-butyl (2-((benzyl)(3-(2-methoxy-5-(pyridin-3-yl)phenylsulfonamide)phenyl)amino)ethyl)carbamate (46.0 mg).
(2) To a solution of tert-butyl (2-((benzyl) (3-(2-methoxy-5-(pyridin-3-yl)phenylsulfonamide)phenyl)amino)ethyl)carbamate (46.0 mg) in 10% hydrogen chloride-methanol (2.0 mL) was added 10% palladium/carbon (23.0 mg), and the mixture was stirred under a hydrogen atmosphere at room temperature for 3 hr. The reaction mixture was filtered through celite, and the filtrate was concentrated. The obtained residue was purified by amine silica gel column chromatography (eluate: chloroform/methanol=10/1) to give N-(3-((2-aminoethyl)amino)phenyl)-2-methoxy-5-(pyridin-3-yl)benzenesulfonamide (128 mg).

Reference Example 34

N-(3-((2-aminoethyl)amino)phenyl)-2-methoxy-5-(5-methoxypyridin-3-yl)benzenesulfonamide

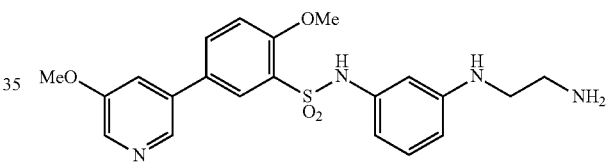

(1) Under an argon atmosphere, to a solution of tert-butyl (2-((benzyl) (3-(5-bromo-2-methoxyphenylsulfonamide) phenyl)amino)ethyl)carbamate (118 mg) in dioxane (4.0 mL) were added 5-methoxy-3-pyridineboronic acid pinacol ester (65.8 mg), sodium carbonate (42.4 mg), water (0.200 mL) and bis(diphenylphosphino)ferrocene palladium dichloride dichloromethane complex (8.2 mg), and the mixture was heated under reflux overnight. The reaction mixture was filtered through celite, and the filtrate was concentrated. The obtained residue was purified by silica gel column chromatography (eluate: ethyl acetate/hexane=3/2→2/1) to give tert-butyl (2-((benzyl)(3-(2-methoxy-5-(5-methoxypyridin-3-yl)phenylsulfonamide)phenyl)amino)ethyl)carbamate (108 mg).
(2) To a solution of tert-butyl (2-((benzyl) (3-(2-methoxy-5-(5-methoxypyridin-3-yl)phenylsulfonamide)phenyl)amino)ethyl)carbamate (108 mg) in 10% hydrogen chloride-methanol (2.0 mL) was added 10% palladium/carbon (53.9 mg), and the mixture was stirred under a hydrogen atmosphere at room temperature overnight. The reaction mixture was filtered through celite, and the filtrate was concentrated. The obtained residue was purified by amine silica gel column chromatography (eluate: ammonia-saturated chloroform/methanol=10/1) to give N-(3-((2-aminoethyl)amino)phenyl)-2-methoxy-5-(5-methoxypyridin-3-yl)benzenesulfonamide (52.1 mg).

Reference Example 35 tert-butyl (2-((benzyl)(3-(5-bromo-2-methoxy-4-methylphenylsulfonamide)phenyl)amino)ethyl)carbamate

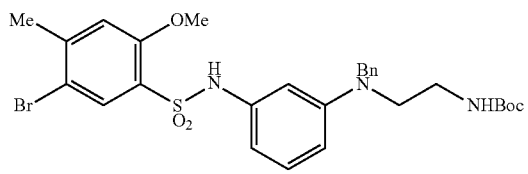 [SMILES: COc1cc(C)c(Br)cc1S(=O)(=O)Nc1cccc(N(CCNC(=O)OC(C)(C)C)Cc2ccccc2)c1]

Under an argon atmosphere, to a solution of tert-butyl (2-((3-aminophenyl)(benzyl)amino)ethyl)carbamate (688 mg) in dichloromethane (10.0 mL) were added pyridine (0.164 mL) and 5-bromo-2-methoxy-4-methylbenzenesulfonyl chloride (581 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/2→2/3) to give tert-butyl (2-((benzyl)(3-(5-bromo-2-methoxy-4-methylphenylsulfonamide)phenyl)amino)ethyl)carbamate (849 mg).

Reference Example 36 tert-butyl (2-((benzyl)(3-(5-bromo-2-methylphenylsulfonamide)phenyl)amino)ethyl)carbamate

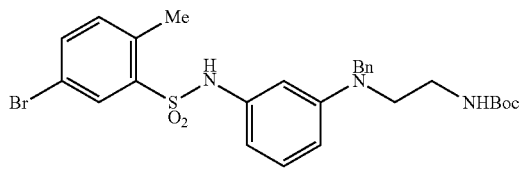 [SMILES: Cc1ccc(Br)cc1S(=O)(=O)Nc1cccc(N(CCNC(=O)OC(C)(C)C)Cc2ccccc2)c1]

Under an argon atmosphere, to a solution of tert-butyl (2-((3-aminophenyl)(benzyl)amino)ethyl)carbamate (275 mg) in dichloromethane (5.0 mL) were added pyridine (0.066 mL) and 5-bromo-2-methylbenzenesulfonyl chloride (200 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/3) to give tert-butyl (2-((benzyl) (3-(5-bromo-2-methylphenylsulfonamide)phenyl)amino)ethyl)carbamate (386 mg).

Reference Example 37 tert-butyl (2-((benzyl)(3-(5-bromo-2-fluorophenylsulfonamide)phenyl)amino)ethyl) carbamate

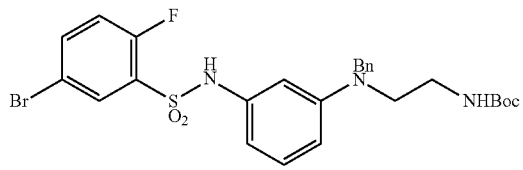 [SMILES: CC(C)(C)OC(=O)NCCN(Cc1ccccc1)c1cccc(NS(=O)(=O)c2cc(Br)ccc2F)c1]

Under an argon atmosphere, to a solution of tert-butyl (2-((3-aminophenyl)(benzyl)amino)ethyl)carbamate (271 mg) in dichloromethane (6.0 mL) were added pyridine (0.064 mL) and 5-bromo-2-fluorobenzenesulfonyl chloride (200 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/3) to give tert-butyl (2-((benzyl)(3-(5-bromo-2-fluorophenylsulfonamide)phenyl)amino)ethyl)carbamate (405 mg).

Reference Example 38 tert-butyl (2-((benzyl)(3-(5-bromo-2-ethoxyphenylsulfonamide)phenyl)amino)ethyl)carbamate

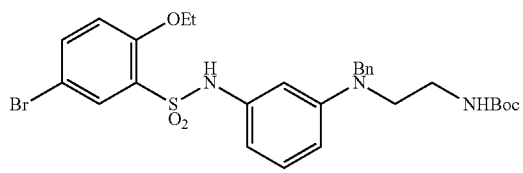 [SMILES: CCOc1ccc(Br)cc1S(=O)(=O)Nc1cccc(N(CCNC(=O)OC(C)(C)C)Cc2ccccc2)c1]

Under an argon atmosphere, to a solution of tert-butyl (2-((3-aminophenyl)(benzyl)amino)ethyl)carbamate (249 mg) in dichloromethane (6.0 mL) were added pyridine (0.060 mL) and 5-bromo-2-ethoxybenzenesulfonyl chloride (200 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/2) to give tert-butyl (2-((benzyl) (3-(5-bromo-2-ethoxyphenylsulfonamide)phenyl)amino)ethyl)carbamate (312 mg).

Reference Example 39

5'-(N-((2-aminoethyl)amino)phenyl)sulfamoyl)-4'-methoxy-N,N,2'-trimethyl-[1,1'-biphenyl]-3-carboxamide dihydrochloride

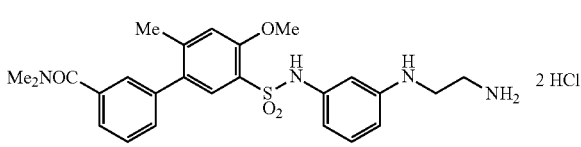

(1) Under an argon atmosphere, to a solution of tert-butyl (2-((benzyl) (3-(5-bromo-2-methoxy-4-methylphenylsulfonamide)phenyl)amino)ethyl)carbamate (424 mg) in dioxane (7.0 mL) were added 3-methoxycarbonylphenylboronic acid pinacol ester (220 mg), sodium carbonate (148 mg), water (0.700 mL) and bis(diphenylphosphino)ferrocene palladium dichloride dichloromethane complex (28.6 mg), and the mixture was heated under reflux overnight. The reaction mixture was filtered through celite, and the filtrate was concentrated. The obtained residue was purified by silica gel column chromatography (eluate: ethyl acetate/hexane=2/3) to give methyl 5'-(N-(3-((benzyl) (2-((tert-butoxycarbonyl)amino)ethyl)amino)phenyl)sulfamoyl)-4'-methoxy-2'-methyl-[1,1'-biphenyl]-3-carboxylate (461 mg).

(2) To a suspension of methyl 5'-(N-(3-((benzyl)(2-((tert-butoxycarbonyl)amino)ethyl)amino)phenyl)sulfamoyl)-4'-methoxy-2'-methyl-[1,1'-biphenyl]-3-carboxylate (461 mg) in methanol (7.0 mL) was added 10% palladium/carbon (138 mg), and the mixture was stirred under a hydrogen atmosphere at room temperature overnight. The reaction mixture was filtered through celite, and the filtrate was concentrated. The obtained residue was purified by amine silica gel column chromatography (eluate: chloroform/methanol=10/1) to give methyl 5'-(N-(3-((2-((tert-butoxycarbonyl)amino)ethyl)amino)phenyl)sulfamoyl)-4'-methoxy-2'-methyl-[1,1'-biphenyl]-3-carboxylate (394 mg).

(3) To a suspension of methyl 5'-(N-(3-((2-((tert-butoxycarbonyl)amino)ethyl)amino)phenyl)sulfamoyl)-4'-methoxy-2'-methyl-[1,1'-biphenyl]-3-carboxylate (394 mg) in methanol (7.0 mL) was added 1N aqueous sodium hydroxide solution (2.07 mL), and the mixture was stirred at 60° C. for 3 hr. To this reaction mixture was added 1N hydrochloric acid, and the mixture was extracted with chloroform. The organic layer was dried over sodium sulfate, filtered, the filtrate was concentrated to give 5'-(N-(3-((2-((tert-butoxycarbonyl)amino)ethyl)amino)phenyl)sulfamoyl)-4'-methoxy-2'-methyl-[1,1'-biphenyl]-3-carboxylic acid (383 mg).

(4) Under an argon atmosphere, to a suspension of 5'-(N-(3-((2-((tert-butoxycarbonyl)amino)ethyl)amino)phenyl)sulfamoyl)-4'-methoxy-2'-methyl-[1,1'-biphenyl]-3-carboxylic acid (383 mg) in dichloromethane (10 mL) were added dimethylamine hydrochloride (113 mg), triethylamine (0.337 mL) and BOP reagent (336 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=3/1→1/0) to give tert-butyl (2-((3-(3'-(dimethylcarbamoyl)-4-methoxy-6-methyl-[1,1'-biphenyl]-3-ylsulfonamide)phenyl)amino)ethyl)carbamate (299 mg).

(5) To tert-butyl (2-((3-(3'-(dimethylcarbamoyl)-4-methoxy-6-methyl-[1,1'-biphenyl]-3-ylsulfonamide)phenyl)amino)ethyl) carbamate (299 mg) was added 10% hydrogen chloride-methanol solution (4.0 mL), and the mixture was stirred at 50° C. for 2 hr. The reaction mixture was concentrated to give 5'-(N-(3-((2-aminoethyl)amino)phenyl)sulfamoyl)-4'-methoxy-N,N,2'-trimethyl-[1,1'-biphenyl]-3-carboxamide dihydrochloride (290 mg).

Reference Example 40

3'-(N-(3-((2-aminoethyl)amino)phenyl)sulfamoyl)-N,N,4'-trimethyl-[1,1'-biphenyl]-3-carboxamide dihydrochloride

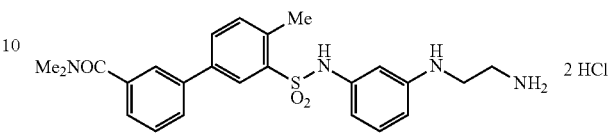

(1) Under an argon atmosphere, to a solution of tert-butyl (2-((benzyl) (3-(5-bromo-2-methoxy-4-methylphenylsulfonamide)phenyl)amino)ethyl)carbamate (386 mg) in dioxane (7.0 mL) were added 3-methoxycarbonylphenylboronic acid pinacol ester (210 mg), sodium carbonate (142 mg), water (0.670 mL) and bis(diphenylphosphino)ferrocene palladium dichloride dichloromethane complex (27.8 mg), and the mixture was heated under reflux overnight. The reaction mixture was filtered through celite, and the filtrate was concentrated. The obtained residue was purified by silica gel column chromatography (eluate: ethyl acetate/hexane=2/5) to give methyl 3'-(N-(3-((benzyl) (2-((tert-butoxycarbonyl)amino)ethyl)amino)phenyl)sulfamoyl)-4'-methyl-[1,1'-biphenyl]-3-carboxylate (419 mg).

(2) To a suspension of methyl 3'-(N-(3-((benzyl) (2-((tert-butoxycarbonyl)amino)ethyl)amino)phenyl)sulfamoyl)-4'-methyl-[1,1'-biphenyl]-3-carboxylate (419 mg) in methanol (7.0 mL) was added 10% palladium/carbon (126 mg), and the mixture was stirred under a hydrogen atmosphere at room temperature overnight. The reaction mixture was filtered through celite, and the filtrate was concentrated. The obtained residue was purified by amine silica gel column chromatography (eluate: chloroform/methanol=10/1) to give methyl 3'-(N-(3-((2-((tert-butoxycarbonyl)amino)ethyl)amino)phenyl)sulfamoyl)-4'-methyl-[1,1'-biphenyl]-3-carboxylate (353 mg).

(3) To a suspension of methyl 3'-(N-(3-((2-((tert-butoxycarbonyl)amino)ethyl)amino)phenyl)sulfamoyl)-4'-methyl-[1,1'-biphenyl]-3-carboxylate (353 mg) in methanol (7.0 mL) was added 1N aqueous sodium hydroxide solution (1.96 mL), and the mixture was stirred at 60° C. for 3 hr. To this reaction mixture was added 1N hydrochloric acid, and the mixture was extracted with chloroform. The organic layer was dried over sodium sulfate, filtered, and the filtrate was concentrated to give 3'-(N-(3-((2-((tert-butoxycarbonyl)amino)ethyl)amino)phenyl)sulfamoyl)-4'-methyl-[1,1'-biphenyl]-3-carboxylic acid (341 mg).

(4) Under an argon atmosphere, to a suspension of 3'-(N-(3-((2-((tert-butoxycarbonyl)amino)ethyl)amino)phenyl)sulfamoyl)-4'-methyl-[1,1'-biphenyl]-3-carboxylic acid (341 mg) in dichloromethane (10 mL) were added dimethylamine hydrochloride (106 mg), triethylamine (0.318 mL) and BOP reagent (318 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=3/1→1/0) to give tert-butyl (2-((3-(3'-(dimethylcarbamoyl)-4-methyl-[1,1'-biphenyl]-3-ylsulfonamide)phenyl)amino)ethyl)carbamate (255 mg).

(5) To tert-butyl (2-((3-(3'-(dimethylcarbamoyl)-4-methyl-[1,1'-biphenyl]-3-ylsulfonamide)phenyl)amino)ethyl)carbamate (255 mg) was added 10% hydrogen chloride-methanol solution (4.0 mL), and the mixture was stirred at 50° C. for 2 hr. The reaction mixture was concentrated to give 3'-(N-(3-((2-aminoethyl)amino)phenyl)sulfamoyl)-N,N,4'-trimethyl-[1,1'-biphenyl]-3-carboxamide dihydrochloride (243 mg).

Reference Example 41

3'-(N-(3-((2-aminoethyl)amino)phenyl)sulfamoyl)-4'-fluoro-N,N-dimethyl-[1,1'-biphenyl]-3-carboxamide dihydrochloride

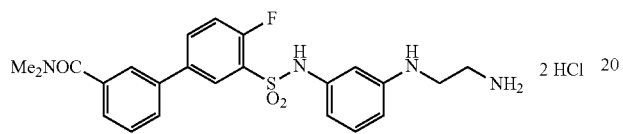

(1) Under an argon atmosphere, to a solution of tert-butyl (2-((benzyl) (3-(5-bromo-2-fluorophenylsulfonamide)phenyl)amino)ethyl)carbamate (405 mg) in dioxane (7.0 mL) were added 3-methoxycarbonylphenylboronic acid pinacol ester (220 mg), sodium carbonate (148 mg), water (0.700 mL) and bis(diphenylphosphino)ferrocene palladium dichloride dichloromethane complex (28.6 mg), and the mixture was heated under reflux overnight. The reaction mixture was filtered through celite, and the filtrate was concentrated. The obtained residue was purified by silica gel column chromatography (eluate: ethyl acetate/hexane=1/2) to give methyl 3'-(N-(3-((benzyl) (2-((tert-butoxycarbonyl)amino)ethyl)amino)phenyl)sulfamoyl)-4'-fluoro-[1,1'-biphenyl]-3-carboxylate (458 mg).
(2) To a suspension of methyl 3'-(N-(3-((benzyl) (2-((tert-butoxycarbonyl)amino)ethyl)amino)phenyl)sulfamoyl)-4'-fluoro-[1,1'-biphenyl]-3-carboxylate (458 mg) in methanol (7.0 mL) was added 10% palladium/carbon (137 mg), and the mixture was stirred under a hydrogen atmosphere at room temperature overnight. The reaction mixture was filtered through celite, and the filtrate was concentrated. The obtained residue was purified by amine silica gel column chromatography (eluate: chloroform/methanol=10/1) to give methyl 3'-(N-(3-((2-((tert-butoxycarbonyl)amino)ethyl)amino)phenyl)sulfamoyl)-4'-fluoro-[1,1'-biphenyl]-3-carboxylate (387 mg).
(3) To a suspension of methyl 3'-(N-(3-((2-((tert-butoxycarbonyl)amino)ethyl)amino)phenyl)sulfamoyl)-4'-fluoro-[1,1'-biphenyl]-3-carboxylate (387 mg) in methanol (7.0 mL) was added 1N aqueous sodium hydroxide solution (2.13 mL), and the mixture was stirred at 60° C. for 3 hr. To this reaction mixture was added 1N hydrochloric acid, and the mixture was extracted with chloroform. The organic layer was dried over sodium sulfate, filtered, and the filtrate was concentrated to give 3'-(N-(3-((2-((tert-butoxycarbonyl)amino)ethyl)amino)phenyl)sulfamoyl)-4'-fluoro-[1,1'-biphenyl]-3-carboxylic acid (346 mg).
(4) Under an argon atmosphere, to a suspension of 3'-(N-(3-((2-((tert-butoxycarbonyl)amino)ethyl)amino)phenyl)sulfamoyl)-4'-fluoro-[1,1'-biphenyl]-3-carboxylic acid (346 mg) in dichloromethane (10 mL) were added dimethylamine hydrochloride (116 mg), triethylamine (0.347 mL) and BOP reagent (345 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate) to give tert-butyl (2-((3-(3'-(dimethylcarbamoyl)-4-fluoro-[1,1'-biphenyl]-3-ylsulfonamide)phenyl)amino)ethyl)carbamate (291 mg).
(5) To tert-butyl (2-((3-(3'-(dimethylcarbamoyl)-4-fluoro-[1,1'-biphenyl]-3-ylsulfonamide)phenyl)amino)ethyl)carbamate (291 mg) was added 10% hydrogen chloride-methanol solution (4.0 mL), and the mixture was stirred at 50° C. for 2 hr. The reaction mixture was concentrated to give 3'-(N-(3-((2-aminoethyl)amino)phenyl)sulfamoyl)-4'-fluoro-N,N-dimethyl-[1,1'-biphenyl]-3-carboxamide dihydrochloride (283 mg).

Reference Example 42

3'-(N-(3-((2-aminoethyl)amino)phenyl)sulfamoyl)-4'-ethoxy-N,N-dimethyl-[1,1'-biphenyl]-3-carboxamide dihydrochloride

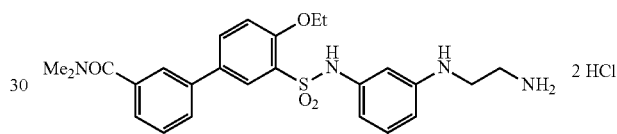

(1) Under an argon atmosphere, to a solution of tert-butyl (2-((benzyl)(3-(5-bromo-2-ethoxyphenylsulfonamide)phenyl)amino)ethyl)carbamate (312 mg) in dioxane (5.0 mL) were added 3-methoxycarbonylphenylboronic acid pinacol ester (163 mg), sodium carbonate (109 mg), water (0.520 mL) and bis(diphenylphosphino)ferrocene palladium dichloride dichloromethane complex (21.2 mg), and the mixture was heated under reflux overnight. The reaction mixture was filtered through celite, and the filtrate was concentrated. The obtained residue was purified by silica gel column chromatography (eluate: ethyl acetate/hexane=1/2→1/1) to give methyl 3'-(N-(3-((benzyl) (2-((tert-butoxycarbonyl)amino)ethyl)amino)phenyl)sulfamoyl)-4'-ethoxy-[1,1'-biphenyl]-3-carboxylate (270 mg).
(2) To a suspension of methyl 3'-(N-(3-((benzyl) (2-((tert-butoxycarbonyl)amino)ethyl)amino)phenyl)sulfamoyl)-4'-ethoxy-[1,1'-biphenyl]-3-carboxylate (270 mg) in methanol (7.0 mL) was added 10% palladium/carbon (81.0 mg), and the mixture was stirred under a hydrogen atmosphere at room temperature overnight. The reaction mixture was filtered through celite, and the filtrate was concentrated. The obtained residue was purified by amine silica gel column chromatography (eluate: chloroform/methanol=10/1) to give methyl 3'-(N-(3-((2-((tert-butoxycarbonyl)amino)ethyl)amino)phenyl)sulfamoyl)-4'-ethoxy-[1,1'-biphenyl]-3-carboxylate (222 mg).
(3) To a suspension of methyl 3'-(N-(3-((2-((tert-butoxycarbonyl)amino)ethyl)amino)phenyl)sulfamoyl)-4'-ethoxy-[1,1'-biphenyl]-3-carboxylate (222 mg) in methanol (7.0 mL) was added 1N aqueous sodium hydroxide solution (1.17 mL), and the mixture was stirred at 60° C. for 2 hr. To this reaction mixture was added 1N hydrochloric acid, and the mixture was extracted with chloroform. The organic layer was dried over sodium sulfate, filtered, and the filtrate was concentrated to give 3'-(N-(3-((2-((tert-butoxycarbonyl)amino)ethyl)amino)phenyl)sulfamoyl)-4'-ethoxy-[1,1'-biphenyl]-3-carboxylic acid (215 mg).

(4) Under an argon atmosphere, to a suspension of 3'-(N-(3-((2-((tert-butoxycarbonyl)amino)ethyl)amino)phenyl)sulfamoyl)-4'-ethoxy-[1,1'-biphenyl]-3-carboxylic acid (215 mg) in dichloromethane (8.0 mL) were added dimethylamine hydrochloride (63.6 mg), triethylamine (0.190 mL) and BOP reagent (190 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate) to give tert-butyl (2-((3-(3'-(dimethylcarbamoyl)-4-ethoxy-[1,1'-biphenyl]-3-ylsulfonamide)phenyl)amino)ethyl)carbamate (191 mg).

(5) To tert-butyl (2-((3-(3'-(dimethylcarbamoyl)-4-ethoxy-[1,1'-biphenyl]-3-ylsulfonamide)phenyl)amino)ethyl)carbamate (191 mg) was added 10% hydrogen chloride-methanol solution (4.0 mL), and the mixture was stirred at 50° C. for 2 hr. The reaction mixture was concentrated to give 3'-(N-(3-((2-aminoethyl)amino)phenyl)sulfamoyl)-4'-ethoxy-N,N-dimethyl-[1,1'-biphenyl]-3-carboxamide dihydrochloride (176 mg).

Reference Example 43

N-(3-((2-aminoethyl)amino)phenyl)-3'-fluoro-4-methoxy-[1,1'-biphenyl]-3-sulfonamide dihydrochloride

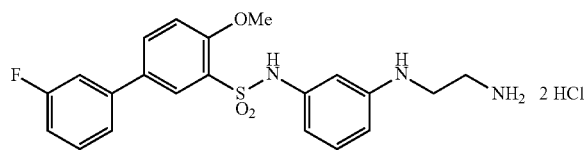 [SMILES: COc1ccc(-c2cccc(F)c2)cc1S(=O)(=O)Nc1cccc(NCCN)c1]

(1) Under an argon atmosphere, to a solution of tert-butyl (2-((3-(5-bromo-2-methoxyphenylsulfonamide)phenyl)(4-methoxybenzyl)amino)ethyl)carbamate (118 mg) in n-propanol (4.0 mL) were added potassium 3-fluorophenyltrifluoroborate (48.5 mg), triethylamine (0.084 mL) and bis(diphenylphosphino)ferrocene palladium dichloride dichloromethane complex (4.9 mg), and the mixture was heated under reflux overnight. The reaction mixture was filtered through celite, and the filtrate was concentrated. The obtained residue was purified by preparative thin layer chromatography (eluate: ammonia-saturated chloroform) to give tert-butyl (2-((3-(3'-fluoro-4-methoxy-[1,1'-biphenyl]-3-ylsulfonamide)phenyl)(4-methoxybenzyl)amino)ethyl)carbamate (67.5 mg).

(2) To a solution of tert-butyl (2-((3-(3'-fluoro-4-methoxy-[1,1'-biphenyl]-3-ylsulfonamide)phenyl) (4-methoxybenzyl)amino)ethyl)carbamate (67.5 mg) in methanol (2.0 mL) was added 10% palladium/carbon (20.3 mg), and the mixture was stirred under a hydrogen atmosphere at room temperature overnight. The reaction mixture was filtered through celite, and the filtrate was concentrated. The obtained residue was purified by amine silica gel column chromatography (eluate: chloroform/methanol=10/1) to give tert-butyl (2-((3-(3'-fluoro-4-methoxy-[1,1'-biphenyl]-3-ylsulfonamide)phenyl)amino)ethyl)carbamate (28.5 mg).

(3) To tert-butyl (2-((3-(3'-fluoro-4-methoxy-[1,1'-biphenyl]-3-ylsulfonamide)phenyl)amino)ethyl)carbamate (28.5 mg) was added 10% hydrogen chloride-methanol solution (2.0 mL), and the mixture was stirred at 50° C. for 2 hr. The reaction mixture was concentrated to give N-(3-((2-aminoethyl)amino)phenyl)-3'-fluoro-4-methoxy-[1,1'-biphenyl]-3-sulfonamide dihydrochloride (26.7 mg).

Reference Example 44 tert-butyl (2-((benzyl)(3-(5-bromo-2-methoxyphenylsulfonamide)phenyl)amino)ethyl)(methyl)carbamate

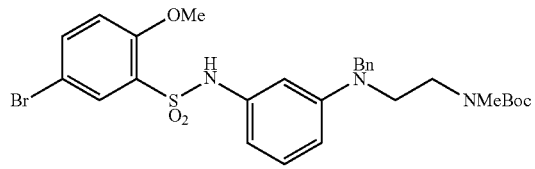

(1) Under an argon atmosphere, to a solution of tert-butyl (2-((3-nitrophenyl)amino)ethyl)carbamate (4.46 g) in dichloromethane (30 mL) were added 50 wt % aqueous sodium hydroxide solution (10 mL), benzyl bromide (2.84 mL) and tetrabutylammonium iodide (587 mg), 20-30° C. for 48 hr. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/6→1/4) to give tert-butyl (2-((benzyl)(3-nitrophenyl)amino)ethyl)carbamate (4.62 g).

(2) Under an argon atmosphere, to a solution of tert-butyl (2-((benzyl) (3-nitrophenyl)amino)ethyl)carbamate (297 mg) in DMF (3.0 mL) were added potassium tert-butoxide (117 mg) and methyl iodide (0.065 mL), and the mixture was stirred at room temperature for 2 hr. To this reaction mixture was added saturated brine, the mixture was extracted with ethyl acetate, and the organic layer was washed with water. The organic layer was dried over sodium sulfate, filtered, and the filtrate was concentrated. The obtained residue was purified by preparative thin layer chromatography (eluate: ethyl acetate/hexane=1/5) to give tert-butyl (2-((benzyl) (3-nitrophenyl)amino)ethyl) (methyl) carbamate (218 mg).

(3) Under an argon atmosphere, to a mixed suspension of (2-((benzyl) (3-nitrophenyl)amino)ethyl)(methyl)carbamate (218 mg) in ethanol (2.5 mL) and water (1.0 mL) were added ammonium chloride (305 mg) and iron powder (221 mg), and the mixture was heated under reflux for 2 hr. The reaction mixture was filtered through celite, the filtrate was concentrated, and the obtained residue was purified by amine silica gel column chromatography (eluate: chloroform/methanol=10/1) to give tert-butyl (2-((3-aminophenyl)(benzyl)amino)ethyl)(methyl)carbamate (200 mg).

(4) Under an argon atmosphere, to a solution of tert-butyl (2-((3-aminophenyl) (benzyl)amino)ethyl)(methyl)carbamate (200 mg) in dichloromethane (6.0 mL) were added pyridine (0.050 mL) and 5-bromo-2-methoxybenzenesulfonyl chloride (160 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/2) to give tert-butyl (2-((benzyl) (3-(5-bromo-2-methoxyphenylsulfonamide)phenyl)amino)ethyl)(methyl)carbamate (260 mg).

Reference Example 45

4'-methoxy-N,N-dimethyl-3'-(N-(3-((2-methyl-amino)ethyl)amino)phenyl)sulfamoyl)-[1,1'-biphenyl]-3-carboxamide dihydrochloride

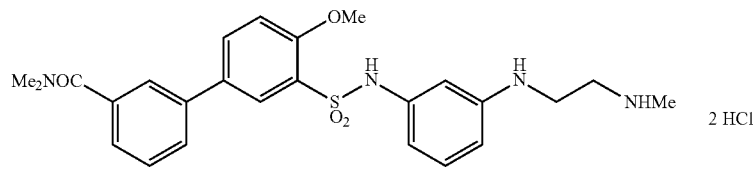

(1) Under an argon atmosphere, to a solution of tert-butyl (2-((benzyl) (3-(5-bromo-2-ethoxyphenylsulfonamide)phenyl)amino)ethyl) (methyl) carbamate (260 mg) in dioxane (4.0 mL) were added 3-methoxycarbonylphenylboronic acid pinacol ester (136 mg), sodium carbonate (91.2 mg), water (0.430 mL) and bis(diphenylphosphino)ferrocene palladium dichloride dichloromethane complex (17.6 mg), and the mixture was heated under reflux overnight. The reaction mixture was filtered through celite, and the filtrate was concentrated. The obtained residue was purified by silica gel column chromatography (eluate: ethyl acetate/hexane=1/2→3/5) to give methyl 3'-(N-(3-((benzyl)(2-((tert-butoxycarbonyl) (methyl)amino)ethyl)amino)phenyl)sulfamoyl)-4'-methoxy-[1,1'-biphenyl]-3-carboxylate (246 mg).

(2) To a suspension of methyl 3'-(N-(3-((benzyl) (2-((tert-butoxycarbonyl) (methyl)amino)ethyl)amino)phenyl)sulfamoyl)-4'-ethoxy-[1,1'-biphenyl]-3-carboxylate (246 mg) in methanol (5.0 mL) was added 10% palladium/carbon (73.8 mg), and the mixture was stirred under a hydrogen atmosphere at room temperature overnight. The reaction mixture was filtered through celite, and the filtrate was concentrated. The obtained residue was purified by amine silica gel column chromatography (eluate: chloroform/methanol=10/1) to give methyl 3'-(N-(3-((2-((tert-butoxycarbonyl) (methyl)amino)ethyl)amino)phenyl)sulfamoyl)-4'-methoxy-[1,1'-biphenyl]-3-carboxylate (217 mg).

(3) To a suspension of methyl 3'-(N-(3-((2-((tert-butoxycarbonyl) (methyl)amino)ethyl)amino)phenyl)sulfamoyl)-4'-methoxy-[1,1'-biphenyl]-3-carboxylate (217 mg) in methanol (7.0 mL) was added 1N aqueous sodium hydroxide solution (1.14 mL), and the mixture was stirred at 60° C. for 2 hr. To this reaction mixture was added 1N hydrochloric acid, and the mixture was extracted with chloroform. The organic layer was dried over sodium sulfate, filtered, and the filtrate was concentrated to give 3'-(N-(3-((2-((tert-butoxycarbonyl) (methyl)amino)ethyl)amino)phenyl)sulfamoyl)-4'-methoxy-[1,1'-biphenyl]-3-carboxylic acid (208 mg).

(4) Under an argon atmosphere, to a suspension of 3'-(N-(3-((2-((tert-butoxycarbonyl) (methyl)amino)ethyl)amino)phenyl)sulfamoyl)-4'-methoxy-[1,1'-biphenyl]-3-carboxylic acid (208 mg) in dichloromethane (5.0 mL) were added dimethylamine hydrochloride (61.1 mg), triethylamine (0.183 mL) and BOP reagent (181 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate) to give tert-butyl (2-((3-(3'-(dimethylcarbamoyl)-4-methoxy-[1,1'-biphenyl]-3-ylsulfonamide)phenyl)amino)ethyl)(methyl)carbamate (160 mg).

(5) To tert-butyl (2-((3-(3'-(dimethylcarbamoyl)-4-methoxy-[1,1'-biphenyl]-3-ylsulfonamide)phenyl)amino)ethyl) (methyl)carbamate (160 mg) was added 10% hydrogen chloride-methanol solution (4.0 mL), and the mixture was stirred at 50° C. for 2 hr. The reaction mixture was concentrated to give 4'-methoxy-N,N-dimethyl-3'-(N-(3-((2-methylamino)ethyl)amino)phenyl)sulfamoyl)-[1,1'-biphenyl]-3-carboxamide dihydrochloride (150 mg).

Reference Example 46 tert-butyl (2-((benzyl)(3-(3-bromophenylsulfonamide)phenyl)amino)ethyl) carbamate

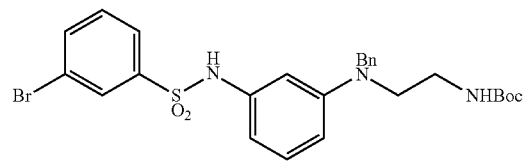 [SMILES: CC(C)(C)OC(=O)NCCN(Cc1ccccc1)c1cccc(NS(=O)(=O)c2cccc(Br)c2)c1]

Under an argon atmosphere, to a solution of tert-butyl (2-((3-aminophenyl)(benzyl)amino)ethyl)carbamate (300 mg) in dichloromethane (8.0 mL) were added pyridine (0.078 mL) and 3-bromobenzenesulfonyl chloride (0.116 mL), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=1/3) to give tert-butyl (2-((benzyl)(3-(3-bromophenylsulfonamide)phenyl)amino)ethyl)carbamate (423 mg).

Reference Example 47

3'-(N-(3-((2-aminoethyl)amino)phenyl)sulfamoyl)-N,N-dimethyl-[1,1'-biphenyl]-3-carboxamide dihydrochloride

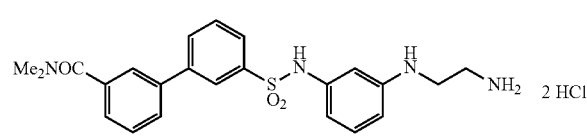

(1) To a solution of tert-butyl (2-((benzyl)(3-(3-bromophenylsulfonamide)phenyl)amino)ethyl)carbamate (423 mg) in dioxane (7.0 mL) were added 3-methoxycarbonylphenylboronic acid pinacol ester (239 mg), sodium carbonate (160 mg), water (0.754 mL) and bis(diphenylphosphino)ferrocene palladium dichloride dichloromethane complex (30.8 mg), and the mixture was heated under reflux overnight. The reaction mixture was filtered through celite, and the filtrate was concentrated. The obtained residue was purified by silica gel column chromatography (eluate: ethyl acetate/hexane=1/3→1/2) to give methyl 3'-(N-(3-((benzyl) (2-((tert-butoxycarbonyl)amino)ethyl)amino)phenyl)sulfamoyl)-[1,1'-biphenyl]-3-carboxylate (297 mg).

(2) To a suspension of methyl 3'-(N-(3-((benzyl) (2-((tert-butoxycarbonyl)amino)ethyl)amino)phenyl)sulfamoyl)-[1,1'-biphenyl]-3-carboxylate (297 mg) in methanol (7.0 mL) was added 10% palladium/carbon (100 mg), and the mixture was stirred under a hydrogen atmosphere at room temperature overnight. The reaction mixture was filtered through celite, and the filtrate was concentrated. The obtained residue was purified by amine silica gel column chromatography (eluate: chloroform/methanol=10/1) to give methyl 3'-(N-(3-((2-((tert-butoxycarbonyl)amino)ethyl)amino)phenyl)sulfamoyl)-[1,1'-biphenyl]-3-carboxylate (238 mg).

(3) To a suspension of methyl 3'-(N-(3-((2-((tert-butoxycarbonyl)amino)ethyl)amino)phenyl)sulfamoyl)-[1,1'-biphenyl]-3-carboxylate (238 mg) in methanol (5.0 mL) was added 1N aqueous sodium hydroxide solution (1.36 mL), and the mixture was stirred at 60° C. for 2 hr. To this reaction mixture was added 1N hydrochloric acid, and the mixture was extracted with chloroform. The organic layer was dried over sodium sulfate, filtered, and the filtrate was concentrated to give 3'-(N-(3-((2-((tert-butoxycarbonyl)amino)ethyl)amino)phenyl)sulfamoyl)-[1,1'-biphenyl]-3-carboxylic acid (222 mg).

(4) Under an argon atmosphere, to a suspension of 3'-(N-(3-((2-((tert-butoxycarbonyl)amino)ethyl)amino)phenyl)sulfamoyl)-[1,1'-biphenyl]-3-carboxylic acid (222 mg) in dichloromethane (6.0 mL) were added dimethylamine hydrochloride (70.1 mg), triethylamine (0.210 mL) and BOP reagent (208 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=4/1) to give tert-butyl (2-((3-(3'-(dimethylcarbamoyl)-[1,1'-biphenyl]-3-ylsulfonamide)phenyl)amino)ethyl)carbamate (185 mg).

(5) To tert-butyl (2-((3-(3'-(dimethylcarbamoyl)-[1,1'-biphenyl]-3-ylsulfonamide)phenyl)amino)ethyl)carbamate (185 mg) was added 10% hydrogen chloride-methanol solution (4.0 mL), and the mixture was stirred at 50° C. for 2 hr. The reaction mixture was concentrated to give 3'-(N-(3-((2-aminoethyl)amino)phenyl)sulfamoyl)-N,N-dimethyl-[1,1'-biphenyl]-3-carboxamide dihydrochloride (142 mg).

Example 1

N-(2-((3-(2'-fluoro-4-methoxy-[1,1'-biphenyl]-3-ylsulfonamide)phenyl)amino)ethyl)-2-methoxybenzamide

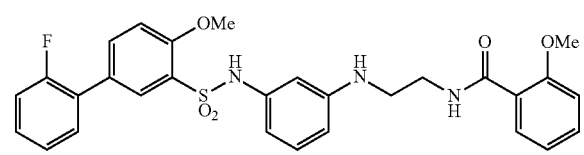

Under an argon atmosphere, to a suspension of N-(3-((2-aminoethyl)amino)phenyl)-2'-fluoro-4-methoxy-[1,1'-biphenyl]-3-sulfonamide dihydrochloride (19.5 mg) in dichloromethane (1.0 mL) were added o-anisic acid (6.1 mg), triethylamine (0.018 mL) and BOP reagent (19.5 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=3/2→3/1) to give N-(2-((3-(2'-fluoro-4-methoxy-[1,1'-biphenyl]-3-ylsulfonamide)phenyl)amino)ethyl)-2-methoxybenzamide (22.0 mg).

Example 2

N-(2-((3-(2'-fluoro-4-methoxy-[1,1'-biphenyl]-3-ylsulfonamide)phenyl)amino)ethyl)-3-methoxybenzamide

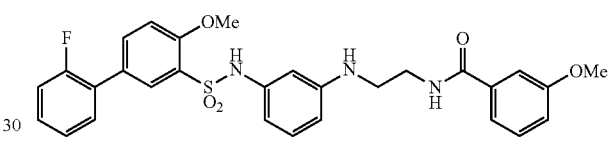

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with m-anisic acid (6.1 mg) to give N-(2-((3-(2'-fluoro-4-methoxy-[1,1'-biphenyl]-3-ylsulfonamide)phenyl)amino)ethyl)-3-methoxybenzamide (21.9 mg).

Example 3

N-(2-((3-(2'-fluoro-4-methoxy-[1,1'-biphenyl]-3-ylsulfonamide)phenyl)amino)ethyl)-4-methoxybenzamide

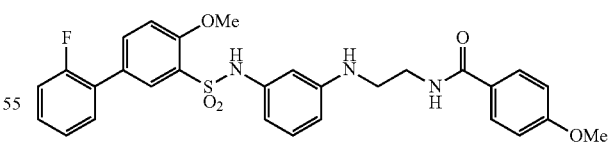

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with p-anisic acid (6.1 mg) to give N-(2-((3-(2'-fluoro-4-methoxy-[1,1'-biphenyl]-3-ylsulfonamide)phenyl)amino)ethyl)-4-methoxybenzamide (16.8 mg).

Example 4

5-bromo-N-(2-((3-(2'-fluoro-4-methoxy-[1,1'-biphenyl]-3-ylsulfonamide)phenyl)amino)ethyl)-2-methoxybenzamide

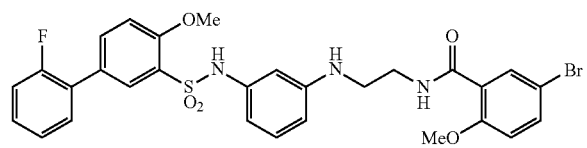 [SMILES: COc1ccc(Br)cc1C(=O)NCCNc1cccc(NS(=O)(=O)c2cc(-c3ccccc3F)ccc2OC)c1]

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with 5-bromo-2-methoxybenzoic acid (9.2 mg) to give 5-bromo-N-(2-((3-(2'-fluoro-4-methoxy-[1,1'-biphenyl]-3-ylsulfonamide)phenyl)amino)ethyl)-2-methoxybenzamide (24.8 mg). For purification, silica gel column chromatography (eluate: chloroform/ethyl acetate=1/0→3/1) was used.

Example 5

5-(dimethylamino)-N-(2-((3-(2'-fluoro-4-methoxy-[1,1'-biphenyl]-3-ylsulfonamide)phenyl)amino)ethyl)-2-methoxybenzamide

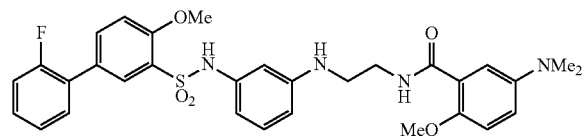 [SMILES: COc1ccc(N(C)C)cc1C(=O)NCCNc1cccc(NS(=O)(=O)c2cc(-c3ccccc3F)ccc2OC)c1]

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with 5-dimethylamino-2-methoxybenzoic acid (7.8 mg) to give 5-(dimethylamino)-N-(2-((3-(2'-fluoro-4-methoxy-[1,1'-biphenyl]-3-ylsulfonamide)phenyl)amino)ethyl)-2-methoxybenzamide (21.3 mg). For purification, silica gel column chromatography (eluate: ethyl acetate) was used.

Example 6

N-(2-((3-(2'-fluoro-4-methoxy-[1,1'-biphenyl]-3-ylsulfonamide)phenyl)amino)ethyl)-2-hydroxybenzamide

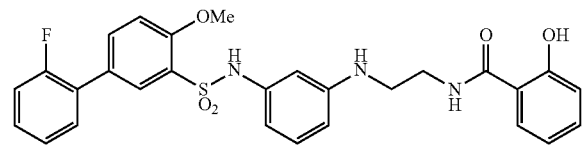

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with salicylic acid (5.5 mg) to give N-(2-((3-(2'-fluoro-4-methoxy-[1,1'-biphenyl]-3-ylsulfonamide)phenyl)amino)ethyl)-2-hydroxybenzamide (18.8 mg). For purification, silica gel column chromatography (eluate: ethyl acetate/hexane=1/1) was used.

Example 7

2-chloro-N-(2-((3-(2'-fluoro-4-methoxy-[1,1'-biphenyl]-3-ylsulfonamide)phenyl)amino)ethyl)benzamide

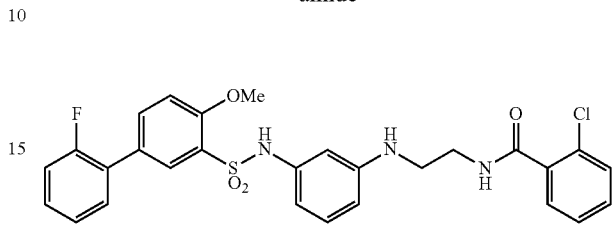

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with 2-chlorobenzoic acid (6.3 mg) to give 2-chloro-N-(2-((3-(2'-fluoro-4-methoxy-[1,1'-biphenyl]-3-ylsulfonamide)phenyl)amino)ethyl)benzamide (20.3 mg). For purification, silica gel column chromatography (eluate: ethyl acetate/hexane=2/1) was used.

Example 8

3-chloro-N-(2-((3-(2'-fluoro-4-methoxy-[1,1'-biphenyl]-3-ylsulfonamide)phenyl)amino)ethyl)benzamide

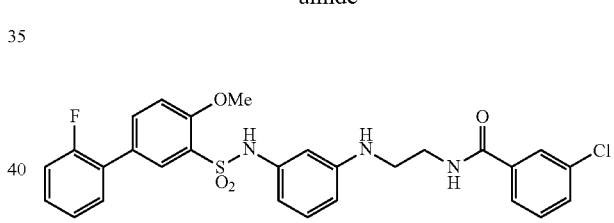

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with 3-chlorobenzoic acid (6.3 mg) to give 3-chloro-N-(2-((3-(2'-fluoro-4-methoxy-[1,1'-biphenyl]-3-ylsulfonamide)phenyl)amino)ethyl)benzamide (15.0 mg). For purification, silica gel column chromatography (eluate: ethyl acetate) was used.

Example 9

4-chloro-N-(2-((3-(2'-fluoro-4-methoxy-[1,1'-biphenyl]-3-ylsulfonamide)phenyl)amino)ethyl)benzamide

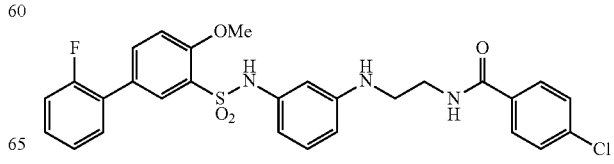

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with 4-chlorobenzoic acid (6.3 mg) to give 4-chloro-N-(2-((3-(2'-fluoro-4-methoxy-[1,1'-biphenyl]-3-ylsulfonamide)phenyl)amino)ethyl)benzamide (21.3 mg). For purification, silica gel column chromatography (eluate: ethyl acetate) was used.

Example 10

N-(2-((3-(2'-chloro-4-methoxy-[1,1'-biphenyl]-3-ylsulfonamide)phenyl)amino)ethyl)-2-methoxybenzamide

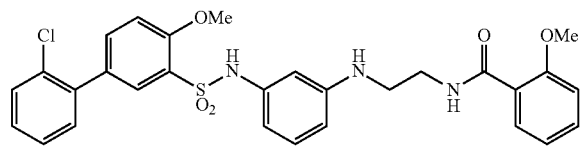 [SMILES: COc1ccc(-c2ccccc2F)cc1S(=O)(=O)Nc1cccc(NCCNC(=O)c2ccccc2O)c1]

In the same manner as in Example 1, N-(3-((2-aminoethyl)amino)phenyl)-2'-chloro-4-methoxy-[1,1'-biphenyl]-3-sulfonamide dihydrochloride (23.0 mg) was amidated with o-anisic acid (7.0 mg) to give N-(2-((3-(2'-chloro-4-methoxy-[1,1'-biphenyl]-3-ylsulfonamide)phenyl)amino)ethyl)-2-methoxybenzamide (20.2 mg). For purification, preparative thin layer chromatography (eluate: ammonia-saturated chloroform/methanol=40/1) was used.

Example 11

N-(2-((3-(2'-chloro-4-methoxy-[1,1'-biphenyl]-3-ylsulfonamide)phenyl)amino)ethyl)-3-methoxybenzamide

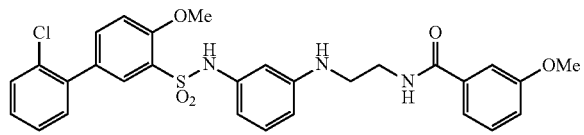

In the same manner as in Example 1, N-(3-((2-aminoethyl)amino)phenyl)-2'-chloro-4-methoxy-[1,1'-biphenyl]-3-sulfonamide dihydrochloride (26.9 mg) was amidated with m-anisic acid (8.1 mg) to give N-(2-((3-(2'-chloro-4-methoxy-[1,1'-biphenyl]-3-ylsulfonamide)phenyl)amino)ethyl)-3-methoxybenzamide (21.5 mg). For purification, silica gel column chromatography (eluate: ethyl acetate) was used.

Example 12

N-(2-((3-(2',4-dimethoxy-[1,1'-biphenyl]-3-ylsulfonamide)phenyl)amino)ethyl)-2-methoxybenzamide

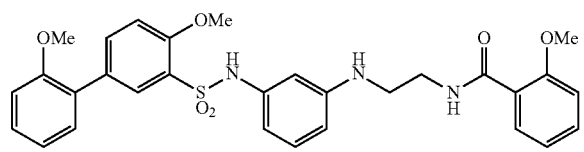

To a solution of tert-butyl (2-((3-(2',4-dimethoxy-[1,1'-biphenyl]-3-ylsulfonamide)phenyl) (4-methoxybenzyl)amino)ethyl)carbamate (136 mg) in dichloromethane (3.0 mL) was added trifluoroacetic acid (TFA) (0.500 mL), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. Under an argon atmosphere, to a solution of the obtained residue in dichloromethane (2.0 mL) were added o-anisic acid (18.3 mg), triethylamine (0.020 mL) and BOP reagent (61.9 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=2/1→1/0) to give N-(2-((3-(2',4-dimethoxy-[1,1'-biphenyl]-3-ylsulfonamide)phenyl)amino)ethyl)-2-methoxybenzamide (20.3 mg).

Example 13

N-(2-((3-(2',4-dimethoxy-[1,1'-biphenyl]-3-ylsulfonamide)phenyl)amino)ethyl)-3-methoxybenzamide

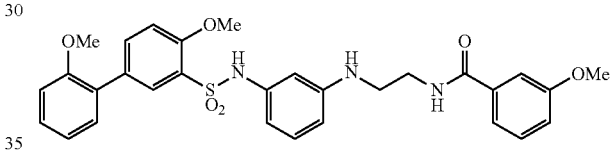

In the same manner as in Example 12, tert-butyl (2-((3-(2',4-dimethoxy-[1,1'-biphenyl]-3-ylsulfonamide)phenyl) (4-methoxybenzyl)amino)ethyl)carbamate (136 mg) was deprotected with TFA, and amidated with m-anisic acid (18.3 mg) to give N-(2-((3-(2',4-dimethoxy-[1,1'-biphenyl]-3-ylsulfonamide)phenyl)amino)ethyl)-3-methoxybenzamide (22.3 mg).

Example 14

N-(2-((3-(2'-fluoro-4-methoxy-[1,1'-biphenyl]-3-ylsulfonamide)phenyl)amino)ethyl)picolinamide

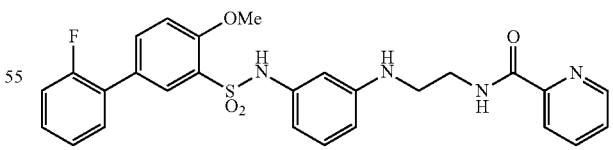

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with picolinic acid (4.9 mg) to give N-(2-((3-(2'-fluoro-4-methoxy-[1,1'-biphenyl]-3-ylsulfonamide)phenyl)amino)ethyl)picoline amide (19.2 mg). For purification, silica gel column chromatography (eluate: ethyl acetate/hexane=2/1→1/0) was used.

Example 15

N-(2-((3-(2'-fluoro-4-methoxy-[1,1'-biphenyl]-3-ylsulfonamide)phenyl)amino)ethyl)nicotineamide

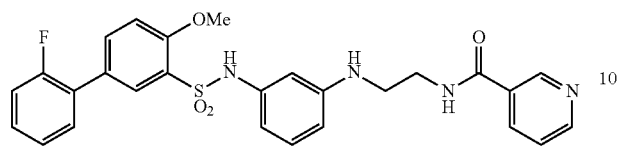 [SMILES: COc1ccc(-c2ccccc2F)cc1S(=O)(=O)Nc1cccc(NCCNC(=O)c2cccc(Cl)c2)c1]

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with nicotinic acid (4.9 mg) to give N-(2-((3-(2'-fluoro-4-methoxy-[1,1'-biphenyl]-3-ylsulfoneamide)phenyl)amino)ethyl)nicotinamide (20.2 mg). For purification, preparative thin layer chromatography (eluate: ammonia-saturated chloroform/methanol=40/1) was used.

Example 16

N-(2-((3-(2'-fluoro-4-methoxy-[1,1'-biphenyl]-3-ylsulfonamide)phenyl)amino)ethyl)isonicotinamide

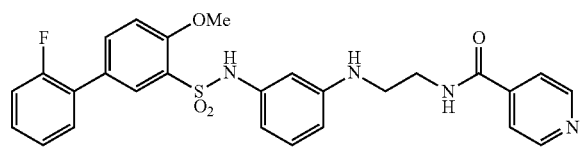 [SMILES: COc1ccc(-c2ccccc2F)cc1S(=O)(=O)Nc1cccc(NCCNC(=O)c2ccncc2)c1]

In the same manner as in Example 1, N-(3-((2-aminoethyl)amino)phenyl)-2'-fluoro-4-methoxy-[1,1'-biphenyl]-3-sulfonamide dihydrochloride (19.5 mg) was amidated with isonicotinic acid (4.9 mg) to give N-(2-((3-(2'-fluoro-4-methoxy-[1,1'-biphenyl]-3-ylsulfonamide)phenyl)amino)ethyl)isonicotinamide (21.6 mg). For purification, preparative thin layer chromatography (eluate: ammonia-saturated chloroform/methanol=40/1) was used.

Example 17

N-(2-((3-(2',6'-difluoro-4-methoxy-[1,1'-biphenyl]-3-ylsulfonamide)phenyl)amino)ethyl)-2-methoxybenzamide

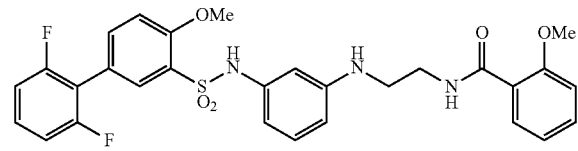 [SMILES: COc1ccccc1C(=O)NCCNc1cccc(NS(=O)(=O)c2cc(-c3c(F)cccc3F)ccc2OC)c1]

In the same manner as in Example 12, tert-butyl (2-((3-(2',6'-difluoro-4-dimethoxy-[1,1'-biphenyl]-3-ylsulfonamide)phenyl)(4-methoxybenzyl)amino)ethyl)carbamate (69.6 mg) was deprotected with TFA, and amidated with o-anisic acid (11.4 mg) to give N-(2-((3-(2',6'-difluoro-4-methoxy-[1,1'-biphenyl]-3-ylsulfonamide)phenyl)amino)ethyl)-2-methoxybenzamide (15.2 mg).

Example 18

N-(2-((3-(2',6'-difluoro-4-methoxy-[1,1'-biphenyl]-3-ylsulfonamide)phenyl)amino)ethyl)-3-methoxybenzamide

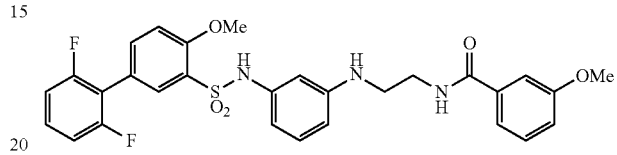

In the same manner as in Example 12, tert-butyl (2-((3-(2',6'-difluoro-4-dimethoxy-[1,1'-biphenyl]-3-ylsulfonamide)phenyl)(4-methoxybenzyl)amino)ethyl)carbamate (69.6 mg) was deprotected with TFA, and amidated with m-anisic acid (11.4 mg) to give N-(2-((3-(2',6'-difluoro-4-methoxy-[1,1'-biphenyl]-3-ylsulfonamide)phenyl)amino)ethyl)-3-methoxybenzamide (13.0 mg).

Example 19

N-(2-((3-(2',5'-difluoro-4-methoxy-[1,1'-biphenyl]-3-ylsulfonamide)phenyl)amino)ethyl)-2-methoxybenzamide

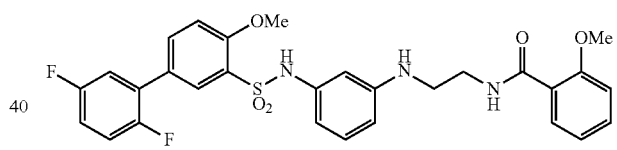

In the same manner as in Example 12, tert-butyl (2-((3-(2',5'-difluoro-4-methoxy-[1,1'-biphenyl]-3-ylsulfonamide)phenyl)(4-methoxybenzyl)amino)ethyl)carbamate (70.1 mg) was deprotected with TFA, and amidated with o-anisic acid (11.4 mg) to give N-(2-((3-(2',5'-difluoro-4-methoxy-[1,1'-biphenyl]-3-ylsulfonamide)phenyl)amino)ethyl)-2-methoxybenzamide (9.8 mg).

Example 20

N-(2-((3-(2',5'-difluoro-4-methoxy-[1,1'-biphenyl]-3-ylsulfonamide)phenyl)amino)ethyl)-3-methoxybenzamide

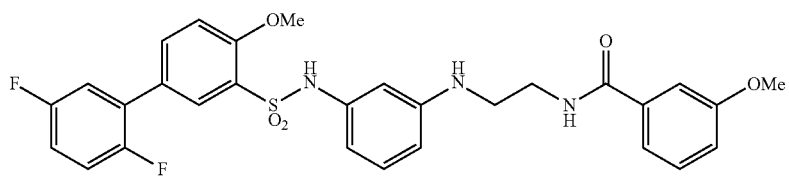

In the same manner as in Example 12, tert-butyl (2-((3-(2',5'-difluoro-4-methoxy-[1,1'-biphenyl]-3-ylsulfonamide)phenyl)(4-methoxybenzyl)amino)ethyl)carbamate (70.1 mg) was deprotected with TFA, and amidated with m-anisic acid (11.4 mg) to give N-(2-((3-(2',5'-difluoro-4-methoxy-[1,1'-biphenyl]-3-ylsulfonamide)phenyl)amino)ethyl)-3-methoxybenzamide (11.9 mg).

Example 21

3-methoxy-N-(2-((3-(4-methoxy-2'-methyl-[1,1'-biphenyl]-3-ylsulfonamide)phenyl)amino)ethyl)benzamide

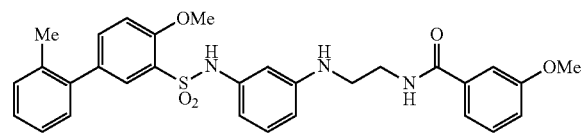

To tert-butyl (2-((3-(4-methoxy-2'-methyl-[1,1'-biphenyl]-3-ylsulfonamide)phenyl)amino)ethyl)carbamate (11.7 mg) was added 10% hydrogen chloride-methanol solution (2.0 mL), and the mixture was stirred at 50° C. for 2 hr. The reaction mixture was concentrated, to a suspension of the obtained residue in dichloromethane (1.0 mL) were added m-anisic acid (3.5 mg), triethylamine (0.011 mL) and BOP reagent (11.1 mg), and the mixture was stirred at room temperature overnight under an argon atmosphere. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by preparative thin layer chromatography (eluate: ethyl acetate/hexane=3/2) to give 3-methoxy-N-(2-((3-(4-methoxy-2'-methyl-[1,1'-biphenyl]-3-ylsulfonamide)phenyl)amino)ethyl)benzamide (5.0 mg).

Example 22

N-(2-((3-(2'-hydroxy-4-methoxy-[1,1'-biphenyl]-3-ylsulfonamide)phenyl)amino)ethyl)-3-methoxybenzamide

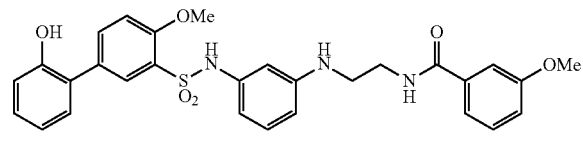

In the same manner as in Example 21, tert-butyl (2-((3-(2'-hydroxy-4-methoxy-[1,1'-biphenyl]-3-ylsulfonamide)phenyl)amino)ethyl)carbamate (7.2 mg) was deprotected with 10% hydrogen chloride-methanol solution, and amidated with m-anisic acid (2.1 mg) to give N-(2-((3-(2'-hydroxy-4-methoxy-[1,1'-biphenyl]-3-ylsulfonamide)phenyl)amino)ethyl)-3-methoxybenzamide (8.2 mg). For purification, silica gel column chromatography (eluate: ethyl acetate/chloroform=1/0→1/1) was used.

Example 23

N-(2-((3-(2'-fluoro-4,6'-dimethoxy-[1,1'-biphenyl]-3-ylsulfonamide)phenyl)amino)ethyl)-2-methoxybenzamide

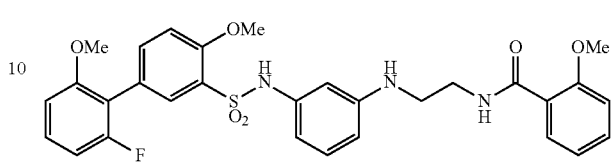 [SMILES: COc1ccccc1C(=O)NCCNc1cccc(NS(=O)(=O)c2cc(-c3cc(F)ccc3F)ccc2OC)c1]

In the same manner as in Example 1, N-(3-((2-aminoethyl)amino)phenyl)-2'-fluoro-4,6'-dimethoxy-[1,1'-biphenyl]-3-sulfonamide dihydrochloride (19.5 mg) was amidated with o-anisic acid (5.8 mg) to give N-(2-((3-(2'-fluoro-4,6'-dimethoxy-[1,1'-biphenyl]-3-ylsulfonamide)phenyl)amino)ethyl)-2-methoxybenzamide (15.8 mg). For purification, silica gel column chromatography (eluate: ethyl acetate/hexane=1/2→1/1) was used.

Example 24

N-(2-((3-(2'-fluoro-4,6'-dimethoxy-[1,1'-biphenyl]-3-ylsulfonamide)phenyl)amino)ethyl)-3-methoxybenzamide

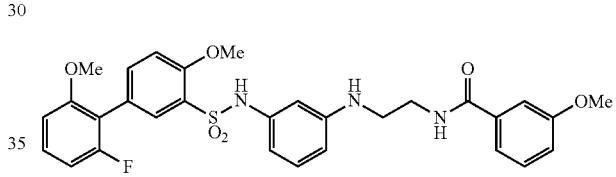

In the same manner as in Example 1, N-(3-((2-aminoethyl)amino)phenyl)-2'-fluoro-4,6'-dimethoxy-[1,1'-biphenyl]-3-sulfonamide dihydrochloride (17.1 mg) was amidated with m-anisic acid (5.0 mg) to give N-(2-((3-(2'-fluoro-4,6'-dimethoxy-[1,1'-biphenyl]-3-ylsulfonamide)phenyl)amino)ethyl)-3-methoxybenzamide (14.6 mg). For purification, silica gel column chromatography (eluate: ethyl acetate/hexane=1/2→1/1) was used.

Example 25

N-(2-((3-(2',5'-dichloro-4-methoxy-[1,1'-biphenyl]-3-ylsulfonamide)phenyl)amino)ethyl)-2-methoxybenzamide

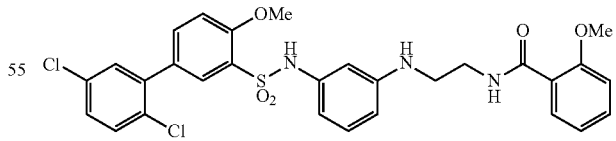

In the same manner as in Example 21, tert-butyl (2-((3-(2',5'-dichloro-4-methoxy-[1,1'-biphenyl]-3-ylsulfonamide)phenyl)(4-methoxybenzyl)amino)ethyl)carbamate (177 mg) was deprotected with 10% hydrogen chloride-methanol solution, and amidated with o-anisic acid (19.8 mg) to give N-(2-((3-(2',5'-dichloro-4-methoxy-[1,1'-biphenyl]-3-ylsulfonamide)phenyl)amino)ethyl)-2-methoxybenzamide (35.8 mg). For purification, silica gel column chromatography (eluate: ethyl acetate/hexane=3/2→2/1) was used.

Example 26

N-(2-((3-(2',5'-dichloro-4-methoxy-[1,1'-biphenyl]-3-ylsulfonamide)phenyl)amino)ethyl)-3-methoxybenzamide

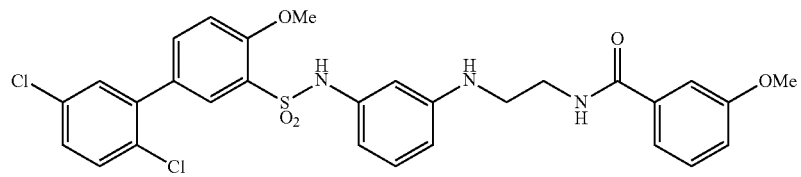 [SMILES: COc1cccc(C(=O)NCCNc2cccc(NS(=O)(=O)c3cc(-c4cc(Cl)ccc4Cl)ccc3OC)c2)c1]

In the same manner as in Example 21, tert-butyl (2-((3-(2',5'-dichloro-4-methoxy-[1,1'-biphenyl]-3-ylsulfonamide)phenyl)(4-methoxybenzyl)amino)ethyl)carbamate (177 mg) was deprotected with 10% hydrogen chloride-methanol solution, and amidated with m-anisic acid (19.8 mg) to give N-(2-((3-(2',5'-dichloro-4-methoxy-[1,1'-biphenyl]-3-ylsulfonamide)phenyl)amino)ethyl)-3-methoxybenzamide (13.8 mg). For purification, silica gel column chromatography (eluate: ethyl acetate/hexane=3/2→2/1) was used.

Example 27

N-(2-((3-(3',5'-dichloro-4-methoxy-[1,1'-biphenyl]-3-ylsulfonamide)phenyl)amino)ethyl)-2-methoxybenzamide

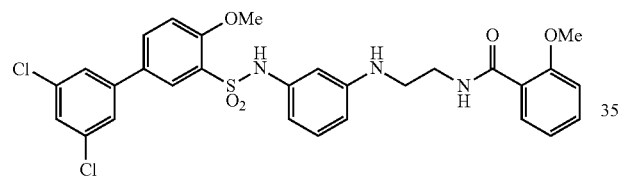

In the same manner as in Example 21, tert-butyl (2-((3-(3',5'-dichloro-4-methoxy-[1,1'-biphenyl]-3-ylsulfonamide)phenyl) (4-methoxybenzyl)amino)ethyl)carbamate (137 mg) was deprotected with 10% hydrogen chloride-methanol solution, and amidated with o-anisic acid (15.2 mg) to give N-(2-((3-(3',5'-dichloro-4-methoxy-[1,1'-biphenyl]-3-ylsulfonamide)phenyl)amino)ethyl)-2-methoxybenzamide (42.5 mg). For purification, silica gel column chromatography (eluate: ethyl acetate/hexane=3/2→2/1) was used.

Example 28

N-(2-((3-(3',5'-dichloro-4-methoxy-[1,1'-biphenyl]-3-ylsulfonamide)phenyl)amino)ethyl)-3-methoxybenzamide

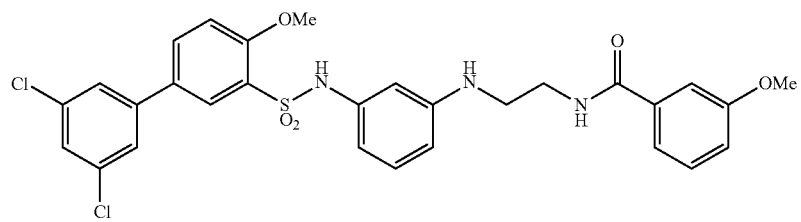 [SMILES: COc1cccc(C(=O)NCCNc2cccc(NS(=O)(=O)c3cc(-c4cc(Cl)cc(Cl)c4)ccc3OC)c2)c1]

In the same manner as in Example 21, tert-butyl (2-((3-(3',5'-dichloro-4-methoxy-[1,1'-biphenyl]-3-ylsulfonamide)phenyl) (4-methoxybenzyl)amino)ethyl)carbamate (137 mg) was deprotected with 10% hydrogen chloride-methanol solution, and amidated with m-anisic acid (15.2 mg) to give N-(2-((3-(3',5'-dichloro-4-methoxy-[1,1'-biphenyl]-3-ylsulfonamide)phenyl)amino)ethyl)-3-methoxybenzamide (20.5 mg). For purification, silica gel column chromatography (eluate: ethyl acetate/hexane=3/2→2/1) was used.

Example 29

N-(2-((3-(3'-chloro-4-methoxy-[1,1'-biphenyl]-3-ylsulfonamide)phenyl)amino)ethyl)-3-methoxybenzamide

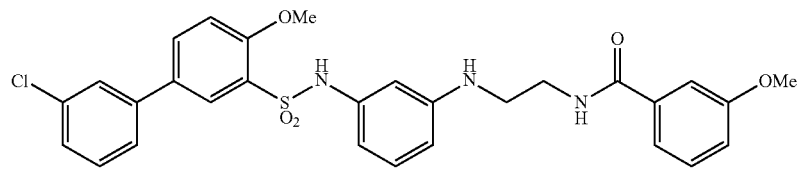 [SMILES: COc1cccc(C(=O)NCCNc2cccc(NS(=O)(=O)c3cc(-c4cccc(Cl)c4)ccc3OC)c2)c1]

In the same manner as in Example 21, tert-butyl (2-((3-(3'-chloro-4-methoxy-[1,1'-biphenyl]-3-ylsulfonamide)phenyl) (4-methoxybenzyl)amino)ethyl)carbamate (104 mg) was deprotected with 10% hydrogen chloride-methanol solution, and amidated with m-anisic acid (8.5 mg) to give N-(2-((3-(3'-chloro-4-methoxy-[1,1'-biphenyl]-3-ylsulfonamide)phenyl)amino)ethyl)-3-methoxybenzamide (13.5 mg). For purification, silica gel column chromatography (eluate: ethyl acetate/hexane=1/1) was used.

Example 30

N-(2-((3-(3',4-dimethoxy-[1,1'-biphenyl]-3-ylsulfonamide)phenyl)amino)ethyl)-2-methoxybenzamide

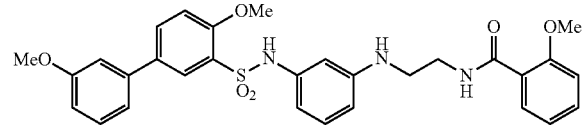

In the same manner as in Example 1, N-(3-((2-aminoethyl)amino)phenyl)-3',4-dimethoxy-[1,1'-biphenyl]-3-sulfonamide dihydrochloride (16.4 mg) was amidated with o-anisic acid (5.0 mg) to give N-(2-((3-(3',4-dimethoxy-[1,1'-biphenyl]-3-ylsulfonamide)phenyl)amino)ethyl)-2-methoxybenzamide (4.1 mg).

Example 31

N-(2-((3-(3',4-dimethoxy-[1,1'-biphenyl]-3-ylsulfonamide)phenyl)amino)ethyl)-3-methoxybenzamide

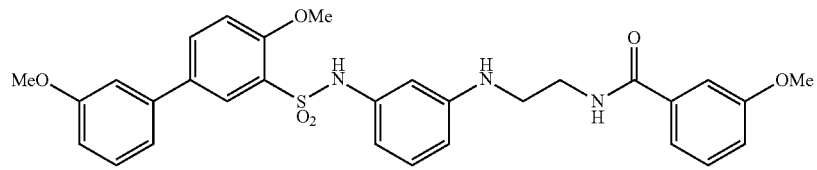 [SMILES: COc1cccc(C(=O)NCCNc2cccc(NS(=O)(=O)c3cc(-c4cccc(OC)c4)ccc3OC)c2)c1]

In the same manner as in Example 1, N-(3-((2-aminoethyl)amino)phenyl)-3',4-dimethoxy-[1,1'-biphenyl]-3-sulfonamide dihydrochloride (16.4 mg) was amidated with m-anisic acid (5.0 mg) to give N-(2-((3-(3',4-dimethoxy-[1,1'-biphenyl]-3-ylsulfonamide)phenyl)amino)ethyl)-3-methoxybenzamide (6.9 mg).

Example 32

N-(2-((3-(2'-chloro-5'-fluoro-4-methoxy-[1,1'-biphenyl]-3-ylsulfonamide)phenyl)amino)ethyl)-2-methoxybenzamide

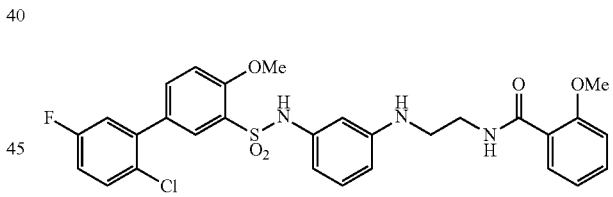

In the same manner as in Example 21, tert-butyl (2-((3-(2'-chloro-5'-fluoro-4-methoxy-[1,1'-biphenyl]-3-ylsulfonamide)phenyl)(4-methoxybenzyl)amino)ethyl)carbamate (127 mg) was deprotected with 10% hydrogen chloride-methanol solution, and amidated with o-anisic acid (16.7 mg) to give N-(2-((3-(2'-chloro-5'-fluoro-4-methoxy-[1,1'-biphenyl]-3-ylsulfonamide)phenyl)amino)ethyl)-2-methoxybenzamide (15.6 mg). For purification, silica gel column chromatography (eluate: ethyl acetate/hexane=3/2) was used.

Example 33

N-(2-((3-(2'-chloro-5'-fluoro-4-methoxy-[1,1'-biphenyl]-3-ylsulfonamide)phenyl)amino)ethyl)-3-methoxybenzamide

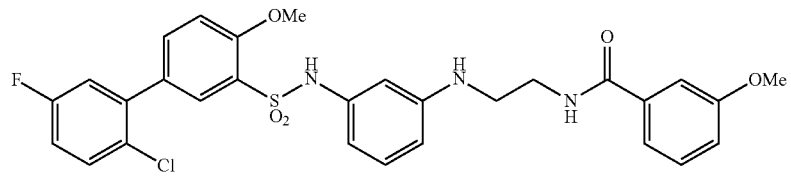 [SMILES: COc1cccc(C(=O)NCCNc2cccc(NS(=O)(=O)c3cc(-c4cc(F)ccc4Cl)ccc3OC)c2)c1]

In the same manner as in Example 21, tert-butyl (2-((3-(2'-chloro-5'-fluoro-4-methoxy-[1,1'-biphenyl]-3-ylsulfonamide)phenyl)(4-methoxybenzyl)amino)ethyl)carbamate (127 mg) was deprotected with 10% hydrogen chloride-methanol solution, and amidated with m-anisic acid (16.7 mg) to give N-(2-((3-(2'-chloro-5'-fluoro-4-methoxy-[1,1'-biphenyl]-3-ylsulfonamide)phenyl)amino)ethyl)-3-methoxybenzamide (10.4 mg). For purification, silica gel column chromatography (eluate: ethyl acetate/hexane=3/2) was used.

Example 34

N-(2-((3-(2'-fluoro-4,5'-dimethoxy-[1,1'-biphenyl]-3-ylsulfonamide)phenyl)amino)ethyl)-2-methoxybenzamide

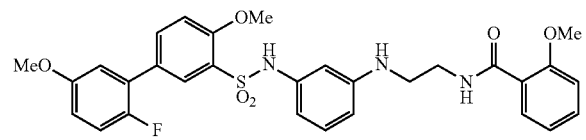 [SMILES: COc1ccc(F)c(-c2ccc(OC)c(S(=O)(=O)Nc3cccc(NCCNC(=O)c4ccccc4OC)c3)c2)c1]

In the same manner as in Example 1, N-(3-((2-aminoethyl)amino)phenyl)-2'-fluoro-4,5'-dimethoxy-[1,1'-biphenyl]-3-sulfonamide dihydrochloride (18.1 mg) was amidated with o-anisic acid (5.3 mg) to give N-(2-((3-(2'-fluoro-4,5'-dimethoxy-[1,1'-biphenyl]-3-ylsulfonamide)phenyl)amino)ethyl)-2-methoxybenzamide (8.2 mg). For purification, silica gel column chromatography (eluate: ethyl acetate/hexane=3/1) was used.

Example 35

N-(2-((3-(2'-fluoro-4,5'-dimethoxy-[1,1'-biphenyl]-3-ylsulfonamide)phenyl)amino)ethyl)-3-methoxybenzamide

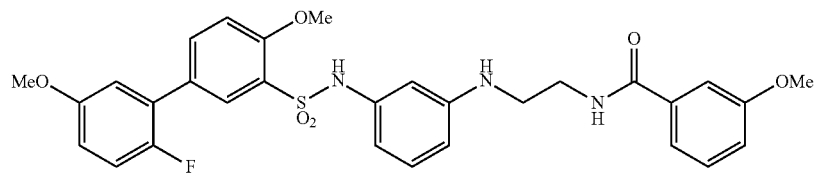 [SMILES: COc1cccc(C(=O)NCCNc2cccc(NS(=O)(=O)c3cc(-c4cc(OC)ccc4F)ccc3OC)c2)c1]

In the same manner as in Example 1, N-(3-((2-aminoethyl)amino)phenyl)-2'-fluoro-4,5'-dimethoxy-[1,1'-biphenyl]-3-sulfonamide dihydrochloride (18.1 mg) was amidated with m-anisic acid (5.3 mg) to give N-(2-((3-(2'-fluoro-4,5'-dimethoxy-[1,1'-biphenyl]-3-ylsulfonamide)phenyl)amino)ethyl)-3-methoxybenzamide (12.9 mg). For purification, silica gel column chromatography (eluate: ethyl acetate/hexane=3/1) was used.

Example 36

2-methoxy-N-(2-((3-(3',4',5'-trimethoxy-[1,1'-biphenyl]-3-ylsulfonamide)phenyl)amino)ethyl)benzamide

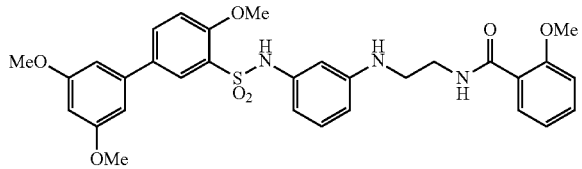 [SMILES: COc1cc(OC)cc(-c2ccc(OC)c(S(=O)(=O)Nc3cccc(NCCNC(=O)c4ccccc4OC)c3)c2)c1]

In the same manner as in Example 1, N-(3-((2-aminoethyl)amino)phenyl)-3',4',5'-trimethoxy-[1,1'-biphenyl]-3-sulfonamide dihydrochloride (16.2 mg) was amidated with o-anisic acid (4.7 mg) to give 2-methoxy-N-(2-((3-(3',4',5'-trimethoxy-[1,1'-biphenyl]-3-ylsulfonamide)phenyl)amino)ethyl)benzamide (12.4 mg). For purification, silica gel column chromatography (eluate: ethyl acetate/hexane=2/1→1/0) was used.

Example 37

N-(2-((3-(3'-amino-4-methoxy-[1,1'-biphenyl]-3-ylsulfonamide)phenyl)amino)ethyl)-2-methoxybenzamide

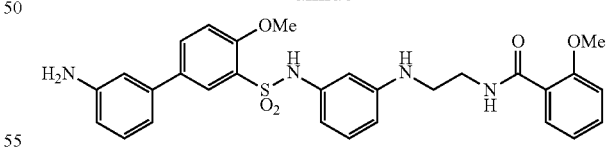

In the same manner as in Example 1, 3'-amino-N-(3-((2-aminoethyl)amino)phenyl)-4-methoxy-[1,1'-biphenyl]-3-sulfonamide (44.9 mg) was amidated with o-anisic acid (16.7 mg) to give N-(2-((3-(3'-amino-4-methoxy-[1,1'-biphenyl]-3-ylsulfonamide)phenyl)amino)ethyl)-2-methoxybenzamide (53.1 mg). For purification, silica gel column chromatography (eluate: ethyl acetate) was used.

Example 38

N-(2-((3-(3'-(isobutylamino)-4-methoxy-[1,1'-biphenyl]-3-ylsulfonamide)phenyl)amino)ethyl)-2-methoxybenzamide

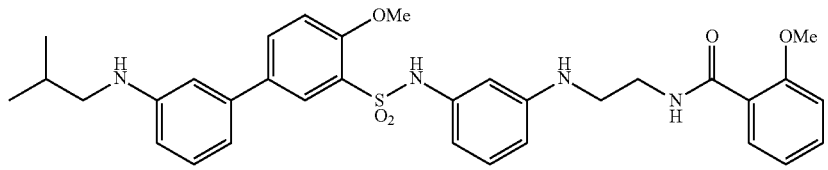 [SMILES: COc1ccccc1C(=O)NCCNc1cccc(NS(=O)(=O)c2cc(-c3cccc(NCC(C)C)c3)ccc2OC)c1]

To a solution of N-(2-((3-(3'-amino-4-methoxy-[1,1'-biphenyl]-3-ylsulfonamide)phenyl)amino)ethyl)-2-methoxybenzamide (53.6 mg) in 1,2-dichloroethane (2.0 mL) were added isobutylaldehyde (0.01 mL) and sodium triacetoxyborohydride (31.8 mg), and the mixture was stirred at room temperature for 4 hr. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by preparative thin layer chromatography (ammonia-saturated chloroform/methanol=40/1) to give N-(2-((3-(3'-(isobutylamino)-4-methoxy-[1,1'-biphenyl]-3-ylsulfonamide)phenyl)amino)ethyl)-2-methoxybenzamide (32.3 mg).

Example 39

N-(2-((3-(3'-(hydroxymethyl)-4-methoxy-[1,1'-biphenyl]-3-ylsulfonamide)phenyl)amino)ethyl)-2-methoxybenzamide

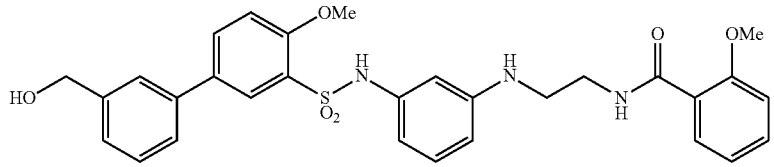 [SMILES: COc1ccccc1C(=O)NCCNc1cccc(NS(=O)(=O)c2cc(-c3cccc(CO)c3)ccc2OC)c1]

In the same manner as in Example 1, N-(3-((2-aminoethyl)amino)phenyl)-3'-hydroxymethyl-4-methoxy-[1,1'-biphenyl]-3-sulfonamide (25.3 mg) was amidated with o-anisic acid (9.0 mg) to give N-(2-((3-(3'-(hydroxymethyl)-4-methoxy-[1,1'-biphenyl]-3-ylsulfonamide)phenyl)amino)ethyl)-2-methoxybenzamide (20.6 mg). For purification, silica gel column chromatography (eluate: ethyl acetate) was used.

Example 40

4'-methoxy-3'-(N-(3-((2-(2-methoxybenzamido)ethyl)amino)phenyl)sulfamoyl)-N,N-dimethyl-[1,1'-biphenyl]-3-carboxamide

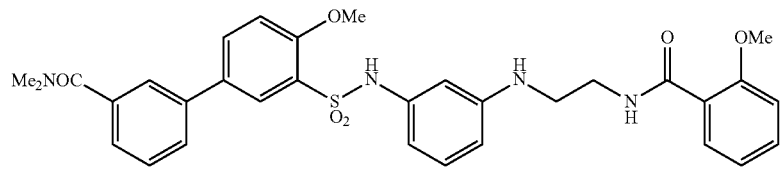

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (86.6 mg) was amidated with o-anisic acid (24.3 mg) to give 4'-methoxy-3'-(N-(3-((2-(2-methoxybenzamido)ethyl)amino)phenyl)sulfamoyl)-N,N-dimethyl-[1,1'-biphenyl]-3-carboxamide (85.3 mg). For purification, silica gel column chromatography (eluate: ethyl acetate) was used.

Example 41

4'-methoxy-3'-(N-(3-((2-(3-methoxybenzamido)ethyl)amino)phenyl)sulfamoyl)-N,N-dimethyl-[1,1'-biphenyl]-3-carboxamide

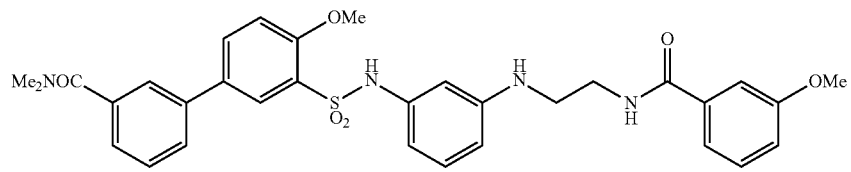

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with m-anisic acid (5.3 mg) to give 4'-methoxy-3'-(N-(3-((2-(3-methoxybenzamido)ethyl)amino)phenyl)sulfamoyl)-N,N-dimethyl-[1,1'-biphenyl]-3-carboxamide (17.9 mg). For purification, silica gel column chromatography (eluate: ethyl acetate) was used.

Example 42

3'-(N-(3-((2-(2-chlorobenzamido)ethyl)amino)phenyl)sulfamoyl)-4'-methoxy-N,N-dimethyl-[1,1'-biphenyl]-3-carboxamide

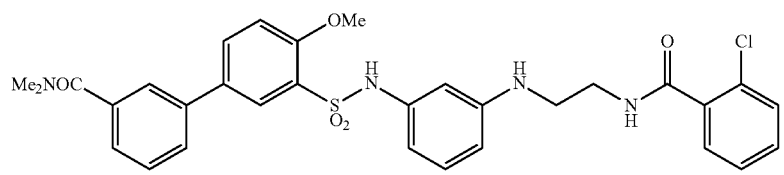

In the same manner as in Example 1, 3'-(N-(3-((2-amino-ethyl)amino)phenyl)sulfamoyl)-4'-methoxy-N,N-dimethyl-[1,1'-biphenyl]-3-carboxamide dihydrochloride (19.0 mg) was amidated with 2-chlorobenzoic acid (5.5 mg) to give 3'-(N-(3-((2-(2-chlorobenzamido)ethyl)amino)phenyl)sulfamoyl)-4'-methoxy-N,N-dimethyl-[1,1'-biphenyl]-3-carboxamide (17.2 mg). For purification, silica gel column chromatography (eluate: ethyl acetate) was used.

Example 43

3'-(N-(3-((2-(2-fluorobenzamido)ethyl)amino)phenyl)sulfamoyl)-4'-methoxy-N,N-dimethyl-[1,1'-biphenyl]-3-carboxamide

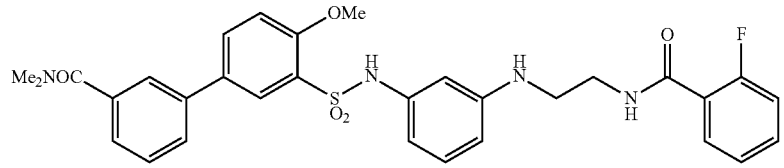

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-fluorobenzoic acid (4.9 mg) to give 3'-(N-(3-((2-(2-fluorobenzamido)ethyl)amino)phenyl)sulfamoyl)-4'-methoxy-N,N-dimethyl-[1,1'-biphenyl]-3-carboxamide (19.9 mg). For purification, silica gel column chromatography (eluate: ethyl acetate) was used.

Example 44

4'-methoxy-3'-(N-(3-((2-(4-methoxybenzamido)ethyl)amino)phenyl)sulfamoyl)-N,N-dimethyl-[1,1'-biphenyl]-3-carboxamide

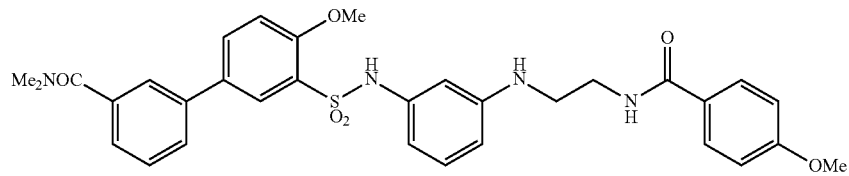

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with p-anisic acid (5.5 mg) to give 4'-methoxy-3'-(N-(3-((2-(4-methoxybenzamido)ethyl)amino)phenyl)sulfamoyl)-N,N-dimethyl-[1,1'-biphenyl]-3-carboxamide (20.6 mg). For purification, preparative thin layer chromatography (eluate: ammonia-saturated chloroform/methanol=40/1) was used.

Example 45

3'-(N-(3-((2-(2,6-difluorobenzamido)ethyl)amino)phenyl)sulfamoyl)-4'-methoxy-N,N-dimethyl-[1,1'-biphenyl]-3-carboxamide

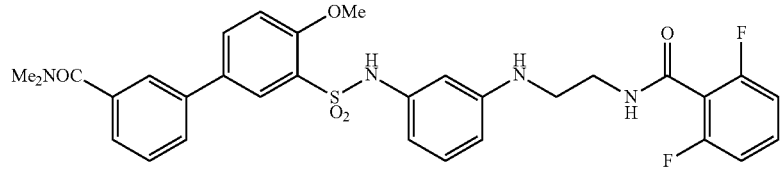

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (22.3 mg) was amidated with 2,6-difluorobenzoic acid (6.5 mg) to give 3'-(N-(3-((2-(2,6-difluorobenzamido)ethyl)amino)phenyl)sulfamoyl)-4'-methoxy-N,N-dimethyl-[1,1'-biphenyl]-3-carboxamide (22.1 mg). For purification, silica gel column chromatography (eluate: ethyl acetate) was used.

Example 46

N-(2-((3-(3'-(dimethylcarbamoyl)-4-methoxy-[1,1'-biphenyl]-3-ylsulfonamide)phenyl)amino)ethyl)-2-methoxynicotinamide

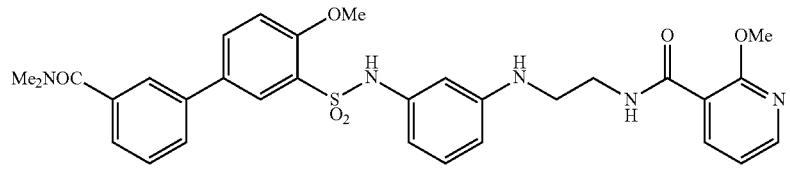

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-methoxypyridine-3-carboxylic acid (5.4 mg) to give N-(2-((3-(3'-(dimethylcarbamoyl)-4-methoxy-[1,1'-biphenyl]-3-ylsulfonamide)phenyl)amino)ethyl)-2-methoxynicotinamide (20.6 mg). For purification, preparative thin layer chromatography (eluate: ammonia-saturated chloroform/methanol=40/1) was used.

Example 47

N-(2-((3-(3'-(dimethylcarbamoyl)-4-methoxy-[1,1'-biphenyl]-3-yl sulfonamide)phenyl)amino)ethyl)-2-methoxyisonicotinamide

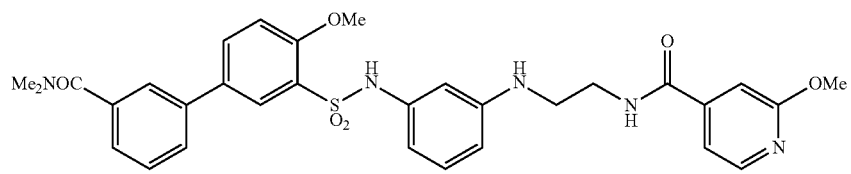

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-methoxypyridine-4-carboxylic acid (5.4 mg) to give N-(2-((3-(3'-(dimethylcarbamoyl)-4-methoxy-[1,1'-biphenyl]-3-ylsulfonamide)phenyl)amino)ethyl)-2-methoxynicotinamide (20.1 mg). For purification, preparative thin layer chromatography (eluate: ammonia-saturated chloroform/methanol=40/1) was used.

Example 48

N-(2-((3-(3'-(dimethylcarbamoyl)-4-methoxy-[1,1'-biphenyl]-3-ylsulfonamide)phenyl)amino)ethyl)-6-methoxypicolinamide

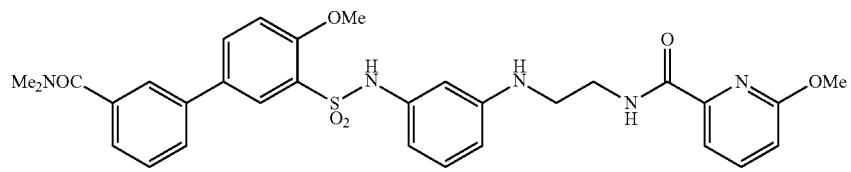

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 6-methoxypyridine-2-carboxylic acid (5.4 mg) to give N-(2-((3-(3'-(dimethylcarbamoyl)-4-methoxy-[1,1'-biphenyl]-3-ylsulfonamide)phenyl)amino)ethyl)-6-methoxynicotinamide (18.3 mg). For purification, preparative thin layer chromatography (eluate: ammonia saturated chloroform/methanol=40/1) was used.

Example 49

N-(2-((3-(3'-(dimethylcarbamoyl)-4-methoxy-[1,1'-biphenyl]-3-ylsulfonamide)phenyl)amino)ethyl)-5-methoxynicotinamide

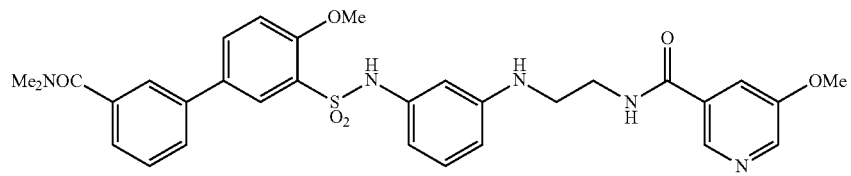

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 5-methoxypyridine-3-carboxylic acid (5.4 mg) to give N-(2-((3-(3'-(dimethylcarbamoyl)-4-methoxy-[1,1'-biphenyl]-3-ylsulfonamide)phenyl)amino)ethyl)-5-methoxynicotinamide (18.3 mg). For purification, preparative thin layer chromatography (eluate: ammonia-saturated chloroform/methanol=40/1) was used.

Example 50

2-chloro-N-(2-((3-(3'-(dimethylcarbamoyl)-4-methoxy-[1,1'-biphenyl]-3-ylsulfonamido)phenyl)amino)ethyl)nicotinamide

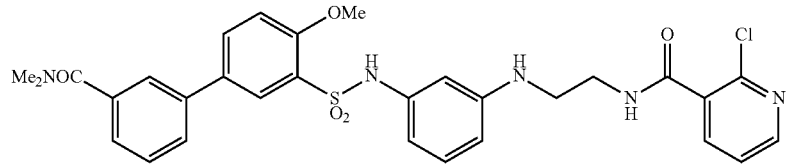

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-chloronicotinic acid (5.5 mg) to give 2-chloro-N-(2-((3-(3'-(dimethylcarbamoyl)-4-methoxy-[1,1'-biphenyl]-3-ylsulfonamido)phenyl)amino)ethyl)nicotinamide (20.1 mg). For purification, amine silica gel column chromatography (eluate: chloroform/methanol=1/0→50/1) was used.

Example 51

3-chloro-N-(2-((3-(3'-(dimethylcarbamoyl)-4-methoxy-[1,1'-biphenyl]-3-ylsulfonamido)phenyl)amino)ethyl)picolinamide

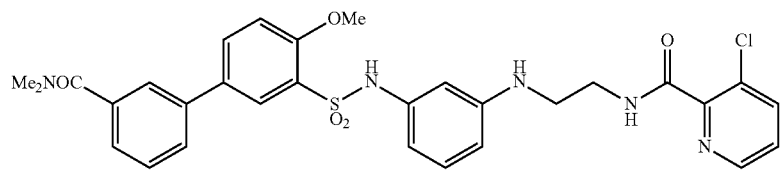

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 3-chloropyridine-2-carboxylic acid (5.5 mg) to give 3-chloro-N-(2-((3-(3'-(dimethylcarbamoyl)-4-methoxy-[1,1'-biphenyl]-3-ylsulfonamido)phenyl)amino)ethyl)picolinamide (18.2 mg). For purification, amine silica gel column chromatography (eluate: chloroform/methanol=1/0→100/1) was used.

Example 52

3'-(N-(3-((2-(3-fluorobenzamido)ethyl)amino)phenyl)sulfamoyl)-4'-methoxy-N,N-dimethyl-[1,1'-biphenyl]-3-carboxamide

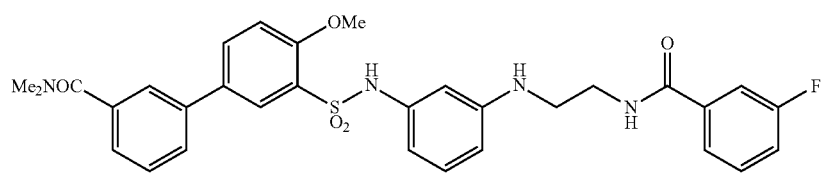

In the same manner as in Example 1, 3'-(N-(3-((2-amino-ethyl)amino)phenyl)sulfamoyl)-4'-methoxy-N,N-dimethyl-[1,1'-biphenyl]-3-carboxamide dihydrochloride (19.0 mg) was amidated with 3-fluorobenzoic acid (4.9 mg) to give 3'-(N-(3-((2-(3-fluorobenzamido)ethyl)amino)phenyl)sulfamoyl)-4'-methoxy-N,N-dimethyl-[1,1'-biphenyl]-3-carboxamide (13.5 mg). For purification, silica gel column chromatography (eluate: ethyl acetate) was used.

Example 53

3'-(N-(3-((2-(2,5-difluorobenzamido)ethyl)amino) phenyl)sulfamoyl)-4'-methoxy-N,N-dimethyl-[1,1'-biphenyl]-3-carboxamide

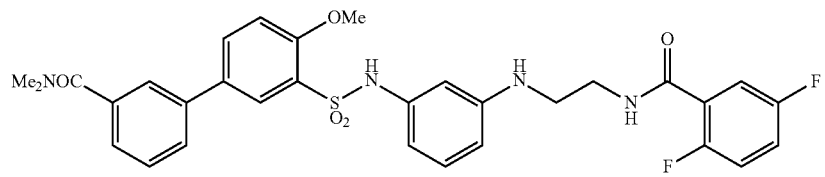

In the same manner as in Example 1, 3'-(N-(3-((2-amino-ethyl)amino)phenyl)sulfamoyl)-4'-methoxy-N,N-dimethyl-[1,1'-biphenyl]-3-carboxamide dihydrochloride (19.0 mg) was amidated with 2,5-difluorobenzoic acid (5.5 mg) to give 3'-(N-(3-((2-(2,5-difluorobenzamido)ethyl)amino)phenyl) sulfamoyl)-4'-methoxy-N,N-dimethyl-[1,1'-biphenyl]-3-carboxamide (15.3 mg). For purification, silica gel column chromatography (eluate: ethyl acetate) was used.

Example 54

3'-(N-(3-((2-(3,5-difluorobenzamido)ethyl)amino) phenyl)sulfamoyl)-4'-methoxy-N,N-dimethyl-[1,1'-biphenyl]-3-carboxamide

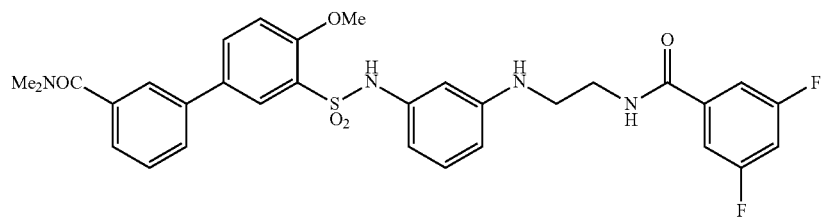

In the same manner as in Example 1, 3' (N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 3,5-difluorobenzoic acid (5.5 mg) to give 3'-(N-(3-((2-(3,5-difluorobenzamido)ethyl) amino)phenyl)sulfamoyl)-4'-methoxy-N,N-dimethyl-[1,1'-biphenyl]-3-carboxamide (18.3 mg). For purification, silica gel column chromatography (eluate: ethyl acetate) was used.

Example 55

6-chloro-N-(2-((3-(3'-(dimethylcarbamoyl)-4-methoxy-[1,1'-biphenyl]-3-ylsulfonamido)phenyl)amino)ethyl)picolinamide

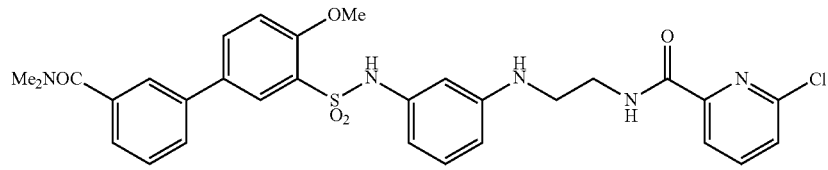

In the same manner as in Example 1, —(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 6-chloropyridine-2-carboxylic acid (5.5 mg) to give 6-chloro-N-(2-((3-(3'-(dimethylcarbamoyl)-4-methoxy-[1,1'-biphenyl]-3-ylsulfonamido)phenyl)amino)ethyl)picolinamide (20.3 mg). For purification, amine silica gel column chromatography (eluate: chloroform/methanol=1/0→100/1) was used.

Example 56

3-chloro-N-(2-((3-(3'-(dimethylcarbamoyl)-4-methoxy-[1,1'-biphenyl]-3-ylsulfonamido)phenyl)amino)ethyl) isonicotinamide

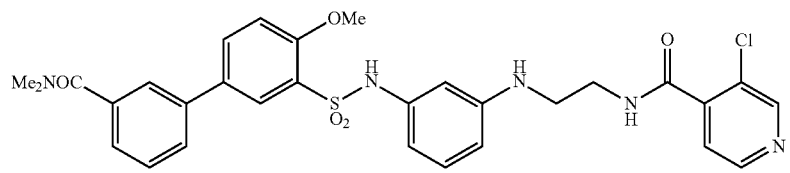

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 3-chloropyridine-4-carboxylic acid (5.5 mg) to give 3-chloro-N-(2-((3-(3'-(dimethylcarbamoyl)-4-methoxy-[1,1'-biphenyl]-3-ylsulfonamido)phenyl)amino)ethyl)isonicotinamide (18.5 mg). For purification, amine silica gel column chromatography (eluate: chloroform/methanol=1/0→100/1) was used.

Example 57

4-chloro-N-(2-((3-(3'-(dimethylcarbamoyl)-4-methoxy-[1,1'-biphenyl]-3-ylsulfonamido)phenyl)amino)ethyl)nicotinamide

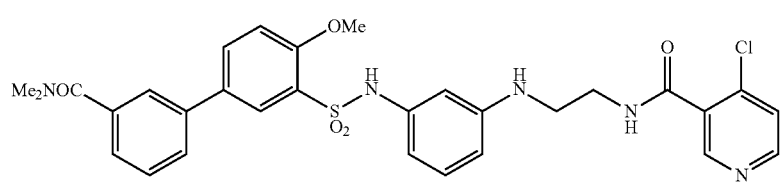

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 4-chloropyridine-3-carboxylic acid (5.5 mg) to give 4-chloro-N-(2-((3-(3'-(dimethylcarbamoyl)-4-methoxy-[1,1'-biphenyl]-3-ylsulfonamido)phenyl)amino)ethyl)nicotinamide (12.9 mg). For purification, amine silica gel column chromatography (eluate: chloroform/methanol=1/0→100/1) was used.

Example 58

5-chloro-N-(2-((3-(3'-(dimethylcarbamoyl)-4-methoxy-[1,1'-biphenyl]-3-ylsulfonamido)phenyl)amino)ethyl)nicotinamide

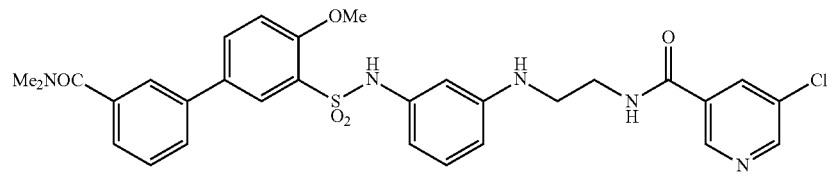

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 5-chloropyridine-3-carboxylic acid (5.5 mg) to give 5-chloro-N-(2-((3-(3'-(dimethylcarbamoyl)-4-methoxy-[1,1'-biphenyl]-3-ylsulfonamido)phenyl)amino)ethyl)nicotinamide (18.0 mg). For purification, amine silica gel column chromatography (eluate: chloroform/methanol=1/0→100/1) was used.

Example 59

N-(2-((3-(3'-(dimethylcarbamoyl)-4-methoxy-[1,1'-biphenyl]-3-ylsulfonamido)phenyl)amino)ethyl)-1-methyl-1H-pyrazole-5-carboxamide

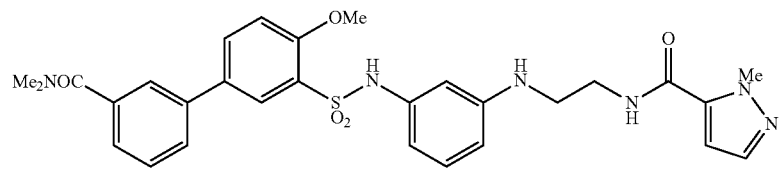

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 1-methyl-1H-pyrazole-5-carboxylic acid (4.4 mg) to give N-(2-((3-(3'-(dimethylcarbamoyl)-4-methoxy-[1,1'-biphenyl]-3-ylsulfonamido)phenyl)amino)ethyl)-1-methyl-1H-pyrazole-5-carboxamide (15.7 mg). For purification, amine silica gel column chromatography (eluate: chloroform/methanol=1/0→100/1) was used.

Example 60

N-(2-((3-(3'-(dimethylcarbamoyl)-4-methoxy-[1,1'-biphenyl]-3-ylsulfonamido)phenyl)amino)ethyl)-3-methylthiophene-2-carboxamide

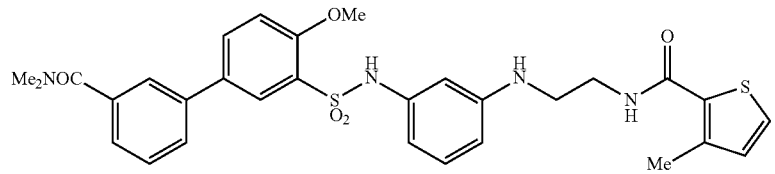

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 3-methylthiophene-2-carboxylic acid (5.0 mg) to give N-(2-((3-(3'-(dimethylcarbamoyl)-4-methoxy-[1,1'-biphenyl]-3-ylsulfonamido)phenyl)amino)ethyl)-3-methylthiophene-2-carboxamide (16.4 mg). For purification, silica gel column chromatography (eluate: ethyl acetate) was used.

Example 61

5-chloro-N-(2-((3-(3'-(dimethylcarbamoyl)-4-methoxy-[1,1'-biphenyl]-3-ylsulfonamido)phenyl)amino)ethyl)thiophene-2-carboxamide

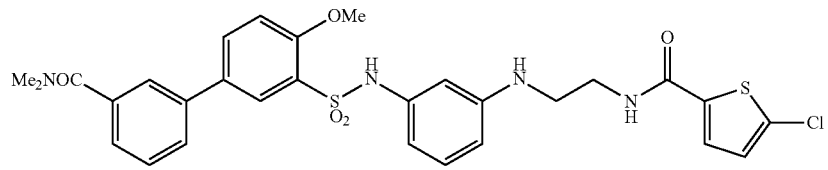

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 5-chlorothiophene-2-carboxylic acid (5.7 mg) to give 5-chloro-N-(2-((3-(3'-(dimethylcarbamoyl)-4-methoxy-[1,1'-biphenyl]-3-ylsulfonamido)phenyl)amino)ethyl)thiophene-2-carboxamide (15.8 mg). For purification, silica gel column chromatography (eluate: ethyl acetate) was used.

Example 62

3-chloro-N-(2-((3-(3'-(dimethylcarbamoyl)-4-methoxy-[1,1'-biphenyl]-3-ylsulfonamido)phenyl)amino)ethyl)thiophene-2-carboxamide

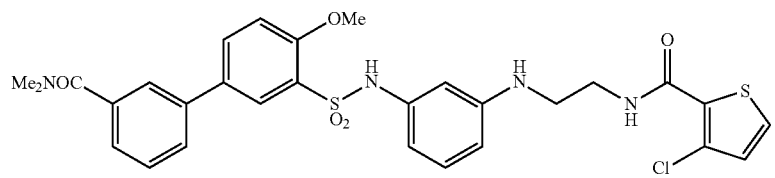

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 3-chlorothiophene-2-carboxylic acid (5.7 mg) to give 3-chloro-N-(2-((3-(3'-(dimethylcarbamoyl)-4-methoxy-[1,1'-biphenyl]-3-ylsulfonamido)phenyl)amino)ethyl)thiophene-2-carboxamide (19.7 mg). For purification, silica gel column chromatography (eluate: ethyl acetate) was used.

Example 63

N-(2-((3-(3'-(dimethylcarbamoyl)-4-methoxy-[1,1'-biphenyl]-3-ylsulfonamido)phenyl)amino)ethyl)-1-methyl-1H-imidazole-2-carboxamide

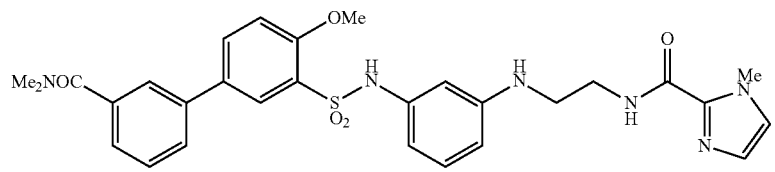

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 1-methyl-1H-imidazole-2-carboxylic acid (4.9 mg) to give N-(2-((3-(3'-(dimethylcarbamoyl)-4-methoxy-[1,1'-biphenyl]-3-ylsulfonamido)phenyl)amino)ethyl)-1-methyl-1H-imidazole-2-carboxamide (20.3 mg). For purification, preparative thin layer chromatography (eluate: ammonia-saturated chloroform/methanol=40/1) was used.

Example 64

N-(2-((3-(3'-(dimethylcarbamoyl)-4-methoxy-[1,1'-biphenyl]-3-ylsulfonamido)phenyl)amino)ethyl)-1-methyl-1H-imidazole-4-carboxamide

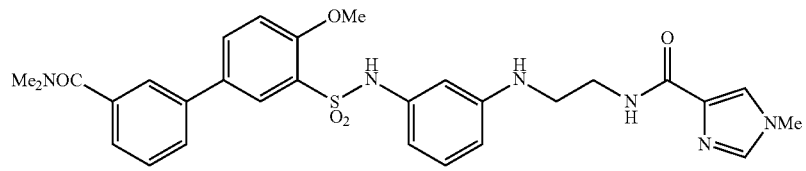

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 1-methyl-1H-imidazole-4-carboxylic acid (4.4 mg) to give N-(2-((3-(3'-(dimethylcarbamoyl)-4-methoxy-[1,1'-biphenyl]-3-ylsulfonamido)phenyl)amino)ethyl)-1-methyl-1H-imidazole-4-carboxamide (19.7 mg). For purification, preparative thin layer chromatography (eluate: ammonia-saturated chloroform/methanol=40/1) was used.

Example 65

4'-methoxy-N,N-dimethyl-3'-(N-(3-((2-(2-methyl-benzamido)ethyl)amino)phenyl)sulfamoyl)-[1,1'-biphenyl]-3-carboxamide

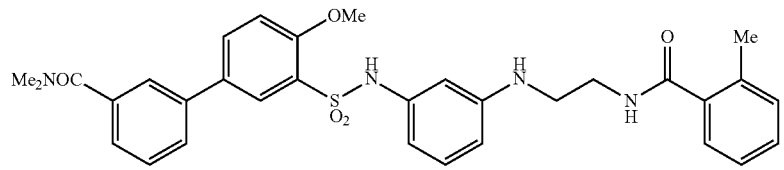

In the same manner as in Example 1, 3'-(N-(3-((2-amino-ethyl)amino)phenyl)sulfamoyl)-4'-methoxy-N,N-dimethyl-[1,1'-biphenyl]-3-carboxamide dihydrochloride (19.0 mg) was amidated with 2-toluic acid (4.8 mg) to give 4'-methoxy-N,N-dimethyl-3'-(N-(3-((2-(2-methylbenzamido)ethyl)amino)phenyl)sulfamoyl)-[1,1'-biphenyl]-3-carboxamide (20.1 mg). For purification, silica gel column chromatography (eluate: ethyl acetate) was used.

Example 66

4'-methoxy-N,N-dimethyl-3-(N-(3-((2-(3-methyl-benzamido)ethyl)amino)phenyl)sulfamoyl)-[1,1'-biphenyl]-3-carboxamide

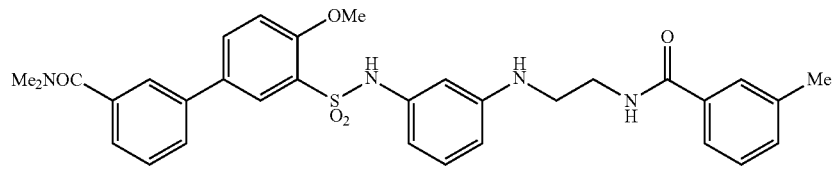

In the same manner as in Example 1, 3'-(N-(3-((2-amino-ethyl)amino)phenyl)sulfamoyl)-4'-methoxy-N,N-dimethyl-[1,1'-biphenyl]-3-carboxamide dihydrochloride (19.0 mg) was amidated with 3-toluic acid (4.8 mg) to give 4'-methoxy-N,N-dimethyl-3'-(N-(3-((2-(3-methylbenzamido)ethyl)amino)phenyl)sulfamoyl)-[1,1'-biphenyl]-3-carboxamide (15.8 mg). For purification, silica gel column chromatography (eluate: ethyl acetate) was used.

Example 67

N-(2-((3-(3'-(dimethylcarbamoyl)-4-methoxy-[1,1'-biphenyl]-3-ylsulfonamido)phenyl)amino)ethyl)-2-methylfuran-3-carboxamide

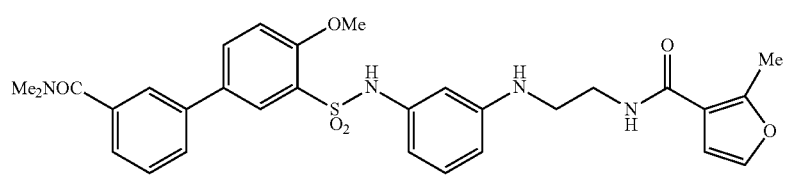

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-methylfuran-3-carboxylic acid (4.4 mg) to give N-(2-((3-(3'-(dimethylcarbamoyl)-4-methoxy-[1,1'-biphenyl]-3-ylsulfonamido)phenyl)amino)ethyl)-2-methylfuran-3-carboxamide (18.0 mg). For purification, silica gel column chromatography (eluate: ethyl acetate) was used.

Example 68

N-(2-((3-(3'-(dimethylcarbamoyl)-4-methoxy-[1,1'-biphenyl]-3-ylsulfonamido)phenyl)amino)ethyl)-3-methylfuran-2-carboxamide

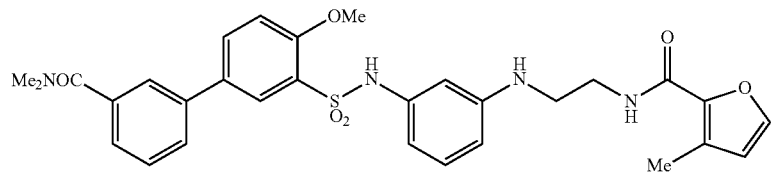

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 3-methylfuran-2-carboxylic acid (4.4 mg) to give N-(2-((3-(3'-(dimethylcarbamoyl)-4-methoxy-[1,1'-biphenyl]-3-ylsulfonamido)phenyl)amino)ethyl)-3-methylfuran-2-carboxamide (20.0 mg). For purification, silica gel column chromatography (eluate: ethyl acetate) was used.

Example 69

4'-methoxy-N,N-dimethyl-3'-(N-(3-((2-(2-(trifluoromethyl)benzamido)ethyl)amino)phenyl)sulfamoyl)-[1,1'-biphenyl]-3-carboxamide

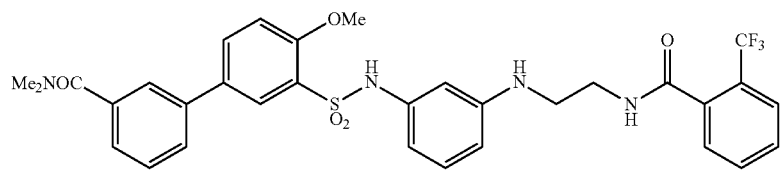

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-trifluoromethylbenzoic acid (6.7 mg) to give 4'-methoxy-N,N-dimethyl-3'-(N-(3-((2-(2-(trifluoromethyl)benzamido)ethyl)amino)phenyl)sulfamoyl)-[1,1'-biphenyl]-3-carboxamide (21.0 mg). For purification, silica gel column chromatography (eluate: ethyl acetate) was used.

Example 70

3'-(N-(3-((2-(2-fluoro-6-methoxybenzamido)ethyl)amino)phenyl)sulfamoyl)-4'-methoxy-N,N-dimethyl-[1,1'-biphenyl]-3-carboxamide

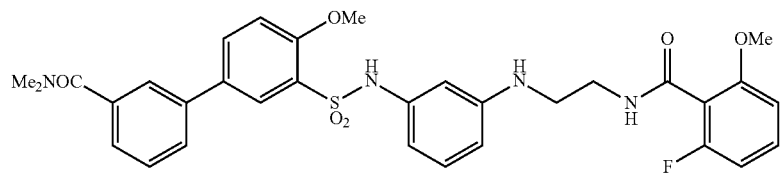

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-fluoro-6-methoxybenzoic acid (6.0 mg) to give 3'-(N-(3-((2-(2-fluoro-6-methoxybenzamido)ethyl)amino)phenyl)sulfamoyl)-4'-methoxy-N,N-dimethyl-[1,1'-biphenyl]-3-carboxamide (23.6 mg). For purification, preparative thin layer chromatography (eluate: ammonia-saturated chloroform/methanol=80/1) was used.

Example 71

3'-(N-(3-((2-(2-cyanobenzamido)ethyl)amino)phenyl)sulfamoyl)-4'-methoxy-N,N-dimethyl-[1,1'-biphenyl]-3-carboxamide

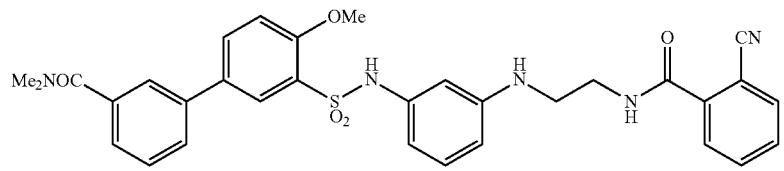

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 2-cyanobenzoic acid (5.1 mg) to give 3'-(N-(3-((2-(2-cyanobenzamido)ethyl)amino)phenyl)sulfamoyl)-4'-methoxy-N,N-dimethyl-[1,1'-biphenyl]-3-carboxamide (19.2 mg). For purification, amine silica gel column chromatography (eluate: chloroform/methanol=1/0→100/1) was used

Example 72

3'-(N-(3-((2-(3-cyanobenzamido)ethyl)amino)phenyl)sulfamoyl)-4'-methoxy-N,N-dimethyl-[1,1'-biphenyl]-3-carboxamide

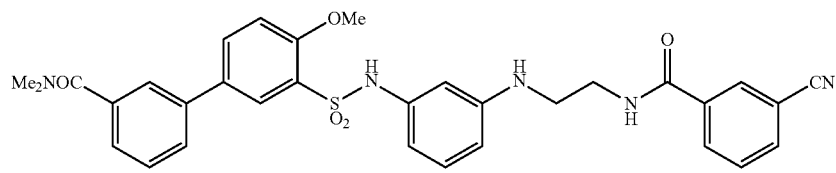

In the same manner as in Example 1, 3'-(N-(3-((2-aminoethyl)amino)phenyl)sulfamoyl)-4'-methoxy-N,N-dimethyl-[1,1'-biphenyl]-3-carboxamide dihydrochloride (19.0 mg) was amidated with 3-cyanobenzoic acid (5.1 mg) to give 3'-(N-(3-((2-(3-cyanobenzamido)ethyl)amino)phenyl)sulfamoyl)-4'-methoxy-N,N-dimethyl-[1,1'-biphenyl]-3-carboxamide (21.3 mg). For purification, preparative thin layer chromatography (eluate: ammonia-saturated chloroform/methanol=100/1) was used.

Example 73

4'-methoxy-3'-(N-(3-((2-(2-methoxybenzamido)ethyl)amino)phenyl)sulfamoyl)-N-methyl-[1,1'-biphenyl]-3-carboxamide

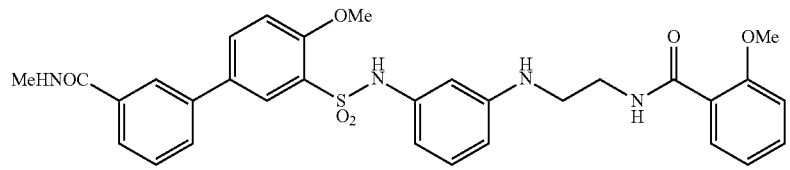

To a suspension of 4'-methoxy-3'-(N-(3-((2-(2-methoxybenzamido)ethyl)amino)phenyl)sulfamoyl)-[1,1'-biphenyl]-3-carboxylic acid (19.0 mg) in dichloromethane (2.0 mL) were added methylamine hydrochloride (7.4 mg), triethylamine (0.021 mL) and BOP reagent (17.2 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate) to give 4'-methoxy-3'-(N-(3-((2-(2-methoxybenzamido)ethyl)amino)phenyl)sulfamoyl)-N-methyl-[1,1'-biphenyl]-3-carboxamide (21.8 mg).

Example 74

N-(2-hydroxyethyl)-4'-methoxy-3'-(N-(3-((2-(2-methoxybenzamido)ethyl)amino)phenyl)sulfamoyl)-[1,1'-biphenyl]-3-carboxamide

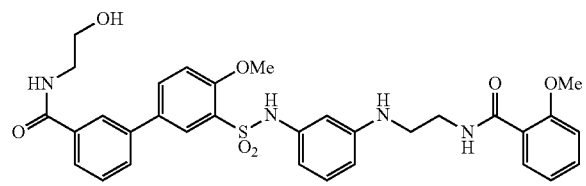 [SMILES: COc1ccccc1C(=O)NCCNc1cccc(NS(=O)(=O)c2cc(-c3cccc(C(=O)NCCO)c3)ccc2OC)c1]

In the same manner as in Example 73, 4'-methoxy-3'-(N-(3-((2-(2-methoxybenzamido)ethyl)amino)phenyl)sulfamoyl)-[1,1'-biphenyl]-3-carboxylic acid (20.1 mg) was amidated with 2-aminoethanol (0.006 mL) to give N-(2-hydroxyethyl)-4'-methoxy-3'-(N-(3-((2-(2-methoxybenzamido)ethyl)amino)phenyl)sulfamoyl)-[1,1'-biphenyl]-3-carboxamide (18.2 mg). For purification, preparative thin layer chromatography (eluate: ammonia-saturated chloroform/methanol=20/1) was used.

Example 75

2-methoxy-N-(2-((3-(4-methoxy-3'-(pyrrolidine-1-carbonyl)-1-[1,1'-biphenyl]-3-ylsulfonamide)phenyl)amino)ethyl)benzamide

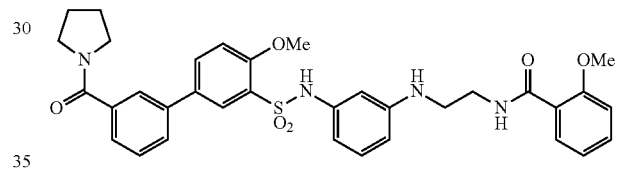

In the same manner as in Example 73, 4'-methoxy-3'-(N-(3-((2-(2-methoxybenzamido)ethyl)amino)phenyl)sulfamoyl)-[1,1'-biphenyl]-3-carboxylic acid (20.1 mg) was amidated with pyrrolidine (0.009 mL) to give 2-methoxy-N-(2-((3-(4-methoxy-3'-(pyrrolidine-1-carbonyl)-1-[1,1'-biphenyl]-3-ylsulfonamido)phenyl)amino)ethyl)benzamide (18.4 mg). For purification, preparative thin layer chromatography (eluate: ammonia-saturated chloroform/methanol=40/1) was used.

Example 76

N-(tert-butyl)-4'-methoxy-3'-(N-(3-((2-(2-methoxybenzamido)ethyl)amino)phenyl)sulfamoyl)-N-methyl-[1,1'-biphenyl]-3-carboxamide

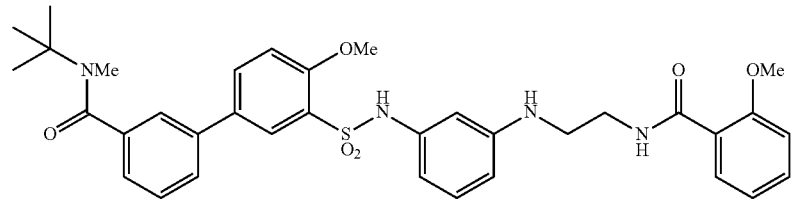 [SMILES: COc1ccccc1C(=O)NCCNc1cccc(NS(=O)(=O)c2cc(-c3cccc(C(=O)N(C)C(C)(C)C)c3)ccc2OC)c1]

In the same manner as in Example 73, 4'-methoxy-3'-(N-(3-((2-(2-methoxybenzamido)ethyl)amino)phenyl)sulfamoyl)-[1,1'-biphenyl]-3-carboxylic acid (20.1 mg) was amidated with tert-butylmethylamine (0.008 mL) to give N-(tert-butyl)-4'-methoxy-3'-(N-(3-((2-(2-methoxybenzamido)ethyl)amino)phenyl)sulfamoyl)-N-methyl-[1,1'-biphenyl]-3-carboxamide (21.6 mg). For purification, silica gel column chromatography (eluate: ethyl acetate) was used.

Example 77

4'-methoxy-3'-(N-(3-((2-(2-methoxybenzamido) ethyl)amino)phenyl)sulfamoyl)-N-(2-methoxyethyl)-N-methyl-[1,1'-biphenyl]-3-carboxamide

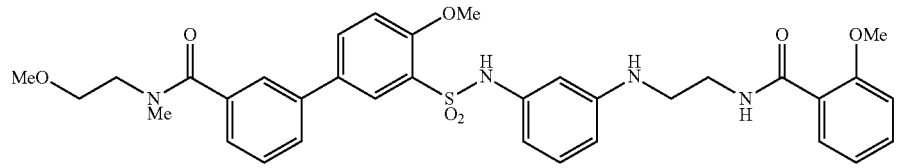 [SMILES: COCCN(C)C(=O)c1cccc(-c2ccc(OC)c(S(=O)(=O)Nc3cccc(NCCNC(=O)c4ccccc4OC)c3)c2)c1]

In the same manner as in Example 73, 4'-methoxy-3'-(N-(3-((2-(2-methoxybenzamido)ethyl)amino)phenyl)sulfamoyl)-[1,1'-biphenyl]-3-carboxylic acid (20.1 mg) was amidated with N-(2-methoxyethyl)-N-methylamine (0.004 mL) to give 4'-methoxy-3'-(N-(3-((2-(2-methoxybenzamido)ethyl)amino)phenyl)sulfamoyl)-N-(2-methoxyethyl)-N-methyl-[1,1'-biphenyl]-3-carboxamide (21.3 mg). For purification, preparative thin layer chromatography (eluate: ethyl acetate) was used.

Example 78

4'-methoxy-3'-(N-(3-((2-(2-methoxybenzamido) ethyl)amino)phenyl)sulfamoyl)-N-(2,2,2-trifluoroethyl)-[1,1'-biphenyl]-3-carboxamide

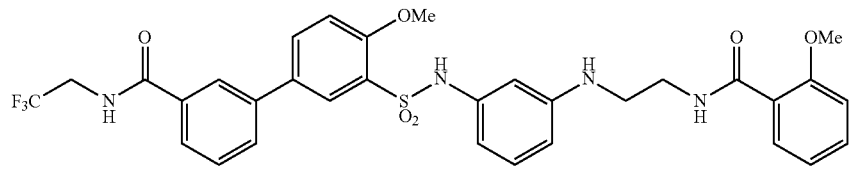 [SMILES: COc1ccccc1C(=O)NCCNc1cccc(NS(=O)(=O)c2cc(-c3cccc(C(=O)NCC(F)(F)F)c3)ccc2OC)c1]

In the same manner as in Example 73, 4'-methoxy-3'-(N-(3-((2-(2-methoxybenzamido)ethyl)amino)phenyl)sulfamoyl)-[1,1'-biphenyl]-3-carboxylic acid (22.4 mg) was amidated with 2,2,2-trifluoroethylamine hydrochloride (5.3 mg) to give 4'-methoxy-3'-(N-(3-((2-(2-methoxybenzamido)ethyl)amino)phenyl)sulfamoyl)-N-(2,2,2-trifluoroethyl)-[1,1'-biphenyl]-3-carboxamide (20.1 mg). For purification, silica gel column chromatography (eluate: ethyl acetate/hexane=3/1→1/0) was used.

Example 79

4'-methoxy-3'-(N-(3-((2-(2-methoxybenzamido) ethyl)amino)phenyl)sulfamoyl)-N,N-dimethyl-[1,1'-biphenyl]-2-carboxamide

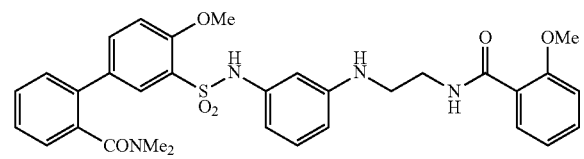

In the same manner as in Example 1, 3'-(N-(3-((2-aminoethyl)amino)phenyl)sulfamoyl)-4'-methoxy-N,N-dimethyl-[1,1'-biphenyl]-2-carboxamide dihydrochloride (19.0 mg) was amidated with o-anisic acid (5.3 mg) to give 4'-methoxy-3'-(N-(3-((2-(2-methoxybenzamido)ethyl)amino)phenyl)sulfamoyl)-N,N-dimethyl-[1,1'-biphenyl]-2-carboxamide (19.7 mg). For purification, silica gel column chromatography (eluate: ethyl acetate/hexane=3/1→1/0) was used.

Example 80

2-methoxy-N-(2-((3-(4-methoxy-3'-(piperidine-1-carbonyl)-1-[1,1'-biphenyl]-3-ylsulfonamido)phenyl)amino)ethyl)benzamide

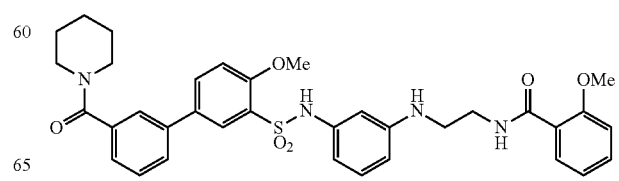

In the same manner as in Example 73, 4'-methoxy-3'-(N-(3-((2-(2-methoxybenzamido)ethyl)amino)phenyl)sulfamoyl)-[1,1'-biphenyl]-3-carboxylic acid (20.7 mg) was amidated with piperidine (0.004 mL) to give 2-methoxy-N-(2-((3-(4-methoxy-3'-(piperidine-1-carbonyl)-1-[1,1'-biphenyl]-3-ylsulfonamido)phenyl)amino)ethyl)benzamide (14.0 mg). For purification, silica gel column chromatography (eluate: ethyl acetate) was used.

Example 81

N-(2-((3-(3'-(azetidine-1-carbonyl)-4-methoxy-[1,1'-biphenyl]-3-ylsulfonamido)phenyl)amino)ethyl)-2-methoxybenzamide

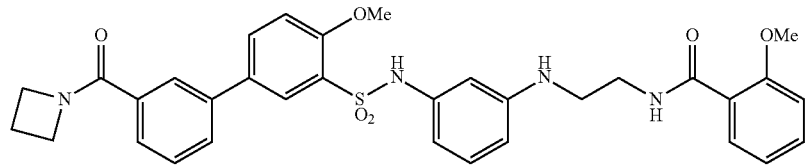 [SMILES: COc1ccccc1C(=O)NCCNc1cccc(NS(=O)(=O)c2cc(-c3cccc(C(=O)N4CCC4)c3)ccc2OC)c1]

In the same manner as in Example 73, 4'-methoxy-3'-(N-(3-((2-(2-methoxybenzamido)ethyl)amino)phenyl)sulfamoyl)-[1,1'-biphenyl]-3-carboxylic acid (20.7 mg) was amidated with azetidine hydrochloride (3.4 mg) to give N-(2-((3-(3'-(azetidine-1-carbonyl)-4-methoxy-[1,1'-biphenyl]-3-ylsulfonamido)phenyl)amino)ethyl)-2-methoxybenzamide (12.0 mg). For purification, preparative thin layer chromatography (eluate: ammonia-saturated chloroform/methanol=40/1) was used.

Example 82

N-(2-((3-(3'-(azetidine-1-carbonyl)-4-methoxy-[1,1'-biphenyl]-3-ylsulfonamido)phenyl)amino)ethyl)-2-chlorobenzamide

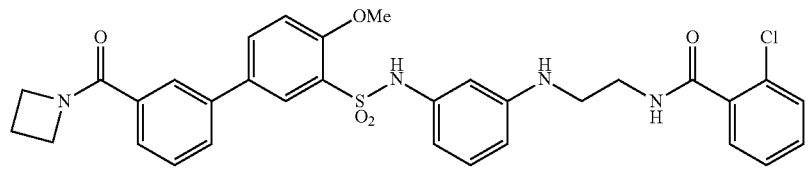 [SMILES: COc1ccc(-c2cccc(C(=O)N3CCC3)c2)cc1S(=O)(=O)Nc1cccc(NCCNC(=O)c2ccccc2Cl)c1]

In the same manner as in Example 1, N-(3-((2-aminoethyl)amino)phenyl)-3'-(azetidine-1-carbonyl)-4-methoxy-[1,1'-biphenyl]-3-sulfonamide dihydrochloride (19.4 mg) was amidated with 2-chlorobenzoic acid (5.5 mg) to give N-(2-((3-(3'-(azetidine-1-carbonyl)-4-methoxy-[1,1'-biphenyl]-3-ylsulfonamido)phenyl)amino)ethyl)-2-chlorobenzamide (13.2 mg). For purification, silica gel column chromatography (eluate: ethyl acetate/hexane=3/1-4/1) was used.

Example 83

N-(2-((3-(3'-(azetidine-1-carbonyl)-4-methoxy-[1,1'-biphenyl]-3-ylsulfonamido)phenyl)amino)ethyl)-6-methoxypicolinamide

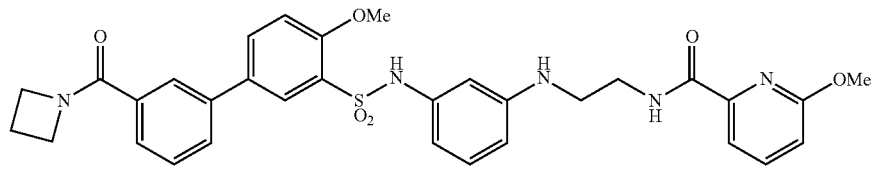 [SMILES: COc1cccc(C(=O)NCCNc2cccc(NS(=O)(=O)c3cc(-c4cccc(C(=O)N5CCC5)c4)ccc3OC)c2)n1]

In the same manner as in Example 1, N-(3-((2-aminoethyl)amino)phenyl)-3'-(azetidine-1-carbonyl)-4-methoxy-[1,1'-biphenyl]-3-sulfonamide dihydrochloride (19.4 mg) was amidated with 6-methoxypyridine-2-carboxylic acid (5.4 mg) to give N-(2-((3-(3'-(azetidine-1-carbonyl)-4-methoxy-[1,1'-biphenyl]-3-ylsulfonamido)phenyl)amino)ethyl)-6-methoxypicolinamide (16.1 mg). For purification, silica gel column chromatography (eluate: ethyl acetate/hexane=4/1) was used.

Example 84

N-(2-((3-(3'-(azetidine-1-carbonyl)-4-methoxy-[1,1'-biphenyl]-3-ylsulfonamido)phenyl)amino)ethyl)-3-fluorobenzamide

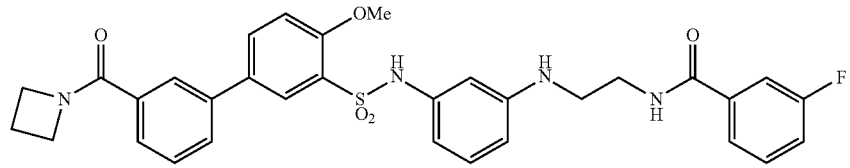 [SMILES: COc1ccc(-c2cccc(C(=O)N3CCC3)c2)cc1S(=O)(=O)Nc1cccc(NCCNC(=O)c2cccc(F)c2)c1]

In the same manner as in Example 1, N-(3-((2-aminoethyl)amino)phenyl)-3'-(azetidine-1-carbonyl)-4-methoxy-[1,1'-biphenyl]-3-sulfonamide dihydrochloride (19.4 mg) was amidated with 3-fluorobenzoic acid (4.9 mg) to give N-(2-((3-(3'-(azetidine-1-carbonyl)-4-methoxy-[1,1'-biphenyl]-3-ylsulfonamido)phenyl)amino)ethyl)-3-fluorobenzamide (15.0 mg). For purification, silica gel column chromatography (eluate: ethyl acetate/hexane=3/1→1/0) was used.

Example 85

N-(2-((3-(3'-(azetidine-1-carbonyl)-4-methoxy-[1,1'-biphenyl]-3-ylsulfonamido)phenyl)amino)ethyl)-2,6-dimethoxybenzamide

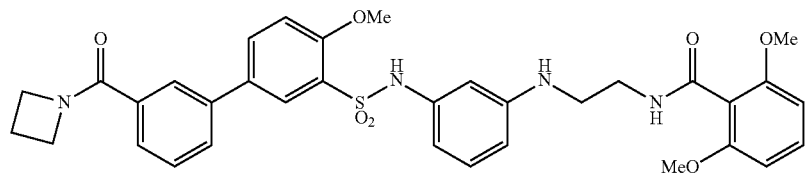 [SMILES: COc1ccc(-c2cccc(C(=O)N3CCC3)c2)cc1S(=O)(=O)Nc1cccc(NCCNC(=O)c2c(OC)cccc2OC)c1]

In the same manner as in Example 1, N-(3-((2-aminoethyl)amino)phenyl)-3'-(azetidine-1-carbonyl)-4-methoxy-[1,1'-biphenyl]-3-sulfonamide dihydrochloride (19.4 mg) was amidated with 2,6-dimethoxybenzoic acid (6.4 mg) to give N-(2-((3-(3'-(azetidine-1-carbonyl)-4-methoxy-[1,1'-biphenyl]-3-ylsulfonamido)phenyl)amino)ethyl)-2,6-dimethoxybenzamide (15.2 mg). For purification, silica gel column chromatography (eluate: ethyl acetate) was used.

Example 86

3-methoxy-N-(2-((3-(4-methoxy-3'-(pyrrolidine-1-carbonyl)-[1,1'-biphenyl]-3-ylsulfonamido)phenyl)amino)ethyl)benzamide

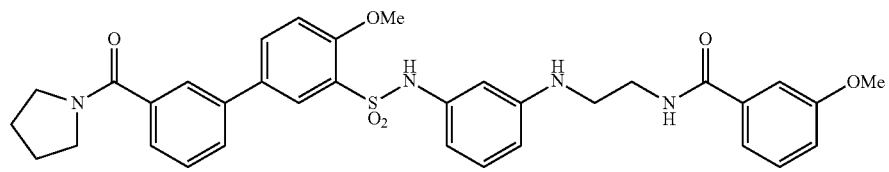 [SMILES: COc1cccc(C(=O)NCCNc2cccc(NS(=O)(=O)c3cc(-c4cccc(C(=O)N5CCCC5)c4)ccc3OC)c2)c1]

In the same manner as in Example 1, N-(3-((2-aminoethyl)amino)phenyl)-4-methoxy-3'-(pyrrolidine-1-carbonyl)-[1,1'-biphenyl]-3-sulfonamide dihydrochloride (19.9 mg) was amidated with m-anisic acid (5.3 mg) to give 3-methoxy-N-(2-((3-(4-methoxy-3'-(pyrrolidine-1-carbonyl)-[1,1'-biphenyl]-3-ylsulfonamido)phenyl)amino)ethyl)benzamide (16.3 mg). For purification, silica gel column chromatography (eluate: ethyl acetate/hexane=3/1→1/0) was used.

Example 87

2-chloro-N-(2-((3-(4-methoxy-3'-(pyrrolidine-1-carbonyl)-[1,1'-biphenyl]-3-ylsulfonamido)phenyl)amino)ethyl)benzamide

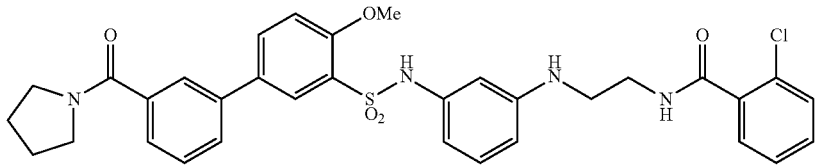 [SMILES: COc1ccc(-c2cccc(C(=O)N3CCCC3)c2)cc1S(=O)(=O)Nc1cccc(NCCNC(=O)c2ccccc2Cl)c1]

In the same manner as in Example 1, N-(3-((2-aminoethyl)amino)phenyl)-4-methoxy-3'-(pyrrolidine-1-carbonyl)-[1,1'-biphenyl]-3-sulfonamide dihydrochloride (19.9 mg) was amidated with 2-chlorobenzoic acid (5.5 mg) to give 2-chloro-N-(2-((3-(4-methoxy-3'-(pyrrolidine-1-carbonyl)-[1,1'-biphenyl]-3-ylsulfonamido)phenyl)amino)ethyl)benzamide (16.7 mg). For purification, silica gel column chromatography (eluate: ethyl acetate) was used.

Example 88

2,6-difluoro-N-(2-((3-(4-methoxy-3'-(pyrrolidine-1-carbonyl)-[1,1'-biphenyl]-3-ylsulfonamido)phenyl)amino)ethyl)benzamide

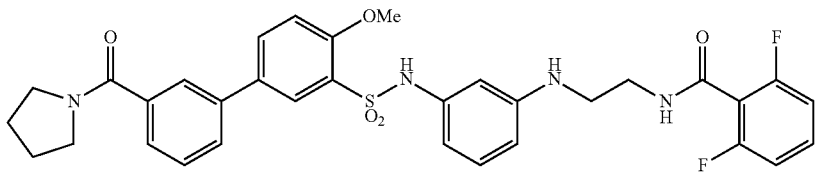 [SMILES: COc1ccc(-c2cccc(C(=O)N3CCCC3)c2)cc1S(=O)(=O)Nc1cccc(NCCNC(=O)c2c(F)cccc2F)c1]

In the same manner as in Example 1, N-(3-((2-aminoethyl)amino)phenyl)-4-methoxy-3'-(pyrrolidine-1-carbonyl)-[1,1'-biphenyl]-3-sulfonamide dihydrochloride (19.9 mg) was amidated with 2,6-difluorobenzoic acid (5.5 mg) to give 2,6-difluoro-N-(2-((3-(4-methoxy-3'-(pyrrolidine-1-carbonyl)-[1,1'-biphenyl]-3-ylsulfonamido)phenyl)amino)ethyl)benzamide (16.8 mg). For purification, silica gel column chromatography (eluate: ethyl acetate) was used.

Example 89

3-chloro-N-(2-((3-(4-methoxy-3'-(pyrrolidine-1-carbonyl)-[1,1'-biphenyl]-3-ylsulfonamido)phenyl)amino)ethyl)thiophene-2-carboxamide

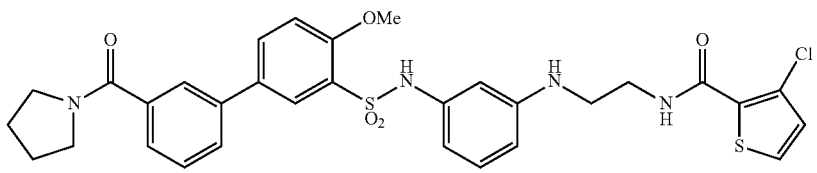 [SMILES: COc1ccc(-c2cccc(C(=O)N3CCCC3)c2)cc1S(=O)(=O)Nc1cccc(NCCNC(=O)c2sccc2Cl)c1]

In the same manner as in Example 1, N-(3-((2-aminoethyl)amino)phenyl)-4-methoxy-3'-(pyrrolidine-1-carbonyl)-[1,1'-biphenyl]-3-sulfonamide dihydrochloride (19.9 mg) was amidated with 3-chlorothiophene-2-carboxylic acid (5.7 mg) to give 3-chloro-N-(2-((3-(4-methoxy-3'-(pyrrolidine-1-carbonyl)-[1,1'-biphenyl]-3-ylsulfonamido)phenyl)amino)ethyl)thiophene-2-carboxamide (15.9 mg). For purification, silica gel column chromatography (eluate: ethyl acetate) was used.

Example 90

2-fluoro-N-(2-((3-(4-methoxy-3'-(piperidine-1-carbonyl)-[1,1'-biphenyl]-3-ylsulfonamido)phenyl)amino)ethyl)benzamide

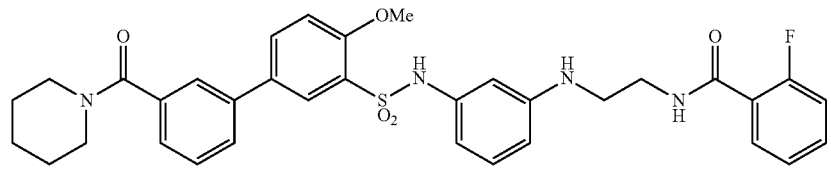 [SMILES: COc1ccc(-c2cccc(C(=O)N3CCCCC3)c2)cc1S(=O)(=O)Nc1cccc(NCCNC(=O)c2ccccc2F)c1]

In the same manner as in Example 1, N-(3-((2-aminoethyl)amino)phenyl)-4-methoxy-3'-(piperidine-1-carbonyl)-[1,1'-biphenyl]-3-sulfonamide dihydrochloride (20.4 mg) was amidated with 2-fluorobenzoic acid (4.9 mg) to give 2-fluoro-N-(2-((3-(4-methoxy-3'-(piperidine-1-carbonyl)-[1,1'-biphenyl]-3-ylsulfonamido)phenyl)amino)ethyl)benzamide (14.4 mg). For purification, silica gel column chromatography (eluate: ethyl acetate/hexane=3/1→1/0) was used.

Example 91

2-methoxy-N-(2-((3-(4-methoxy-3'-(piperidine-1-carbonyl)-[1,1'-biphenyl]-3-ylsulfonamido)phenyl)amino)ethyl)nicotinamide

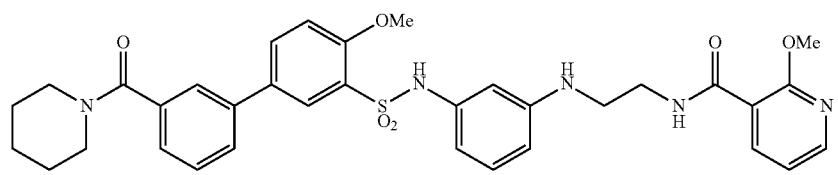 [SMILES: COc1ccc(-c2cccc(C(=O)N3CCCCC3)c2)cc1S(=O)(=O)Nc1cccc(NCCNC(=O)c2cccnc2OC)c1]

In the same manner as in Example 1, N-(3-((2-aminoethyl)amino)phenyl)-4-methoxy-3'-(piperidine-1-carbonyl)-[1,1'-biphenyl]-3-sulfonamide dihydrochloride (20.4 mg) was amidated with 2-methoxypyridine-3-carboxylic acid (5.4 mg) to give 2-methoxy-N-(2-((3-(4-methoxy-3'-(piperidine-1-carbonyl)-[1,1'-biphenyl]-3-ylsulfonamido)phenyl)amino)ethyl)nicotinamide (16.7 mg). For purification, silica gel column chromatography (eluate: ethyl acetate) was used.

Example 92

3-fluoro-N-(2-((3-(4-methoxy-3'-(piperidine-1-carbonyl)-[1,1'-biphenyl]-3-ylsulfonamido)phenyl)amino)ethyl)benzamide

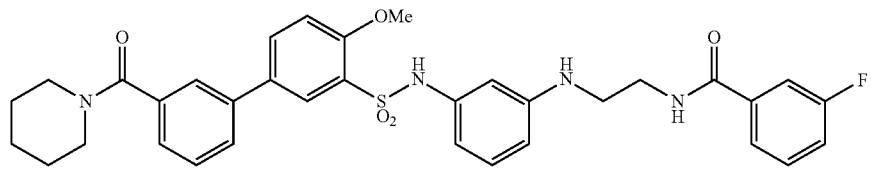 [SMILES: COc1ccc(-c2cccc(C(=O)N3CCCCC3)c2)cc1S(=O)(=O)Nc1cccc(NCCNC(=O)c2cccc(F)c2)c1]

In the same manner as in Example 1, N-(3-((2-aminoethyl)amino)phenyl)-4-methoxy-3'-(piperidine-1-carbonyl)-[1,1'-biphenyl]-3-sulfonamide dihydrochloride (20.4 mg) was amidated with 3-fluorobenzoic acid (4.9 mg) to give 3-fluoro-N-(2-((3-(4-methoxy-3'-(piperidine-1-carbonyl)-[1,1'-biphenyl]-3-ylsulfonamido)phenyl)amino)ethyl)benzamide (17.4 mg). For purification, silica gel column chromatography (eluate: ethyl acetate/hexane-3/1→1/0) was used.

In the same manner as in Example 1, N-(3-((2-aminoethyl)amino)phenyl)-2-methoxy-5-(6-methoxypyridin-2-yl)benzenesulfonamide (27.0 mg) was amidated with o-anisic acid (9.6 mg) to give 2-methoxy-N-(2-((3-(2-methoxy-5-(6-methoxypyridin-2-yl)phenylsulfonamido)phenyl)amino)ethyl)benzamide (28.4 mg). For purification, silica gel column chromatography (eluate: ethyl acetate/hexane=3/1) was used.

Example 93

N-(2-((3-(5-(3-fluoropyridin-2-yl)-2-methoxyphenylsulfonamido)phenyl)amino)ethyl)-3-methoxybenzamide

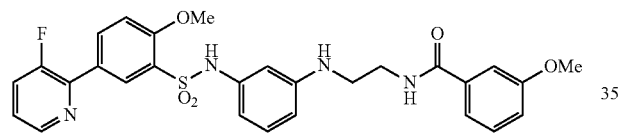

Example 95

3-methoxy-N-(2-((3-(2-methoxy-5-(6-methoxypyridin-2-yl)phenylsulfonamido)phenyl)amino)ethyl)benzamide

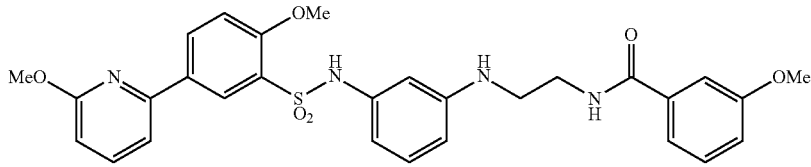

In the same manner as in Example 1, N-(3-((2-aminoethyl)amino)phenyl)-5-(3-fluoropyridin-2-yl)-2-methoxybenzenesulfonamide trihydrochloride (16.7 mg) was amidated with m-anisic acid (5.5 mg) to give N-(2-((3-(5-(3-fluoropyridin-2-yl)-2-methoxyphenylsulfonamido)phenyl)amino)ethyl)-3-methoxybenzamide (12.2 mg). For purification, silica gel column chromatography (eluate: ethyl acetate/hexane=3/1→1/0) was used.

In the same manner as in Example 1, N-(3-((2-aminoethyl)amino)phenyl)-2-methoxy-5-(6-methoxypyridin-2-yl)benzenesulfonamide (27.0 mg) was amidated with m-anisic acid (9.6 mg) to give 3-methoxy-N-(2-((3-(2-methoxy-5-(6-methoxypyridin-2-yl)phenylsulfonamido)phenyl)amino)ethyl)benzamide (32.3 mg). For purification, silica gel column chromatography (eluate: ethyl acetate/hexane=1/1→3/1) was used.

Example 94

2-methoxy-N-(2-((3-(2-methoxy-5-(6-methoxypyridin-2-yl)phenylsulfonamido)phenyl)amino)ethyl)benzamide

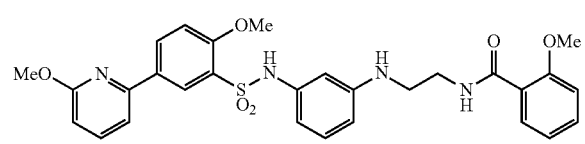 [SMILES: COc1cccc(-c2ccc(OC)c(S(=O)(=O)Nc3cccc(NCCNC(=O)c4ccccc4OC)c3)c2)n1]

Example 96

2-methoxy-N-(2-((3-(2-methoxy-5-(pyridin-3-yl)phenylsulfonamido)phenyl)amino)ethyl)benzamide

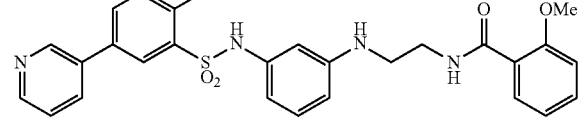

In the same manner as in Example 1, N-(3-((2-aminoethyl)amino)phenyl)-2-methoxy-5-(pyridin-3-yl)benzenesulfonamide (14.0 mg) was amidated with o-anisic acid (5.3 mg) to give 2-methoxy-N-(2-((3-(2-methoxy-5-(pyridin-3-yl)phenylsulfonamido)phenyl)amino)ethyl)benzamide (13.5 mg). For purification, silica gel column chromatography (eluate: ethyl acetate/chloroform=9/1) was used.

Example 97

2-methoxy-N-(2-((3-(2-methoxy-5-(5-methoxypyridin-3-yl)phenylsulfonamido)phenyl)amino)ethyl)benzamide

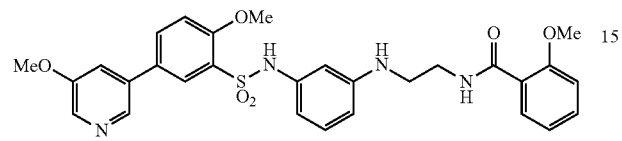

In the same manner as in Example 1, N-(3-((2-aminoethyl)amino)phenyl)-2-methoxy-5-(5-methoxypyridin-3-yl)benzenesulfonamide (17.0 mg) was amidated with o-anisic acid (6.1 mg) to give 2-methoxy-N-(2-((3-(2-methoxy-5-(5-methoxypyridin-3-yl)phenylsulfonamido)phenyl)amino)ethyl)benzamide (19.0 mg). For purification, silica gel column chromatography (eluate: ethyl acetate) was used.

Example 98

3-methoxy-N-(2-((3-(2-methoxy-5-(5-methoxypyridin-3-yl)phenylsulfonamido)phenyl)amino)ethyl)benzamide

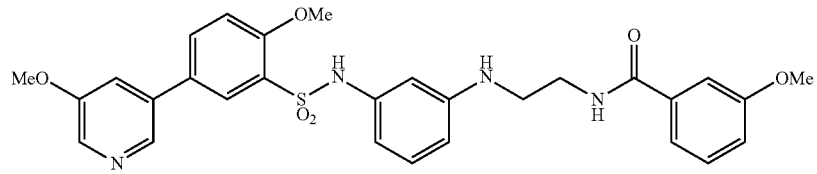 [SMILES: COc1cccc(C(=O)NCCNc2cccc(NS(=O)(=O)c3cc(-c4cncc(OC)c4)ccc3OC)c2)c1]

In the same manner as in Example 1, N-(3-((2-aminoethyl)amino)phenyl)-2-methoxy-5-(5-methoxypyridin-3-yl)benzenesulfonamide (17.0 mg) was amidated with m-anisic acid (6.1 mg) to give 3-methoxy-N-(2-((3-(2-methoxy-5-(5-methoxypyridin-3-yl)phenylsulfonamido)phenyl)amino)ethyl)benzamide (18.3 mg). For purification, silica gel column chromatography (eluate: ethyl acetate) was used.

Example 99

4'-methoxy-5'-(N-(3-((2-(2-methoxybenzamido)ethyl)amino)phenyl)sulfamoyl)-N,N,2'-trimethyl-[1,1'-biphenyl]-3-carboxamide

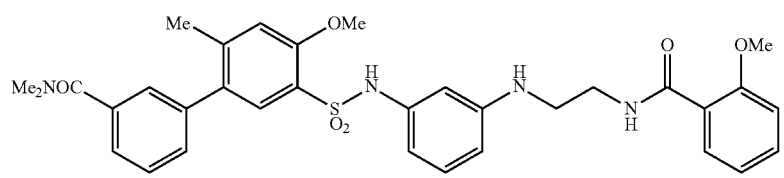

In the same manner as in Example 1, 5'-(N-(3-((2-amino-ethyl)amino)phenyl)sulfamoyl)-4'-methoxy-N,N,2'-trimethyl-[1,1'-biphenyl]-3-carboxamide dihydrochloride (19.4 mg) was amidated with o-anisic acid (5.3 mg) to give 4'-methoxy-5'-(N-(3-((2-(2-methoxybenzamido)ethyl)amino)phenyl)sulfamoyl)-N,N,2'-trimethyl-[1,1'-biphenyl]-3-carboxamide (9.3 mg). For purification, silica gel column chromatography (eluate: ethyl acetate) was used.

Example 100

4'-methoxy-5'-(N-(3-((2-(3-methoxybenzamido)ethyl)amino)phenyl)sulfamoyl)-N,N,2'-trimethyl-[1,1'-biphenyl]-3-carboxamide

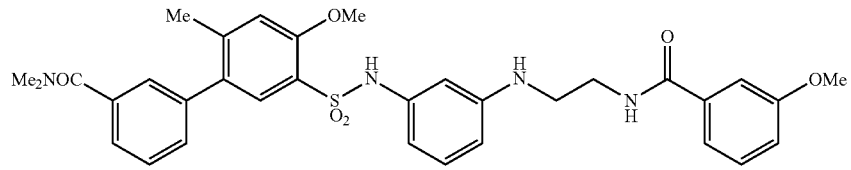

In the same manner as in Example 1, 5'-(N-(3-((2-amino-ethyl)amino)phenyl)sulfamoyl)-4'-methoxy-N,N,2'-trimethyl-[1,1'-biphenyl]-3-carboxamide dihydrochloride (27.0 mg) was amidated with m-anisic acid (7.5 mg) to give 4'-methoxy-5'-(N-(3-((2-(3-methoxybenzamido)ethyl)amino)phenyl)sulfamoyl)-N,N,2'-trimethyl-[1,1'-biphenyl]-3-carboxamide (19.5 mg). For purification, silica gel column chromatography (eluate: ethyl acetate) was used.

Example 101

4'-methoxy-N,N,2'-trimethyl-5'-(N-(3-((2-(3-methylbenzamido)ethyl)amino)phenyl)sulfamoyl)-[1,1'-biphenyl]-3-carboxamide

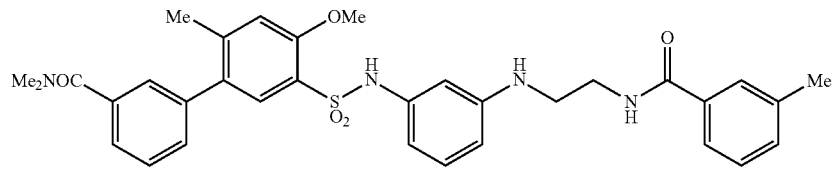

In the same manner as in Example 1, 5'-(N-(3-((2-amino-ethyl)amino)phenyl)sulfamoyl)-4'-methoxy-N,N,2'-trimethyl-[1,1'-biphenyl]-3-carboxamide dihydrochloride (19.4 mg) was amidated with 3-toluic acid (4.8 mg) to give 4'-methoxy-N,N,2'-trimethyl-5'-(N-(3-((2-(3-methylbenzamido)ethyl)amino)phenyl)sulfamoyl)-[1,1'-biphenyl]-3-carboxamide (16.6 mg). For purification, silica gel column chromatography (eluate: ethyl acetate) was used.

Example 102

5'-(N-(3-((2-(3-fluorobenzamido)ethyl)amino)phenyl)sulfamoyl)-4'-methoxy-N,N,2'-trimethyl-[1,1'-biphenyl]-3-carboxamide

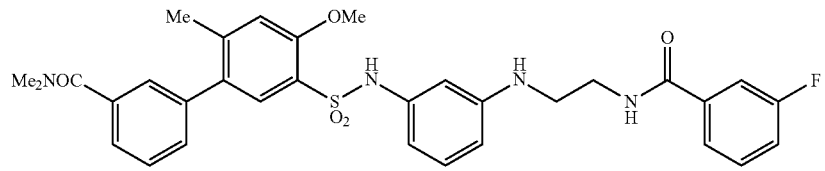

In the same manner as in Example 1, 5'-(N-(3-((2-aminoethyl)amino)phenyl)sulfamoyl)-4'-methoxy-N,N,2'-trimethyl-[1,1'-biphenyl]-3-carboxamide dihydrochloride (19.4 mg) was amidated with 3-fluorobenzoic acid (4.9 mg) to give 5'-(N-(3-((2-(3-fluorobenzamido)ethyl)amino)phenyl)sulfamoyl)-4'-methoxy-N,N,2'-trimethyl-[1,1'-biphenyl]-3-carboxamide (22.0 mg). For purification, silica gel column chromatography (eluate: ethyl acetate) was used.

Example 103

N-(2-((3-(3'-(dimethylcarbamoyl)-4-methoxy-6-methyl-[1,1'-biphenyl]-3-ylsulfonamido)phenyl)amino)ethyl)-2-methoxynicotinamide

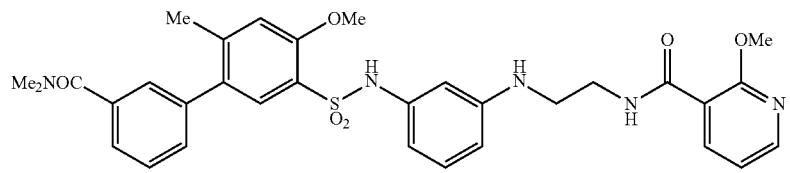

In the same manner as in Example 1, 5'-(N-(3-((2-aminoethyl)amino)phenyl)sulfamoyl)-4'-methoxy-N,N,2'-trimethyl-[1,1'-biphenyl]-3-carboxamide dihydrochloride (19.4 mg) was amidated with 2-methoxypyridine-3-carboxylic acid (5.4 mg) to give N-(2-((3-(3'-(dimethylcarbamoyl)-4-methoxy-6-methyl-[1,1'-biphenyl]-3-ylsulfonamido)phenyl)amino)ethyl)-2-methoxynicotinamide (21.1 mg). For purification, amine silica gel column chromatography (eluate: chloroform/ethyl acetate=1/1) was used.

Example 104

5'-(N-(3-((2-(2-chlorobenzamido)ethyl)amino)phenyl)sulfamoyl)-4'-methoxy-N,N,2'-trimethyl-[1,1'-biphenyl]-3-carboxamide

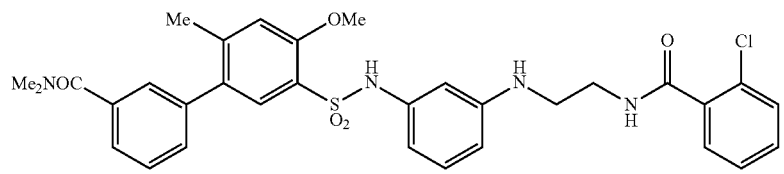

In the same manner as in Example 1, 5'-(N-(3-((2-aminoethyl)amino)phenyl)sulfamoyl)-4'-methoxy-N,N,2'-trimethyl-[1,1'-biphenyl]-3-carboxamide dihydrochloride (19.4 mg) was amidated with 2-chlorobenzoic acid (5.5 mg) to give 5'-(N-(3-((2-(2-chlorobenzamido)ethyl)amino)phenyl)sulfamoyl)-4'-methoxy-N,N,2'-trimethyl-[1,1'-biphenyl]-3-carboxamide (17.4 mg). For purification, silica gel column chromatography (eluate: ethyl acetate) was used.

Example 105

3-chloro-N-(2-((3-(3'-(dimethylcarbamoyl)-4-methoxy-6-methyl-[1,1'-biphenyl]-3-ylsulfonamido)phenyl)amino)ethyl)thiophene-2-carboxamide

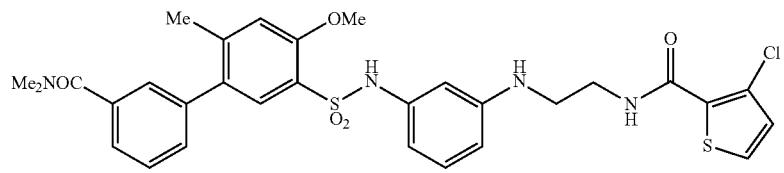

In the same manner as in Example 1, 5'-(N-(3-((2-aminoethyl)amino)phenyl)sulfamoyl)-4'-methoxy-N,N,2'-trimethyl-[1,1'-biphenyl]-3-carboxamide dihydrochloride (19.4 mg) was amidated with 3-chlorothiophene-2-carboxylic acid (5.7 mg) to give 3-chloro-N-(2-((3-(3'-(dimethylcarbamoyl)-4-methoxy-6-methyl-[1,1'-biphenyl]-3-ylsulfonamido)phenyl)amino)ethyl)thiophene-2-carboxamide (20.4 mg). For purification, silica gel column chromatography (eluate: ethyl acetate) was used.

Example 106

3'-(N-(3-((2-(2-methoxybenzamido)ethyl)amino)phenyl)sulfamoyl)-N,N,4'-trimethyl-[1,1'-biphenyl]-3-carboxamide

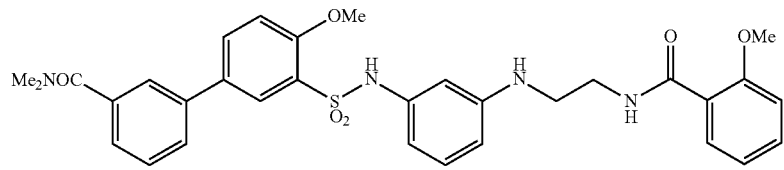

In the same manner as in Example 1, 3'-(N-(3-((2-aminoethyl)amino)phenyl)sulfamoyl)-N,N,4'-trimethyl-[1,1'-biphenyl]-3-carboxamide dihydrochloride (18.4 mg) was amidated with o-anisic acid (5.3 mg) to give 3'-(N-(3-((2-(2-methoxybenzamido)ethyl)amino)phenyl)sulfamoyl)-N,N,4'-trimethyl-[1,1'-biphenyl]-3-carboxamide (20.3 mg). For purification, silica gel column chromatography (eluate: ethyl acetate) was used.

Example 107

4'-fluoro-3'-(N-(3-((2-(2-methoxybenzamido)ethyl)amino)phenyl)sulfamoyl)-N,N-dimethyl-[1,1'-biphenyl]-3-carboxamide

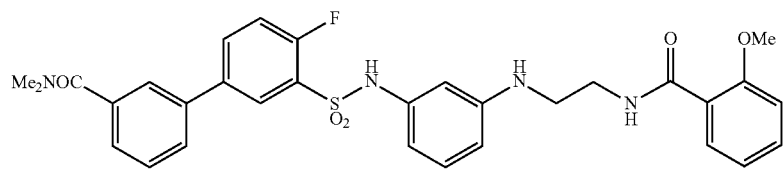

In the same manner as in Example 1, 3'-(N-(3-((2-amino-ethyl)amino)phenyl)sulfamoyl)-4'-fluoro-N,N-dimethyl-[1,1'-biphenyl]-3-carboxamide dihydrochloride (18.5 mg) was amidated with o-anisic acid (5.3 mg) to give 4'-fluoro-3'-(N-(3-((2-(2-methoxybenzamido)ethyl)amino)phenyl)sulfamoyl)-N,N-dimethyl-[1,1'-biphenyl]-3-carboxamide (20.1 mg). For purification, silica gel column chromatography (eluate: ethyl acetate) was used.

Example 108

4'-ethoxy-3'-(N-(3-((2-(2-methoxybenzamido)ethyl)amino)phenyl)sulfamoyl)-N,N-dimethyl-[1,1'-biphenyl]-3-carboxamide

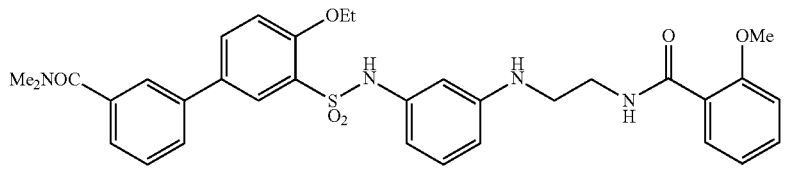

In the same manner as in Example 1, 3'-(N-(3-((2-amino-ethyl)amino)phenyl)sulfamoyl)-4'-ethoxy-N,N-dimethyl-[1,1'-biphenyl]-3-carboxamide dihydrochloride (19.4 mg) was amidated with o-anisic acid (5.3 mg) to give 4'-ethoxy-3'-(N-(3-((2-(2-methoxybenzamido)ethyl)amino)phenyl)sulfamoyl)-N,N-dimethyl-[1,1'-biphenyl]-3-carboxamide (15.5 mg). For purification, silica gel column chromatography (eluate: ethyl acetate) was used.

Example 109

N-(2-((3-(3'-fluoro-4-methoxy-[1,1'-biphenyl]-3-ylsulfonamido)phenyl)amino)ethyl)-2-methoxybenzamide

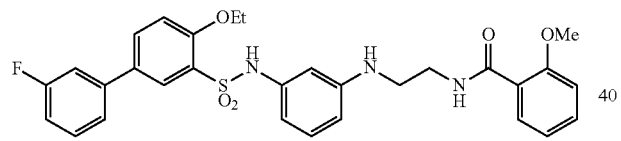

In the same manner as in Example 1, N-(3-((2-amino-ethyl)amino)phenyl)-3'-fluoro-4-methoxy-[1,1'-biphenyl]-3-sulfonamide dihydrochloride (26.9 mg) was amidated with o-anisic acid (8.4 mg) to give N-(2-((3-(3'-fluoro-4-methoxy-[1,1'-biphenyl]-3-ylsulfonamido)phenyl)amino)ethyl)-2-methoxybenzamide (13.0 mg). For purification, silica gel column chromatography (eluate: ammonia-saturated chloroform) was used.

Example 110

3'-(N-(3-((2-(2-methoxybenzamido)ethyl)amino)phenyl)sulfamoyl)-N,N-dimethyl-[1,1'-biphenyl]-3-carboxamide

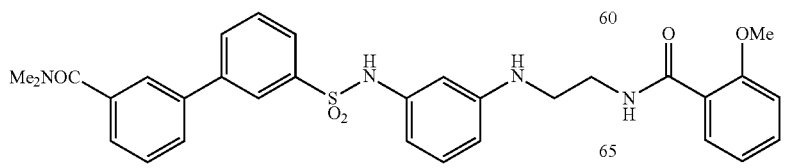

In the same manner as in Example 1, 3'-(N-(3-((2-amino-ethyl)amino)phenyl)sulfamoyl)-N,N-dimethyl-[1,1'-biphenyl]-3-carboxamide dihydrochloride (17.9 mg) was amidated with o-anisic acid (5.3 mg) to give 3'-(N-(3-((2-(2-methoxybenzamido)ethyl)amino)phenyl)sulfamoyl)-N,N-dimethyl-[1,1'-biphenyl]-3-carboxamide (16.9 mg). For purification, silica gel column chromatography (eluate: ethyl acetate) was used.

Example 111

4'-methoxy-3'-(N-(3-((2-(2-methoxy-N-methylbenzamido)ethyl)amino)phenyl)sulfamoyl)-N,N-dimethyl-[1,1'-biphenyl]-3-carboxamide

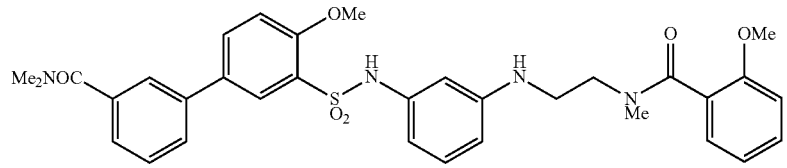

In the same manner as in Example 1, 4'-methoxy-N,N-dimethyl-3'-(N-(3-((2-methylamino)ethyl)amino)phenyl)sulfamoyl)-[1,1'-biphenyl]-3-carboxamide dihydrochloride (19.4 mg) was amidated with o-anisic acid (5.3 mg) to give 4'-methoxy-3'-(N-(3-((2-(2-methoxy-N-methylbenzamido)ethyl)amino)phenyl)sulfamoyl)-N,N-dimethyl-[1,1'-biphenyl]-3-carboxamide (19.3 mg). For purification, preparative thin layer chromatography (eluate: ammonia-saturated chloroform/methanol=50/1) was used.

Example 112

4'-methoxy-3'-(N-(3-((2-(2-methoxybenzamido)ethyl)(methyl)amino)phenyl)sulfamoyl)-N,N-dimethyl-[1,1'-biphenyl]-3-carboxamide

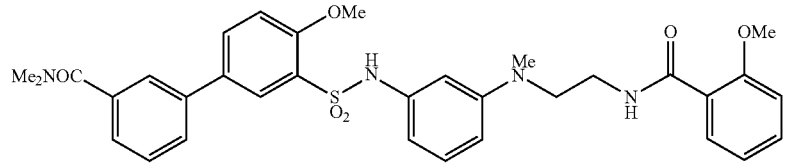

To a solution of 4'-methoxy-3'-(N-(3-((2-(2-methoxybenzamido)ethyl)amino)phenyl)sulfamoyl)-N,N-dimethyl-[1,1'-biphenyl]-3-carboxamide (17.2 mg) in acetonitrile (1.0 mL) were added 37% formalin aqueous solution (0.035 mL), acetic acid (0.007 mL) and sodium cyanoborohydride (8.2 mg), and the mixture was stirred at room temperature for 2 days. To this reaction mixture was added saturated aqueous sodium hydrogen carbonate solution, and the mixture was extracted m with chloroform. The organic layer was dried over sodium sulfate, filtered, and the filtrate was concentrated. The obtained residue was purified by preparative thin layer chromatography (eluate: ammonia-saturated chloroform/methanol=80/1) to give 4'-methoxy-3'-(N-(3-((2-(2-methoxybenzamido)ethyl)(methyl)amino)phenyl)sulfamoyl)-N,N-dimethyl-[1,1'-biphenyl]-3-carboxamide (12.8 mg).

Example 113

4'-methoxy-3'-(N-(3-((2-(2-methoxybenzamido)ethyl)amino)phenyl)sulfamoyl)-[1,1'-biphenyl]-3-carboxylic acid

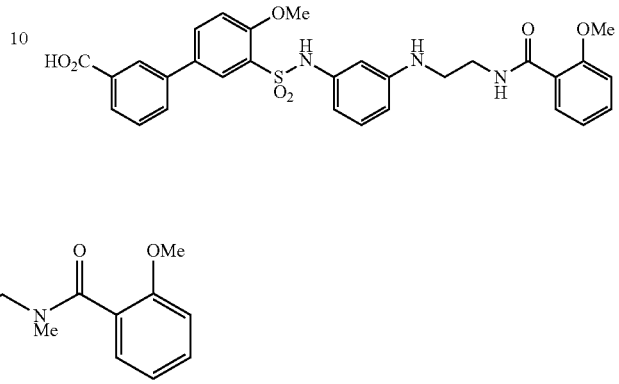

(1) To methyl 3'-(N-(3-((2-((tert-butoxycarbonyl)amino)ethyl)amino)phenyl)sulfamoyl)-4'-methoxy-[1,1'-biphenyl]-3-carboxylate was added 10% hydrogen chloride-methanol (6.0 mL) solution, and the mixture was stirred at 50° C. for 2 hr. The reaction mixture was concentrated to give methyl 3'-(N-(3-((2-aminoethyl)amino)phenyl)sulfamoyl)-4'-methoxy-[1,1'-biphenyl]-3-carboxylate dihydrochloride (356 mg).

(2) To a suspension of methyl 3'-(N-(3-((2-aminoethyl)amino)phenyl)sulfamoyl)-4'-methoxy-[1,1'-biphenyl]-3-carboxylate dihydrochloride (178 mg) in dichloromethane (4.0 mL) were added o-anisic acid (51.7 mg), triethylamine (0.155 mL) and BOP reagent (164 mg), and the mixture was stirred at room temperature overnight. To this reaction mixture was added saturated aqueous sodium hydrogen carbonate solution, and the mixture was extracted with chloroform. The organic layer was dried over sodium sulfate, filtered, and the filtrate was concentrated. The obtained residue was purified by silica gel column chromatography (eluate: ethyl acetate/hexane=2/1→1/0) to give methyl 4'-methoxy-3'-(N-(3-((2-(2-methoxybenzamido)ethyl)amino)phenyl)sulfamoyl)-[1,1'-biphenyl]-3-carboxylate (176 mg).

(3) To a suspension of methyl 4'-methoxy-3'-(N-(3-((2-(2-methoxybenzamido)ethyl)amino)phenyl)sulfamoyl)-[1,1'-biphenyl]-3-carboxylate (176 mg) in methanol (3.0 mL) was added 1N aqueous sodium hydroxide solution (0.900 mL), and the mixture was stirred at 60° C. for 3 hr. To this reaction mixture was added 1N hydrochloric acid, and the mixture was extracted with chloroform. The organic layer was dried over sodium sulfate, filtered, and the filtrate was concentrated to give 4'-methoxy-3'-(N-(3-((2-(2-methoxybenzamido)ethyl)amino)phenyl)sulfamoyl)-[1,1'-biphenyl]-3-carboxylic acid (161 mg).

The structural formulas and physical property data of the Example compounds are shown in Table 9 to Table 24.

TABLE 9

| Example No. | Structure | ESI-MS (M + H)+ | ¹H-NMR Chemical Shift (400 MHz, CDCl₃) |
|---|---|---|---|
| 1 | 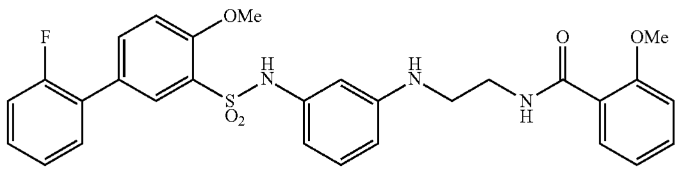 [SMILES: COc1ccccc1C(=O)NCCNc1cccc(NS(=O)(=O)c2cc(-c3ccccc3F)ccc2OC)c1] | 550 | δ 3.31 (2H, t, J = 6.0 Hz), 3.62-3.65 (2H, m), 3.81 (3H, s), 4.06 (3H, s), 4.25 (1H, brs), 6.31-6.36 (2H, m), 6.48 (1H, t, J = 2.4 Hz), 6.86 (1H, brs), 6.91-6.98 (2H, m), 7.04-7.18 (4H, m), 7.25-7.37 (2H, m), 7.44 (1H, td, J = 7.6, 2.0 Hz), 7.68 (1H, td, J = 8.4, 2.0 Hz), 8.03 (1H, dd, J = 8.4, 2.0 Hz), 8.08-8.16 (1H, m), 8.20 (1H, dd, J = 8.0, 2.0 Hz) |
| 2 | 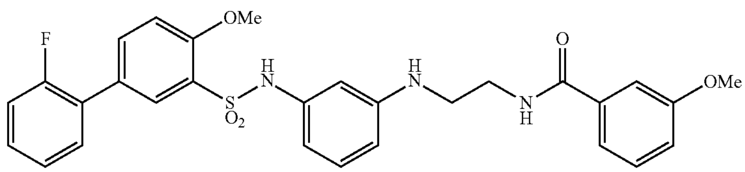 [SMILES: COc1cccc(C(=O)NCCNc2cccc(NS(=O)(=O)c3cc(-c4ccccc4F)ccc3OC)c2)c1] | 550 | δ 3.31 (2H, t, J = 5.6 Hz), 3.62-3.65 (2H, m), 3.83 (3H, s), 4.06 (3H, s), 6.31-6.36 (4H, m), 6.50 (1H, t, J = 2.4 Hz), 6.88 (1H, brs), 6.97 (1H, t, J = 8.0 Hz), 7.01-7.08 (3H, m), 7.17-7.22 (2H, m), 7.26-7.35 (4H, m), 7.68 (1H, td, J = 9.2, 2.0 Hz), 8.04 (1H, d, J = 0.8 Hz) |
| 3 | 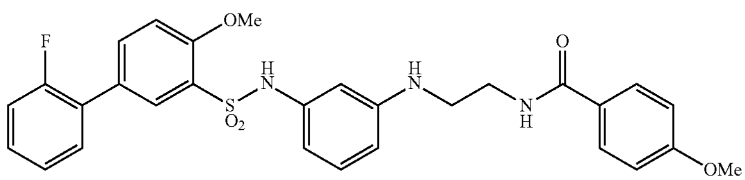 [SMILES: COc1ccc(C(=O)NCCNc2cccc(NS(=O)(=O)c3cc(-c4ccccc4F)ccc3OC)c2)cc1] | 550 | δ 3.30 (2H, t, J = 6.0 Hz), 3.59-3.65 (2H, m), 3.84 (3H, s), 4.06 (3H, s), 4.15 (1H, brs), 6.32-6.48 (3H, m), 6.49 (1H, t, J = 2.0 Hz), 6.88-6.90 (3H, m), 6.96 (1H, t, J = 8.0 Hz), 7.04-7.11 (2H, m), 7.17 (1H, t, J = 7.2 Hz), 7.28-7.35 (2H, m), 7.67-7.69 (3H, m), 8.04 (1H, dd, J = 4.8, 0.8 Hz) |
| 4 | 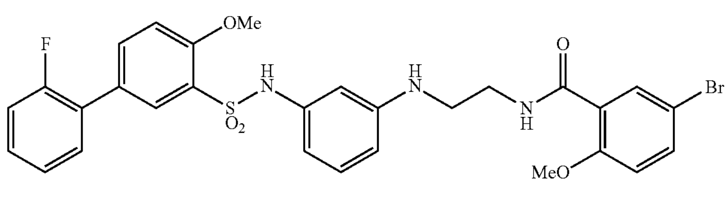 [SMILES: COc1ccc(Br)cc1C(=O)NCCNc1cccc(NS(=O)(=O)c2cc(-c3ccccc3F)ccc2OC)c1] | 628 | δ 3.29-3.32 (2H, m), 3.60-3.65 (2H, m), 3.78 (3H, s), 4.07 (3H, s), 4.18 (1H, brs), 6.30-6.35 (2H, m), 6.50 (1H, t, J = 2.4 Hz), 6.79 (1H, d, J = 8.8 Hz), 6.89 (1H, brs), 6.96 (1H, t, J = 8.0 Hz), 7.04-7.18 (3H, m), 7.26-7.34 (2H, m), 7.52 (1H, dd, J = 8.8, 2.4 Hz), 7.69 (1H, td, J = 8.4, 2.0 Hz), 8.02-8.03 (2H, m), 8.29 (1H, d, J = 4.2 Hz) |
| 5 | 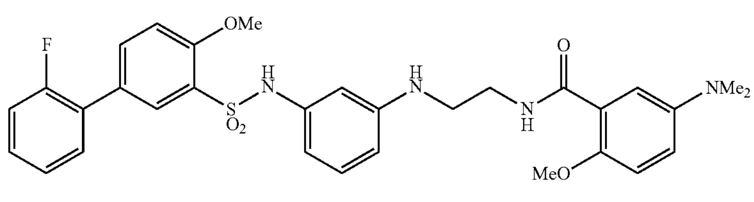 [SMILES: COc1ccc(N(C)C)cc1C(=O)NCCNc1cccc(NS(=O)(=O)c2cc(-c3ccccc3F)ccc2OC)c1] | 593 | δ 1.73 (1H, brs), 2.97 (6H, s), 3.30 (2H, t, J = 6.0 Hz), 3.61-3.66 (2H, m), 3.76 (3H, s), 4.06 (3H, s), 6.32-6.36 (2H, m), 6.49 (1H, t, J = 2.0 Hz), 6.86-6.90 (2H, m), 6.96 (1H, t, J = 8.0 Hz), 7.00-7.18 (4H, m), 7.26-7.37 (2H, m), 7.68 (1H, td, J = 8.8, 2.0 Hz), 7.73-7.75 (1H, m), 8.02 (1H, d, J = 0.6 Hz), 8.22-8.25 (1H, m) |

TABLE 9-continued

| Example No. | Structure | ESI-MS (M + H)+ | 1H-NMR Chemical Shift (400 MHz, CDCl3) |
|---|---|---|---|
| 6 | 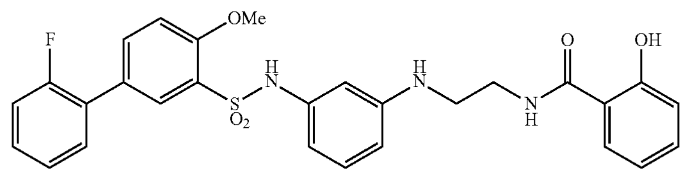 [SMILES: COc1ccc(-c2ccccc2F)cc1S(=O)(=O)Nc1cccc(NCCNC(=O)c2ccccc2O)c1] | 536 | δ 3.34 (2H, t, J = 6.0 Hz), 3.59-3.64 (2H, m), 4.00 (1H, brs), 4.06 (3H, s), 4.25 (1H, brs), 6.31-6.36 (2H, m), 6.53 (1H, t, J = 2.0 Hz), 6.58 (1H, brs), 6.77 (1H, t, J = 8.0 Hz), 6.87 (1H, brs), 6.96-7.19 (4H, m), 7.27-7.40 (4H, m), 7.68 (1H, td, J = 8.8, 2.4 Hz), 8.04 (1H, d, J = 1.2 Hz), 12.21 (1H, brs) |
| 7 | 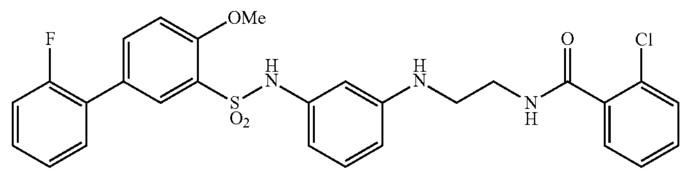 [SMILES: COc1ccc(-c2ccccc2F)cc1S(=O)(=O)Nc1cccc(NCCNC(=O)c2ccccc2Cl)c1] | 554 | δ 3.33 (2H, t, J = 6.0 Hz), 3.61-3.66 (2H, m), 4.07 (3H, s), 4.09 (1H, brs), 6.32-6.36 (3H, m), 6.49 (1H, t, J = 2.4 Hz), 6.89 (1H, brs), 6.97 (1H, t, J = 8.0 Hz), 7.05-7.19 (3H, m), 7.26-7.39 (5H, m), 7.59 (1H, td, J = 8.0, 1.2 Hz), 7.68 (1H, td, J = 10.8, 2.0 Hz), 8.04 (1H, dd, J = 2.4, 0.8 Hz) |

TABLE 10

| | | | |
|---|---|---|---|
| 8 | | 554 | δ 3.32 (2H, t, J = 6.0 Hz), 3.60-3.64 (2H, m), 4.06 (3H, s), 4.09 (1H, brs), 6.30-6.36 (3H, m), 6.52 (1H, t, J = 2.0 Hz), 6.87 (1H, brs), 6.97 (1H, t, J = 8.0 Hz), 7.05-7.19 (3H, m), 7.26-7.36 (3H, m), 7.45 (1H, ddd, J = 8.0, 2.0, 0.8 Hz), 7.56 (1H, dt, J = 5.6, 1.2 Hz), 7.67-7.70 (2H, m), 8.04 (1H, dd, J = 2.0, 0.8 Hz) |
| 9 | | 554 | δ 3.32 (2H, t, J = 6.0 Hz), 3.60-3.64 (2H, m), 4.07 (3H, s), 4.09 (1H, brs), 6.30-6.36 (3H, m), 6.49 (1H, t, J = 2.0 Hz), 6.89 (1H, brs), 6.97 (1H, t, J = 8.0 Hz), 7.05-7.19 (3H, m), 7.26-7.38 (4H, m), 7.62-7.65 (2H, m), 7.68 (1H, dt, J = 8.8, 2.0 Hz), 8.04 (1H, dd, J = 2.0, 0.8 Hz) |
| 10 | | 566 | δ 3.31 (2H, t, J = 6.0 Hz), 3.62-3.67 (2H, m), 3.83 (3H, s), 4.06 (3H, s), 4.25 (1H, brs), 6.31 (1H, dd, J = 8.0, 1.6 Hz), 6.35 (1H, dd, J = 8.0, 1.6 Hz), 6.47 (1H, t, J = 2.4 Hz), 6.83 (1H, brs), 6.92-7.10 (4H, m), 7.21-7.26 (3H, m), 7.37-7.39 (1H, m), 7.44 (1H, td, J = 8.4, 2.0 Hz), 7.55 (1H, dd, J = 8.4, 2.0 Hz), 7.92 (1H, d, J = 2.4 Hz), 8.08-8.12 (1H, m), 8.20 (1H, dd, J = 8.0, 2.0 Hz) |
| 11 | | 566 | δ 3.33 (2H, t, J = 6.0 Hz), 3.64-3.69 (2H, m), 3.84 (3H, s), 4.06 (3H, s), 4.24 (1H, brs), 6.32 (1H, dd, J = 7.2, 1.6 Hz), 6.41-6.44 (3H, m), 6.54 (1H, brs), 7.00-7.06 (2H, m), 7.24-7.35 (7H, m), 7.63 (1H, ddd, J = 8.0, 2.0, 1.2 Hz), 7.67 (1H, ddd, J = 8.0, 2.0, 0.8 Hz), 7.94 (1H, d, J = 2.0 Hz) |

TABLE 10-continued

| | | | |
|---|---|---|---|
| 12 | 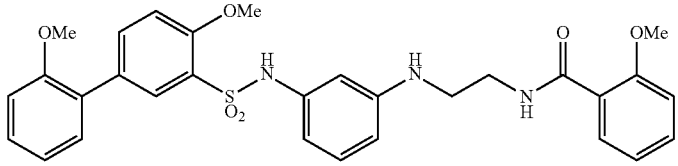 [SMILES: COc1ccccc1C(=O)NCCNc1cccc(NS(=O)(=O)c2cc(-c3ccccc3OC)ccc2OC)c1] | 562 | δ 3.31 (2H, t, J = 6.0 Hz), 3.61-3.65 (2H, m), 3.81 (6H, s), 4.08 (3H, s), 6.34 (1H, d, J = 8.4 Hz), 6.47-6.48 (1H, m), 6.80-6.84 (1H, m), 6.90-7.10 (6H, m), 7.21-7.31 (4H, m), 7.44 (1H, td, J = 7.6, 2.0 Hz), 7.66 (1H, dd, J = 8.4, 2.0 Hz), 8.03 (1H, dd, J = 5.6, 2.4 Hz), 8.06-8.13 (1H, m), 8.18 (1H, dd, J = 8.0, 1.6 Hz) |
| 13 | 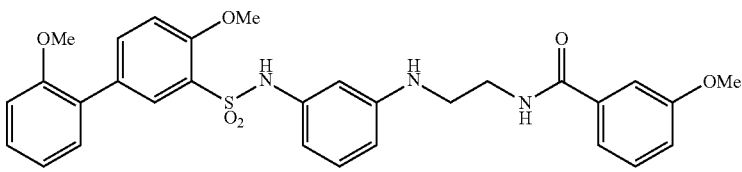 [SMILES: COc1cccc(C(=O)NCCNc2cccc(NS(=O)(=O)c3cc(-c4ccccc4OC)ccc3OC)c2)c1] | 562 | δ 3.31 (2H, t, J = 6.0 Hz), 3.61-3.65 (2H, m), 3.83 (6H, s), 4.08 (3H, s), 4.25 (1H, brs), 6.33-6.36 (3H, m), 6.47-6.49 (1H, m), 6.81-6.86 (2H, m), 6.92-7.08 (5H, m), 7.20-7.23 (1H, m), 7.26-7.32 (3H, m), 7.67 (1H, dd, J = 8.8, 2.4 Hz), 8.02 (1H, dd, J = 7.2, 2.0 Hz) |
| 14 | 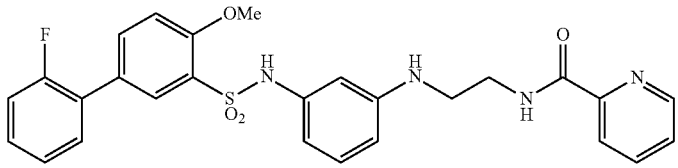 [SMILES: COc1ccc(-c2ccccc2F)cc1S(=O)(=O)Nc1cccc(NCCNC(=O)c2ccccn2)c1] | 521 | δ 3.31 (2H, t, J = 6.0 Hz), 3.63-3.68 (2H, m), 4.06 (3H, s), 6.33-6.36 (2H, m), 6.47 (1H, t, J = 2.0 Hz), 6.86 (1H, brs), 6.96 (1H, t, J = 8.0 Hz), 7.05-7.19 (3H, m), 7.26-7.29 (2H, m), 7.34 (1H, td, J = 9.2, 1.6 Hz), 7.43 (1H, ddd, J = 8.0, 4.8, 1.2 Hz), 7.68 (1H, dt, J = 8.8, 2.0 Hz), 7.85 (1H, td, J = 9.6, 2.0 Hz), 8.04 (1H, t, J = 1.6 Hz), 8.18 (1H, d, J = 7.6 Hz), 8.20-8.28 (1H, m), 8.52 (1H, ddd, J = 4.0, 1.6, 0.8 Hz) |

TABLE 11

| | | | |
|---|---|---|---|
| 15 | 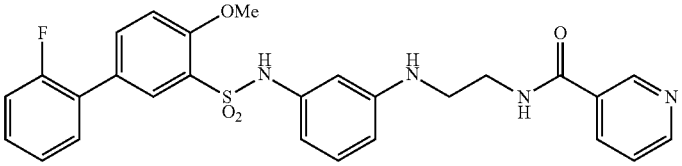 [SMILES: COc1ccc(-c2ccccc2F)cc1S(=O)(=O)Nc1cccc(NCCNC(=O)c2cccnc2)c1] | 521 | δ 3.34 (2H, t, J = 6.0 Hz), 3.63-3.70 (2H, m), 4.06 (3H, s), 4.25 (1H, brs), 6.30-6.36 (2H, m), 6.41-6.50 (1H, m), 6.54 (1H, t, J = 2.0 Hz), 6.93-6.99 (2H, m), 7.05-7.19 (3H, m), 7.26-7.36 (3H, m), 7.68 (1H, dt, J = 8.8, 2.0 Hz), 8.02-8.05 (2H, m), 8.71 (1H, dd, J = 4.8, 2.0 Hz), 8.90 (1H, d, J = 1.6 Hz) |
| 16 | 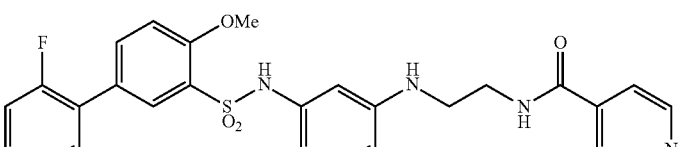 | 521 | δ 3.34 (2H, t, J = 6.0 Hz), 3.62-3.66 (2H, m), 4.02 (1H, brs), 4.06 (3H, s), 6.29 (1H, dd, J = 8.4, 2.0 Hz), 6.34 (1H, dd, J = 8.0, 2.0 Hz), 6.46-6.53 (1H, m), 6.56 (1H, t, J = 2.0 Hz), 6.92-6.99 (2H, m), 7.05-7.19 (3H, m), 7.26-7.36 (2H, m), 7.52-7.53 (2H, m), 7.68 (1H, dt, J = 8.8, 2.0 Hz), 8.04 (1H, t, J = 0.8 Hz), 8.68-8.70 (2H, m) |
| 17 | 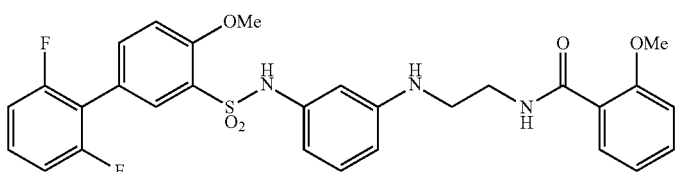 | 568 | δ 3.31 (2H, t, J = 6.0 Hz), 3.62-3.67 (2H, m), 3.81 (3H, s), 4.05 (3H, s), 4.20 (1H, brs), 6.30-6.36 (2H, m), 6.48 (1H, t, J = 2.0 Hz), 6.84 (1H, brs), 6.89-7.00 (3H, m), 7.04-7.10 (2H, m), 7.22-7.28 (2H, m), 7.42-7.47 (1H, m), 7.58 (1H, dt, J = 8.8, 1.2 Hz), 7.99-8.01 (1H, m), 8.06-8.14 (1H, m), 8.19 (1H, dd, J = 8.0, 2.0 Hz) |

TABLE 11-continued

| | | | |
|---|---|---|---|
| 18 | (structure) | 568 | δ 3.30 (2H, t, J = 6.0 Hz), 3.60-3.65 (2H, m), 3.83 (3H, s), 4.07 (3H, s), 4.15 (1H, brs), 6.30-6.35 (2H, m), 6.37-6.43 (1H, m), 6.49 (1H, t, J = 2.0 Hz), 6.70-7.07 (6H, m), 7.20-7.32 (4H, m), 7.57-7.60 (1H, m), 8.00 (1H, dd, J = 2.4, 1.2 Hz) |
| 19 | (structure) | 568 | δ 3.31 (2H, t, J = 6.0 Hz), 3.63-3.69 (2H, m), 3.84 (3H, s), 4.07 (3H, s), 4.25 (1H, brs), 6.31-6.37 (2H, m), 6.48 (1H, t, J = 2.0 Hz), 6.86 (1H, brs), 6.93-6.99 (3H, m), 7.02-7.10 (4H, m), 7.44 (1H, td, J = 6.4, 1.2 Hz), 7.65 (1H, dt, J = 8.4, 2.0 Hz), 8.01 (1H, dd, J = 2.0, 0.8 Hz), 8.07-8.13 (1H, m), 8.19 (1H, dd, J = 8.0, 1.6 Hz) |
| 20 | (structure) | 568 | δ 3.31 (2H, t, J = 6.0 Hz), 3.61-3.65 (2H, m), 3.83 (3H, s), 4.07 (3H, s), 4.20 (1H, brs), 6.31-6.36 (2H, m), 6.37-6.44 (1H, m), 6.49 (1H, t, J = 2.0 Hz), 6.91 (1H, brs), 6.95-7.07 (5H, m), 7.20-7.32 (4H, m), 7.65 (1H, dt, J = 8.4, 2.0 Hz), 8.01 (1H, dd, J = 2.0, 1.2 Hz) |
| 21 | (structure) | 546 | δ 2.91 (3H, s), 3.50-3.53 (2H, m), 3.56-3.59 (2H, m), 3.83 (3H, s), 4.02 (3H, s), 4.15 (1H, brs), 6.29-6.32 (2H, m), 6.42-6.49 (1H, m), 6.59 (1H, brs), 6.89 (1H, brs), 6.94-7.13 (4H, m), 7.13-7.14 (1H, m), 7.26-7.28 (5H, m), 7.45 (1H, td, J = 7.2, 1.6 Hz), 7.80 (1H, dd, J = 8.0, 1.6 Hz) |

TABLE 12

| | | | |
|---|---|---|---|
| 22 | (structure) | 548 | δ 3.28 (2H, t, J = 6.0 Hz), 3.66-3.70 (2H, m), 3.82 (3H, s), 4.10 (3H, s), 4.13 (1H, brs), 6.17 (1H, dd, J = 8.0, 1.6 Hz), 6.23 (1H, dd, J = 8.0, 1.6 Hz), 6.52-6.59 (1H, m), 6.66 (1H, t, J = 2.0 Hz), 6.85 (1H, brs), 6.91-7.09 (5H, m), 7.18-7.35 (5H, m), 7.46-7.52 (1H, m), 7.55 (1H, dd, J = 8.4, 2.4 Hz), 8.32 (1H, d, J = 2.4 Hz) |
| 23 | (structure) | 580 | δ 3.31 (2H, t, J = 6.0 Hz), 3.60-3.65 (2H, m), 3.82 (6H, s), 4.09 (3H, s), 4.11-4.15 (1H, m), 6.34 (1H, d, J = 8.0 Hz), 6.47-6.48 (1H, m), 6.80-6.86 (1H, m), 6.91-7.11 (4H, m), 7.21-7.31 (4H, m), 7.44 (1H, td, J = 7.6, 2.0 Hz), 7.68 (1H, dd, J = 8.4, 2.0 Hz), 8.06 (1H, dd, J = 5.6, 2.0 Hz), 8.08-8.15 (1H, m), 8.20 (1H, dd, J = 8.0, 1.2 Hz) |

TABLE 12-continued

| # | Structure | MS | NMR |
|---|---|---|---|
| 24 | 2-F-6-OMe-biphenyl-OMe-SO2NH-C6H4-NH-CH2CH2-NHC(O)-C6H4-3-OMe | 580 | δ 3.32 (2H, t, J = 6.0 Hz), 3.60-3.66 (2H, m), 3.81 (6H, s), 4.08 (3H, s), 4.20 (1H, brs), 6.33-6.36 (3H, m), 6.47-6.49 (1H, m), 6.80-6.84 (2H, m), 6.90-7.05 (4H, m), 7.18-7.20 (1H, m), 7.24-7.30 (3H, m), 7.70 (1H, dd, J = 8.8, 2.4 Hz), 8.02 (1H, dd, J = 7.2, 2.0 Hz) |
| 25 | 2,5-diCl-biphenyl-OMe-SO2NH-C6H4-NH-CH2CH2-NHC(O)-C6H4-2-OMe | 600 | δ 3.31 (2H, t, J = 6.0 Hz), 3.63-3.68 (2H, m), 3.86 (3H, s), 4.07 (3H, s), 4.23 (1H, brs), 6.30 (1H, dd, J = 8.0, 1.6 Hz), 6.35 (1H, dd, J = 8.0, 1.6 Hz), 6.50 (1H, t, J = 2.0 Hz), 6.86 (1H brs), 6.93-7.11 (4H, m), 7.20-7.32 (3H, m), 7.43-7.47 (1H, m), 7.52 (1H, dd, J = 8.4, 2.0 Hz), 7.90 (1H, d, J = 2.4 Hz), 8.07-8.13 (1H, m), 8.19 (1H, dd, J = 8.4, 2.0 Hz) |
| 26 | 2,5-diCl-biphenyl-OMe-SO2NH-C6H4-NH-CH2CH2-NHC(O)-C6H4-3-OMe | 600 | δ 3.31 (2H, t, J = 6.0 Hz), 3.62-3.68 (2H, m), 3.84 (3H, s), 4.08 (3H, s), 4.13 (1H, brs), 6.29-6.36 (2H, m), 6.37-6.44 (1H, m), 6.49 (1H, t, J = 2.0 Hz), 6.88 (1H, brs), 6.96 (1H, t, J = 8.0 Hz), 7.02-7.05 (2H, m), 7.21-7.33 (6H, m), 7.52 (1H, dd, J = 8.4, 2.4 Hz), 7.90 (1H, d, J = 2.0 Hz) |
| 27 | 3,5-diCl-biphenyl-OMe-SO2NH-C6H4-NH-CH2CH2-NHC(O)-C6H4-2-OMe | 600 | δ 3.30 (2H, t, J = 6.0 Hz), 3.62-3.68 (2H, m), 3.84 (3H, s), 4.08 (3H, s), 4.28 (1H, brs), 6.31-6.37 (2H, m), 6.45-6.47 (1H, m), 6.65-6.68 (1H, m), 6.84 (1H, brs), 6.93-7.10 (4H, m), 7.29-7.35 (2H, m), 7.45 (1H, td, J = 8.0, 2.0 Hz), 7.61-7.65 (1H, m), 7.99 (1H, d, J = 2.4 Hz), 8.06-8.12 (1H, m), 8.17-8.21 (1H, m) |
| 28 | 3,5-diCl-biphenyl-OMe-SO2NH-C6H4-NH-CH2CH2-NHC(O)-C6H4-3-OMe | 600 | δ 3.32-3.25 (2H, m), 3.64-3.68 (2H, m), 3.85 (3H, s), 4.08 (3H, s), 4.18 (1H, brs), 6.31-6.37 (3H, m), 6.48 (1H, t, J = 2.0 Hz), 6.87 (1H, brs), 6.95-7.08 (3H, m), 7.20-7.35 (6H, m), 7.63 (1H, dd, J = 8.8, 2.4 Hz), 8.00 (1H, d, J = 2.4 Hz) |

TABLE 13

| # | Structure | MS | NMR |
|---|---|---|---|
| 29 | 3-Cl-biphenyl-OMe-SO2NH-C6H4-NH-CH2CH2-NHC(O)-C6H4-3-OMe | 566 | δ 3.31 (2H, t, J = 6.0 Hz), 3.61-3.67 (2H, m), 3.84 (3H, s), 4.06 (3H, s), 4.18 (1H, brs), 6.32-6.36 (3H, m), 6.48 (1H, t, J = 2.0 Hz), 6.88 (1H, brs), 6.94-7.07 (3H, m), 7.19-7.37 (6H, m), 7.46 (1H, t, J = 1.6 Hz), 7.65 (1H, dd, J = 8.8, 2.4 Hz), 8.03 (1H, d, J = 2.4 Hz) |

TABLE 13-continued

| | | | |
|---|---|---|---|
| 30 | (structure) | 562 | δ 3.30 (2H, t, J = 6.0 Hz), 3.62-3.66 (2H, m), 3.80 (3H, s), 3.88 (3H, s), 4.06 (3H, s), 4.15 (1H, brs), 6.32-6.36 (2H, m), 6.48 (1H, t, J = 2.0 Hz), 6.84-7.10 (7H, m), 7.28-7.32 (2H, m), 7.42-7.46 (1H, m), 7.66 (1H, dd, J = 8.4, 2.4 Hz), 8.05 (1H, d, J = 2.4 Hz), 8.06-8.12 (1H, m), 8.18 (1H, dd, J = 7.6, 2.0 Hz) |
| 31 | (structure) | 562 | δ 3.30 (2H, t, J = 6.0 Hz), 3.59-3.64 (2H, m), 3.81 (3H, s), 3.88 (3H, s), 4.06 (3H, s), 4.16 (1H, brs), 6.31-6.35 (2H, m), 6.36-6.41 (1H, m), 6.48-6.50 (1H, m), 6.85-7.08 (7H, m), 7.18-7.34 (4H, m), 7.67 (1H, dd, J = 8.8, 2.4 Hz), 8.06 (1H, d, J = 2.4 Hz) |
| 32 | (structure) | 584 | δ 3.31 (2H, t, J = 6.0 Hz), 3.63-3.68 (2H, m), 3.86 (3H, s), 4.07 (3H, s), 4.25 (1H, brs), 6.33-6.36 (2H, m), 6.47 (1H, t, J = 2.4 Hz), 6.86 (1H, brs), 6.94-6.98 (3H, m), 7.03-7.11 (3H, m), 7.32-7.35 (1H, m), 7.43-7.47 (1H, m), 7.53 (1H, dd, J = 8.4, 2.4 Hz), 7.91 (1H, d, J = 2.4 Hz), 8.07-8.13 (1H, m), 8.20 (1H, dd, J = 8.0, 2.0 Hz) |
| 33 | (structure) | 584 | δ 3.32 (2H, t, J = 6.0 Hz), 3.62-3.68 (2H, m), 3.84 (3H, s), 4.07 (3H, s), 4.15 (1H, brs), 6.30-6.36 (2H, m), 6.36-6.44 (1H, m), 6.49 (1H, t, J = 2.0 Hz), 6.85-6.86 (1H, m), 6.94-7.04 (5H, m), 7.06-7.35 (4H, m), 7.52-7.55 (1H, m), 7.91 (1H, d, J = 2.4 Hz) |
| 34 | (structure) | 580 | δ 3.31 (2H, t, J = 6.0 Hz), 3.62-3.66 (2H, m), 3.79 (3H, s), 3.87 (3H, s), 4.06 (3H, s), 4.24 (1H, brs), 6.31-6.36 (2H, m), 6.45-6.49 (1H, m), 6.77-6.85 (3H, m), 6.91-7.11 (5H, m), 7.42-7.48 (1H, m), 7.66 (1H, dt, J = 8.4, 2.0 Hz), 8.01-8.03 (1H, m), 8.06-8.13 (1H, m), 8.10-8.20 (1H, m) |
| 35 | (structure) | 580 | δ 3.31 (2H, t, J = 6.0 Hz), 3.60-3.65 (2H, m), 3.79 (3H, s), 3.84 (3H, s), 4.05 (3H, s), 4.25 (1H, brs), 6.33-6.35 (2H, m), 6.39-6.46 (1H, brs), 6.50 (1H, t, J = 2.0 Hz), 6.78-6.85 (2H, m), 6.91-7.05 (5H, m), 7.20-7.34 (3H, m), 7.67 (1H, dt, J = 8.4, 2.0 Hz), 8.03 (1H, dd, J = 2.4, 1.2 Hz) |

TABLE 14

| | | | |
|---|---|---|---|
| 36 | (structure) | 592 | δ 2.97 (3H, s), 3.30 (2H, t, J = 6.0 Hz), 3.62-3.66 (2H, m), 3.80 (3H, s), 3.83 (3H, s), 4.06 (3H, s), 4.22 (1H, brs), 6.31-6.36 (2H, m), 6.46-6.48 (1H, m), 6.60-6.62 (1H, m), 6.86 (1H, brs), 6.89-7.09 (5H, m), 7.18-7.25 (1H, m), 7.42-7.46 (1H, td, J = 8.4, 2.0 Hz), 7.64-7.68 (1H, m), 8.04-8.06 (1H, m), 8.06-8.12 (1H, m), 8.18-8.20 (1H, m) |
| 37 | (structure) | 547 | δ 3.30 (2H, t, J = 6.0 Hz), 3.62-3.67 (2H, m), 3.76 (2H, brs), 3.80 (3H, s), 4.07 (3H, s), 4.21 (1H, brs), 6.29-6.35 (2H, m), 6.49 (1H, t, J = 2.0 Hz), 6.63 (1H, ddd, J = 8.0, 2.4, 0.8 Hz), 6.80-7.10 (7H, m), 7.16 (1H, t, J = 8.0 Hz), 7.44 (1H, ddd, J = 8.8, 5.2, 1.6 Hz), 7.66 (1H, dd, J = 8.8, 2.4 Hz), 8.03 (1H, d, J = 2.4 Hz), 8.07-8.10 (1H, m), 8.19 (1H, dd, J = 8.0, 2.0 Hz) |
| 38 | (structure) | 603 | δ 0.98 (6H, d, J = 6.8 Hz), 1.86-1.90 (1H, m), 2.94 (2H, d, J = 6.8 Hz), 3.30 (2H, t, J = 6.0 Hz), 3.61-3.66 (2H, m), 3.78 (3H, s), 4.05 (3H, s), 4.18 (1H, brs), 6.31-6.35 (2H, m), 6.47 (1H, t, J = 2.04 Hz), 6.56 (1H, ddd, J = 8.0, 2.4, 0.8 Hz), 6.69 (1H, t, J = 2.0 Hz), 6.76 (1H, dd, J = 8.4, 1.6 Hz), 6.88-6.96 (4H, m), 7.01-7.09 (2H, m), 7.17 (1H, t, J = 8.0 Hz), 7.41-7.46 (1H, m), 7.66 (1H, dd, J = 8.8, 2.4 Hz), 8.04 (1H, d, J = 2.4 Hz), 8.06-8.12 (1H, m), 8.19 (1H, dd, J = 8.0, 2.0 Hz) |
| 39 | (structure) | 562 | δ 2.37 (2H, brs), 2.39 (1H, brs), 3.30-3.32 (2H, m), 3.61-3.66 (2H, m), 3.79 (3H, s), 4.06 (3H, s), 4.23 (1H, brs), 6.32-6.35 (2H, m), 6.47 (1H, t, J = 2.0 Hz), 6.88-6.97 (3H, m), 7.03-7.14 (3H, m), 7.26-7.30 (3H, m), 7.44 (1H, ddd, J = 9.2, 7.2, 1.6 Hz), 7.66 (1H, dd, J = 8.8, 2.4 Hz), 8.05 (1H, d, J = 2.4 Hz), 8.06-8.11 (1H, m), 8.18 (1H, dd, J = 8.0, 2.0 Hz) |

TABLE 14-continued

| | | | |
|---|---|---|---|
| 40 | *[structure]* | 603 | δ 2.98 (3H, brs), 3.12 (3H, brs), 3.30 (2H, t, J = 6.0 Hz), 3.63-3.67 (2H, m), 3.82 (3H, s), 4.07 (3H, s), 4.31 (1H, brs), 6.31-6.36 (2H, m), 6.47 (1H, t, J = 2.4 Hz), 6.88 (1H, brs), 6.92-6.97 (2H, m), 7.04-7.09 (2H, m), 7.33-7.46 (3H, m), 7.51-7.54 (2H, m), 7.68 (1H, dd, J = 8.8, 2.4 Hz), 8.05 (1H, d, J = 2.4 Hz), 8.08-8.14 (1H, m), 8.18 (1H, dd, J = 8.0, 2.0 Hz) |
| 41 | *[structure]* | 603 | δ 3.02 (3H, brs), 3.13 (3H, brs), 3.21 (2H, t, J = 5.2 Hz), 3.58-3.63 (2H, m), 3.79 (3H, s), 4.04 (3H, s), 4.48 (1H, brs), 6.21 (1H, dd, J = 7.6, 1.6 Hz), 6.31 (1H, dd, J = 8.0, 1.6 Hz), 6.47 (1H, t, J = 2.4 Hz), 6.87 (1H, brs), 6.92 (1H, t, J = 8.0 Hz), 6.97-7.05 (2H, m), 7.18-7.28 (3H, m), 7.30-7.36 (2H, m), 7.42 (1H, t, J = 8.0 Hz), 7.54-7.57 (2H, m), 7.67 (1H, dd, J = 8.4, 2.4 Hz), 8.11 (1H, d, J = 2.4 Hz) |
| 42 | *[structure]* | 607 | δ 2.99 (3H, brs), 3.08 (3H, brs), 3.28 (2H, t, J = 6.0 Hz), 3.61-3.65 (2H, m), 4.06 (3H, s), 4.28 (1H, brs), 6.27 (1H, dd, J = 8.0, 1.6 Hz), 6.33 (1H, dd, J = 8.0, 1.6 Hz), 6.47 (1H, t, J = 2.0 Hz), 6.85-6.87 (2H, m), 6.92 (1H, t, J = 8.0 Hz), 7.07 (1H, d, J = 8.8 Hz), 7.23-7.43 (5H, m), 7.50-7.55 (3H, m), 7.69 (1H, dd, J = 8.4, 2.4 Hz), 8.09 (1H, d, J = 2.4 Hz) |

TABLE 15

| | | | |
|---|---|---|---|
| 43 | *[structure]* | 591 | δ 2.99 (3H, brs), 3.12 (3H, brs), 3.29 (2H, t, J = 6.0 Hz), 3.64-3.67 (2H, m), 4.07 (3H, s), 4.24 (1H, brs), 6.31 (1H, dd, J = 8.0, 1.6 Hz), 6.35 (1H, dd, J = 8.4, 2.0 Hz), 6.46 (1H, t, J = 2.0 Hz), 6.84 (1H, brs), 6.96 (1H, t, J = 8.0 Hz), 7.05-7.11 (3H, m), 7.23-7.35 (2H, m), 7.40-7.47 (2H, m), 7.52-7.55 (2H, m), 7.68 (1H, dd, J = 8.8, 2.0 Hz), 8.02-8.08 (2H, m) |

TABLE 15-continued

| | Structure | MS | NMR |
|---|---|---|---|
| 44 | (Biphenyl with Me₂NOC, OMe, SO₂NH-phenyl-NH-CH₂CH₂-NHC(O)-phenyl-OMe) | 603 | δ 3.02 (3H, brs), 3.14 (3H, brs), 3.20 (2H, t, J = 5.6 Hz), 3.57-3.62 (2H, m), 3.82 (3H, s), 3.86 (1H, brs), 4.04 (3H, s), 4.50 (1H, brs), 6.22 (1H, dd, J = 8.0, 1.2 Hz), 6.31 (1H, dd, J = 8.0, 1.6 Hz), 6.45 (1H, t, J = 2.0 Hz), 6.84-6.95 (4H, m), 7.04 (1H, d, J = 8.8 Hz), 7.09-7.17 (1H, m), 7.32-7.34 (1H, m), 7.43 (1H, t, J = 7.6 Hz), 7.54-7.57 (2H, m), 7.67-7.79 (2H, m), 8.12 (1H, d, J = 2.4 Hz) |
| 45 | (Biphenyl with Me₂NOC, OMe, SO₂NH-phenyl-NH-CH₂CH₂-NHC(O)-2,6-difluorophenyl) | 609 | δ 2.99 (3H, brs), 3.07 (3H, brs), 3.24-3.26 (2H, m), 3.58-3.62 (2H, m), 4.06 (3H, s), 4.17 (1H, brs), 6.28 (1H, dd, J = 8.0, 1.6 Hz), 6.33 (1H, dd, J = 8.0, 1.6 Hz), 6.45 (1H, t, J = 2.0 Hz), 6.85-6.97 (4H, m), 7.07 (1H, d, J = 8.8 Hz), 7.26-7.35 (3H, m), 7.41 (1H, t, J = 7.6 Hz), 7.53-7.55 (2H, m), 7.70 (1H, dd, J = 8.4, 2.4 Hz), 8.09 (1H, d, J = 2.0 Hz) |
| 46 | (Biphenyl with Me₂NOC, OMe, SO₂NH-phenyl-NH-CH₂CH₂-NHC(O)-2-methoxypyridin-3-yl) | 604 | δ 2.99 (3H, brs), 3.13 (3H, brs), 3.31 (2H, t, J = 6.0 Hz), 3.63-3.73 (2H, m), 3.97 (3H, s), 4.07 (3H, s), 4.30 (1H, brs), 6.31 (1H, dd, J = 8.0, 1.2 Hz), 6.35 (1H, dd, J = 8.0, 1.2 Hz), 6.49 (1H, t, J = 2.0 Hz), 6.93-6.97 (2H, m), 7.03-7.07 (2H, m), 7.33-7.35 (1H, m), 7.42 (1H, t, J = 7.6 Hz), 7.51-7.55 (2H, m), 7.69 (1H, dd, J = 8.4, 2.0 Hz), 8.07 (1H, d, J = 2.4 Hz), 8.18-8.25 (1H, m), 8.26 (1H, dd, J = 8.8, 2.0 Hz), 8.49 (1H, dd, J = 7.6, 2.0 Hz) |
| 47 | (Biphenyl with Me₂NOC, OMe, SO₂NH-phenyl-NH-CH₂CH₂-NHC(O)-2-methoxypyridin-4-yl) | 604 | δ 3.04 (3H, brs), 3.15 (3H, brs), 3.15-3.17 (2H, m), 3.55-3.59 (2H, m), 3.92 (3H, s), 4.02 (3H, s), 4.44 (1H, brs), 6.17 (1H, dd, J = 8.0, 1.2 Hz), 6.29 (1H, dd, J = 8.0, 1.6 Hz), 6.46 (1H, t, J = 2.0 Hz), 6.86 (1H, brs), 6.92 (1H, t, J = 8.0 Hz), 7.03 (3H, m), 7.32 (1H, dt, J = 7.6, 1.2 Hz), 7.43 (1H, t, J = 8.0 Hz), 7.55-7.57 (2H, m), 7.70 (1H, dd, J = 8.8, 2.4 Hz), 7.74-7.81 (1H, m), 8.12-8.16 (2H, m) |

TABLE 15-continued

| | | | | |
|---|---|---|---|---|
| 48 | 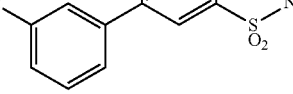 | | 604 | δ 2.99 (3H, brs), 3.12 (3H, brs), 3.31 (2H, t, J = 6.0 Hz), 3.64-3.69 (2H, m), 3.86 (3H, s), 4.07 (3H, s), 4.33 (1H, brs), 6.30 (1H, dd, J = 8.0, 1.6 Hz), 6.35 (1H, dd, J = 8.0, 2.0 Hz), 6.48 (1H, t, J = 2.0 Hz), 6.87-6.89 (2H, m), 6.94 (1H, t, J = 8.0 Hz), 7.06 (1H, d, J = 8.8 Hz), 7.32-7.35 (1H, m), 7.44 (1H, t, J = 8.0 Hz), 7.51-7.55 (2H, m), 7.68-7.79 (3H, m), 8.06 (1H, d, J = 2.4 Hz), 8.07-8.13 (1H, m) |
| 49 | | | 604 | δ 3.04 (3H, brs), 3.14 (3H, brs), 3.14-3.18 (2H, m), 3.58-3.61 (2H, m), 3.82 (3H, s), 4.02 (3H, s), 4.56 (1H, brs), 6.15 (1H, dd, J = 8.0, 1.2 Hz), 6.29 (1H, dd, J = 8.4, 1.6 Hz), 6.48 (1H, t, J = 2.0 Hz), 6.89-6.94 (2H, m), 7.03 (1H, d, J = 8.8 Hz), 7.25-7.31 (2H, m), 7.42 (1H, t, J = 8.0 Hz), 7.54-7.57 (1H, m), 7.64-7.70 (2H, m), 7.91-7.97 (1H, m), 8.15 (1H, d, J = 2.4 Hz), 8.35 (1H, d, J = 2.8 Hz), 8.53 (1H, d, J = 1.6 Hz) |

TABLE 16

| | | | | |
|---|---|---|---|---|
| 50 | 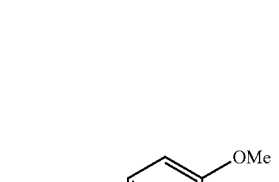 | | 608 | δ 299 (3H, brs), 3.06 (3H, brs), 3.23-3.27 (2H, m), 3.59-3.64 (2H, m), 4.05 (3H, s), 4.23-4.29 (1H, m), 6.22 (1H, dd, J = 7.6, 1.2 Hz), 6.31 (1H, dd, J = 8.0, 1.6 Hz), 6.48 (1H, t, J = 2.0 Hz), 6.88 (1H, brs), 6.94 (1H, t, J = 8.0 Hz), 7.05 (1H, d, J = 8.8 Hz), 7.21-7.26 (2H, m), 7.40 (1H, dd, J = 7.6, 3.2 Hz), 7.43-7.50 (1H, m), 7.54-7.57 (2H, m), 7.72 (1H, dd, J = 8.8, 2.4 Hz), 7.85 (1H, dd, J = 7.6, 2.0 Hz), 8.11 (1H, d, J = 2.4 Hz), 8.39 (1H, dd, J = 8.8, 2.0 Hz) |
| 51 | | | 608 | δ 2.99 (3H, brs), 3.12 (3H, brs), 3.29-3.31 (2H, m), 3.61-3.66 (2H, m), 4.07 (3H, s), 4.18 (1H, brs), 6.33-6.36 (2H, m), 6.45 (1H, t, J = 2.0 Hz), 6.90 (1H, brs), 6.95 (1H, t, J = 8.0 Hz), 7.07 (1H, d, J = 8.8 Hz), 7.32-7.44 (3H, m), 7.52-7.54 (2H, m), 7.70 (1H, dd, J = 8.4, 2.0 Hz), 7.80 (1H, dd, J = 8.4, 1.6 Hz), 8.00-8.06 (1H, m), 8.06 (1H, d, J = 2.0 Hz), 8.41 (1H, dd, J = 8.4, 1.2 Hz) |

TABLE 16-continued

| | | | |
|---|---|---|---|
| 52 | [structure] | 591 | δ 3.04 (3H, brs), 3.15 (3H, brs), 3.15-3.18 (2H, m), 3.57-3.61 (2H, m), 4.03 (3H, s), 4.54 (1H, brs), 6.17 (1H, dd, J = 8.0, 1.6 Hz), 6.30 (1H, dd, J = 8.0, 2.4 Hz), 6.46 (1H, t, J = 2.0 Hz), 6.82 (1H, brs), 6.92 (1H, t, J = 8.0 Hz), 7.04 (1H, d, J = 8.4 Hz), 7.12-7.13 (1H, m), 7.26-7.34 (3H, m), 7.41-7.61 (5H, m), 7.68 (1H, dd, J = 8.8, 2.4 Hz), 8.15 (1H, d, J = 2.4 Hz) |
| 53 | [structure] | 609 | δ 3.00 (3H, brs), 3.12 (3H, brs), 3.29 (2H, t, J = 6.0 Hz), 3.63-3.66 (2H, m), 407 (3H, s), 4.22 (1H, brs), 6.30 (1H, dd, J = 8.0, 1.6 Hz), 6.34 (1H, dd, J = 8.4, 1.6 Hz), 6.48 (1H, t, J = 2.0 Hz), 6.86 (1H, brs), 6.96 (1H, d, J = 8.0 Hz), 7.05-7.16 (4H, m), 7.32-7.34 (1H, m), 7.42 (1H, t, J = 7.6 Hz), 7.52-7.55 (2H, m), 7.69-7.72 (2H, m), 8.08 (1H, d, J = 2.4 Hz) |
| 54 | [structure] | 609 | δ 3.06 (3H, brs), 3.11 (2H, t, J = 5.6 Hz), 3.16 (3H, brs), 3.53-3.57 (2H, m), 4.02 (3H, s), 4.52 (1H, brs), 6.15 (1H, dd, J = 8.0, 1.6 Hz), 6.28 (1H, dd, J = 8.4, 2.4 Hz), 6.43 (1H, t, J = 2.0 Hz), 6.84-6.93 (3H, m), 7.03 (1H, d, J = 8.4 Hz), 7.31-7.34 (3H, m), 7.44 (1H, t, J = 8.0 Hz), 7.57-7.59 (2H, m), 7.68 (1H, dd, J = 8.4, 2.4 Hz), 7.97-8.03 (1H, m), 8.17 (1H, d, J = 2.4 Hz) |
| 55 | [structure] | 608 | δ 3.00 (3H, brs), 3.13 (3H, brs), 3.28-3.32 (2H, m), 3.63-3.67 (2H, m), 4.07 (3H, s), 4.17-4.23 (1H, m), 6.33-6.36 (2H, m), 6.45 (1H, t, J = 2.0 Hz), 6.86 (1H, brs), 6.96 (1H, t, J = 8.0 Hz), 7.08 (1H, d, J = 8.8 Hz), 7.35 (1H, dt, J = 7.2, 1.2 Hz), 7.41-7.55 (4H, m), 7.71 (1H, dd, J = 8.8, 2.4 Hz), 7.82 (1H, t, J = 8.0 Hz), 8.07-8.10 (2H, m), 8.11 (1H, d, J = 1.2 Hz) |
| 56 | [structure] | 608 | δ 2.99 (3H, brs), 305 (3H, brs), 3.22-3.24 (2H, m), 3.59-3.63 (2H, m), 4.05 (3H, s), 4.22-4.29 (1H, m), 6.19 (1H, dd, J = 8.0, 1.6 Hz), 6.30 (1H, dd, J = 8.0, 2.0 Hz), 6.50 (1H, brs), 6.85 (1H, brs), 6.93 (1H, t, J = 8.0 Hz), 6.94 (1H, d, J = 8.8 Hz), 7.19 (1H, dt, J = 7.6, 1.6 Hz), 7.26-7.29 (1H, m), 7.40 (1H, t, J = 8.0 Hz), 7.52-7.58 (2H, m), 7.66-7.72 (1H, m), 7.72 (1H, dd, J = 8.4, 2.4 Hz), 8.13 (1H, d, J = 2.4 Hz), 8.42 (1H, d, J = 8.8 Hz), 8.51 (1H, s) |

TABLE 17

| | | | |
|---|---|---|---|
| 57 | 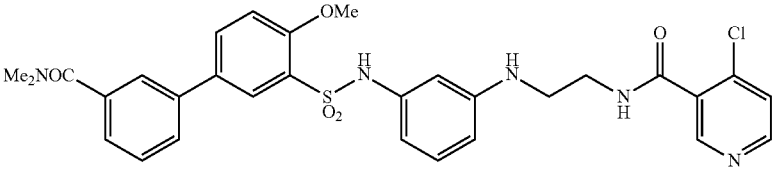 | 608 | δ 2.98 (3H, brs), 3.06 (3H, brs), 3.28 (2H, t, J = 5.6 Hz), 3.69-3.74 (2H, m), 4.04 (3H, s), 4.36-4.41 (1H, m), 6.18 (1H, dd, J = 8.0, 1.6 Hz), 6.28-6.32 (2H, m), 6.45 (1H, brs), 6.87 (1H, t, J = 8.0 Hz), 7.02 (1H, d, J = 8.8 Hz), 7.14-7.17 (1H, m), 7.24-7.33 (1H, m), 7.41-7.52 (2H, m), 7.65 (1H, dd, J = 8.4, 2.4 Hz), 7.96-8.03 (1H, m), 8.09-8.13 (2H, m), 8.47 (1H, d, J = 6.0 Hz), 9.06 (1H, s) |
| 58 | 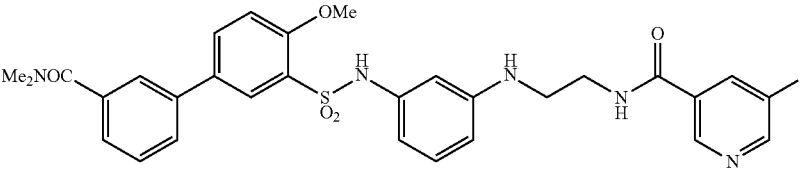 | 608 | δ 3.07 (3H, brs), 3.07-3.10 (2H, m), 3.17 (3H, brs), 3.53-3.58 (2H, m), 4.01 (3H, s), 4.55-4.61 (1H, m), 6.12 (1H, dd, J = 7.6, 1.2 Hz), 6.29 (1H, dd, J = 8.0, 1.6 Hz), 6.43 (1H, t, J = 6.0 Hz), 6.86 (1H, brs), 6.91 (1H, t, J = 8.0 Hz), 7.03 (1H, d, J = 8.8 Hz), 7.29-7.31 (1H, m), 7.42 (1H, td, J = 7.6, 0.8 Hz), 7.57-7.59 (2H, m), 7.69 (1H, dd, J = 8.4, 2.0 Hz), 8.11 (1H, t, J = 2.0 Hz), 8.18 (1H, d, J = 2.4 Hz), 8.36-8.42 (1H, m), 8.59 (1H, d, J = 2.4 Hz), 8.84 (1H, d, J = 1.6 Hz) |
| 59 | 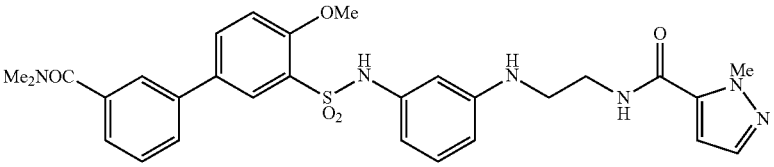 | 577 | δ 3.05 (3H, brs), 3.07-3.17 (5H, m), 3.51-3.56 (2H, m), 4.03 (3H, s), 4.10 (3H, s), 4.22-4.29 (1H, m), 6.16 (1H, d, J = 7.6 Hz), 6.28 (1H, dd, J = 8.0, 2.0 Hz), 6.48-6.51 (2H, m), 6.86 (1H, brs), 6.92 (1H, t, J = 8.0 Hz), 7.04 (1H, d, J = 8.8 Hz), 7.30-7.33 (2H, m), 7.42 (2H, m), 7.56-7.58 (2H, m), 7.68 (1H, dd, J = 8.4, 2.4 Hz), 8.14 (1H, d, J = 2.4 Hz) |
| 60 | 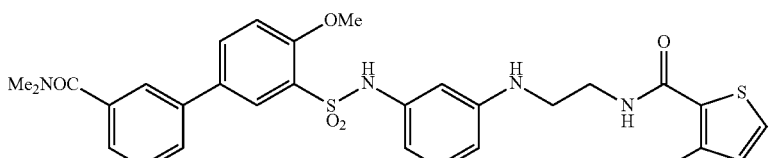 | 593 | δ 2.44 (3H, s), 3.00 (3H, brs), 3.13 (3H, brs), 3.24 (2H, t, J = 5.6 Hz), 3.57-3.61 (2H, m), 4.06 (3H, s), 4.31-4.38 (1H, m), 6.28 (1H, dd, J = 8.0, 2.0 Hz), 6.33 (1H, dd, J = 8.0, 2.0 Hz), 6.44-6.46 (2H, m), 6.84-6.87 (2H, m), 6.95 (1H, t, J = 8.0 Hz), 7.05 (1H, d, J = 8.8 Hz), 7.23 (1H, d, J = 4.8 Hz), 7.33 (1H, dt, J = 7.6, 1.2 Hz), 7.42 (1H, t, J = 8.0 Hz), 7.53-7.56 (2H, m), 7.69 (1H, dd, J = 8.4, 2.0 Hz), 8.09 (1H, d, J = 2.4 Hz) |

TABLE 17-continued

| | | | |
|---|---|---|---|
| 61 | [structure] | 613 | δ 3.06 (3H, brs), 3.12-3.16 (2H, m), 3.16 (3H, brs), 3.50-3.54 (2H, m), 4.03 (3H, s), 4.49 (1H, brs), 6.15 (1H, dd, J = 8.0, 1.2 Hz), 6.28 (1H, dd, J = 8.0, 1.6 Hz), 6.46 (1H, t, J = 2.0 Hz), 6.78 (1H, d, J = 3.6 Hz), 6.82 (1H, brs), 6.91 (1H, t, J = 8.0 Hz), 7.04 (1H, d, J = 8.8 Hz), 7.26-7.35 (3H, m), 7.45 (1H, t, J = 7.6 Hz), 7.56-7.60 (2H, m), 7.68 (1H, dd, J = 8.8, 2.4 Hz), 8.15 (1H, d, J = 2.4 Hz) |
| 62 | [structure] | 613 | δ 3.00 (3H, brs), 3.13 (3H, brs), 3.29-3.32 (2H, m), 3.62-3.67 (2H, m), 4.07 (3H, s), 4.20 (1H, brs), 6.32-6.36 (2H, m), 6.47 (1H, t, J = 2.0 Hz), 6.86 (1H, brs), 6.93-6.98 (2H, m), 7.07 (1H, d, J = 8.8 Hz), 7.25 (1H, brs), 7.33-7.35 (1H, m), 7.40-7.46 (2H, m), 7.52-7.55 (2H, m), 7.69 (1H, dd, J = 8.8, 2.4 Hz), 8.07 (1H, d, J = 2.4 Hz) |
| 63 | [structure] | 577 | δ 2.99 (3H, brs), 3.13 (3H, brs), 3.23-3.26 (2H, m), 3.56-3.61 (2H, m), 3.73 (3H, s), 4.06 (3H, s), 4.29 (1H, brs), 6.31-6.40 (3H, m), 6.93-6.97 (2H, m), 7.07 (1H, d, J = 8.8 Hz), 7.26-7.38 (3H, m), 7.41-7.45 (1H, m), 7.50-7.55 (3H, m), 7.69 (1H, dd, J = 8.4, 2.4 Hz), 8.05 (1H, d, J = 2.4 Hz) |

TABLE 18

| | | | |
|---|---|---|---|
| 64 | [structure] | 577 | δ 2.99 (3H, brs), 3.13 (3H, brs), 3.23-3.27 (2H, m), 3.54-3.59 (2H, m), 4.04 (3H, s), 4.06 (3H, s), 4.20 (1H, brs), 6.31 (1H, dd, J = 8.0, 2.0 Hz), 6.35 (1H, dd, J = 8.0, 1.6 Hz), 6.43 (1H, t, J = 2.0 Hz), 6.94-6.98 (4H, m), 7.07 (1H, d, J = 8.4 Hz), 7.34 (1H, dt, J = 7.6, 1.2 Hz), 7.41-7.45 (1H, m), 7.52-7.55 (2H, m), 7.59-7.64 (1H, m), 7.70 (1H, dd, J = 8.8, 2.4 Hz), 8.06 (1H, d, J = 2.4 Hz) |
| 65 | [structure] | 587 | δ 2.35 (3H, s), 2.99 (3H, brs), 3.07 (3H, brs), 3.21-3.24 (2H, m), 3.59-3.61 (2H, m), 4.07 (3H, s), 4.39 (1H, brs), 6.26 (1H, d, J = 7.2 Hz), 6.32 (1H, d, J = 8.0 Hz), 6.45-6.47 (1H, m), 6.62-6.70 (1H, m), 6.92-6.96 (2H, m), 7.04-7.16 (3H, m), 7.22-7.28 (3H, m), 7.40 (1H, t, J = 7.6 Hz), 7.52-7.55 (2H, m), 7.69 (1H, dd, J = 8.8, 2.0 Hz), 8.10 (1H, d, J = 2.0 Hz) |

TABLE 18-continued

| | | | |
|---|---|---|---|
| 66 | *(structure)* | 587 | δ 2.34 (3H, s), 3.02 (3H, brs), 3.13 (3H, brs), 3.19-3.22 (2H, m), 3.58-3.63 (2H, m), 4.04 (3H, s), 4.47 (1H, brs), 6.22 (1H, dd, J = 8.0, 1.6 Hz), 6.32 (1H, dd, J = 8.4, 1.6 Hz), 6.45 (1H, t, J = 2.0 Hz), 6.88 (1H, brs), 6.92 (1H, t, J = 8.0 Hz), 7.04 (1H, d, J = 8.4 Hz), 7.13-7.18 (1H, m), 7.21-7.34 (3H, m), 7.42 (1H, t, J = 8.0 Hz), 7.50-7.58 (4H, m), 7.68 (1H, dd, J = 8.4, 2.4 Hz), 8.12 (1H, d, J = 2.4 Hz) |
| 67 | *(structure)* | 577 | δ 2.55 (3H, s), 3.03 (3H, brs), 3.14 (3H, brs), 3.14-3.19 (2H, m), 3.51-3.55 (2H, m), 4.04 (3H, s), 4.53 (1H, brs), 6.19 (1H, dd, J = 7.6, 1.6 Hz), 6.30 (1H, dd, J = 7.6, 2.0 Hz), 6.45-6.46 (2H, m), 6.81-6.83 (2H, m), 6.92 (1H, t, J = 8.0 Hz), 7.04 (1H, d, J = 8.4 Hz), 7.16 (1H, d, J = 2.0 Hz), 7.32 (1H, d, J = 8.0 Hz), 7.44 (1H, t, J = 8.0 Hz), 7.55-7.57 (2H, m), 7.70 (1H, dd, J = 8.4, 2.0 Hz), 8.12 (1H, d, J = 1.6 Hz) |
| 68 | *(structure)* | 577 | δ 2.38 (3H, s), 3.00 (3H, brs), 3.13 (3H, brs), 3.24-3.28 (2H, m), 3.56-3.60 (2H, m), 4.07 (3H, s), 4.24 (1H, brs), 6.30-6.35 (2H, m), 6.46 (1H, t, J = 2.0 Hz), 6.64-6.71 (1H, m), 6.88 (1H, brs), 6.95 (1H, t, J = 8.0 Hz), 7.06 (1H, d, J = 8.4 Hz), 7.24-7.26 (2H, m), 7.34 (1H, dt, J = 7.6, 1.2 Hz), 7.43 (1H, t, J = 7.6 Hz), 7.52-7.55 (2H, m), 7.69 (1H, dd, J = 8.8, 2.4 Hz), 8.07 (1H, d, J = 2.4 Hz) |
| 69 | *(structure)* | 641 | δ 2.98 (3H, brs), 3.06 (3H, brs), 3.20-3.25 (2H, m), 3.57-3.62 (2H, m), 4.06 (3H, s), 4.26 (1H, brs), 6.27 (1H, dd, J = 8.0, 1.6 Hz), 6.31 (1H, dd, J = 8.0, 1.6 Hz), 6.45 (1H, t, J = 2.0 Hz), 6.74-6.79 (1H, m), 6.87 (1H, brs), 6.95 (1H, t, J = 8.0 Hz), 7.05 (1H, d, J = 8.8 Hz), 7.23-7.26 (2H, m), 7.37-7.41 (2H, m), 7.48-7.54 (3H, m), 7.63-7.66 (1H, m), 7.69 (1H, dd, J = 8.8, 2.4 Hz), 8.12 (1H, d, J = 2.4 Hz) |

TABLE 18-continued

| # | Structure | MS | NMR |
|---|---|---|---|
| 70 | Me₂NOC-biphenyl-OMe, SO₂NH-phenyl-NH-CH₂CH₂-NHC(O)-phenyl(OMe)(F) | 621 | δ 2.98 (3H, brs), 3.08 (3H, brs), 3.27-3.29 (2H, m), 3.57-3.64 (2H, m), 3.75 (3H, s), 4.07 (3H, s), 4.20 (1H, brs), 6.30 (1H, dd, J = 8.0, 1.6 Hz), 6.34 (1H, dd, J = 8.0, 2.4 Hz), 6.47 (1H, brs), 6.49-6.55 (1H, m), 6.66-6.72 (2H, m), 6.86 (1H, brs), 6.96 (1H, t, J = 8.0 Hz), 7.07 (1H, d, J = 8.4 Hz), 7.25-7.33 (2H, m), 7.42 (1H, t, J = 8.0 Hz), 7.52-7.54 (2H, m), 7.70 (1H, dd, J = 8.4, 2.4 Hz), 8.07 (1H, d, J = 2.0 Hz) |

TABLE 19

| # | Structure | MS | NMR |
|---|---|---|---|
| 71 | Me₂NOC-biphenyl-OMe, SO₂NH-phenyl-NH-CH₂CH₂-NHC(O)-phenyl-CN (ortho) | 598 | δ 2.99 (3H, brs), 3.13 (3H, brs), 3.34-3.38 (2H, m), 4.06 (3H, s), 4.07-4.11 (2H, m), 4.50-4.55 (1H, m), 6.30 (2H, d, J = 8.0 Hz), 6.39 (1H, brs), 6.81 (1H, brs), 6.92 (1H, t, J = 8.0 Hz), 7.05 (1H, d, J = 8.8 Hz), 7.33-7.35 (1H, m), 7.43 (1H, t, J = 7.6 Hz), 7.52-7.55 (2H, m), 7.63-7.70 (4H, m), 7.81-7.83 (1H, m), 8.07 (1H, d, J = 2.0 Hz), 8.68 (1H, brs) |
| 72 | Me₂NOC-biphenyl-OMe, SO₂NH-phenyl-NH-CH₂CH₂-NHC(O)-phenyl-CN (meta) | 598 | δ 3.07 (3H, brs), 3.07-3.11 (2H, m), 3.18 (3H, brs), 3.54-3.58 (2H, m), 4.01 (3H, s), 4.63 (1H, brs), 6.11 (1H, d, J = 7.6 Hz), 6.28 (1H, dd, J = 8.0, 1.6 Hz), 6.44 (1H, t, J = 2.0 Hz), 6.81 (1H, brs), 6.91 (1H, t, J = 8.0 Hz), 7.03 (1H, d, J = 8.8 Hz), 7.33-7.36 (1H, m), 7.42-7.48 (2H, m), 7.58-7.61 (2H, m), 7.68-7.71 (2H, m), 8.02-8.05 (1H, m), 8.10 (1H, t, J = 1.2 Hz), 8.19-8.20 (1H, m), 8.25-8.30 (1H, m) |

TABLE 19-continued

| | | | |
|---|---|---|---|
| 73 | [structure] | 589 | δ 3.01 (3H, d, J = 4.8 Hz), 3.24-3.28 (2H, m), 3.55-3.60 (2H, m), 3.80 (3H, s), 4.06 (3H, s), 4.22-4.33 (1H, m), 6.30-6.35 (2H, m), 6.46-6.48 (2H, m), 6.87 (1H, brs), 6.91-6.98 (2H, m), 7.04-7.08 (2H, m), 7.41-7.46 (2H, m), 7.58-7.60 (1H, m), 7.68-7.71 (2H, m), 7.88 (1H, t, J = 1.6 Hz), 8.09-8.12 (2H, m), 8.13 (1H, dd, J = 8.0, 2.0 Hz) |
| 74 | [structure] | 619 | δ 3.22-3.25 (2H, m), 3.47-3.51 (2H, m), 3.70-3.74 (2H, m), 3.76 (3H, s), 3.82 (3H, s), 3.92-3.95 (2H, m), 4.06-4.16 (2H, m), 6.26 (1H, dd, J = 7.2, 1.6 Hz), 6.46-6.48 (2H, m), 6.73 (1H, d, J = 8.8 Hz), 6.91-6.97 (2H, m), 7.06-7.10 (1H, m), 7.40-7.48 (2H, m), 7.52-7.55 (3H, m), 7.85-7.87 (2H, m), 7.98 (1H, brs), 8.06-8.12 (3H, m) |
| 75 | [structure] | 629 | δ 1.85-1.89 (2H, m), 1.95-1.99 (2H, m), 3.30 (2H, t, J = 6.0 Hz), 3.40-3.44 (2H, m), 3.62-3.67 (4H, m), 3.81 (3H, s), 4.07 (3H, s), 4.38 (1H, brs), 6.32-6.36 (2H, m), 6.47 (1H, t, J = 2.0 Hz), 6.90-6.97 (3H, m), 7.04-7.09 (2H, m), 7.40-7.46 (3H, m), 7.52 (1H, dt, J = 7.2, 1.6 Hz), 7.63 (1H, d, J = 1.2 Hz), 7.69 (1H, dd, J = 8.8, 1.6 Hz), 8.06 (1H, d, J = 2.4 Hz), 8.09-8.15 (1H, m), 8.18 (1H, dd, J = 8.0, 2.0 Hz) |

TABLE 19-continued

| # | Structure | MS | ¹H NMR |
|---|---|---|---|
| 76 | (structure) | 645 | δ 1.52 (9H, s), 2.87 (3H, s), 3.28-3.31 (2H, m), 3.62-3.67 (2H, m), 3.81 (3H, s), 4.07 (3H, s), 4.36 (1H, brs), 6.31-6.36 (2H, m), 6.47 (1H, t, J = 2.0 Hz), 6.89 (1H, brs), 6.91-6.95 (2H, m), 7.04-7.09 (2H, m), 7.32-7.50 (4H, m), 7.54 (1H, d, J = 1.2 Hz), 7.68 (1H, dd, J = 8.8, 2.4 Hz), 8.06 (1H, d, J = 2.4 Hz), 8.11-8.14 (1H, m), 8.18 (1H, dd, J = 7.6, 2.0 Hz) |
| 77 | (structure) | 647 | δ 3.03-3.13 (3H, m), 3.30-3.49 (7H, m), 3.64-3.73 (4H, m), 3.82 (3H, s), 4.07 (3H, s), 4.30 (1H, brs), 6.32-6.36 (2H, m), 6.47 (1H, t, J = 2.0 Hz), 6.86 (1H, d, J = 4.8 Hz), 6.92-6.97 (2H, m), 7.04-7.09 (2H, m), 7.35-7.52 (5H, m), 7.67 (1H, dd, J = 8.4, 1.6 Hz), 8.06 (1H, d, J = 2.0 Hz), 8.09-8.16 (1H, m), 8.19 (1H, dd, J = 8.0, 1.6 Hz) |

TABLE 20

| # | Structure | MS | ¹H NMR |
|---|---|---|---|
| 78 | (structure) | 657 | δ 3.24 (2H, t, J = 6.0 Hz), 3.53-3.64 (2H, m), 3.80 (3H, s), 4.05 (3H, s), 4.08-4.17 (2H, m), 4.25-4.31 (1H, m), 6.29-6.34 (2H, m), 6.44-6.48 (1H, m), 6.85 (1H, brs), 6.91-7.07 (5H, m), 7.41-7.52 (3H, m), 7.63-7.65 (1H, m), 7.69 (1H, dd, J = 8.4, 2.4 Hz), 7.74 (1H, m), 8.06-8.13 (3H, m) |
| 79 | (structure) | 603 | δ 1.55 (6H, s), 3.30 (2H, t, J = 6.0 Hz), 3.62-3.67 (2H, m), 3.83 (3H, s), 4.06 (3H, s), 4.38 (1H, brs), 6.30-6.36 (2H, m), 6.46 (1H, t, J = 2.4 Hz), 6.82 (1H, brs), 6.91-7.02 (4H, m), 7.08 (1H, t, J = 7.6 Hz), 7.36-7.50 (4H, m), 7.78-7.83 (2H, m), 8.07-8.13 (1H, m), 8.19 (1H, dd, J = 8.0, 2.0 Hz) |

TABLE 20-continued
| | | | |
|---|---|---|---|
| 80 | 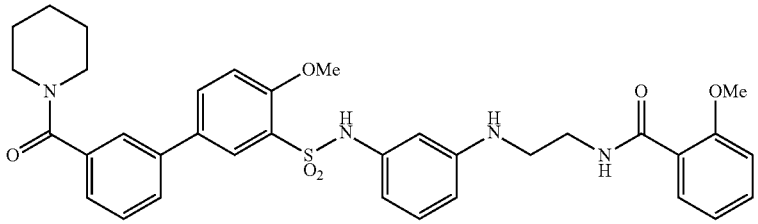 [SMILES: COc1ccccc1C(=O)NCCNc1cccc(NS(=O)(=O)c2cc(-c3cccc(C(=O)N4CCCCC4)c3)ccc2OC)c1] | 643 | δ 1.52-1.68 (6H, m), 3.10 (1H, brs), 3.28-3.35 (4H, m), 3.63-3.72 (4H, m), 3.82 (3H, s), 4.07 (3H, s), 4.29 (1H, brs), 6.31-6.36 (2H, m), 6.46-6.49 (1H, m), 6.92-7.00 (2H, m), 7.05-7.09 (2H, m), 7.30-7.32 (1H, m), 7.38-7.47 (2H, m), 7.50-7.53 (2H, m), 7.68 (1H, dd, J = 7.6, 2.4 Hz), 8.06 (1H, d, J = 2.4 Hz), 8.11-8.16 (1H, m), 8.18 (1H, dd, J = 8.0, 2.0 Hz) |
| 81 | 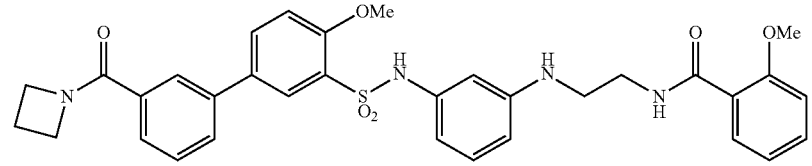 [SMILES: COc1ccccc1C(=O)NCCNc1cccc(NS(=O)(=O)c2cc(-c3cccc(C(=O)N4CCC4)c3)ccc2OC)c1] | 615 | δ 2.32-3.36 (2H, m), 3.30 (2H, t, J = 6.0 Hz), 3.62-3.67 (2H, m), 3.81 (3H, s), 4.07 (3H, s), 4.21-4.31 (5H, m), 6.31 (1H, dd, J = 8.0, 2.0 Hz), 6.34 (1H, dd, J = 8.0, 2.0 Hz), 6.47 (1H, t, J = 2.0 Hz), 6.85 (1H, brs), 6.91-6.97 (2H, m), 7.05-7.09 (2H, m), 7.39-7.46 (2H, m), 7.51-7.58 (2H, m), 7.69 (1H, dd, J = 8.4, 2.0 Hz), 7.76 (1H, t, J = 1.6 Hz), 8.05 (1H, d, J = 2.4 Hz), 8.08-8.13 (1H, m), 8.18 (1H, dd, J = 8.0, 2.0 Hz) |
| 82 | 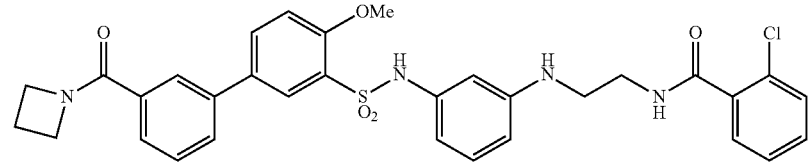 [SMILES: COc1ccc(-c2cccc(C(=O)N3CCC3)c2)cc1S(=O)(=O)Nc1cccc(NCCNC(=O)c2ccccc2Cl)c1] | 619 | δ 2.05-2.11 (2H, m), 3.31 (2H, t, J = 6.0 Hz), 3.54-3.64 (6H, m), 4.07 (3H, s), 4.17-4.24 (1H, m), 6.28 (1H, dd, J = 8.0, 1.6 Hz), 6.34 (1H, dd, J = 8.0, 2.0 Hz), 6.50-6.53 (1H, m), 6.57-6.63 (1H, m), 6.74-6.78 (1H, m), 6.88 (1H, brs), 6.96 (1H, t, J = 8.0 Hz), 7.07 (1H, d, J = 8.8 Hz), 7.21-7.30 (2H, m), 7.43-7.47 (2H, m), 7.60-7.63 (2H, m), 7.70 (1H, dd, J = 8.4, 2.4 Hz), 7.90 (1H, s), 8.10 (1H, d, J = 2.4 Hz) |
| 83 | 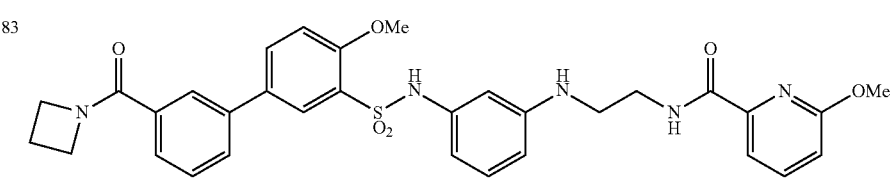 | 616 | δ 2.11-2.18 (2H, m), 3.31 (2H, t, J = 5.6 Hz), 3.59-3.67 (6H, m), 3.84 (3H, s), 4.06 (3H, s), 4.18-4.25 (1H, m), 6.29 (1H, dd, J = 8.0, 1.6 Hz), 6.33 (1H, dd, J = 8.4, 1.6 Hz), 6.48 (1H, t, J = 2.0 Hz), 6.66-6.72 (1H, m), 6.87-6.89 (2H, m), 6.95 (1H, t, J = 8.0 Hz), 7.04 (1H, d, J = 8.4 Hz), 7.46 (1H, t, J = 8.0 Hz), 7.60-7.63 (1H, m), 7.64-7.74 (3H, m), 7.90 (1H, t, J = 1.6 Hz), 8.01-8.07 (1H, m), 8.09-8.11 (1H, m) |

TABLE 20-continued
| 84 | 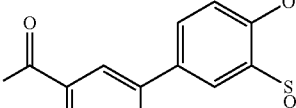 | 603 | δ 2.09-2.13 (2H, m), 3.26 (2H, t, J = 5.6 Hz), 3.59-3.65 (6H, m), 4.02 (3H, s), 4.35 (1H, brs), 6.22 (1H, dd, J = 8.0, 1.6 Hz), 6.30 (1H, dd, J = 8.0, 1.6 Hz), 6.54 (1H, t, J = 2.0 Hz), 6.68-6.76 (1H, m), 6.91-7.03 (3H, m), 7.13-7.31 (2H, m), 7.38-7.47 (3H, m), 7.58-7.66 (3H, m), 7.91 (1H, s), 8.10 (1H, d, J = 2.4 Hz) |
TABLE 21
| 85 | 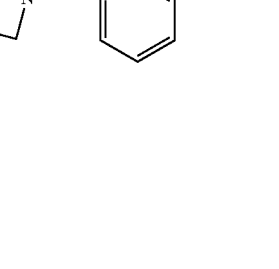 | 645 | δ 2.04-2.11 (2H, m), 3.24-3.30 (2H, m), 3.51-3.62 (6H, m), 3.63 (3H, s), 3.64 (3H, s), 4.06 (3H, s), 4.28 (1H, brs), 6.14-6.18 (1H, m), 6.28 (2H, m), 6.43-6.51 (3H, m), 6.83-6.90 (1H, m), 6.93-6.97 (1H, m), 7.05-7.09 (1H, m), 7.20 (1H, t, J = 8.4 Hz), 7.42 (1H, t, J = 8.0 Hz), 7.56-7.59 (1H, m), 7.66-7.71 (2H, m), 7.90 (1H, s), 8.08 (1H, d, J = 2.4 Hz) |
| 86 | 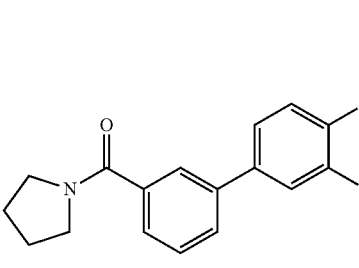 | 629 | δ 1.90-2.01 (4H, m), 3.22 (2H, t, J = 5.6 Hz), 3.45-3.48 (2H, m), 3.61-3.67 (4H, m), 3.79 (3H, s), 4.04 (3H, s), 4.40-4.49 (1H, m), 6.19 (1H, dd, J = 8.0, 1.2 Hz), 6.31 (1H, dd, J = 8.0, 1.6 Hz), 6.49 (1H, t, J = 2.0 Hz), 6.82 (1H, brs), 6.92 (1H, t, J = 8.0 Hz), 6.98 (1H, ddd, J = 8.0, 6.8, 1.2 Hz), 7.03 (1H, d, J = 8.8 Hz), 7.21-7.28 (2H, m), 7.36 (1H, t, J = 2.0 Hz), 7.41-7.43 (3H, m), 7.54-7.55 (1H, m), 7.66-7.70 (2H, m), 8.12-8.13 (1H, m) |

TABLE 21-continued
| 87 | 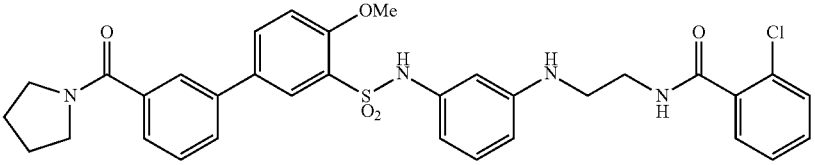 [SMILES: COc1ccc(-c2cccc(C(=O)N3CCCC3)c2)cc1S(=O)(=O)Nc1cccc(NCCNC(=O)c2ccccc2Cl)c1] | 633 | δ 1.86-1.97 (4H, m), 3.28 (2H, t, J = 5.6 Hz), 3.40-3.44 (2H, m), 3.62-3.66 (4H, m), 4.06 (3H, s), 4.30 (1H, brs), 6.26 (1H, dd, J = 8.0, 1.2 Hz), 6.32 (1H, dd, J = 8.0, 2.0 Hz), 6.48 (1H, t, J = 2.0 Hz), 6.87 (1H, brs), 6.95 (1H, t, J = 8.0 Hz), 6.98-7.04 (1H, m), 7.05 (1H, d, J = 8.4 Hz), 7.22-7.32 (3H, m), 7.37-7.42 (2H, m), 7.49-7.56 (2H, m), 7.64 (1H, s), 7.69 (1H, dd, J = 8.8, 2.4 Hz), 8.09 (1H, d, J = 2.4 Hz) |
| --- | --- | --- | --- |
| 88 | 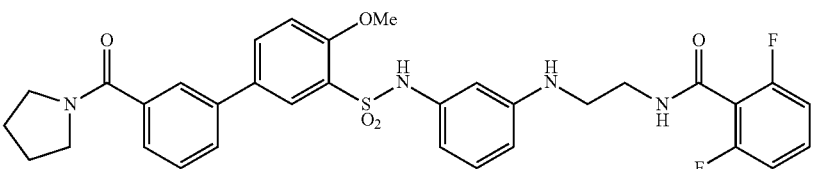 | 635 | δ 1.87-1.98 (4H, m), 3.24-3.27 (2H, m), 3.41-3.44 (2H, m), 3.55-3.63 (4H, m), 4.06 (3H, s), 4.20 (1H, brs), 6.27 (1H, dd, J = 8.0, 1.6 Hz), 6.33 (1H, dd, J = 8.0, 2.0 Hz), 6.46 (1H, t, J = 2.0 Hz), 6.85-7.00 (5H, m), 7.06 (1H, d, J = 8.4 Hz), 7.29-7.42 (3H, m), 7.54 (1H, dt, J = 7.2, 1.6 Hz), 7.62 (1H, s), 7.69 (1H, dd, J = 8.8, 2.4 Hz), 8.09 (1H, d, J = 2.0 Hz) |
| 89 | 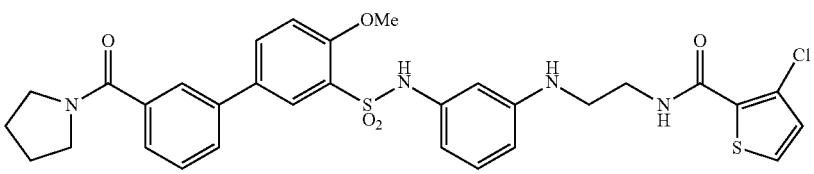 [SMILES: COc1ccc(-c2cccc(C(=O)N3CCCC3)c2)cc1S(=O)(=O)Nc1cccc(NCCNC(=O)c2sccc2Cl)c1] | 639 | δ 1.87-1.98 (4H, m), 3.22-3.29 (2H, m), 3.41-3.45 (2H, m), 3.63-3.67 (4H, m), 4.07 (3H, s), 4.23 (1H, brs), 6.32-6.36 (2H, m), 6.47 (1H, t, J = 2.0 Hz), 6.90-6.98 (3H, m), 7.06 (1H, d, J = 8.8 Hz), 7.42-7.45 (4H, m), 7.52-7.55 (1H, m), 7.65 (1H, s), 7.69 (1H, dd, J = 8.4, 2.4 Hz), 8.08 (1H, d, J = 2.4 Hz) |
| 90 | 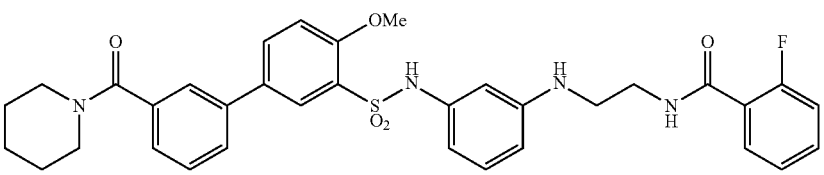 [SMILES: COc1ccc(-c2cccc(C(=O)N3CCCCC3)c2)cc1S(=O)(=O)Nc1cccc(NCCNC(=O)c2ccccc2F)c1] | 631 | δ 1.53-1.68 (6H, m), 3.28-3.36 (4H, m), 3.64-3.71 (4H, m), 4.07 (3H, s), 4.25 (1H, brs), 6.31-6.36 (2H, m), 6.46 (1H, t, J = 2.0 Hz), 6.84 (1H, brs), 6.96 (1H, t, J = 8.0 Hz), 7.05-7.11 (3H, m), 7.23-7.32 (2H, m), 7.39-7.47 (2H, m), 7.52-7.54 (2H, m), 7.69 (1H, dd, J = 8.4, 2.0 Hz), 8.02-8.08 (2H, m) |

TABLE 21-continued
| | | | |
|---|---|---|---|
| 91 | 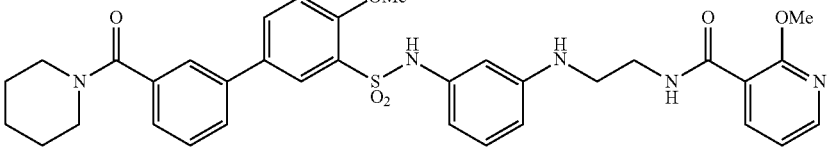 | 644 | δ 1.52-1.68 (6H, m), 3.29-3.51 (4H, m), 3.64-3.72 (4H, m), 3.98 (3H, s), 4.07 (3H, s), 4.30 (1H, brs), 6.31 (1H, dd, J = 8.0, 1.6 Hz), 6.35 (1H, dd, J = 8.0, 2.4 Hz), 6.50 (1H, t, J = 2.0 Hz), 6.89 (1H, brs), 6.96 (1H, t, J = 8.0 Hz), 7.04-7.07 (2H, m), 7.30-7.32 (1H, m), 7.41 (1H, t, J = 8.0 Hz), 7.51-7.53 (2H, m), 7.70 (1H, dd, J = 8.8, 2.4 Hz), 8.07 (1H, d, J = 2.4 Hz), 8.14-8.19 (1H, m), 8.26 (1H, dd, J = 8.8, 2.0 Hz), 8.49 (1H, dd, J = 7.6, 2.0 Hz) |
TABLE 22
| | | | |
|---|---|---|---|
| 92 | 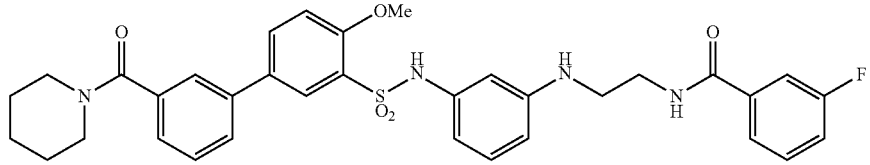 [SMILES: COc1ccc(-c2cccc(C(=O)N3CCCCC3)c2)cc1S(=O)(=O)Nc1cccc(NCCNC(=O)c2cccc(F)c2)c1] | 631 | δ 1.56-1.71 (6H, m), 3.10-3.19 (2H, m), 3.38-3.43 (2H, m), 3.55-3.60 (2H, m), 3.70-3.77 (2H, m), 4.03 (3H, s), 4.51 (1H, brs), 6.17 (1H, dd, J = 8.0, 1.2 Hz), 6.30 (1H, dd, J = 8.0, 2.4 Hz), 6.44 (1H, t, J = 2.0 Hz), 6.82 (1H, brs), 6.92 (1H, t, J = 8.0 Hz), 7.04 (1H, d, J = 8.8 Hz), 7.11-7.16 (1H, m), 7.26-7.33 (2H, m), 7.40-7.52 (3H, m), 7.55-7.57 (2H, m), 7.60-7.66 (1H, m), 7.69 (1H, dd, J = 8.4, 2.0 Hz), 8.15-8.16 (1H, m) |
| 93 | 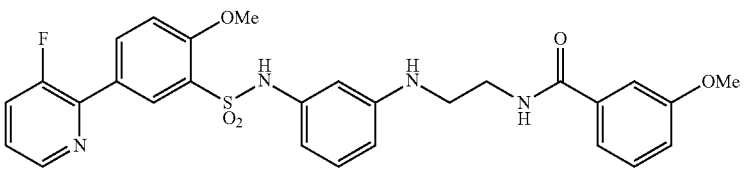 [SMILES: COc1cccc(C(=O)NCCNc2cccc(NS(=O)(=O)c3cc(-c4ncccc4F)ccc3OC)c2)c1] | 551 | δ 3.30 (2H, t, J = 6.0 Hz), 3.53-3.61 (2H, m), 3.83 (3H, s), 4.07 (3H, s), 6.28-6.33 (2H, m), 6.50-6.54 (2H, m), 6.91-6.96 (1H, m), 7.02 (1H, ddd, J = 8.4, 6.4, 1.2 Hz), 7.08 (1H, d, J = 8.8 Hz), 7.18-7.31 (6H, m), 7.40-7.45 (1H, m), 8.15 (1H, ddd, J = 8.8, 6.4, 1.2 Hz), 8.41 (1H, dt, J = 8.4, 1.6 Hz), 8.54 (1H, dd, J = 2.0, 1.2 Hz) |

TABLE 22-continued

| | | | |
|---|---|---|---|
| 94 | (structure) | 563 | δ 3.30 (2H, t, J = 6.0 Hz), 3.61-3.66 (2H, m), 3.79 (3H, s), 3.98 (3H, s), 4.08 (3H, s), 4.25-4.32 (1H, m), 6.33 (2H, dd, J = 8.0, 2.0 Hz), 6.49 (1H, t, J = 2.0 Hz), 6.64 (1H, d, J = 8.4 Hz), 6.89-6.96 (3H, m), 7.06-7.10 (2H, m), 7.24-7.26 (1H, m), 7.41-7.46 (1H, m), 7.57 (1H, t, J = 4.0 Hz), 8.05-8.11 (1H, m), 8.18 (1H, dd, J = 7.6, 2.0 Hz), 8.23 (1H, dd, J = 8.8, 2.4 Hz), 8.45 (1H, d, J = 2.0 Hz) |
| 95 | (structure) | 563 | δ 3.30 (2H, t, J = 6.0 Hz), 3.59-3.63 (2H, m), 3.83 (3H, s), 3.98 (3H, s), 4.07 (3H, s), 4.26-4.32 (1H, m), 6.32-6.34 (2H, m), 6.34-6.37 (1H, m), 6.50 (1H, t, J = 2.0 Hz), 6.64 (1H, dd, J = 8.0, 0.8 Hz), 6.91-6.96 (2H, m), 7.01 (1H, ddd, J = 8.0, 2.8, 0.8 Hz), 7.07 (1H, d, J = 8.8 Hz), 7.17-7.20 (1H, m), 7.24-7.31 (3H, m), 7.57 (1H, dd, J = 8.4, 3.6 Hz), 8.23 (1H, dd, J = 8.8, 2.4 Hz), 8.46 (1H, d, J = 2.4 Hz) |
| 96 | (structure) | 533 | δ 3.30 (2H, t, J = 6.0 Hz), 3.63-3.67 (2H, m), 3.85 (3H, s), 4.08 (3H, s), 429-4.37 (1H, m), 6.33-6.36 (2H, m), 6.47 (1H, s), 6.93-6.98 (3H, m), 7.07-7.11 (2H, m), 7.32 (1H, dd, J = 8.0, 4.8 Hz), 7.43-7.47 (1H, m), 7.67 (1H, dd, J = 8.8, 2.4 Hz), 7.77 (1H, dd, J = 8.0, 1.6 Hz), 8.04 (1H, d, J = 2.4 Hz), 8.05-8.14 (1H, m), 8.18 (1H, dd, J = 8.0, 1.6 Hz), 8.55 (1H, d, J = 4.4 Hz), 8.74 (1H, s) |

TABLE 22-continued
| | | | | |
|---|---|---|---|---|
| 97 | 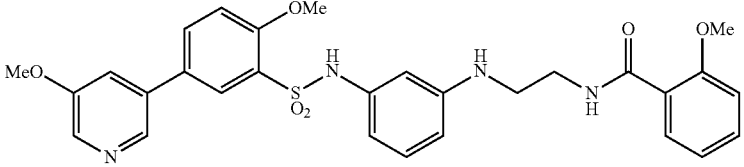 [SMILES: COc1cncc(-c2ccc(OC)c(S(=O)(=O)Nc3cccc(NCCNC(=O)c4ccccc4OC)c3)c2)c1] | | 563 | δ 3.28-3.31 (2H, m), 3.63-3.67 (2H, m), 3.84 (3H, s), 3.89 (3H, s), 4.08 (3H, s), 4.29-4.37 (1H, m), 6.32-6.37 (2H, m), 6.46 (1H, t, J = 2.0 Hz), 6.85-6.90 (1H, m), 6.93-6.98 (2H, m), 7.06-7.10 (2H, m), 7.25-7.27 (1H, m), 7.43-7.47 (1H, m), 7.67 (1H, dd, J = 8.4, 2.4 Hz), 8.03 (1H, d, J = 2.4 Hz), 8.06-8.12 (1H, m), 8.18 (1H, dd, J = 8.0, 2.0 Hz), 8.25 (1H, d, J = 2.8 Hz), 8.33 (1H, d, J = 2.0 Hz) |
| 98 | 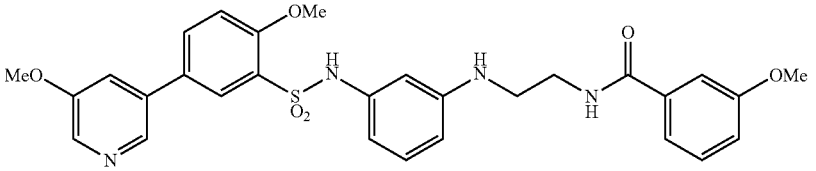 [SMILES: COc1cccc(C(=O)NCCNc2cccc(NS(=O)(=O)c3cc(-c4cncc(OC)c4)ccc3OC)c2)c1] | | 563 | δ 3.29-3.32 (2H, m), 3.61-3.65 (2H, m), 3.83 (3H, s), 3.89 (3H, s), 4.07 (3H, s), 4.18-4.25 (1H, m), 6.31-6.36 (2H, m), 6.50 (1H, t, J = 2.0 Hz), 6.56-6.64 (1H, m), 6.93-6.97 (2H, m), 7.01 (1H, ddd, J = 8.0, 2.4, 0.8 Hz), 7.08 (1H, dd, J = 8.8 Hz), 7.22-7.33 (4H, m), 7.67 (1H, dd, J = 8.8, 2.4 Hz), 8.03 (1H, d, J = 2.4 Hz), 8.26 (1H, d, J = 2.8 Hz), 8.31 (1H, d, J = 2.0 Hz) |
TABLE 23
| | | | | |
|---|---|---|---|---|
| 99 | 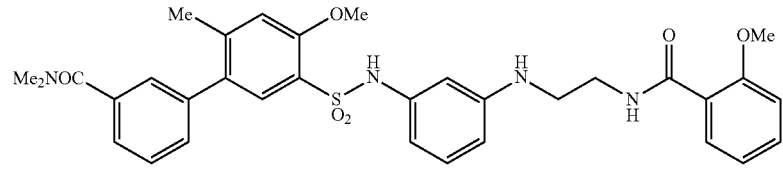 | | 617 | δ 2.27 (3H, s), 2.98 (3H, brs), 3.10 (3H, brs), 3.29-3.33 (2H, m), 3.63-3.68 (2H, m), 3.85 (3H, s), 4.04 (3H, s), 4.31 (1H, brs), 6.31 (1H, dd, J = 7.6, 1.6 Hz), 6.36 (1H, dd, J = 7.6, 1.6 Hz), 6.47 (1H, t, J = 2.0 Hz), 6.81 (1H, brs), 6.86 (1H, s), 6.93-6.99 (2H, m), 7.06-7.10 (1H, m), 7.23-7.26 (2H, m), 7.35-7.47 (3H, m), 7.68 (1H, s), 8.08-8.14 (1H, m), 8.18 (1H, dd, J = 8.0, 1.6 Hz) |
| 100 | 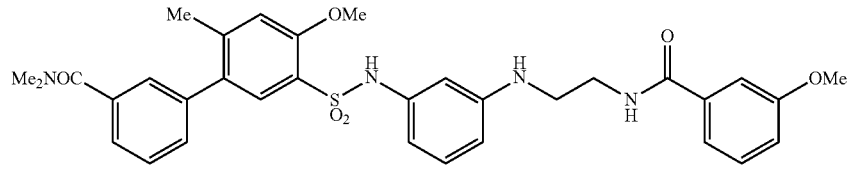 | | 617 | δ 2.26 (3H, s), 3.04 (3H, brs), 3.10 (3H, brs), 3.20-3.23 (2H, m), 3.59-3.63 (2H, m), 3.81 (3H, s), 4.00 (3H, s), 4.52 (1H, brs), 6.20 (1H, dd, J = 8.0, 1.6 Hz), 6.33 (1H, dd, J = 8.0, 1.6 Hz), 6.46 (1H, t, J = 2.0 Hz), 6.81 (1H, brs), 6.84 (1H, s), 6.95 (1H, t, J = 8.0 Hz), 7.00 (1H, ddd, J = 8.0, 2.4, 0.8 Hz), 7.25-7.41 (8H, m), 7.76 (1H, s) |

TABLE 23-continued

| | | | |
|---|---|---|---|
| 101 | (structure) | 601 | δ 2.26 (3H, s), 2.36 (3H, s), 3.03 (3H, brs), 3.10 (3H, brs), 3.20-3.23 (2H, m), 3.59-3.63 (2H, m), 4.01 (3H, s), 4.46 (1H, brs), 6.22 (1H, dd, J = 7.6, 1.6 Hz), 6.33 (1H, dd, J = 8.0, 1.6 Hz), 6.46 (1H, t, J = 2.0 Hz), 6.80 (1H, brs), 6.84 (1H, s), 6.95 (1H, t, J = 8.0 Hz), 7.22-7.30 (1H, m), 7.30-7.41 (6H, m), 7.54-7.58 (1H, m), 7.62 (1H, s), 7.76 (1H, s) |
| 102 | (structure) | 605 | δ 2.26 (3H, s), 3.06 (3H, brs), 3.12 (3H, brs), 3.15-3.18 (2H, m), 3.56-3.62 (2H, m), 3.99 (3H, s), 4.52 (1H, brs), 6.16 (1H, dd, J = 7.6, 1.6 Hz), 6.31 (1H, dd, J = 8.0, 1.6 Hz), 6.45 (1H, t, J = 2.0 Hz), 6.80 (1H, brs), 6.83 (1H, s), 6.94 (1H, t, J = 8.0 Hz), 7.11-7.17 (1H, m), 7.29-7.44 (5H, m), 7.54-7.61 (2H, m), 7.62-7.70 (1H, m), 7.79 (1H, s) |
| 103 | (structure) | 618 | δ 2.27 (3H, s), 2.99 (3H, brs), 3.10 (3H, brs), 3.29-3.33 (2H, m), 3.64-3.69 (2H, m), 3.99 (3H, s), 4.04 (3H, s), 4.27 (1H, brs), 6.30 (1H, dd, J = 7.6, 1.6 Hz), 6.36 (1H, dd, J = 8.0, 1.6 Hz), 6.49 (1H, t, J = 2.0 Hz), 6.82 (1H, brs), 6.86 (1H, s), 6.97 (1H, t, J = 8.0 Hz), 7.05 (1H, dd, J = 7.6, 1.6 Hz), 7.23-7.26 (2H, m), 7.35-7.40 (2H, m), 7.69 (1H, s) 8.14-8.22 (1H, m), 8.27 (1H, dd, J = 8.8, 2.0 Hz), 8.49 (1H, dd, J = 7.6, 2.0 Hz) |
| 104 | (structure) | 621 | δ 2.27 (3H, s), 2.99 (3H, brs), 3.01 (3H, brs), 3.21-3.31 (2H, m), 3.62-3.67 (2H, m), 4.03 (3H, s), 4.29 (1H, brs), 6.25 (1H, dd, J = 8.0, 1.6 Hz), 6.34 (1H, dd, J = 8.0, 2.0 Hz), 6.48 (1H, t, J = 2.0 Hz), 6.83 (1H, brs), 6.86 (1H, s), 6.94-6.98 (2H, m), 7.25-7.42 (7H, m), 7.54-7.57 (1H, m), 7.72 (1H, s) |

TABLE 23-continued

| | | | | |
|---|---|---|---|---|
| 105 | 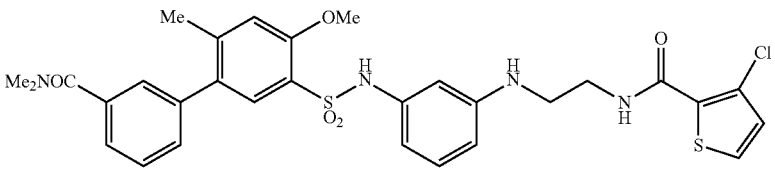 | | 627 | δ 2.27 (3H, s), 3.00 (3H, brs), 3.11 (3H, brs), 3.29-3.33 (2H, m), 3.62-3.67 (2H, m), 4.04 (3H, s), 4.20 (1H, brs), 6.32 (1H, dd, J = 8.0, 2.0 Hz), 6.36 (1H, dd, J = 8.0, 2.0 Hz), 6.47 (1H, t, J = 2.0 Hz), 6.83 (1H, brs), 6.87 (1H, s), 6.94-7.00 (2H, m), 7.25-7.27 (3H, m), 7.36-7.41 (2H, m), 7.45 (1H, d, J = 5.6 Hz), 7.70 (1H, s) |

TABLE 24

| | | | | |
|---|---|---|---|---|
| 106 | 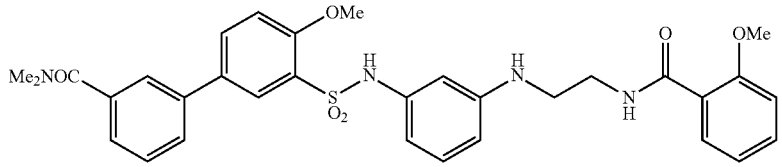 | | 587 | δ 2.68 (3H, s), 2.99 (3H, brs), 3.13 (3H, brs), 3.23-3.27 (2H, m), 3.59-3.65 (2H, m), 3.84 (3H, s), 4.38 (1H, brs), 6.31-6.35 (2H, m), 6.36 (1H, t, J = 2.0 Hz), 6.61 (1H, brs), 6.93-6.99 (2H, m), 7.05-7.09 (1H, m), 7.32-7.38 (2H, m), 7.41-7.47 (2H, m), 7.53-7.56 (2H, m), 7.62 (1H, dd, J = 8.0, 2.0 Hz), 8.08-8.16 (1H, m), 8.16-8.19 (2H, m) |
| 107 | 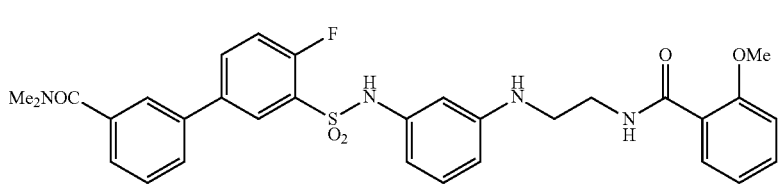 | | 591 | δ 2.99 (3H, brs), 3.13 (3H, brs), 3.28-3.32 (2H, m), 3.63-3.68 (2H, m), 3.85 (3H, s), 4.39 (1H, brs), 6.37-6.41 (2H, m), 6.46 (1H, t, J = 2.0 Hz), 6.78 (1H, brs), 6.93-7.01 (2H, m), 7.05-7.10 (1H, m), 7.21-7.24 (1H, m), 7.38 (1H, dt, J = 7.6, 1.2 Hz), 7.42-7.47 (2H, m), 7.50-7.54 (2H, m), 7.70 (1H, ddd, J = 7.6, 4.4, 2.4 Hz), 8.02 (1H, dd, J = 6.8, 2.4 Hz), 8.08-8.16 (1H, m), 8.18 (1H, dd, J = 8.0, 2.0 Hz) |
| 108 | 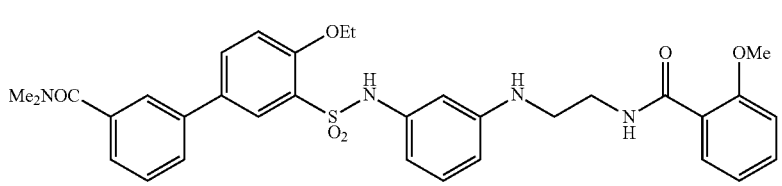 | | 617 | δ 1.60 (3H, t, J = 6.8 Hz), 2.98 (3H, brs), 3.12 (3H, brs), 3.28-3.32 (2H, m), 3.63-3.68 (2H, m), 3.82 (3H, s), 4.30 (2H, q, J = 6.8 Hz), 4.33 (1H, brs), 6.32 (1H, dd, J = 8.0, 1.6 Hz), 6.35 (1H, dd, J = 8.0, 1.6 Hz), 6.49 (1H, t, J = 2.0 Hz), 6.80 (1H, brs), 6.92-6.98 (2H, m), 7.03-7.09 (2H, m), 7.33 (1H, dt, J = 7.6, 1.2 Hz), 7.39-7.46 (2H, m), 7.51-7.54 (2H, m), 7.66 (1H, dd, J = 8.4, 2.4 Hz), 8.05 (1H, d, J = 2.4 Hz), 8.08-8.16 (1H, m), 8.18 (1H, dd, J = 8.0, 1.6 Hz) |
| 109 | 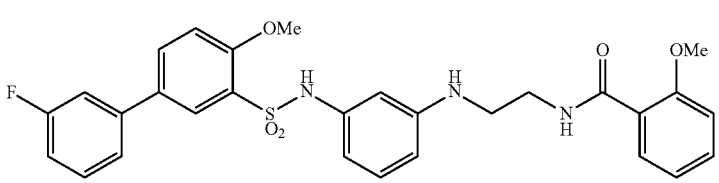 [SMILES: COc1ccccc1C(=O)NCCNc1cccc(NS(=O)(=O)c2cc(-c3cccc(F)c3)ccc2OC)c1] | | 550 | δ 3.28-3.32 (2H, m), 3.62-3.67 (2H, m), 3.83 (3H, s), 4.02 (3H, s), 4.25 (1H, brs), 6.31-6.36 (2H, m), 6.45-6.47 (1H, m), 6.83-7.10 (6H, m), 7.17 (1H, dt, J = 10.0, 2.4 Hz), 7.25-7.27 (1H, m), 7.32-7.37 (1H, m), 7.42-7.47 (1H, m) 7.65 (1H, dd, J = 8.8, 2.4 Hz), 8.04 (1H, d, J = 2.4 Hz), 8.06-8.17 (1H, m), 8.18-8.22 (1H, m) |

TABLE 24-continued

| | | | |
|---|---|---|---|
| 110 | Me₂NOC-[biphenyl]-S(O₂)NH-[phenyl]-NH-CH₂CH₂-NHC(O)-[phenyl-OMe] | 573 | δ 2.98 (3H, brs), 3.14 (3H, brs), 3.26-3.31 (2H, m), 3.62-3.68 (2H, m), 3.86 (3H, s), 6.41 (2H, d, J = 7.6 Hz), 6.47 (1H, s), 6.50-6.57 (1H, m), 6.91-6.95 (2H, m), 7.00 (1H, t, J = 8.0 Hz), 7.05-7.09 (1H, m), 7.36-7.51 (6H, m), 7.69 (1H, d, J = 7.6 Hz), 7.77 (1H, d, J = 8.0 Hz), 7.94 (1H, s), 8.10-8.17 (1H, m), 8.18 (1H, dd, J = 8.0, 2.0 Hz) |
| 111 | Me₂NOC-[biphenyl-OMe]-S(O₂)NH-[phenyl]-N(Me)-CH₂CH₂-NHC(O)-[phenyl-OMe] | 617 | δ 2.78 (3H, s), 2.99 (3H, brs), 3.06-3.11 (5H, m), 3.30-3.40 (2H, m), 3.76 (3H, s), 4.07 (3H, s), 6.31-6.37 (3H, m), 6.47 (1H, t, J = 2.0 Hz), 6.85-6.99 (4H, m), 7.07 (1H, d, J = 8.8 Hz), 7.16 (1H, dd, J = 7.6, 1.6 Hz), 7.32-7.36 (2H, m), 7.40-7.44 (1H, m), 7.51-7.54 (2H, m), 7.69-7.72 (1H, m), 8.04-8.06 (1H, m) |
| 112 | Me₂NOC-[biphenyl-OMe]-S(O₂)NH-[phenyl]-N(Me)-CH₂CH₂-NHC(O)-[phenyl-OMe] | 617 | δ 2.92 (3H, s), 2.97 (3H, brs), 3.11 (3H, brs), 3.48-3.51 (2H, m), 3.56-3.59 (2H, m), 3.70 (3H, s), 4.08 (3H, s), 6.36 (1H, dd, J = 8.0, 1.6 Hz), 6.50 (1H, dd, J = 8.0, 2.0 Hz), 6.58 (1H, t, J = 2.0 Hz), 6.88 (1H, brs), 6.89 (1H, d, J = 8.0 Hz), 7.00-7.10 (3H, m), 7.33 (1H, dt, J = 7.6, 1.6 Hz), 7.37-7.45 (2H, m), 7.50-7.54 (2H, m), 7.68 (1H, dd, J = 8.4, 2.0 Hz), 7.99-8.04 (1H, m), 8.05-8.06 (1H, m), 8.20 (1H, dd, J = 8.0, 2.0 Hz) |

Experimental Example 1

Evaluation of Agonist Activity Against OX2R

NFAT-luciferase gene and OX2R gene were each constitutively expressed in CHO cell, which is a cell line derived from Chinese hamster ovary to establish a cell line (CHOOX2R). The cells thereof were sown on a 96 well plate at 10000 cells/well, and cultured in a 5% FBS-added DMEM medium for 48 hr. The cells were dissolved in Fura2AM (final concentration 40 μM), HEPE buffer (HEPES Buffer containing 20 mM HEPES, 115 mM NaCl, 5.4 mM KCl, 0.8 mM MgCl2, 1.8 mM CaCl2, 13.8 mM D-glucose, 2.5 mM probenecid acid and 0.1% BSA), and fluorescence labeled at 37° C. for 60 min. After washing, HEPES buffer (75 μL) was added, a test compound solution (25 μL) was added, and changes in the fluorescence intensity were measured by FDSS3000 (Hamamatsu Photonics K.K.). The test compound was dissolved in DMSO (final concentration of DMSO was 1%), and diluted with HEPES buffer to a final concentration of 0.1 μM, 1.0 μM or 10 μM. The agonist activity value of each compound is shown in Table 25 to Table 29.

TABLE 25

| Example No. | Response (10 μM (%)) | Response (1.0 μM (%)) | Response (0.1 μM (%)) |
|---|---|---|---|
| 1 | 57 | 21 | <5 |
| 2 | 67 | 27 | <5 |
| 3 | 50 | 11 | <5 |
| 4 | 17 | <5 | <5 |
| 5 | 23 | <5 | <5 |

TABLE 25-continued

| Example No. | Response (10 μM (%)) | Response (1.0 μM (%)) | Response (0.1 μM (%)) |
|---|---|---|---|
| 6 | 7 | <5 | <5 |
| 7 | 145 | 62 | 10 |
| 8 | 46 | 9 | <5 |
| 9 | <5 | <5 | <5 |
| 10 | 41 | <5 | <5 |
| 11 | 23 | 17 | <5 |
| 12 | 73 | 44 | <5 |
| 13 | 99 | 64 | <5 |
| 14 | 8 | <5 | <5 |
| 15 | 6 | <5 | <5 |
| 16 | <5 | <5 | <5 |
| 17 | 182 | 18 | <5 |
| 18 | 151 | 13 | <5 |
| 19 | 143 | 8 | <5 |
| 20 | 180 | 13 | <5 |
| 21 | 11 | <5 | <5 |
| 22 | 21 | 15 | <5 |
| 23 | <5 | <5 | <5 |
| 24 | <5 | <5 | <5 |
| 25 | 38 | 7 | <5 |
| 26 | 29 | 5 | <5 |
| 27 | <5 | <5 | <5 |
| 28 | <5 | <5 | <5 |
| 29 | 73 | 16 | <5 |
| 31 | 103 | 67 | 6 |
| 32 | 75 | 26 | <5 |
| 33 | 93 | 31 | <5 |

TABLE 26

| Example No. | Response (10 μM (%)) | Response (1.0 μM (%)) | Response (0.1 μM (%)) |
|---|---|---|---|
| 34 | 123 | 64 | 13 |
| 35 | 127 | 68 | 13 |
| 36 | 68 | 11 | <5 |
| 37 | 163 | 102 | 16 |
| 38 | 113 | 37 | 8 |
| 39 | 102 | 27 | <5 |
| 40 | 74 | 74 | 35 |
| 41 | 115 | 107 | 70 |
| 42 | 114 | 103 | 65 |
| 43 | 94 | 55 | <5 |
| 44 | 94 | 28 | <5 |
| 45 | 98 | 80 | <5 |
| 46 | 91 | 89 | 18 |
| 47 | 82 | 89 | 14 |
| 48 | 84 | 91 | 44 |
| 49 | 88 | 84 | 9 |
| 50 | 76 | 71 | <5 |
| 51 | 87 | 9 | <5 |
| 52 | 64 | 79 | 40 |
| 53 | 66 | 89 | 46 |
| 54 | 126 | 168 | 33 |
| 55 | 122 | 144 | 23 |
| 56 | 122 | 22 | <5 |
| 57 | 87 | 9 | <5 |
| 58 | 119 | 130 | <5 |
| 59 | 64 | <5 | <5 |
| 60 | 75 | 43 | <5 |
| 61 | 69 | 18 | <5 |
| 62 | 94 | 92 | 71 |
| 63 | 82 | 81 | <5 |
| 64 | 72 | 68 | <5 |
| 65 | 74 | 96 | 74 |

TABLE 27

| Example No. | Response (10 μM (%)) | Response (1.0 μM (%)) | Response (0.1 μM (%)) |
|---|---|---|---|
| 66 | 67 | 88 | 97 |
| 67 | 76 | 96 | 55 |
| 68 | 74 | 86 | 42 |
| 69 | 111 | 123 | 67 |
| 70 | 85 | 105 | 34 |
| 71 | 80 | 39 | <5 |
| 72 | 88 | 16 | <5 |
| 73 | 98 | 90 | 45 |
| 74 | 92 | 51 | <5 |
| 75 | 76 | 87 | 49 |
| 76 | 98 | 95 | 24 |
| 77 | 82 | 91 | 42 |
| 78 | 49 | 33 | <5 |
| 79 | 34 | 18 | <5 |
| 80 | 91 | 91 | 37 |
| 81 | 98 | 98 | 75 |
| 82 | 74 | 51 | <5 |
| 83 | 71 | 10 | <5 |
| 84 | 70 | 58 | 7 |
| 85 | 90 | 90 | 19 |
| 86 | 81 | 89 | 10 |
| 87 | 80 | 90 | 42 |
| 88 | 86 | 100 | 76 |
| 89 | 97 | 96 | 93 |
| 90 | 88 | 68 | 51 |
| 91 | 80 | 90 | 42 |
| 92 | 94 | 92 | 27 |
| 93 | 73 | 33 | <5 |
| 94 | 22 | <5 | <5 |
| 95 | 30 | <5 | <5 |
| 96 | 88 | 61 | <5 |
| 97 | 37 | 12 | <5 |

TABLE 28

| Example No. | Response (10 μM (%)) | Response (1.0 μM (%)) | Response (0.1 μM (%)) |
|---|---|---|---|
| 98 | 91 | 22 | <5 |
| 102 | 85 | 83 | 61 |
| 103 | 80 | 93 | 77 |
| 104 | 86 | 88 | 67 |
| 105 | 79 | 84 | 78 |
| 106 | 39 | 27 | <5 |
| 107 | 82 | 79 | 65 |
| 108 | 82 | 81 | 44 |
| 109 | 47 | 46 | 13 |
| 110 | 28 | <5 | <5 |
| 112 | 139 | 131 | <5 |

(As used herein, Response in Table 25 to Table 28 is a value obtained by dividing the agonist activity value, when the test compound is evaluated with orexin-A as a full-agonist (maximum value of agonist activity: 100%), at 10 μM, 1.0 μM, 0.1 μM by the agonist activity value of orexin-A.)

TABLE 29

| Example No. | $EC_{50}$ (μM) | Emax (%) |
|---|---|---|
| 29 | 0.8 | 54 |
| 40 | 0.05 | 74 |
| 41 | 0.033 | 57 |
| 42 | 0.031 | 90 |
| 43 | 0.3 | 94 |
| 44 | 1.047 | 94 |
| 45 | 0.115 | 100 |
| 46 | 0.1 | 94 |
| 48 | 0.36 | 87 |
| 51 | 3.277 | 87 |
| 52 | 0.783 | 84 |
| 53 | 1.149 | 87 |
| 54 | 0.63 | 94 |
| 62 | 0.102 | 99 |
| 65 | 0.8 | 85 |
| 66 | 0.023 | 98 |
| 73 | 0.182 | 98 |
| 75 | 0.077 | 87 |
| 81 | 0.365 | 85 |
| 96 | 0.268 | 88 |
| orexin-A | 0.001 | 100 |

(As used herein, Emax in Table 29 is a value by conversion with orexin-A as a full agonist (maximum value of agonist activity: 100%)).

As is clear from the results of Table 25 to Table 29, the compound of the present invention has an OX2R agonist activity.

INDUSTRIAL APPLICABILITY

The compound of the present invention shows an orexin agonist activity, and is useful as an agent for the treatment or prophylaxis of narcolepsy.

This application is based on a patent application No. 2013-257523 filed in Japan (filing date: Dec. 12, 2013), the contents of which are incorporated in full herein.

The invention claimed is:
1. A compound represented by the formula (I)

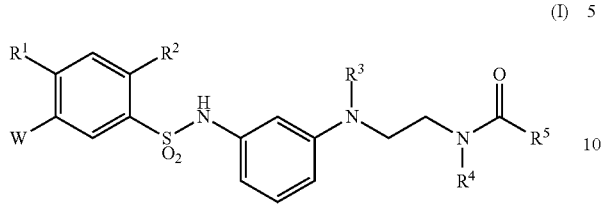 (I)

wherein
R$^1$ is a hydrogen atom, alkyl having 1 to 4 carbon atoms or halogen,
R$^2$ is a hydrogen atom, alkyl having 1 to 4 carbon atoms, alkoxy having 1 to 4 carbon atoms, halogen, —OH, —NR$^{2a}$R$^{2b}$ (wherein R$^{2a}$ is a hydrogen atom, alkyl having 1 to 6 carbon atoms or cycloalkyl having 3 to 8 carbon atoms, R$^{2b}$ is a hydrogen atom, alkyl having 1 to 6 carbon atoms or cycloalkyl having 3 to 8 carbon atoms), or the formula (a) or (b)

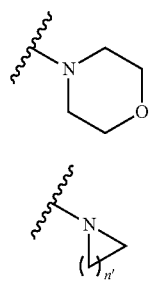 (a)

(b)

(wherein n' is an integer of 1 to 4)
R$^3$ is a hydrogen atom or alkyl having 1 to 4 carbon atoms,
R$^4$ is a hydrogen atom or alkyl having 1 to 4 carbon atoms,
R$^5$ is aryl or heteroaryl (wherein aryl or heteroaryl is optionally substituted by optionally selected 1 to 4 R$^6$),
R$^6$ is a hydrogen atom, alkyl having 1 to 4 carbon atoms, alkoxy having 1 to 4 carbon atoms, halogen, —CN, —CF$_3$, —CH$_2$F, —CHF$_2$, —OCF$_3$, —OH, —NO$_2$ or —NR$^{6a}$R$^{6b}$ (wherein R$^{6a}$ is a hydrogen atom, alkyl having 1 to 4 carbon atoms, —CH$_2$CH$_2$OMe or —CH$_2$CH$_2$OEt, R$^{6b}$ is a hydrogen atom, alkyl having 1 to 4 carbon atoms, —CH$_2$CH$_2$OMe or —CH$_2$CH$_2$OEt),
W is the formula (II):

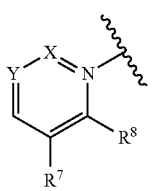 (II)

(wherein
R$^7$ is a hydrogen atom, alkyl having 1 to 4 carbon atoms, alkoxy having 1 to 4 carbon atoms or halogen,
R$^8$ is a hydrogen atom, alkyl having 1 to 4 carbon atoms, alkoxy having 1 to 4 carbon atoms or halogen,
X is —N= or —CR$^9$=,
Y is —N= or —CR$^9$=,
R$^9$ is a hydrogen atom, alkyl having 1 to 4 carbon atoms, alkoxy having 1 to 4 carbon atoms, halogen, —OH, —NR$^{10}$R$^{11}$, —CH$_2$OR$^{10}$, —CF$_3$, —OCF$_3$, —CN, —C(O)OR$^{10}$, —C(O)NR$^{10}$R$^{11}$, the formula (III) or (IV),

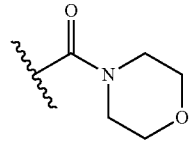 (III)

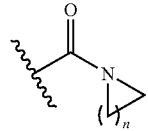 (IV)

(wherein n is an integer of 1 to 4)
X and Y are —CR$^9$=, each R$^9$ may be the same or different,
R$^{11}$ is a hydrogen atom, alkyl having 1 to 4 carbon atoms, —CH$_2$CF$_3$, —CH$_2$CH$_2$OH or —CH$_2$CH$_2$OMe,
R$^{11}$ is a hydrogen atom, alkyl having 1 to 4 carbon atoms, —CH$_2$CF$_3$, —CH$_2$CH$_2$OH or —CH$_2$CH$_2$OMe,
or a pharmaceutically acceptable acid addition salt thereof.
2. The compound according to claim 1, wherein
R$^1$ is a hydrogen atom or alkyl having 1 to 4 carbon atoms,
R$^2$ is a hydrogen atom, alkyl having 1 to 4 carbon atoms, alkoxy having 1 to 4 carbon atoms or halogen,
R$^6$ is alkyl having 1 to 4 carbon atoms, alkoxy having 1 to 4 carbon atoms, halogen, —CN, —CF$_3$, —OH or —NR$^{6a}$R$^{6b}$ (wherein R$^{6a}$ is alkyl having 1 to 4 carbon atoms, R$^{6b}$ is alkyl having 1 to 4 carbon atoms),
W is a compound of the formula (II):

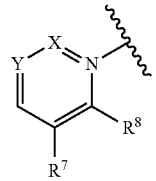 (II)

(wherein
R$^7$ is a hydrogen atom, alkoxy having 1 to 4 carbon atoms or halogen,
R$^8$ is a hydrogen atom, alkyl having 1 to 4 carbon atoms, alkoxy having 1 to 4 carbon atoms or halogen,
X is —CR$^9$= or —N=,
Y is —CR$^9$= or —N=,
R$^9$ is a hydrogen atom, alkyl having 1 to 4 carbon atoms, alkoxy having 1 to 4 carbon atoms, halogen, —OH, —NR$^{10}$R$^{11}$, —CH$_2$OH, —C(O)OR$^{10}$, —C(O)NR$^{10}$R$^{11}$ or the formula (IV):

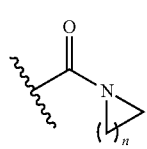 (IV)
(wherein n is an integer of 1 to 4),
$R^{10}$ is a hydrogen atom, alkyl having 1 to 4 carbon atoms, —$CH_2CF_3$, —$CH_2CH_2OH$ or —$CH_2CH_2OMe$, and
$R^{11}$ is a hydrogen atom, alkyl having 1 to 4 carbon atoms, —$CH_2CF_3$, —$CH_2CH_2OH$ or —$CH_2CH_2OMe$,
or a pharmaceutically acceptable acid addition salt thereof.
* * * * *